US012319713B2

(12) United States Patent
Alam

(10) Patent No.: US 12,319,713 B2
(45) Date of Patent: Jun. 3, 2025

(54) 3,4-THIAZOLO-STEROIDS AND METHODS OF MAKING AND USING THE SAME

(71) Applicant: Arkansas State University—Jonesboro, State University, AR (US)

(72) Inventor: Mohammad Abrar Alam, Jonesboro, AR (US)

(73) Assignee: Arkansas State University—Jonesboro, State University, AR (US)

( * ) Notice: Subject to any disclaimer, the term of this patent is extended or adjusted under 35 U.S.C. 154(b) by 964 days.

(21) Appl. No.: 17/261,649

(22) PCT Filed: Jul. 22, 2019

(86) PCT No.: PCT/US2019/042855
§ 371 (c)(1),
(2) Date: Jan. 20, 2021

(87) PCT Pub. No.: WO2020/018997
PCT Pub. Date: Jan. 23, 2020

(65) Prior Publication Data
US 2021/0317160 A1    Oct. 14, 2021

Related U.S. Application Data

(60) Provisional application No. 62/700,967, filed on Jul. 20, 2018.

(51) Int. Cl.
*C07J 71/00* (2006.01)
*A61P 35/00* (2006.01)

(52) U.S. Cl.
CPC ........... *C07J 71/0094* (2013.01); *A61P 35/00* (2018.01)

(58) Field of Classification Search
CPC .............................. C07J 71/0094; A61P 35/00
USPC ....................................................... 514/176
See application file for complete search history.

(56) References Cited

U.S. PATENT DOCUMENTS

| | | | |
|---|---|---|---|
| 3,081,228 | A | 3/1963 | Clinton |
| 3,119,816 | A | 1/1967 | Komeno |
| 3,404,206 | A | 10/1968 | Bertin |
| 3,772,283 | A | 11/1973 | Popper |
| 2009/0270456 | A1 | 10/2009 | Hasegawa et al. |
| 2012/0302569 | A1 | 11/2012 | Jackson et al. |
| 2015/0126564 | A1 | 5/2015 | Hahm et al. |

FOREIGN PATENT DOCUMENTS

| DE | 1169442 B | * | 5/1964 | ......... C07J 71/0094 |
|---|---|---|---|---|
| WO | 2002032897 A1 | | 4/2002 | |

OTHER PUBLICATIONS

Ahmad, M.S., and Alam, Z. "Mass spectral studies on steroidal compounds XIII:[3, 4-d] thiazoles in the cholestane series." OrIDFnic mass spectrometry 24.4 (1989): 279-282.
Alam, M.A. et al. Hexafluoroisopropyl alcohol mediated synthesis of 2,3-dihydro-4H-pyrido[1,2-a]pyrimidin-4-ones. Sci. Rep. 2016, 6, 36316.
Ali, M.A., et al. "Benign synthesis of thiazolo-androstenone derivatives as potent anticancer agents." OrIDFnic letters 20.18 (2018): 5927-5932.
Alley, M.C. et al. Feasibility of Drug Screening with Panels of Human Tumor Cell Lines Using a Microculture Tetrazolium Assay. Cancer Res. Feb. 1, 1988;48(3):589-601.
Allison, D. et al. Synthesis and antimicrobial studies of novel derivatives of 4-(4-formyl-3-phenyl-1Hpyrazol-1-yl) benzoic acid as potent anti-Acinetobacter baumannii agents. Bioorg. Med. Chem. Lett. 2017, 27, 387-392.
Alsharif, Z.A. & Alam, M.A. Modular synthesis of thiazoline and thiazole derivatives by using a cascade protocol. RSC Advances 2017, 7:32647-32651.
Alsharif, Z.A. et al. Hexafluoroisopropanol mediated benign synthesis of 2H-pyrido[1,2-a]pyrimidin-2-ones by using a domino protocol. New J. Chem. 2017, 41:14862-14870.
Ambrose, A.J. et al. Ritterostatin GN1N, a Cephalostatin-Ritterazine Bis-steroidal Pyrazine Hybrid, Selectively Targets GRP78. ChemBioChem 2017, 18(6):506-510.
Ayati, A. et al. Recent applications of 1,3-thiazole core structure in the identification of new lead compounds and drug discovery. Eur. J. Med. Chem. 2015, 97, 699-718.
Bansal, R. and Acharya, P.C. Man-made cytotoxic steroids: exemplary agents for cancer therapy. Chem. Rev. 2014, 114, 6986-7005.
Bastos, D.A. and Antonarakis, E.S. Galeterone for the treatment of advanced prostate cancer: the evidence to date. Drug Des Devel Ther. (2016) 10:2289-97. doi: 10.2147/DDDT.S93941. PMID: 27486306; PMCID: PMC4956059.
Boyd, M.R. et al. Some Practical Considerations and Applications of the National Cancer Institute In Vitro Anticancer Drug Discovery Screen. Drug Development Research 34: 91-109, 1995.
Brider, J. et al. Synthesis and antimicrobial studies of azomethine and N-arylamine derivatives of 4-(4-formyl-3-phenyl-1H-pyrazol-1-yl)benzoic acid as potent antimethicillin-resistant *Staphylococcus aureus* agents. Med. Chem. Res. 2016, 25, 2691-2697.
Calle, J.M. et al. Steroidal Saponins from Furcraea hexapetala Leaves and Their Phytotoxic Activity. J. Nat. Prod. 2016, 79, 2903-2911.
Chen, M. et al. Conversion of human steroid 5beta-reductase (AKR1D1) into 3betahydroxysteroid dehydrogenase by single point mutation E120H: example of perfect enzyme engineering. J. Biol. Chem. 2012, 287, 16609-16622.
Cheskis, B.J. Regulation of cell signalling cascades by steroid hormones. J. Cell. Biochem. 2004, 93, 20-27.
Covell, D.G. et al. Anticancer medicines in development: assessment of bioactivity profiles within the National Cancer Institute anticancer screening data. Molec Cancer Therap 2007; 6: 2261-70.
Dai, J. et al. Pregnane-10,2-carbolactones from a Hawaiian Marine Sponge in the Genus *Myrmekioderma*. J. Nat. Prod. 2016, 79(5):1464-7.

(Continued)

*Primary Examiner* — Kristin A Vajda
(74) *Attorney, Agent, or Firm* — Quarles & Brady, LLP

(57) ABSTRACT

3,4-thiazolo steroids are provided herein. Also provided herein are methods of making and using the same for the inhibition of cell proliferation or the killing of cells.

12 Claims, No Drawings

(56) References Cited

OTHER PUBLICATIONS

El-Desoky, E-S.I, et al. Synthesis and chemical reactions of the steroidal hormone 17alpha-methyltestosterone. Steroids 2016, 105, 68-95.
Fan, N-J. et al. Synthesis and antiproliferative activity of D-ring substituted steroidal benzamidothiazoles. Steroids 2016, 112:103-8.
FDA. FDA approves drug to treat Duchenne muscular dystrophy. https://www.fda.gov/NewsEvents/Newsroom/PressAnnouncements/ucm540945.htm, 2017.
Festa, C. et al. Exploitation of cholane scaffold for the discovery of potent and selective farnesoid X receptor (FXR) and G-protein coupled bile acid receptor 1 (GP-BAR1) liIDFnds. J. Med. Chem. 2014, 57(20):8477-95.
Fuke, C. and Arao, T. In Oleander toxins; Springer GmbH, 2005; pp. 519-526.
Grever, M.R. et al. The National Cancer Institute: Cancer Drug Discovery and Development Program. Seminars in Oncology, 1992, 19(6):622-38.
Hamilton, N.M, et al. Novel Steroid Inhibitors of Glucose 6-Phosphate Dehydrogenase. J. Med. Chem. 2012, 55, 4431-4445.
Heffron, T.P. Small Molecule Kinase Inhibitors for the Treatment of Brain Cancer. J. Med. Chem. 2016, 59, 10030-10066.
Holbeck, S.L. et al. Analysis of Food and Drug Administration-approved anticancer agents in the NCI60 panel of human tumor cell lines. Mol. Cancer Ther. 2010, 9(5):1451-60.
Huang, Y. et al. Synthesis and cytotoxicity of 17a-aza-D-homo-androster-17-one derivatives. Bioorg. Med. Chem. Lett. 2011, 21, 3641-3.
International Search Report and Written Opinion for application PCT/US2019/042855. Mailed on Nov. 22, 2019. 11 pages.
Ji, Z.H. et al. Neuroprotective effect and mechanism of daucosterol palmitate in ameliorating learning and memory impairment in a rat model of Alzheimer's disease. Steroids 2017, 119, 31-35.
Krishnan, K. et al. Neurosteroid Analogues. 17. Inverted Binding Orientations of Androsterone Enantiomers at the Steroid Potentiation Site on γ-Aminobutyric Acid Type A Receptors. J. Med. Chem. 2012, 55(3):1334-45.
Kudova, E. et al. A New Class of Potent N-Methyl-D-Aspartate Receptor Inhibitors: Sulfated Neuroactive Steroids with Lipophilic D-Ring Modifications. J. Med. Chem. 2015, 58, 5950-66.
Kuznetsov, Y.V. et al., New estrogen receptor antagonists. 3,20-Dihydroxy-19-norpregna-1,3,5(10)-trienes: Synthesis, molecular modeling, and biological evaluation. Eur. J. Med. Chem. 2018, 143, 670-682.
Larik, F.A. et al. Synthetic approaches towards the multi target drug spironolactone and its potent analogues/derivatives. Steroids 2017, 118, 76-92.
Le Bideau, F. and Dagorne, S. Synthesis of transition-metal steroid derivatives. Chem. Rev. 2013, 113, 7793-850.
Lei, C. et al. Nickel-Catalyzed Direct Synthesis of Aryl Olefins from Ketones and OrIDFnoboron Reagents under Neutral Conditions. J. Am. Chem. Soc. 2017, 139, 6086-6089.
Li, J. et al. Facile and efficient access to Androsten-17-(1',3',4')-pyrazoles and Androst-17beta-(1',3',4')-pyrazoles via Vilsmeier reagents, and their antiproliferative activity evaluation in vitro. Eur. J. Med. Chem. 2017, 130, 1-14.
Liu, J. et al. Structureactivity relationship of brassinosteroids and their agricultural practical usages. Steroids 2017, 124, 1-17.
Madhra, M.K. et al. Improved Procedure for Preparation of Abiraterone Acetate. Org. Process Res. Dev. 2014, 18, 555-558.
Mendell, A.L. et al. 5a-Androstane-3α, 17β-Diol Inhibits Neurotoxicity in SH-SY5Y Human Neuroblastoma Cells and Mouse Primary Cortical Neurons. Endocrinology 2016, 157(12):4570-4578.
Metz, T.L. et al. An Acid-Catalyzed Addition and Dehydration Sequence for the Synthesis of Heteroarylated Steroidal Dienes. J. Org. Chem. 2018, 83, 1643.
Michalak, K. et al. Synthetic Approach to the Core Structure of Oleandrin and Related Cardiac Glycosides with Highly Functionalized Ring D. Org. Lett. 2016, 18, 6148-6151.

Moreno, Y. et al. Structure-activity relationship analysis of bufadienolide-induced in vitro growth inhibitory effects on mouse and human cancer cells. J. Nat. Prod. 2013, 76, 1078-84.
Ning, X. et al. Development of 17β-hydroxysteroid dehydrogenase type 3 as a target in hormone-dependent prostate cancer therapy. Steroids 2017, 121, 10-16.
Okolo, C. et al. "Hexafluoroisopropanol-mediated domino reaction for the synthesis of thiazolo-androstenones: potent anticancer agents." ACS omeIDF 3.12 (2018): 17991-18001.
Park, E.S. et al. Integrative analysis of proteomic signatures, mutations, and drug responsiveness in the NCI 60 cancer cell lines set. Mol Cancer Ther (2010) 9 (2):257-267.
Phillips, L.R. et al. Liquid chromatographic determination of NSC 737664 (ABT-888: an inhibitor of poly(ADP-ribose) polymerase (PARP)) in plasma and urine in a phase 0 clinical trial. J Liq Chromatogr Relat Technol 2009; 32: 261-72.
Qian, M. et al. Neurosteroid analogues. 18. Structure-activity studies of ent-steroid potentiators of IDFmma-aminobutyric acid type A receptors and comparison of their activities with those of alphaxalone and allopregnanolone. J. Med. Chem. 2014,57(1):171-90.
Reedy, J.L. et al. Synthesis and Evaluation of Tetraarylethylene-based Mono-, Bis-, and Tris (pyridinium) Derivatives for Image-Guided Mitochondria-Specific Targeting and Cytotoxicity of Metastatic Melanoma Cells. Bioconjug. Chem. 2016, 2424-2430.
Rödl, C.B. et al. Multi-dimensional target profiling of N,4-diaryl-1,3-thiazole-2-amines as potent inhibitors of eicosanoid metabolism. (2014) Eur J Med Chem. 84(12):302-311.
Rouf, A. and Tanyeli, C. Bioactive thiazole and benzothiazole derivatives. Eur. J. Med. Chem. 2015, 97:911-927.
Sepe, V. et al. Modification on ursodeoxycholic acid (UDCA) scaffold. discovery of bile acid derivatives as selective agonists of cell-surface Gprotein coupled bile acid receptor 1 (GP-BAR1). J. Med. Chem. 2014, 57(18):7687-701.
Shoemaker, R.H. The NCI60 human tumor cell line anticancer drug screen. Nature Rev Cancer 2006; 6(10):813-23.
Simoben, C.V. et al. Exploring Cancer Therapeutics with Natural Products from African Medicinal Plants, Part I: Xanthones, Quinones, Steroids, Coumarins, Phenolics and other Classes of Compounds. Anti-Cancer Agents Med. Chem. 2015, 15(9):1092-111.
Sipos, A. et al. Synthesis of 1,4-thiazino- and benzo-1,4-thiazinomorphinans: their acid-catalyzed rearrangement and study of the formation of unexpected oxidation products. Tetrahedron 2008, 64:1023-1028.
Søkilde, R. et al. Global microRNA analysis of the NCI-60 cancer cell panel. Mol Cancer Ther (2011) 10(3):375-384.
Su, G. et al. Integrated metabolome and transcriptome analysis of the NCI60 dataset. BMC Bioinformatics 2011; 12 (suppl 1): S36.
Świzdor, A. et al. Microbial Baeyer—Villiger oxidation of 5alpha-steroids using Beauveria bassiana. A stereochemical requirement for the 11alpha-hydroxylation and the lactonization pathway. Steroids 2014, 82:44-52.
Szychowski, J. et al. Natural Products in Medicine: Transformational Outcome of Synthetic Chemistry. J. Med. Chem. 2014, 57:9292-9308.
Terán-Pérez, G. et al. Steroid hormones and sleep regulation. Mini-Rev. Med. Chem. 2012, 12(11):1040-8.
Toth, M. et al. Synthesis and Transformation of Thiazolomorphinanedienes. Lett. Org. Chem. 2007, 4:539-543.
Vitellozzi, L. et al. Organometallic Routes to Novel Steroids Containing Heterocyclic C-17 Side-Chains. Synthesis 2015, 48:48-56.
Wilkenfeld, S.R. et al. Communication between genomic and non-genomic signaling events coordinate steroid hormone actions. Steroids 2018, 133:2-7.
Yadav, M.R. et al. Synthesis and preliminary screening of novel A- and D-ring modified steroids as aromatase inhibitors. Lett. Drug Des. Discovery 2011, 8:943-950.
Zakeyha, A.A. et al. Synthesis and antimicrobial studies of hydrazone derivatives of 4-[3-(2,4-difluorophenyl)-4-formyl-1Hpyrazol-1-yl]benzoic acid and 4-[3-(3,4-difluorophenyl)-4-formyl-1Hpyrazol-1-yl]benzoic acid. Bioorg. Med. Chem. Lett. 2018, 28:2914-2919.
Zhang, B.L. et al. Synthesis and biological evaluation of dehydroepiandrosterone-fused thiazole, imidazo[2,1-b] thiazole, pyridine steroidal analogues. Steroids 2014, 80:92-101.

(56) References Cited

OTHER PUBLICATIONS

Žofková, I. et al. Stanazolol—an anabolic steroid that does not influence parathyroid hormone response to hypercalcemia in postmenopausal women. Calcif. Tissue Int. 1994, 54(6):521-2.

Zolottsev, V. A. et al. Comparison of [17 (20)E]-21—Norpregnene oxazolinyl and benzoxazolyl derivatives as inhibitors of CYP17A1 activity and prostate carcinoma cells growth. Steroids 2018, 129, 24-34.

* cited by examiner

3,4-THIAZOLO-STEROIDS AND METHODS OF MAKING AND USING THE SAME

CROSS-REFERENCE TO RELATED APPLICATIONS

This application is a national stage filing under 35 U.S.C. § 371 of International Patent Application No. PCT/US2019/042855, filed Jul. 22, 2019, which claims the benefit of priority of U.S. Provisional Patent Application No. 62/700,967, filed Jul. 20, 2018, all of which are incorporated by reference herein in their entirety.

BACKGROUND

Several hormones having a steroidal skeleton are found in biological signaling. A large number of steroidal natural products have been isolated from various plants and microorganisms. These molecules are known to show a wide range of biological activities, including cytotoxicity to cancer cells.

SUMMARY OF THE INVENTION 3,4-thiazolo steroids and methods of making and using the same are described herein. One aspect of the invention includes compounds of formula

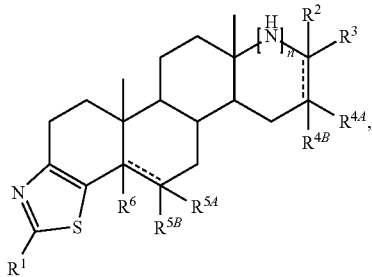

In a particular embodiment, the compound is any compound described herein.

In some embodiments, the thiazolo substituent $R^1$ is selected from $-NR^{7A}R^{7B}$, where $R^{7A}$ and $R^{7B}$ are independently selected from hydrogen; acetyl; a branched or unbranched, substituted or unsubstituted $C_1$-$C_{12}$ alkyl; a branched or unbranched, substituted or unsubstituted $C_2$-$C_{12}$ alkenyl; a branched or unbranched, substituted or unsubstituted $C_2$-$C_{12}$ alkynyl; a branched or unbranched, substituted or unsubstituted $C_3$-$C_{12}$ cycloalkyl; a branched or unbranched, substituted or unsubstituted $C_6$-$C_{12}$ aryl; a branched or unbranched, substituted or unsubstituted $C_6$-$C_{12}$ arylalkyl; a branched or unbranched, substituted or unsubstituted $C_3$-$C_{12}$ heterocyclyl; or a branched or unbranched, substituted or unsubstituted $C_3$-$C_{12}$ heterocyclylalkyl. In certain embodiments, $R^{7A}$ and $R^{7B}$ are selected from the branched or unbranched, substituted or unsubstituted $C_6$-$C_{12}$ aryl or the branched or unbranched, substituted or unsubstituted $C_6$-$C_{12}$ arylalkyl. In particular embodiments, at least one of $R^{7A}$ and $R^{7B}$ is selected from phenyl, 2-phenylethyl, benzyl, 2-fluorophenyl, 3-fluorophenyl, 4-fluorophenyl, 2,4-difluorophenyl, 2-chlorophenyl, 4-chlorophenyl, 2-nitrophenyl, 2,4-dimethylphenyl, 2-methoxyphenyl, 2,5-dimethoxyphenyl, 2-methoxy-5-chlorophenyl, 3-hydroxyphenyl, 4-hydroxyphenyl, 4-methoxyphenyl, 3-trifluoromethoxyphenyl, 4-trifluoromethoxyphenyl, 3-trifluoromethylphenyl, 3-carboxyphenyl, 4-carboxyphenyl, 2,4-dimethylphenyl, or 4-methylphenyl. For example, the compound may be a compound of Formula IIa or Formula IIIa, a C-17 derivative of either Formula IIa or Formula IIIa, a B-ring derivative of either Formula IIa or Formula IIIa, of a D-ring derivative of either Formula IIa or Formula IIIa, as described below.

In some embodiments, the thiazolo substituent $R^1$ is a hydrogen, a branched or unbranched, substituted or unsubstituted $C_1$-$C_{12}$ alkyl, a branched or unbranched, substituted or unsubstituted $C_2$-$C_{12}$ alkenyl, a branched or unbranched, substituted or unsubstituted $C_2$-$C_{12}$ alkynyl, a branched or unbranched, substituted or unsubstituted $C_3$-$C_{12}$ cycloalkyl, a branched or unbranched, substituted or unsubstituted $C_6$-$C_{12}$ aryl, a branched or unbranched, substituted or unsubstituted $C_6$-$C_{12}$ arylalkyl, or a branched or unbranched, substituted or unsubstituted $C_3$-$C_{12}$ heterocyclyl. For example, the compound may be a compound of Formula II or Formula III, a C-17 derivative of either Formula II or Formula III, a B-ring derivative of either Formula II or Formula III, of a D-ring derivative of either Formula II or Formula III, as described below.

In some embodiments, the thiazolo substituent $R^1$ is selected from $-NR^{7A}R^{7B}$, where $R^{7A}$ and $R^{7B}$ together are selected from a branched or unbranched, substituted or unsubstituted $C_2$-$C_{12}$ alkylene; a branched or unbranched, substituted or unsubstituted $C_2$-$C_{12}$ ether; or a branched or unbranched, substituted or unsubstituted, secondary, tertiary, or quaternary amine. For example, the compound may be a compound of Formula IIa or Formula IIIa, a C-17 derivative of either Formula IIa or Formula IIIa, a B-ring derivative of either Formula IIa or Formula IIIa, of a D-ring derivative of either Formula IIa or Formula IIIa, as described below.

In some embodiments, $R^{4A}$ and $R^{4B}$ are each hydrogen and one of $R^2$ or $R^3$ is selected from hydrogen and the other from a hydroxyl group. For example, the compound may be a compound of Formula III or Formula IIIa, a C-17 derivative of either Formula III or Formula IIIa, a B-ring derivative of either Formula III or Formula IIIa, of a D-ring derivative of either Formula III or Formula IIIa.

In some embodiments, $R^{4A}$ and $R^{4B}$ are each hydrogen and $R^2$ and $R^3$ together are selected from an oxo group. Suitably, the compound may be a compound of Formula II. For example, the compound may be a compound of Formula II or Formula IIa, a C-17 derivative of either Formula II or Formula IIa, a B-ring derivative of either Formula II or Formula IIa, of a D-ring derivative of either Formula II or Formula IIa, as described below.

In some embodiments, $R^{4A}$ and $R^{4B}$ are each hydrogen and $R^2$ and $R^3$ together are selected from $=N-NR^{10A}R^{10B}$. $R^{10A}$ and $R^{10B}$ may be independently selected from hydrogen; a branched or unbranched, substituted or unsubstituted $C_1$-$C_{12}$ alkyl; a branched or unbranched, substituted or unsubstituted $C_2$-$C_{12}$ alkenyl; a branched or unbranched, substituted or unsubstituted $C_2$-$C_{12}$ alkynyl; a branched or unbranched, substituted or unsubstituted $C_3$-$C_{12}$ cycloalkyl; a branched or unbranched, substituted or unsubstituted $C_6$-$C_{12}$ aryl; a branched or unbranched, substituted or unsubstituted $C_6$-$C_{12}$ arylalkyl; or a branched or unbranched, substituted or unsubstituted $C_3$-$C_{12}$ heterocyclyl. $R^{10A}$ and $R^{10B}$ together may also be selected from a branched or unbranched, substituted or unsubstituted $C_2$-$C_{12}$ alkylene; a branched or unbranched, substituted or unsubstituted $C_2$-$C_{12}$ ether; a branched or unbranched, substituted or unsubstituted, secondary, tertiary, or quaternary amine. Suitably, the compound may be a compound of Formula IV or Formula IVa, as described below.

In some embodiments, $R^{4A}$ and $R^{4B}$ are each hydrogen and $R^2$ and $R^3$ together are =NOH. Suitably, the compound may be a compound of Formula V or Formula Va, as described below.

In some embodiments, $R^{4A}$ and $R^{4B}$ are each hydrogen and $R^2$ and $R^3$ together are =NN(H)C(=Z)R$^8$, where Z is selected from oxygen and sulfur and $R^8$ is selected from hydrogen; a branched or unbranched, substituted or unsubstituted $C_1$-$C_{12}$ alkyl; a branched or unbranched, substituted or unsubstituted $C_2$-$C_{12}$ alkenyl; a branched or unbranched, substituted or unsubstituted $C_2$-$C_{12}$ alkynyl; a branched or unbranched, substituted or unsubstituted $C_3$-$C_{12}$ cycloalkyl; a branched or unbranched, substituted or unsubstituted $C_6$-$C_{12}$ aryl; a branched or unbranched, substituted or unsubstituted $C_6$-$C_{12}$ arylalkyl; a branched or unbranched, substituted or unsubstituted $C_3$-$C_{12}$ heterocyclyl; or a branched or unbranched, substituted or unsubstituted, secondary, tertiary, or quaternary amine. Suitably, the compound may be a compound of Formula IVb.

In some embodiments, $R^{4A}$ and $R^{4B}$ are each hydrogen and one of $R^2$ or $R^3$ is selected from hydrogen and the other from —OC(=Z)R$^9$ wherein Z is selected from oxygen and sulfur and $R^9$ is selected from hydrogen; a branched or unbranched, substituted or unsubstituted $C_1$-$C_{12}$ alkyl; a branched or unbranched, substituted or unsubstituted $C_2$-$C_{12}$ alkenyl; a branched or unbranched, substituted or unsubstituted $C_2$-$C_{12}$ alkynyl; a branched or unbranched, substituted or unsubstituted $C_3$-$C_{12}$ cycloalkyl; a branched or unbranched, substituted or unsubstituted $C_6$-$C_{12}$ aryl; a branched or unbranched, substituted or unsubstituted $C_6$-$C_{12}$ arylalkyl; a branched or unbranched, substituted or unsubstituted $C_3$-$C_{12}$ heterocyclyl; or a branched or unbranched, substituted or unsubstituted, secondary, tertiary, or quaternary amine. Suitably, the compound may be a compound of Formula VII or Formula VIIa.

In some embodiments, $R^{4A}$ and $R^{4B}$ are each hydrogen and one of $R^2$ or $R^3$ is selected from hydrogen and the other from a branched or unbranched, substituted or unsubstituted $C_1$-$C_{12}$ alkyl. Suitably, the compound may be a compound of Formula Xa.

In some embodiments, $R^{4A}$ and $R^{4B}$ are each hydrogen and one of $R^2$ or $R^3$ is selected from a hydroxyl group and the other from $C_2$-$C_{12}$ alkynyl. Suitably, the compound may be a compound of Formula XIa.

In some embodiments, $R^{4A}$ and $R^{4B}$ are together hydrogen and $R^2$ and $R^3$ together are a cyano group.

In some embodiments, $R^{4A}$ and $R^{4B}$ are together hydrogen and $R^2$ and $R^3$ together are selected from a branched or unbranched, substituted or unsubstituted $C_6$-$C_{12}$ aryl.

In some embodiments, $R^{5A}$ and $R^{5B}$ are together hydrogen and $R^6$ is not present. In other embodiments, each of $R^{5A}$ and $R^{5B}$ is hydrogen and $R^6$ is hydrogen. In yet other embodiments, one of $R^{5A}$ and $R^{5B}$ is hydrogen and the other is a hydroxyl group and $R^6$ is selected from hydrogen or a hydroxyl group. Suitably, the compound may be a compound of Formula VIII or Formula IX.

In some embodiments, n is equal to 0 or 1. Suitably, n may be 0.

Another aspect of the invention includes pharmaceutical compositions comprising a therapeutically effective amount of any of the compounds described herein.

Another aspect of the invention is a method for inhibiting proliferation of or killing a cell. The method comprises contacting the cell with any of the compounds described herein. Suitably, the cell is a cancer cell, such as melanoma.

Another aspect of the invention is a method for the treatment of a subject. The method comprises administering to the subject a therapeutically effective amount of any of the compounds described herein or a pharmaceutical composition comprising any of the compounds described herein. Suitably, the subject may have a cell proliferative disorder, such as a cancer.

Another aspect of the invention is a method for the preparation of a 3,4-thiazolo steroid. The method comprises contacting a 6-bromo-4-en-3-one steroid with a thiourea or a thioamide to prepare the compounds described herein. Suitably, the 6-bromo-4-en-3-one steroid is 6-bromoandrostendione. The 6-bromo-4-en-3-one steroid may be contacted with the thiourea or the thioamide in a polar protic solvent, such as HFIP, TFE, $CH_3CO_2H$, and other suitably polar protic solvents.

These and further aspects of the invention will be described in detail below.

DETAILED DESCRIPTION OF THE INVENTION

Disclosed herein are 3,4-thiazolo-steroid compounds and methods of making and using the same. The thiazolo-steroids may be prepared via the reaction of a 6β-bromosteroid with thioamides and thioureas to form the 3,4-thiazolo-deriviates. Screening the compounds against a cancer panel reveals that these compounds are potent cytotoxic and anticancer agents, particularly anti-melanoma cancer agents.

As used herein "steroid" is a compound possessing the skeleton of cyclopenta[a]phenanthrene or a skeleton derived therefrom by one or more bond scissions or ring expansions or contractions (as shown below). Steroids typically comprise a core skeletal structure composed of 17 carbon atoms bonding through four fused rings. As shown below, the skeletal structure comprises three fused cyclohexyl rings (rings A, B, and C) and one fused cyclopenyl ring (ring D).

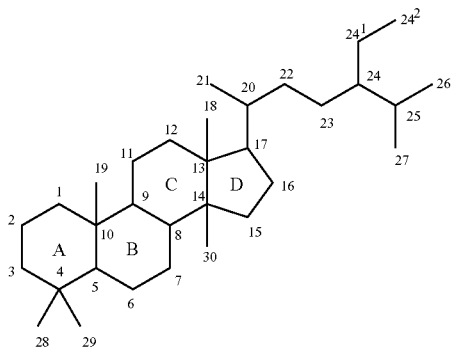

Methyl groups are often present at C-10 and C-13, and a side chain may also be present at C-17. Numerous modifications of the cyclopenta[a]phenanthrene skeleton are known in the art. By varying the functional groups attached to the four-ring core and saturation of the rings, the steroid's biological activity is modified.

Described herein are 3,4-thiazolo steroids. Suitably, 3,4-thiazolo steroid comprises a substituted or unsubstituted thiazolo fused to a steroid at the 3- and 4-carbon positions. In one aspect of the invention, the 3,4-thiazolo steroids have the formula

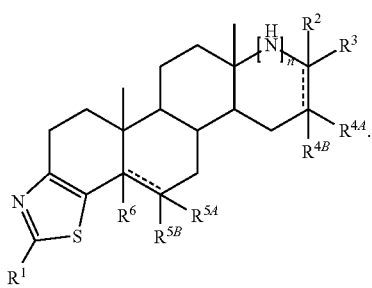

Also provided herein are 3,4-thozolo-modified salts.

In some embodiments, the thiazolo substituent $R^1$ may be any of the following: hydrogen, a branched or unbranched, substituted or unsubstituted $C_1$-$C_{12}$ alkyl, a branched or unbranched, substituted or unsubstituted $C_2$-$C_{12}$ alkenyl, a branched or unbranched, substituted or unsubstituted $C_2$-$C_{12}$ alkynyl, a branched or unbranched, substituted or unsubstituted $C_3$-$C_{12}$ cycloalkyl, a branched or unbranched, substituted or unsubstituted $C_6$-$C_{12}$ aryl, a branched or unbranched, substituted or unsubstituted $C_6$-$C_{12}$ arylalkyl, or a branched or unbranched, substituted or unsubstituted $C_3$-$C_{12}$ heterocyclyl. Compounds of this type may be prepared from the reaction of 6-bromo-4-en-3-one steroids with thioamides (e.g., as shown in Scheme 3).

In other embodiments, thiazolo substituent $R^1$ may be an amine of formula —NRR'. In certain embodiments, R and R' may be independently selected from hydrogen; acetyl; a branched or unbranched, substituted or unsubstituted $C_1$-$C_{12}$ alkyl; a branched or unbranched, substituted or unsubstituted $C_2$-$C_{12}$ alkenyl; a branched or unbranched, substituted or unsubstituted $C_2$-$C_{12}$ alkynyl; a branched or unbranched, substituted or unsubstituted $C_3$-$C_{12}$ cycloalkyl; a branched or unbranched, substituted or unsubstituted $C_6$-$C_{12}$ aryl; a branched or unbranched, substituted or unsubstituted $C_6$-$C_{12}$ arylalkyl; a branched or unbranched, substituted or unsubstituted $C_3$-$C_{12}$ heterocyclyl; or a branched or unbranched, substituted or unsubstituted $C_3$-$C_{12}$ heterocyclylalkyl. In other embodiments, R and R' together may be selected from a branched or unbranched, substituted or unsubstituted $C_2$-$C_{12}$ alkylene; a branched or unbranched, substituted or unsubstituted $C_2$-$C_{12}$ ether; or a branched or unbranched, substituted or unsubstituted, secondary, tertiary, or quaternary amine. Compounds of this type may be prepared from the reaction of 6-bromo-4-en-3-one steroids with thioamides (Scheme 6).

The D-ring may also be modified. In some embodiments, n equals 0 and the D-ring is a cyclopentyl ring. In this case, each of $R^{4A}$ and $R^{4B}$ at position C-16 are hydrogen. In other embodiments, n equals 0 and the D-ring is a cyclopentenyl ring having a double bond between the C-16 and C-17 positions. In yet other cases, n equals 1 and the D-ring is a lactam having the amine diradical inserted between the C-13 and C-17 positions of the D-ring.

The B-ring may also be modified. In some embodiments, the B-ring is a cyclohexenyl having a double bond between the C-5 and C-6 positions. In these embodiments, $R^{5A}$ and $R^{5B}$ together comprise hydrogen and $R^6$ is not present. In other embodiments, B-ring is a cyclohexyl. In these embodiments, $R^{5A}$, $R^{5B}$, and $R^6$ are each independently selected from hydrogen or hydroxyl. Suitably, all of $R^{5A}$, $R^{5B}$, and $R^6$ may be hydrogen, one of $R^{5A}$ and $R^{5B}$ is a hydroxyl and the other is hydrogen and $R^6$ is hydrogen or a hydroxyl, one of $R^{5A}$ and $R^{5B}$ is a hydroxyl and the other is hydrogen and $R^6$ is hydrogen, or one of $R^{5A}$ and $R^{5B}$ is a hydroxyl and the other is hydrogen and $R^6$ is a hydroxyl.

The substituents, $R^2$ and $R^3$, at the C-17 position may also be modified. In embodiments, $R^2$ and $R^3$ together comprise a substituent. Suitably $R^2$ and $R^3$ together may be selected from: an oxo group (=O), an oxime group (=NOH), a cyano group (—CN), a branched or unbranched, substituted or unsubstituted $C_6$-$C_{12}$ aryl, or a hydrazone group such as =N—NRR' or =NN(H)C(=O)R.

When $R^2$ and $R^3$ together form =N—NRR', R and R' may be independently selected from hydrogen; a branched or unbranched, substituted or unsubstituted $C_1$-$C_{12}$ alkyl; a branched or unbranched, substituted or unsubstituted $C_2$-$C_{12}$ alkenyl; a branched or unbranched, substituted or unsubstituted $C_2$-$C_{12}$ alkynyl; a branched or unbranched, substituted or unsubstituted $C_3$-$C_{12}$ cycloalkyl; a branched or unbranched, substituted or unsubstituted $C_6$-$C_{12}$ aryl; a branched or unbranched, substituted or unsubstituted $C_6$-$C_{12}$ arylalkyl; or a branched or unbranched, substituted or unsubstituted $C_3$-$C_{12}$ heterocyclyl; or R and R' together is selected a branched or unbranched, substituted or unsubstituted $C_2$-$C_{12}$ alkylene; a branched or unbranched, substituted or unsubstituted $C_2$-$C_{12}$ ether; or a branched or unbranched, substituted or unsubstituted, secondary, tertiary, or quaternary amine.

When $R^2$ and $R^3$ together form =NN(H)C(=O)R, R may be selected from hydrogen; a branched or unbranched, substituted or unsubstituted $C_1$-$C_{12}$ alkyl; a branched or unbranched, substituted or unsubstituted $C_2$-$C_{12}$ alkenyl; a branched or unbranched, substituted or unsubstituted $C_2$-$C_{12}$ alkynyl; a branched or unbranched, substituted or unsubstituted $C_3$-$C_{12}$ cycloalkyl; a branched or unbranched, substituted or unsubstituted $C_6$-$C_{12}$ aryl; a branched or unbranched, substituted or unsubstituted $C_6$-$C_{12}$ arylalkyl; a branched or unbranched, substituted or unsubstituted $C_3$-$C_{12}$ heterocyclyl; or a branched or unbranched, substituted or unsubstituted, secondary, tertiary, or quaternary amine.

In embodiments where $R^2$ and $R^3$ separately comprise a substituent, $R^2$ and $R^3$ may be independently selected from hydrogen and a hydroxyl group; hydrogen and a carboxylate (—OC(=O)R), a hydroxyl group and a branched or unbranched, substituted or unsubstituted $C_2$-$C_{12}$ alkynyl group, or hydrogen and a branched or unbranched, substituted or unsubstituted $C_2$-$C_{12}$ alkylyl group. When one of $R^2$ and $R^3$ is the carboxylate —OC(=O)R, R may be selected from hydrogen; a branched or unbranched, substituted or unsubstituted $C_1$-$C_{12}$ alkyl; a branched or unbranched, substituted or unsubstituted $C_2$-$C_{12}$ alkenyl; a branched or unbranched, substituted or unsubstituted $C_2$-$C_{12}$ alkynyl; a branched or unbranched, substituted or unsubstituted $C_3$-$C_{12}$ cycloalkyl; a branched or unbranched, substituted or unsubstituted $C_6$-$C_{12}$ aryl; a branched or unbranched, substituted or unsubstituted $C_6$-$C_{12}$ arylalkyl; a branched or unbranched, substituted or unsubstituted $C_3$-$C_{12}$ heterocyclyl; or a branched or unbranched, substituted or unsubstituted, secondary, tertiary, or quaternary amine.

The compounds described herein may prepared from the reaction of thioamides and thioureas with 6-bromo-4-en-3-one steroids such as 6-bromoandrostendione. Bromonated steroids may be used to prepare the 3,4-thiazolo steroid of the present invention. As exemplified with 6-bromoandrostendione, Schemes 1A and 1B demonstrate the formation of 3,4-thiazolo-androstenone derivative from thioamides and thioureas, respectively. These reactions prepare 3,4-thiazolo steroid derivatives from 6-bromo-4-en-3-one steroids such as 6-bromoandrostendione.

Scheme 1A: Reaction of thioamide with bromoandrostenedione.

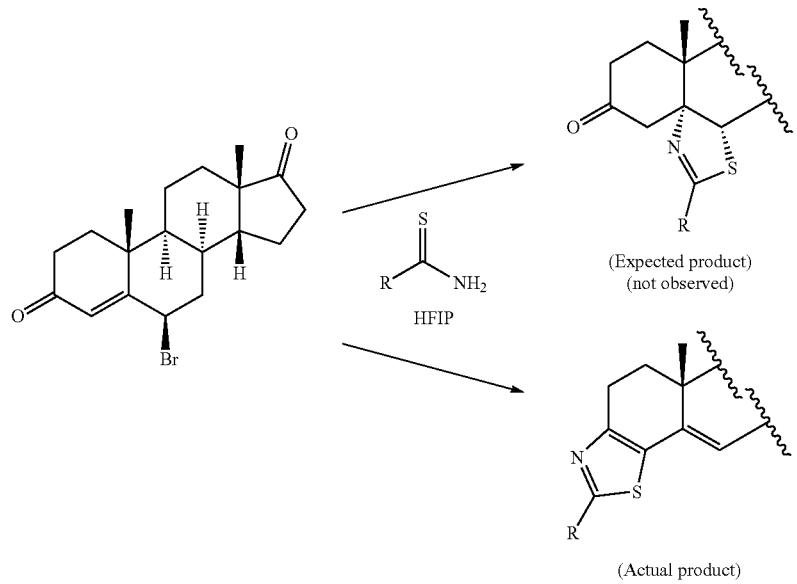

Scheme 1B: Reaction of thiourea with bromoandrostenedione.

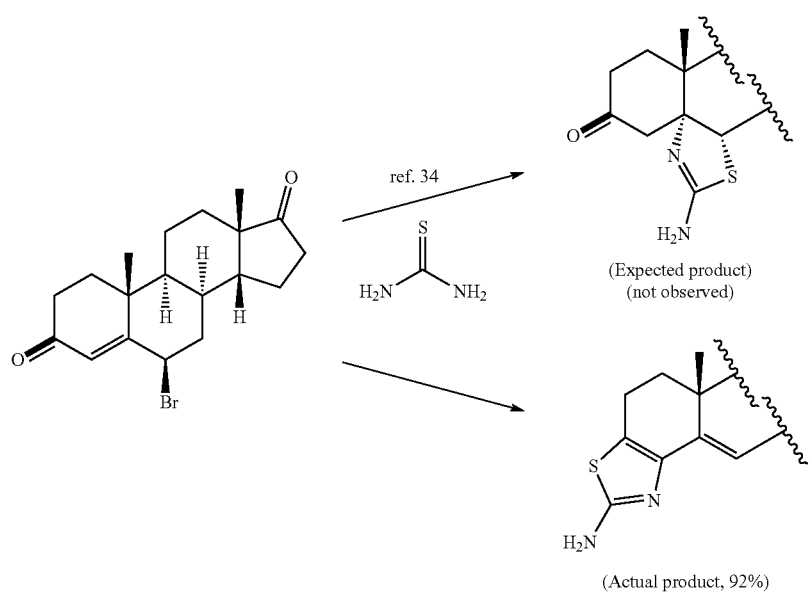

Alsharif and Alam (Modular synthesis of thiazoline and thiazole derivatives by using a cascade protocol. *RSC Advances* 2017, 7, 32647-32651) disclose the preparation of thiazoline derivatives from the γ-bromo-enones with thioamides and thioureas. The reaction proceeds through $S_n2$ substitution of the 4-bromocrontonate derivative followed by intramolecular Michael addition (Scheme 2).

Scheme 2: Reaction of thioamide with 4-bromocronate.

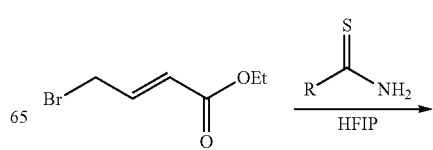

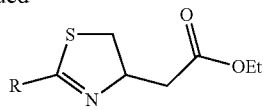

It was expected, therefore, that the reaction of thioureas and thioamides would react with bromoandrostenedione to prepare a 5,6-thiazolo-androstenone (Schemes 1A and 1B). Surprisingly, this was not the case. As the Examples below demonstrate, the actual products 3,4-thiazolo-androstenone were formed.

The reactions described in Schemes 1A and 1B do not require anhydrous solvent and inert atmosphere. The products formed cleanly and the pure material was isolated simply by distilling out HFIP followed by washing with methanol and water.

Formation of 3,4-Thiazolo Steroids from Thioamides

Thioamide derived 3,4-thiazolo steroids may be prepared by the reaction of 6-bromo-4-en-3-ones such as bromoandrostenedione. As shown in Scheme 3, the reactions do not require anhydrous solvent and inert atmosphere.

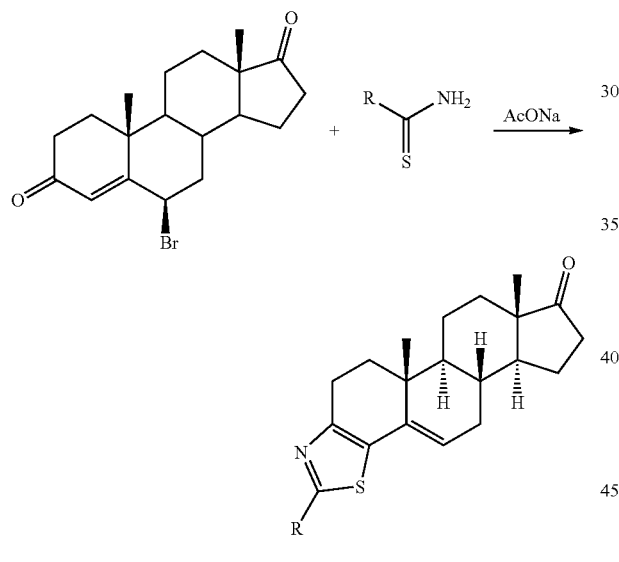

Scheme 3: Reaction of 3 with thioamides.

Numerous 3,4-thiazolo derivatives of Formula I

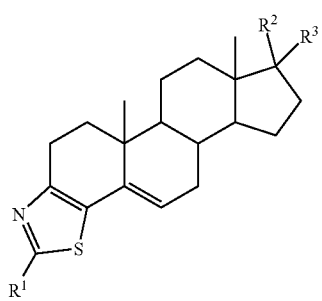

(Formula I)

may be prepared depending on the choice of thioamide reactant. $R^1$ may be selected from hydrogen, a branched or unbranched, substituted or unsubstituted $C_1$-$C_{12}$ alkyl, a branched or unbranched, substituted or unsubstituted $C_2$-$C_{12}$ alkenyl, a branched or unbranched, substituted or unsubstituted $C_2$-$C_{12}$ alkynyl, a branched or unbranched, substituted or unsubstituted $C_3$-$C_{12}$ cycloalkyl, a branched or unbranched, substituted or unsubstituted $C_6$-$C_{12}$ aryl, a branched or unbranched, substituted or unsubstituted $C_6$-$C_{12}$ arylalkyl, or a branched or unbranched, substituted or unsubstituted $C_3$-$C_{12}$ heterocyclyl. Exemplary $R^1$ groups include, without limitation, hydrogen, methyl, ethyl, n-propyl, n-butyl, phenyl, methylphenyl, methoxyphenyl, hydroxyphenyl, dihydroxyphenyl, carboxyphenyl, nitrophenyl, fluorophenyl, trifluoromethylphenyl, chlorophenyl, bromophenyl, phenylmethyl, tolylmethyl, and pyridyl.

Suitably, the 3,4-thiazolo derivatives are compounds of Formula II

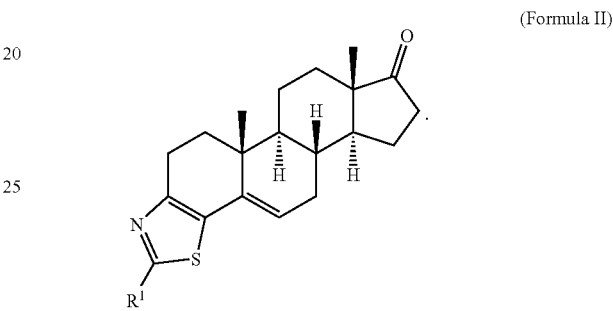

(Formula II)

Exemplary compounds of Formula II are shown in Table 1.

TABLE 1

Exemplary compounds of Formula II

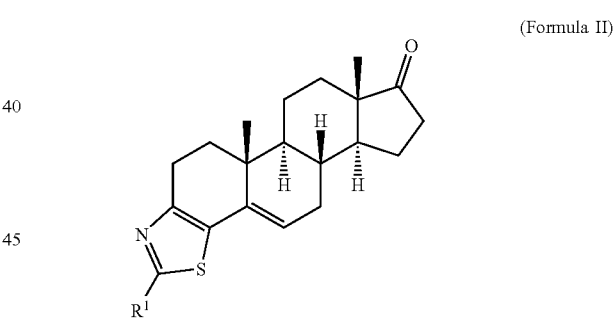

(Formula II)

| Compound ID | R = |
|---|---|
| II.1 | methyl |
| II.2 | benzyl |
| II.3 | pyrind-2-yl |
| II.4 | 4-hydroxy-phenyl |
| II.5 | 2-chloro-phenyl |
| II.6 | 4-carboxy-phenyl |
| II.7 | 3-methyl-phenyl |
| II.8 | 4-methyl-phenyl |
| II.9 | 3-methoxy-phenyl |
| II.10 | 4-methoxy-phenyl |
| II.11 | 2-hydroxy-phenyl |
| II.12 | 3-fluoro-phenyl |
| II.13 | 4-fluoro-phenyl |
| II.14 | 3-chloro-phenyl |
| II.15 | 4-chloro-phenyl |
| II.16 | 4-bromo-phenyl |
| II.17 | 3-hydroxy-phenyl |
| II.18 | 2-methyl-benzyl |
| II.19 | phenyl |
| II.20 | 3,4-dihydroxy-phenyl |

TABLE 1-continued

Exemplary compounds of Formula II (Formula II)

| Compound ID | R = |
|---|---|
| II.21 | 4-trifluoromethyl-phenyl |
| II.22 | 3-nitro-phenyl |
| II.23 | 3-ethoxy-phenyl |
| II.24 | (pyridine-oxy-phenyl structure with F$_3$C substituent) |
| II.25 | 3,5-dichloro-phenyl |

Reaction of thiobenzamide with the electrophile, 6-bromoandrostendione, in HFIP afforded the product (II.19) in 61% yield (Scheme 4). After the identification of the product as thiazolo-androstenone in HFIP, we carried out the reaction in different solvents including different alcohols, and polar aprotic solvents: THF, DMSO, and DMF (see Examples below). Refluxing the reaction mixture in DMF gave the decomposed products. Nevertheless, 20% product was also obtained in acetic acid. Based on these observations, we can conclude that polar protic solvents are required for the product formation of this domino methodology and HFIP has the option properties for the success of this reaction.

Scheme 4: Reaction of electrophile with thiobenzamide.

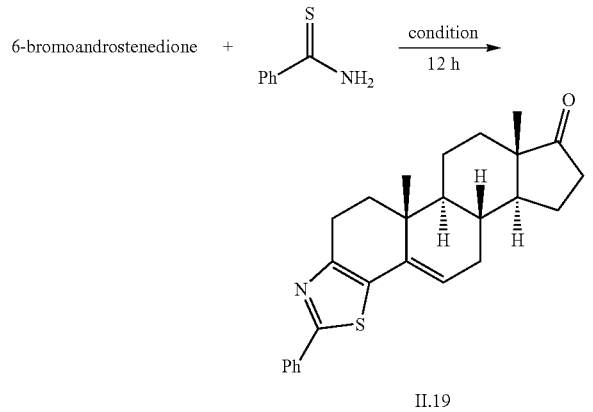

II.19

The results of reactions of different thioamide derivatives are shown in Scheme 4. Reaction of thioacetamide and 2-phenylthioacetamide with 6β-bromoandrostenone formed the products (II.1 and II.2) in 52% and 56% yield respec-tively. 2-(2-Methylphenyl)thioacetamide also reacted with the electrophile to give the benzyl derivative (II.18) in 61% yield. Substituted thiobenzamide derivatives were isolated under the established reaction condition. m-Methyl and p-methyl substituted aryl products formed (II.7 and II.8) in 59% and 61% yield respectively. Similarly, methoxy substituted products (II.9 and II.10) formed in an average of 63% yield. Hydroxy substituted products (II.11, II.4, and II.17) were obtained in good yields. Furthermore dihydroxy thiobenzamide also reacted smoothly to give the expected product (II.20) in 58% yield. The number and position of hydroxy group did not alter the outcome of the corresponding products.

Products containing electron withdrawing substituents were obtained under the established reaction condition. 3-Fluoro substituted thiazolo-androstenone derivative (II.12) formed in 60% yield and 4-fluorophenyl substituted compound (II.13) was obtained in 61% yield. 3-Chloro and 4-chloro substituted products (II.14 and II.15) formed in an average of 50% yield. 4-Bromophenyl product (II.16) was obtained 45% yield. 4-(Trifluoromethyl)thiobenzamide reacted with the electrophile to give the corresponding product (II.21). 3-Nitro-thiobenzamide also reacted with the electrophile to give the corresponding product (II.22). Last but not the least, heterocycle based thioamide formed the product (II.3), albeit low yield (38%) was obtained. Thioisonicotinamide (pyridine-4-thiocarboxamide) failed to react with the 6β-bromoandrostenone to give a product and starting materials were recovered even after refluxing for 24 hours. The product formation of this methodology is in ~50% yield and the remaining starting material, 6β-bromoandrostenone, was recovered. Surprising, refluxing for longer periods of time did not improve the yield of the reactions.

This methodology generates a new class of novel molecules based on fused thiazolo-steroid scaffold. These molecules can be further transformed into new entities by simple reactions, e.g., as shown in Scheme 5. 17-Hydroxy and 17-aceloxy derivatives of androstane skeleton are integral parts of drugs, hormones, natural products, and synthetic bioactive molecules. We reacted some of the molecules with NaBH$_4$ and stereospecific product (III.15) was obtained in excellent yield. Further acetylation with Ac$_2$O/pyridine afforded the acetylated product in quantitative yield. Structure was confirmed by X-ray crystallography data.

Scheme 5: Reduction of acetylation of ketone derivative (II.12)

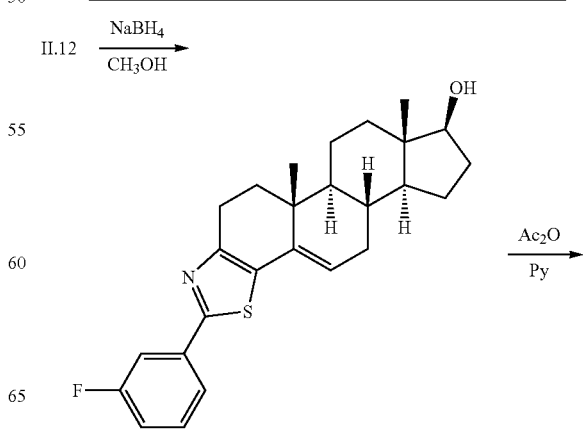

-continued

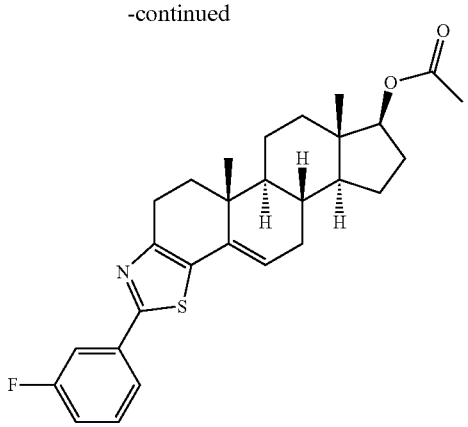

The structures of compounds (II.12, II.13, and acetylated product) unequivocally confirmed by single-crystal X-ray diffraction analysis, which has helped to establish the regiochemistry and stereochemistry of the reactions.

Formation of 3,4-Thiazolo Steroids from Thioureas

Thiourea derived 3,4-thiazolo steroids may be prepared by the reaction of 6-bromo-4-en-3-ones such as 6β-bromoandrostenedione. Numerous 3,4-thiazolo derivatives of Formula I

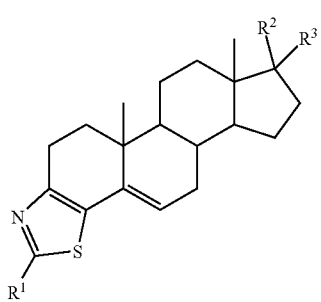

(Formula I)

may be prepared depending on the choice of thiourea reactant where $R^1$ may be selected from —NRR' and R and R' are independently selected from hydrogen; a branched or unbranched, substituted or unsubstituted $C_1$-$C_{12}$ alkyl; a branched or unbranched, substituted or unsubstituted $C_2$-$C_{12}$ alkenyl; a branched or unbranched, substituted or unsubstituted $C_2$-$C_{12}$ alkynyl; a branched or unbranched, substituted or unsubstituted $C_3$-$C_{12}$ cycloalkyl; a branched or unbranched, substituted or unsubstituted $C_6$-$C_{12}$ aryl; a branched or unbranched, substituted or unsubstituted $C_6$-$C_{12}$ arylalkyl; a branched or unbranched, substituted or unsubstituted $C_3$-$C_{12}$ heterocyclyl; a branched or unbranched, substituted or unsubstituted $C_3$-$C_{12}$ heterocyclylalkyl or R and R' together are selected from a branched or unbranched, substituted or unsubstituted $C_2$-$C_{12}$ alkylene; a branched or unbranched, substituted or unsubstituted $C_2$-$C_{12}$ ether; a branched or unbranched, substituted or unsubstituted, secondary, tertiary, or quaternary amine.

Exemplary R and R' groups include, without limitation, hydrogen, methyl, ethyl, n-propyl, butyl, ethenyl, propenyl, butenyl, phenyl, methylphenyl, dimethylphenyl, hydroxyphenyl, carboxyphenyl, methoxyphenyl, dimethoxyphenyl, nitrophenyl, flurophenyl, difluorophenyl, chlorophenyl, bromophenyland trifluoromethoxyphenyl, chloromethoxyphenyl, phenylmethyl, phenylethyl, pyridyl, pryimidinyl, morpholinopropyl, or acetyl.

Suitably, the 3,4-thazolo derivatives may be compounds of Formula IIa

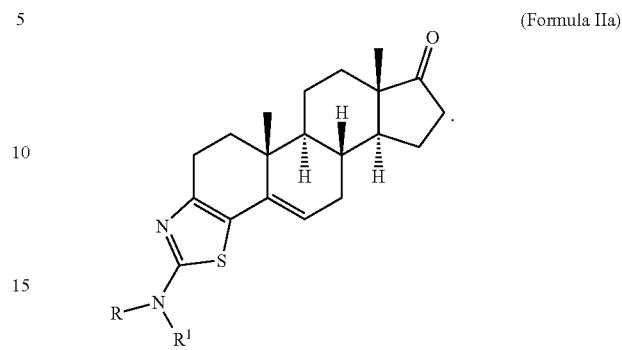

(Formula IIa)

Exemplary compounds of Formula IIa are shown in Table 2.

TABLE 2

Exemplary compounds of Formula IIa

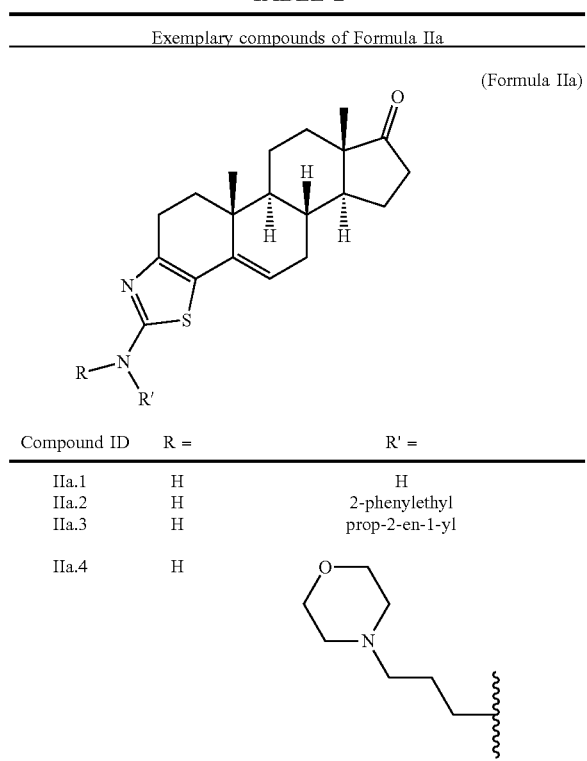

(Formula IIa)

| Compound ID | R = | R' = |
|---|---|---|
| IIa.1 | H | H |
| IIa.2 | H | 2-phenylethyl |
| IIa.3 | H | prop-2-en-1-yl |
| IIa.4 | H | (morpholinopropyl) |
| IIa.5 | H | benzyl |
| IIa.6 | methyl | phenyl |
| IIa.7 | H | phenyl |
| IIa.8 | H | 3-fluoro-phenyl |
| IIa.9 | H | 4-fluoro-phenyl |
| IIa.10 | H | 2,4-difluoro-phenyl |
| IIa.11 | H | 2-chloro-phenyl |
| IIa.12 | H | 4-chloro-phenyl |
| IIa.13 | H | 2-nitro-phenyl |
| IIa.14 | H | 2,4-dimethyl-phenyl |
| IIa.15 | H | 2-methoxy-phenyl |
| IIa.16 | H | 2,6-dimethoxy-phenyl |
| IIa.17 | H | 3-hydroxy-phenyl |
| IIa.18 | H | 4-methoxy-phenyl |
| IIa.19 | H | 4-trifluoromethoxy-phenyl |
| IIa.20 | H | 2-methoxy, 5-chloro-phenyl |
| IIa.21 | H | pyrind-2-yl |
| IIa.22 | H | pyrimidin-2-yl |
| IIa.23 | H | 4-carboxy-phenyl |

TABLE 2-continued

Exemplary compounds of Formula IIa (Formula IIa)

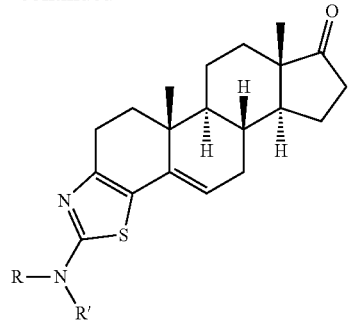

| Compound ID | R = | R' = |
|---|---|---|
| IIa.24 | H | ![piperidinyl] |
| IIa.25 | H | ![morpholinyl] |
| IIa.26 | H | 4-methyl-piperazin-1-yl |
| IIa.27 | H | 4-ethyl-piperazin-1-yl |
| IIa.28 | H | 4-ethan-2-ol-piperazin-1-yl |
| IIa.29 | H | piperazin-1-yl |
| IIa.30 | H | ethyl |
| IIa.31 | H | butyl |
| IIa.32 | H | 4-methyl-phenyl |
| IIa.33 | H | 2-fluoro-phenyl |
| IIa.34 | H | 3-carboxy-phenyl |
| IIa.35 | H | 4-hydroxy-phenyl |

As shown in Scheme 6, the reactions do not require anhydrous solvent and inert atmosphere and may be prepare as follows.

Scheme 6: Reaction of thiourea and its derivatives with 6β-bromoandrostenedione.

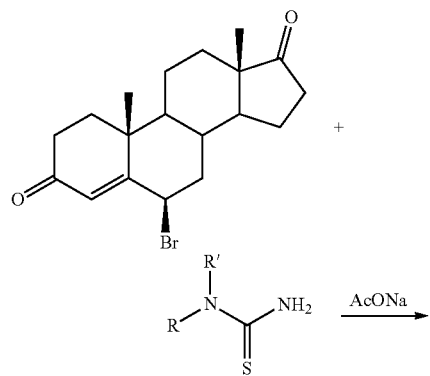

The product (IIa.1) formed in 92% yield and the pure material was isolated simply by filtration followed by washing with ethanol and water. Gram-scale reaction did not alter the outcome of the product. After the identification of the product as thiazolo-androstenone, we carried out the reaction of substituted thiourea derivatives under the same reaction conditions. Expected products formed in good to excellent yield. Reaction of alkyl substituted thiourea with the electrophile afforded the products. Reaction of ethylthiourea and n-butylthiourea afforded the corresponding products (IIa.30 and IIa.31) in 71% and 78% yields respectively. Reaction of allyl and 2-phenylethyl thioureas with the electrophile resulted the products (IIa.3 and IIa.2) in 73% and 75% yields, respectively. The reaction of benzyl thiourea gave the product (IIa.5) in 79% yield. Morpholine, a hydrophilic substituent, attached alkyl thiourea reacted smoothly to give the corresponding product (IIa.4) in 75% yield. We observed that arylthiourea derivatives also reacted with the electrophile and gave the products without affecting the average yield and purity. N-Phenyl thiourea reacted with the electrophile to give the product (IIa.7) in 86% yield. Electron donating groups on the aryl ring of thiourea gave the products without affecting the yield and purity of the desired molecules. Toluenyl product (IIa.32) was obtained in 92% yield. Methoxy, trifluoromethoxy, and hydroxy phenyl substituted products (IIa.15, IIa.19, and IIa.17) also formed to increase the number of compounds in the library. To further study the scope of the methodology, substrates with electron withdrawing groups on the phenyl ring were reacted with the electrophile and the products were formed expectantly. Fluoro and chloro substituted products (IIa.33, IIa.8, and IIa.11) formed in 80%, and 74%, respectively. Carboxylic acid substituted products (IIa.34 and IIa.23) formed in an average of ~73% yield.

This methodology also tolerated the very strong electron withdrawing group, nitro, on the phenyl ring to give the product (IIa.13) in 81% yield. Disubstituted products were also obtained efficiently. Bisfluoro and bismethyl substituted products (IIa.10 and IIa.14) were formed in 77% and 76% yields respectively. Other disubstituted products (IIa.20 and IIa.16) formed in an average of 73% yield. N,N-Disubstitution on thiourea did not hamper the reaction and the expected product (IIa.6) formed in 73% yield. Pyridine and pyrimidine substituted products (IIa.21 and IIa.22) formed by using the same reaction condition. Thus, this methodology is general to generate a library of potential bioactive thiazolo-androstenone derivatives.

To test the scope of the methodology to generate a library of new molecules as potential therapeutic agents, one of compounds (IIa.1) has been synthesized in multi-gram scale and further derivatized by simple transformations. Reaction of the aminothiazolo derivative (IIa.1) with acetic anhydride formed acetamido product (IIb.1), which on NaBH₄ reduction followed by acetylation formed the hydroxy and acetoxy products respectively (Scheme 7). The average yield of these reactions are >90% and the product were obtained simply by filtration and washing with methanol and water.

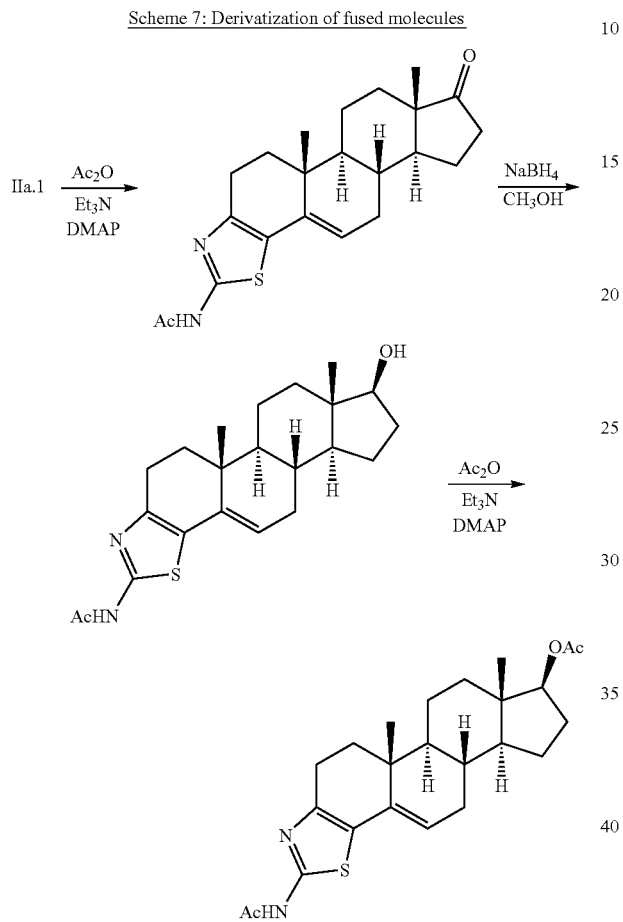

Acetyl Derivatives

Acetyl derivatives of the thiourea derives 3,4-thiazolo derivatives may also be prepared according to Scheme 8.

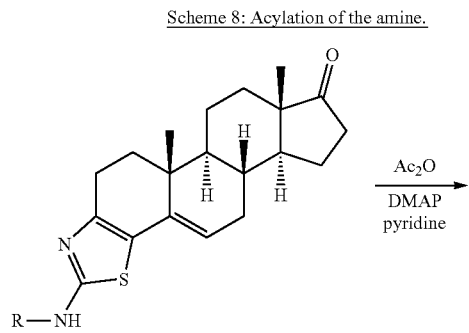

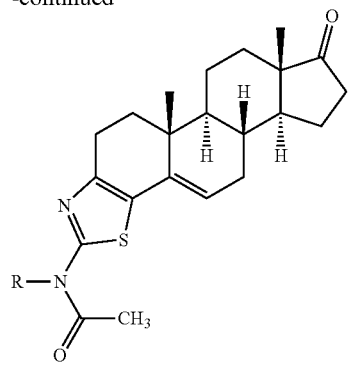

Reaction of amino derivative with Ac₂O in DMAP (cat.) and pyridine for 24 hours resulted the formation of acetyl derivative. Heating (~60° C.) may be required for some starting materials. After the completion of the reaction, methanol was added and addition of water resulted the precipitation of the product. Filtration and washing with water resulted the formation of pure product.

Various acetyl derivatives may be prepared according to this scheme, for example those shown in Table 3.

TABLE 3

Exemplary compounds of Formula IIa having an acetyl group.

(Formula IIa)

| Compound ID | R = | R' = |
|---|---|---|
| IIb.1 | acetyl | H |
| IIb.2 | acetyl | 2-phenylethyl |
| IIb.3 | acetyl | Prop-2-en |
| IIb.4 | acetyl | (morpholinyl-butyl group) |
| IIb.5 | acetyl | benzyl |
| IIb.6 | acetyl | phenyl |
| IIb.8 | acetyl | 3-fluoro-phenyl |
| IIb.9 | acetyl | 4-fluoro-phenyl |
| IIb.10 | acetyl | 2,4-difluoro-phenyl |
| IIb.11 | acetyl | 2-chloro-phenyl |
| IIb.12 | acetyl | 4-chloro-phenyl |
| IIb.13 | acetyl | 2-nitro-phenyl |
| IIb.14 | acetyl | 2,4-dimethyl-phenyl |
| IIb.15 | acetyl | 2-methoxy-phenyl |
| IIb.16 | acetyl | 2,5-dimethoxy-phenyl |
| IIb.17 | acetyl | 3-hydroxy-phenyl |

TABLE 3-continued

Exemplary compounds of Formula IIa having an acetyl group.

(Formula IIa)

| Compound ID | R = | R' = |
|---|---|---|
| IIb.18 | acetyl | 4-methoxy-phenyl |
| IIb.19 | acetyl | 4-trifluoromethyl ether-phenyl |
| IIb.20 | acetyl | 2-methoxy, 5-chloro-phenyl |
| IIb.21 | acetyl | pyrind-2-yl |
| IIb.22 | acetyl | pyrimidin-2-yl |
| IIb.23 | acetyl | 4-carboxy-phenyl |

C-17 Derivatives

Numerous C-17 derivatives may be prepared from the compounds of Formula II or Formula IIa. Suitably, C-17 derivatives include, without limitation, hydroxyl, hydrazine, oxime, carboxylate, cyano, aryl, alkyl, and alkynyl derivatives.

C-17 Hydroxyl Derivatives

C-17 hydroxyl derivatives may also be prepared by reducing the C-17 oxo group of the compounds of Formula II or IIa with a reducing agent. Scheme 9 provides an exemplary method for preparing compounds of Formula III or Formula IIIa starting with a compound of Formula II or Formula IIa, respectively.

Scheme 9: Preparation of hydroxyl derivatives.

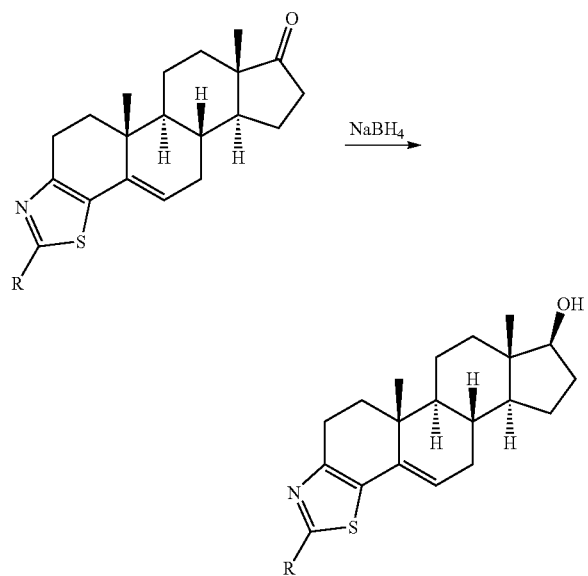

Suitably, the R group may be any thiazolo substituent described herein. Exemplary compounds include, without limitation, those shown in Table 4.

TABLE 4

Exemplary compounds of Formula III and IIIa.

(Formula III)

| Compound ID | R = |
|---|---|
| III.1 | methyl |
| III.2 | phenyl |
| III.3 | benzyl |
| III.4 | pyrind-2-yl |
| III.5 | 4-hydroxy-phenyl |
| III.6 | 2-hydroxy-phenyl |
| III.7 | 3,4-dihydroxy-phenyl |
| III.8 | 2-chloro-phenyl |
| III.9 | 4-carboxy-phenyl |
| III.10 | 3-methyl-phenyl |
| III.11 | 4-methyl-phenyl |
| III.12 | 3-methoxy-phenyl |
| III.13 | 4-methoxy-phenyl |
| III.14 | 2-methyl-phenyl |
| III.15 | 3-fluoro-phenyl |
| III.16 | 4-fluoro-phenyl |
| III.17 | 3-chloro-phenyl |
| III.18 | 4-chloro-phenyl |
| III.19 | 4-bromo-phenyl |
| III.20 | 3-ethoxy-phenyl |

(Formula IIIa)

| Compound ID | R = | R' = |
|---|---|---|
| IIIa.1 | H | H |
| IIIa.2 | H | methyl |
| IIIa.3 | H | ethyl |
| IIIa.4 | H | butyl |
| IIIa.5 | H | 2-phenylethyl |
| IIIa.6 | H | prop-2-en-1-yl |
| IIIa.7 | H | 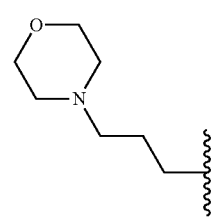 [SMILES: *CCCN1CCOCC1] |
| IIIa.8 | H | benzyl |
| IIIa.9 | methyl | phenyl |

TABLE 4-continued

Exemplary compounds of Formula III and IIIa.

| | | |
|---|---|---|
| IIIa.10 | H | phenyl |
| IIIa.11 | H | 3-fluoro-phenyl |
| IIIa.12 | H | 4-fluoro-phenyl |
| IIIa.13 | H | 2,4-difluoro-phenyl |
| IIIa.14 | H | 2-chloro-phenyl |
| IIIa.15 | H | 4-chloro-phenyl |
| IIIa.16 | H | 2-nitro-phenyl |
| IIIa.17 | H | 2,4-dimethyl-phenyl |
| IIIa.18 | H | 2-methoxy-phenyl |
| IIIa.19 | H | 2,5-dimethoxy-phenyl |
| IIIa.20 | H | 3-hydroxy-phenyl |
| IIIa.21 | H | 4-methoxy-phenyl |
| IIIa.22 | H | 4-trifluoromethyl ether-phenyl |
| IIIa.23 | H | 2-methoxy, 5-chloro-phenyl |
| IIIa.24 | H | pyrind-2-yl |
| IIIa.25 | H | pyrimidin-2-yl |
| IIIa.26 | H | 4-carboxy-phenyl |
| IIIa.27 | H |  |
| IIIa.28 | H | 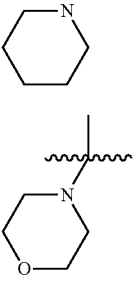 |
| IIIa.29 | H | 4-methyl-piperazin-1-yl |
| IIIa.30 | H | 4-ethyl-piperazin-1-yl |
| IIIa.31 | H | 4-ethan-2-ol-piperazin-1-yl |
| IIIa.32 | H | piperazin-1-yl |
| IIIa.33 | H | 4-methyl-phenyl |
| IIIa.34 | H | 3-trifluoromethyl ether-phenyl |
| IIIa.35 | H | 3-carboxy-phenyl |
| IIIa.36 | H | 3-trifluoromethyl-phenyl |
| IIIa.37 | H | acetyl |
| IIIa.38 | H | 4-hydroxy-phenyl |
| IIIa.39 | H | 3-hydroxy-phenyl |

C-17 Hydrazone Derivatives

C-17 hydrazone derivatives may also be prepared by reacting compounds of Formula II or IIa with a hydrazine of general formula $H_2N—NRR'$. Scheme 10 provides an exemplary method for preparing compounds of Formula IV starting with a compound of Formula IIa.

Scheme 10: Preparation of hydrazone derivatives.

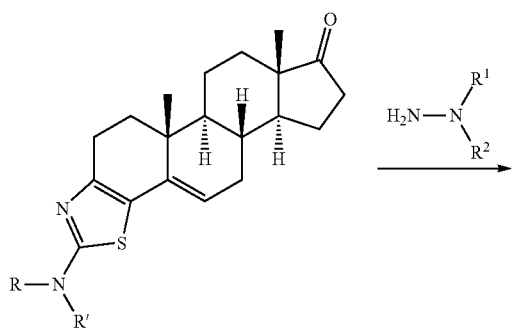

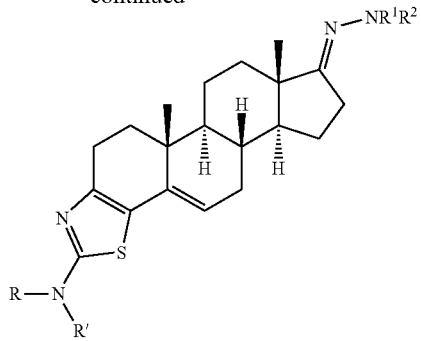

Suitably, compounds of Formula IV

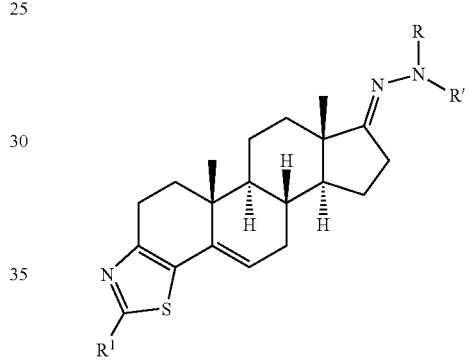

(Formula IV)

may be prepared. Suitably, R and R' are independently selected from hydrogen; a branched or unbranched, substituted or unsubstituted $C_1$-$C_{12}$ alkyl; a branched or unbranched, substituted or unsubstituted $C_2$-$C_{12}$ alkenyl; a branched or unbranched, substituted or unsubstituted $C_2$-$C_{12}$ alkynyl; a branched or unbranched, substituted or unsubstituted $C_3$-$C_{12}$ cycloalkyl; a branched or unbranched, substituted or unsubstituted $C_6$-$C_{12}$ aryl; a branched or unbranched, substituted or unsubstituted $C_6$-$C_{12}$ arylalkyl; or a branched or unbranched, substituted or unsubstituted $C_3$-$C_{12}$ heterocyclyl. In other embodiments, R and R' together are selected from a branched or unbranched, substituted or unsubstituted $C_2$-$C_{12}$ alkylene; a branched or unbranched, substituted or unsubstituted $C_2$-$C_{12}$ ether; a branched or unbranched, substituted or unsubstituted, secondary, tertiary, or quaternary amine. When R and R' are selected together, R and R' with the bridging N may form a substituted or unsubstituted piperdinyl, piperazinyl, or morpholino ring. Suitably, the substituents may be selected from a $C_1$-$C_{12}$ alkyl, $C_1$-$C_{12}$ alkanol, or $C_1$-$C_{12}$ aryl.

Suitably, the $R^1$ group may be any thiazolo substituent described herein. Exemplary compounds include, without limitation, those shown in Table 5.

TABLE 5

Exemplary compounds of Formula IVa.

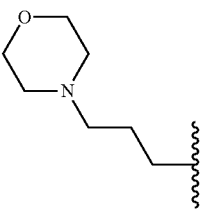 [SMILES: *CCCN1CCOCC1]

(Formula IVa)

| Compound ID | R = | R' = |
|---|---|---|
| IVa.1 | H | H |
| IVa.2 | H | 2-phenylethyl |
| IVa.3 | H | prop-2-en-1-yl |
| IVa.4 | H | 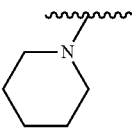 |
| IVa.5 | H | benzyl |
| IVa.6 | methyl | phenyl |
| IVa.7 | H | phenyl |
| IVa.8 | H | 3-fluoro-phenyl |
| IVa.9 | H | 4-fluoro-phenyl |
| IVa.10 | H | 2,4-difluoro-phenyl |
| IVa.11 | H | 2-chloro-phenyl |
| IVa.12 | H | 4-chloro-phenyl |
| IVa.13 | H | 2-nitro-phenyl |
| IVa.14 | H | 2,4-dimethyl-phenyl |
| IVa.15 | H | 2,4,6-trimethyl-phenyl |
| IVa.16 | H | 2-methoxy-phenyl |
| IVa.17 | H | 2,5-dimethoxy-phenyl |
| IVa.18 | H | 3-hydroxy-phenyl |
| IVa.19 | H | 4-methoxy-phenyl |
| IVa.20 | H | 4-trifluoromethyl ether-phenyl |
| IVa.21 | H | 2-methoxy, 5-chloro-phenyl |
| IVa.22 | H | pyrind-2-yl |
| IVa.23 | H | pyrimidin-2-yl |
| IVa.24 | H | 4-carboxy-phenyl |
| IVa.25 | H | 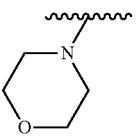 |
| IVa.26 | H | 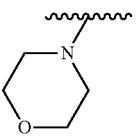 |
| IVa.27 | H | 4-methy-piperazin-1-yl |
| IVa.28 | H | 4-ethyl-piperazin-1-yl |
| IVa.29 | H | 4-ethan-2-ol-piperazin-1-yl |
| IVa.30 | H | piperazin-l-yl |

Alternatively, hydrazone derivatives may be prepared from compounds of Formula III according to Scheme 11.

Scheme 11: Preparation of hydrazone derivatives.

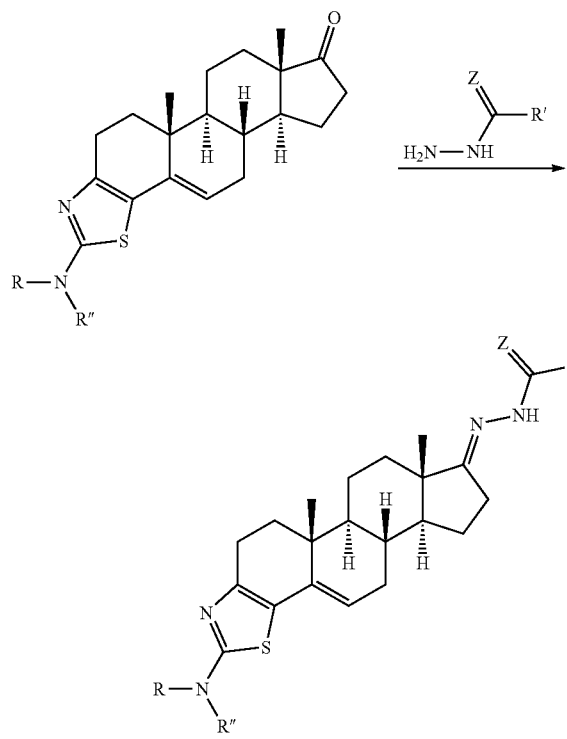

Z = O, and S

Suitably, compounds of Formula VI

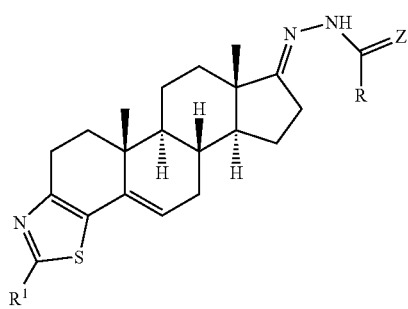

(Formula IV)

may be prepared. Z may be selected from oxygen or sulfur and R may be selected from hydrogen; a branched or unbranched, substituted or unsubstituted $C_1$-$C_{12}$ alkyl; a branched or unbranched, substituted or unsubstituted $C_2$-$C_{12}$ alkenyl; a branched or unbranched, substituted or unsubstituted $C_2$-$C_{12}$ alkynyl; a branched or unbranched, substituted or unsubstituted $C_3$-$C_{12}$ cycloalkyl; a branched or unbranched, substituted or unsubstituted $C_6$-$C_{12}$ aryl; a branched or unbranched, substituted or unsubstituted $C_6$-$C_{12}$ arylalkyl; a branched or unbranched, substituted or unsubstituted $C_3$-$C_{12}$ heterocyclyl; or a branched or unbranched, substituted or unsubstituted, secondary, tertiary, or quaternary amine Suitably, the $R^1$ group may be any thiazolo substituent described herein. Exemplary compounds include, without limitation, those shown in Table 6.

TABLE 6

Exemplary compounds of Formula IVb.

(Formula IVb)

| Compound ID | R = | R' = | $R^1$ = | Z = |
|---|---|---|---|---|
| IVb.1 | H | H | amino | O |
| IVb.2 | H | 2-phenylethyl | amino | O |
| IVb.3 | H | prop-2-en-1-yl | amino | O |
| IVb.4 | H | (morpholinylpropyl) | amino | O |
| IVb.5 | H | benzyl | amino | O |
| IVb.6 | methyl | phenyl | amino | O |
| IVb.7 | H | phenyl | amino | O |
| IVb.8 | H | 3-fluoro-phenyl | amino | O |
| IVb.9 | H | 4-fluoro-phenyl | amino | O |
| IVb.10 | H | 2,4-difluoro-phenyl | amino | O |
| IVb.11 | H | 2-chloro-phenyl | amino | O |
| IVb.12 | H | 4-chloro-phenyl | amino | O |
| IVb.13 | H | 2-nitro-phenyl | amino | O |
| IVb.14 | H | 2,4-dimethyl-phenyl | amino | O |
| IVb.15 | H | 2,4,6-trimethyl-phenyl | amino | O |
| IVb.16 | H | 2-methoxy-phenyl | amino | O |
| IVb.17 | H | 2,5-dimethoxy-phenyl | amino | O |
| IVb.18 | H | 3-hydroxy-phenyl | amino | O |
| IVb.19 | H | 4-methoxy-phenyl | amino | O |
| IVb.20 | H | 4-trifluoromethyl ether-phenyl | amino | O |
| IVb.21 | H | 2-methoxy, 5-chloro-phenyl | amino | O |
| IVb.22 | H | pyrind-2-yl | amino | O |
| IVb.23 | H | pyrimidin-2-yl | amino | O |
| IVb.24 | H | 4-carboxy-phenyl | amino | O |
| IVb.25 | H | piperidinyl | amino | O |
| IVb.26 | H | morpholinyl | amino | O |

TABLE 6-continued

Exemplary compounds of Formula IVb.

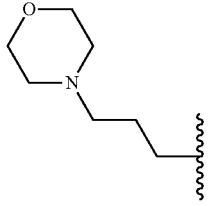 [SMILES: *CCCN1CCOCC1]

(Formula IVb)

| Compound ID | R = | R' = | R¹ = | Z = |
|---|---|---|---|---|
| IVb.27 | H | 4-methyl-piperazin-1-yl | amino | O |
| IVb.28 | H | 4-ethyl-piperazin-1-yl | amino | O |
| IVb.29 | H | 4-ethan-2-ol-piperazin-1-yl | amino | O |
| IVb.30 | H | piperazin-1-yl | amino | O |
| IVb.31 | H | H | amino | S |
| IVb.32 | H | 2-phenylethyl | amino | S |
| IVb.33 | H | prop-2-en-1-yl | amino | S |
| IVb.34 | H | 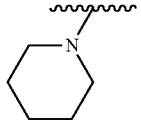 [SMILES: *N1CCCCC1] | amino | S |
| IVb.35 | H | benzyl | amino | S |
| IVb.36 | methyl | phenyl | amino | S |
| IVb.37 | H | phenyl | amino | S |
| IVb.38 | H | 3-fluoro-phenyl | amino | S |
| IVb.39 | H | 4-fluoro-phenyl | amino | S |
| IVb.40 | H | 2,4-difluoro-phenyl | amino | S |
| IVb.41 | H | 2-chloro-phenyl | amino | S |
| IVb.42 | H | 4-chloro-phenyl | amino | S |
| IVb.43 | H | 2-nitro-phenyl | amino | S |
| IVb.44 | H | 2,4-dimethyl-phenyl | amino | S |
| IVb.45 | H | 2,4,6-trimethyl-phenyl | amino | S |
| IVb.46 | H | 2-methoxy-phenyl | amino | S |
| IVb.47 | H | 2,5-dimethoxy-phenyl | amino | S |
| IVb.48 | H | 3-hydroxy-phenyl | amino | S |
| IVb.49 | H | 4-methoxy-phenyl | amino | S |
| IVb.50 | H | 4-trifluoromethyl ether-phenyl | amino | S |
| IVb.51 | H | 2-methoxy, 5-chloro-phenyl | amino | S |
| IVb.52 | H | pyrind-2-yl | amino | S |
| IVb.53 | H | pyrimidin-2-yl | amino | S |
| IVb.54 | H | 4-carboxy-phenyl | amino | S |
| IVb.55 | H | 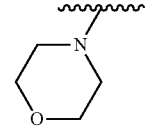 [SMILES: *N1CCOCC1] | amino | S |
| IVb.56 | H | 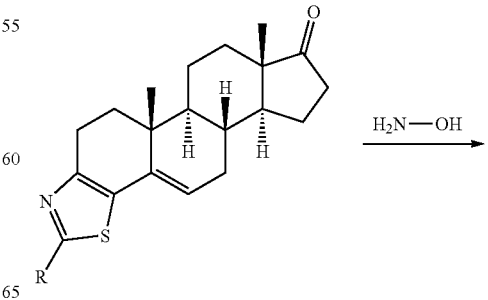 | amino | S |
| IVb.57 | H | 4-methy-piperazin-1-yl | amino | S |
| IVb.58 | H | 4-ethyl- piperazin-1-yl | amino | S |
| IVb.59 | H | 4-ethan-2-ol- piperazin-1-yl | amino | S |
| IVb.60 | H | piperazin-1-yl | amino | S |

C-17 Oxime Derivatives

C-17 oxime derivatives may also be prepared by reacting a compound of Formula II or Formula IIa with a hydroxylamine. Scheme 12 provides an exemplary method for preparing compounds of Formula V starting with a compound of Formula II.

Scheme 12: Preparation of oxime derivatives.

-continued

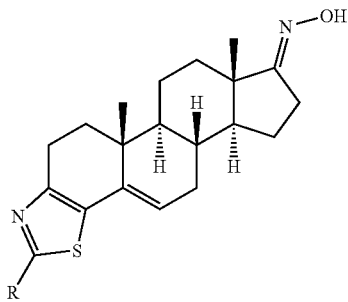

Suitably, compounds of Formula V

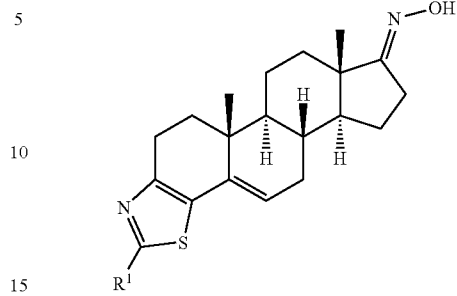
(Formula V)

may be prepared. Suitably, the $R^1$ group may be any thiazolo substituent described herein. Exemplary compounds include, without limitation, those shown in Table 7.

TABLE 7

Exemplary compounds of Formula Va.

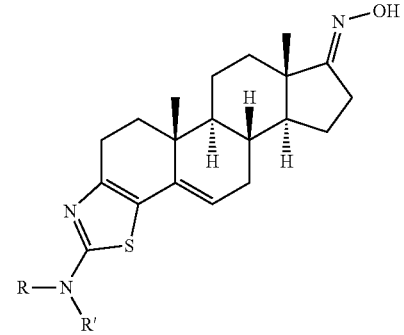
(Formula Va)

| Compound ID | R = | R' = |
|---|---|---|
| Va.1 | H | H |
| Va.2 | H | 2-phenylethyl |
| Va.3 | H | prop-2-en-1-yl |
| Va.4 | H | ![morpholine-propyl] |
| Va.5 | H | benzyl |
| Va.6 | methyl | phenyl |
| Va.7 | H | phenyl |
| Va.8 | H | 3-fluoro-phenyl |
| Va.9 | H | 4-fluoro-phenyl |
| Va.10 | H | 2,4-difluoro-phenyl |
| Va.11 | H | 2-chloro-phenyl |
| Va.12 | H | 4-chloro-phenyl |
| Va.13 | H | 2-nitro-phenyl |
| Va.14 | H | 2,4-dimethyl-phenyl |
| Va.15 | H | 2,4,6-trimethyl-phenyl |
| Va.16 | H | 2-methoxy-phenyl |
| Va.17 | H | 2,5-dimethoxy-phenyl |
| Va.18 | H | 3-hydroxy-phenyl |
| Va.19 | H | 4-methoxy-phenyl |
| Va.20 | H | 4-trifluoromethyl ether-phenyl |
| Va.21 | H | 2-methoxy, 5-chloro-phenyl |
| Va.22 | H | pyrind-2-yl |
| Va.23 | H | pyrimidin-2-yl |

TABLE 7-continued

Exemplary compounds of Formula Va.

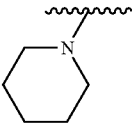 [SMILES: *N1CCCCC1]

(Formula Va)

| Compound ID | R = | R' = |
|---|---|---|
| Va.24 | H | 4-carboxy-phenyl |
| Va.25 | H | 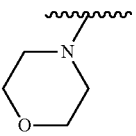 |
| Va.26 | H | |
| Va.27 | H | 4-methy-piperazin-1-yl |
| Va.28 | H | 4-ethyl-piperazin-1-yl |
| Va.29 | H | 4-ethan-2-ol- piperazin-1-yl |
| Va.30 | H | piperazin-1-yl |

C-17 Carboxylate Derivatives

C-17 carboxylate derivatives may also be prepared by reacting a compound of Formula II or Formula IIa with an acyl chloride. Scheme 13 provides an exemplary method for preparing compounds of Formula VIIa starting with a compound of Formula IIa.

Scheme 13: Preparation of carboxylate dervatives.

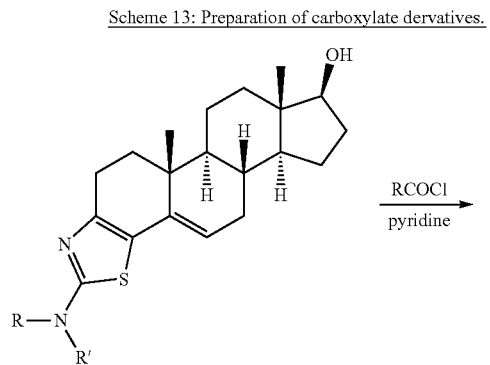

$\xrightarrow{\text{RCOCl}}_{\text{pyridine}}$

-continued

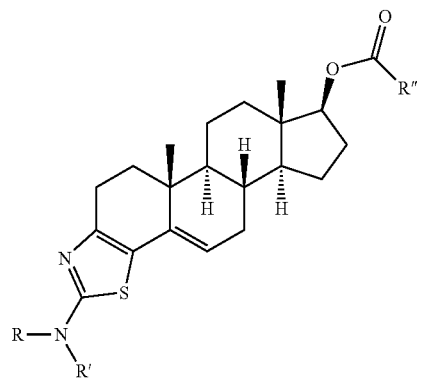

Suitably, compounds of Formula VII

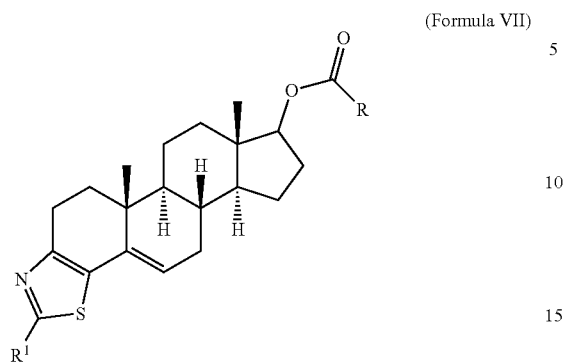

may be prepared. Suitably, the $R^1$ group may be any thiazolo substituents described herein. Exemplary compounds include, without limitation, those shown in Table 8.

TABLE 8

Exemplary compounds of Formula VIIa.

| Compound ID | R = | R' = | $R^2$ = |
| --- | --- | --- | --- |
| VIIa.1 | H | acetyl | methyl |
| VIIa.2 | H | 2-phenylethyl | methyl |
| VIIa.3 | H | prop-2-en-1-yl | methyl |
| VIIa.4 | H. | (morpholinobutyl) | methyl |
| VIIa.5 | H | benzyl | methyl |
| VIIa.6 | methyl | phenyl | methyl |
| VIIa.7 | H | phenyl | methyl |
| VIIa.8 | H | 3 fluoro-phenyl | methyl |
| VIIa.9 | H | 4-fluoro-phenyl | methyl |
| VIIa.10 | H | 2,4-difluoro-phenyl | methyl |
| VIIa.11 | H | 2-chloro-phenyl | methyl |
| VIIa.12 | H | 4-chloro-phenyl | methyl |
| VIIa.13 | H | 2-nitro-phenyl | methyl |
| VIIa.14 | H | 2,4-dimethyl-phenyl | methyl |
| VIIa.15 | H | 2-methoxy-phenyl | methyl |
| VIIa.16 | H | 2,5-dimethoxy-phenyl | methyl |
| VIIa.17 | H | 3-hydroxy-phenyl | methyl |
| VIIa.18 | H | 4-methoxy-phenyl | methyl |
| VIIa.19 | H | 4-trifluoromethyl ether-phenyl | methyl |

TABLE 8-continued

Exemplary compounds of Formula VIIa.

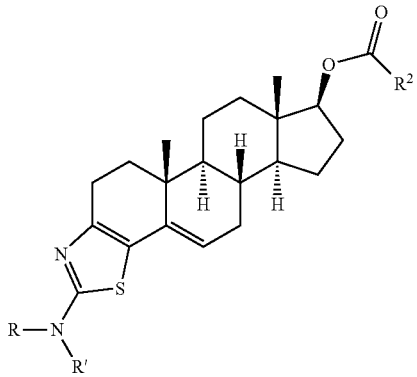

(Formula VIIa)

| Compound ID | R = | R' = | R² = |
|---|---|---|---|
| VIIa.20 | H | 2-methoxy, 5-chloro-phenyl | methyl |
| VIIa.21 | H | pyrind-2-yl | methyl |
| VIIa.22 | H | pyrimidin-2-yl | methyl |
| VIIa.23 | H | 4-carboxy-phenyl | methyl |
| VIIa.24 | H | piperidin-1-yl-methyl | methyl |
| VIIa.25 | H | morpholin-4-yl-methyl | methyl |
| VIIa.26 | H | 4-methyl-piperazin-1-yl | methyl |
| VIIa.27 | H | 4-ethyl-piperazin-1-yl | methyl |
| VIIa.28 | H | 4-ethan-2-ol-piperazin-1-yl | methyl |
| VIIa.29 | H | piperazin-1-yl | methyl |
| VIIa.30 | H | acetyl | ethyl |
| VIIa.31 | H. | 2-phenylethyl | ethyl |
| VIIa.32 | H | prop-2-en-1-yl | ethyl |
| VIIa.33 | H | 4-(morpholin-4-yl)butyl | ethyl |
| VIIa.34 | H | benzyl | ethyl |
| VIIa.35 | methyl | phenyl | ethyl |
| VIIa.36 | H | phenyl | ethyl |
| VIIa.37 | H | 3-fluoro-phenyl | ethyl |
| VIIa.38 | H | 4-fluoro-phenyl | ethyl |
| VIIa.39 | H | 2,4-difluoro-phenyl | ethyl |
| VIIa.40 | H | 2-chloro-phenyl | ethyl |
| VIIa.41 | H | 4-chloro-phenyl | ethyl |
| VIIa.42 | H | 2-nitro-phenyl | ethyl |
| VIIa.43 | H | 2,4-dimethyl-phenyl | ethyl |
| VIIa.44 | H | 2-methoxy-phenyl | ethyl |
| VIIa.45 | H | 2,5-dimethoxy-phenyl | ethyl |
| VIIa.46 | H | 3-hydroxy-phenyl | ethyl |
| VIIa.47 | H | 4-methoxy-phenyl | ethyl |
| VIIa.48 | H | 4-trifluoromethyl ether-phenyl | ethyl |
| VIIa.49 | H. | 2-methoxy, 5-chloro-phenyl | ethyl |
| VIIa.50 | H | pyrind-2-yl | ethyl |
| VIIa.51 | H | pyrind-2-2-yl | ethyl |
| VIIa.52 | H | 4-carboxy-phenyl | ethyl |

TABLE 8-continued

Exemplary compounds of Formula VIIa.

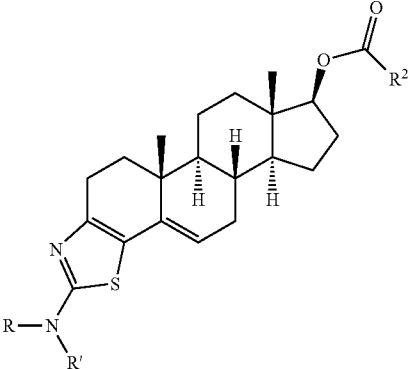

(Formula VIIa)

| Compound ID | R = | R' = | R² = |
|---|---|---|---|
| VIIa.53 | H | piperidin-1-yl | ethyl |
| VIIa.54 | H | morpholin-4-yl | ethyl |
| VIIa.55 | H | 4-methy-piperazin-1-1-yl | ethyl |
| VIIa.56 | H | 4-ethyl- piperazin-1 -yl | ethyl |
| VIIa.57 | H | 4-ethan-2-ol- piperazin-1-yl | ethyl |
| VIIa.58 | H | piperazin-1-yl | ethyl |
| VIIa.59 | H | acetyl | n-propyl |
| VIIa.60 | H | 2-phenylethyl | n-propyl |
| VIIa.61 | H | prop-2-en-1-yl | n-propyl |
| VIIa.62 | H | 3-(morpholin-4-yl)propyl | n-propyl |
| VIIa.63 | H | benzyl | n-propyl |
| VIIa.64 | methyl | phenyl | n-propyl |
| VIIa.65 | H | phenyl | n-propyl |
| VIIa.66 | H | 3-fluoro-phenyl | n-propyl |
| VIIa.67 | H | 4-fluoro-phenyl | n-propyl |
| VIIa.68 | H | 2,4-difluoro-phenyl | n-propyl |
| VIIa.69 | H | 2-chloro-phenyl | n-propyl |
| VIIa.70 | H | 4-chloro-phenyl | n-propyl |
| VIIa.71 | H | 2-nitro-phenyl | n-propyl |
| VIIa.72 | H | 2,4-dimethyl-phenyl | n-propyl |
| VIIa.73 | H | 2-methoxy-phenyl | n-propyl |
| VIIa.74 | H | 2,5-dimethoxy -phenyl | n-propyl |
| VIIa.75 | H | 3-hydroxy-phenyl | n-propyl |
| VIIa.76 | H | 4-methoxy-phenyl | n-propyl |
| VIIa.77 | H | 4-trifluoromethyl ether-phenyl | n-propyl |
| VIIa.78 | H | 2-methoxy, 5-chloro-phenyl | n-propyl |
| VIIa.79 | H | pyrind-2-yl | n-propyl |
| VIIa.80 | H | pyrind-2-2-yl | n-propyl |
| VIIa.81 | H | 4-carboxy-phenyl | n-propyl |

TABLE 8-continued

Exemplary compounds of Formula VIIa.

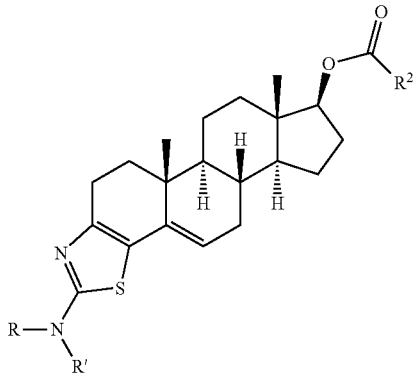

(Formula VIIa)

| Compound ID | R = | R' = | R² = |
| --- | --- | --- | --- |
| VIIa.82 | H | piperidin-1-yl (N-linked) | n-propyl |
| VIIa.83 | H | morpholin-4-yl (N-linked) | n-propyl |
| VIIa.84 | H | 4-methy-piperazin-l-yl | n-propyl |
| VIIa.85 | H | 4-ethyl-piperazin-1-yl | n-propyl |
| VIIa.86 | H | 4-ethan-2-ol-piperazin-1-yl | n-propyl |
| VIIa.87 | H | piperazin-1-yl | n-propyl |
| VIIa.88 | H | acetyl | n-butyl |
| VIIa.89 | H | 2-phenylethyl | n-butyl |
| VIIa.91 | H | prop-2-en-1-yl | n-butyl |
| VIIa.92 | H | 4-(morpholin-4-yl)butyl | n-butyl |
| VIIa.93 | H | benzyl | n-butyl |
| VIIa.94 | methyl | phenyl | n-butyl |
| VIIa.95 | H | phenyl | n-butyl |
| VIIa.96 | H | 3-fluoro-phenyl | n-butyl |
| VIIa.97 | H | 4-fluoro-phenyl | n-butyl |
| VIIa.98 | H | 2,4-difluoro-phenyl | n-butyl |
| VIIa.99 | H | 2-chloro-phenyl | n-butyl |
| VIIa.100 | H | 4-chloro-phenyl | n-butyl |
| VIIa.101 | H | 2-nitro-phenyl | n-butyl |
| VIIa.102 | H | 2,4-dimethyl-phenyl | n-butyl |

TABLE 8-continued

Exemplary compounds of Formula VIIa.

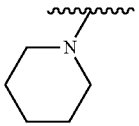 [SMILES: *N1CCCCC1]

(Formula VIIa)

| Compound ID | R = | R' = | R² = |
|---|---|---|---|
| VIIa.103 | H | 2-methoxy-phenyl | n-butyl |
| VIIa.104 | H | 2,5-dimethoxy-phenyl | n-butyl |
| VIIa.105 | H | 3-hydroxy-phenyl | n-butyl |
| VIIa.106 | H | 4-methoxy-phenyl | n-butyl |
| VIIa.107 | H | 4-trifluoromethyl ether-phenyl | n-butyl |
| VIIa.108 | H | 2-methoxy, 5-chloro-phenyl | n-butyl |
| VIIa.109 | H | pyrind-2-yl | n-butyl |
| VIIa.110 | H | pyrimidin-2-yl | n-butyl |
| VIIa.111 | H | 4-carboxy-phenyl | n-butyl |
| VIIa.112 | H. | 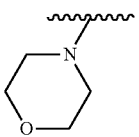 [SMILES: *N1CCOCC1] | n-butyl |
| VIIa.113 | H | 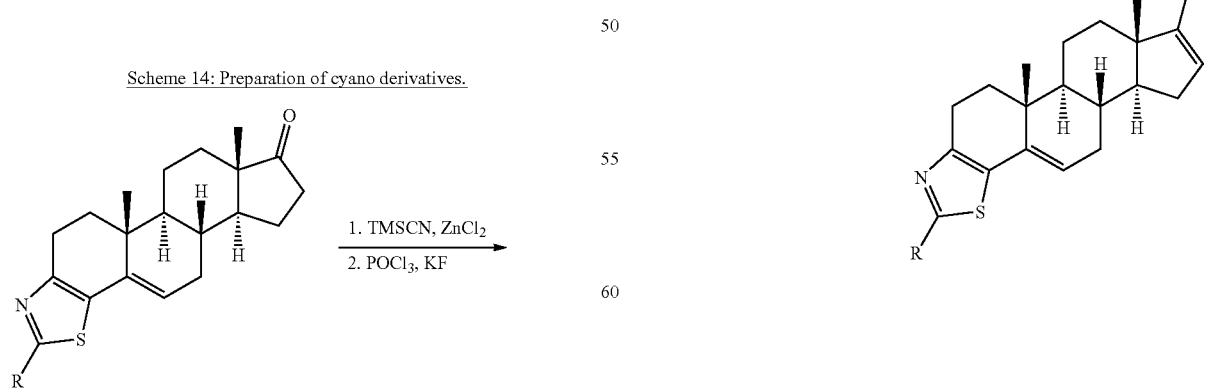 | n-butyl |
| VIIa.114 | H | 4-methy-piperazin-l-yl | n-butyl |
| VIIa.115 | H | 4-ethyl-piperazin-1-yl | n-butyl |
| VIIa.116 | H | 4-ethan-2-ol-piperazin-yl | n-butyl |
| VIIa.117 | H | piperazin-1-yl | n-butyl |

C-17 Cyano Derivatives

C-17 cyano derivatives may also be prepared according to Scheme 14.

Scheme 14: Preparation of cyano derivatives.

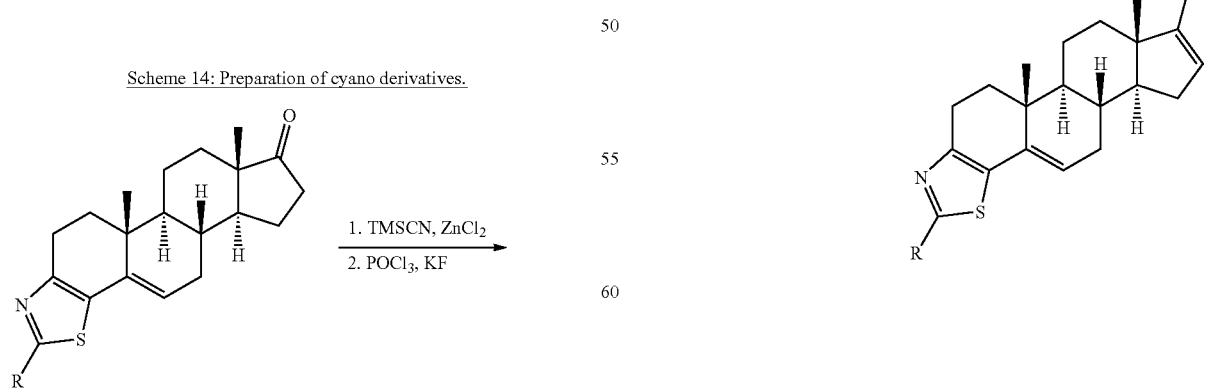

C-17 Aryl Derivatives

C-17 aryl derivatives may also be prepared according to Scheme 15.

Scheme 15: Preparation of aryl derivatives.

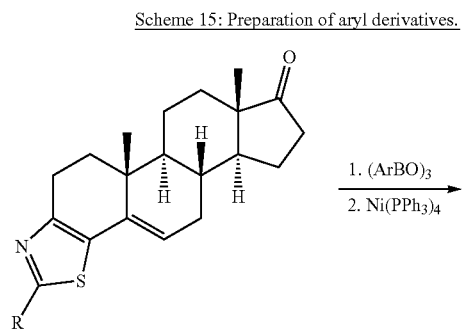

Suitably, the $R^1$ group may be any thiazolo substituent described herein. The Ar group may suitably be any aryl group. Representative aryl groups include substituted or unsubstituted phenyl, naphthyl, anthracenyl, and the like.

C-17 Alkyl Derivatives

Thiazolo-andostenone derivatives may also be prepared from an A-ring epoxide according to Scheme 16 from compounds having a C-17 alkyl-group.

Scheme 16: Preparation of thiazolo-andostenone derivatives.

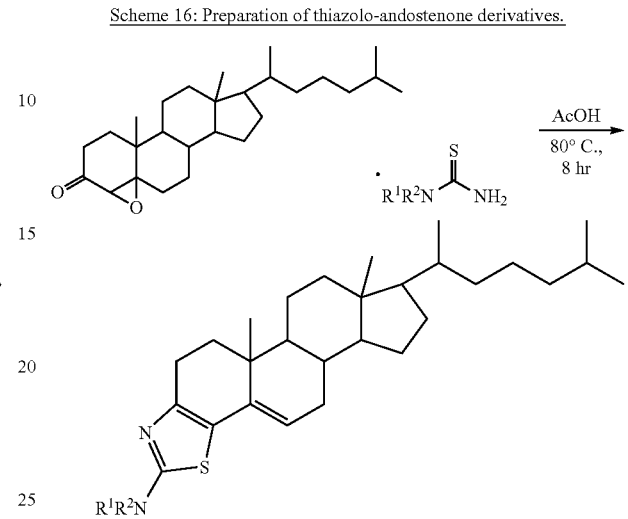

Suitably, the $R^1$ and $R^2$ group may be any substituent described herein. Exemplary compounds include, without limitation, those shown in Table 9.

TABLE 9

Exemplary compounds of Formula Xa.

(Formula Xa)

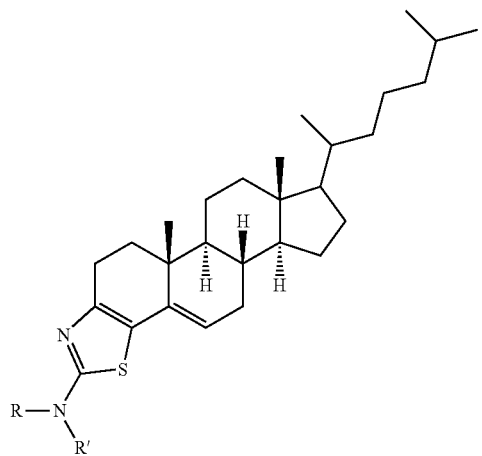

| Compound ID | R = | R' = |
|---|---|---|
| X.1 | H | H |
| X.2 | H | prop-2-en-1-yl |
| X.3 | H | benzyl |
| X.4 | methyl | phenyl |
| X.5 | H | phenyl |
| X.6 | H | 2-trifluoromethyl-phenyl |
| X.7 | H | 4-methyl-phenyl |
| X.8 | H | 2,4-difluoro-phenyl |
| X.9 | H | 2-chloro-phenyl |
| X.10 | H | 3,5-di-trifluoromethyl-phenyl |
| X.11 | H | 2-nitro-phenyl |
| X.12 | H | 2,4-dimethyl-phenyl |
| X.13 | H | 2,4,6-trimethylphenyl |
| X.14 | H | 2-methoxy-phenyl |
| X.15 | H | 2,5-dimethoxy-phenyl |

TABLE 9-continued

Exemplary compounds of Formula Xa.

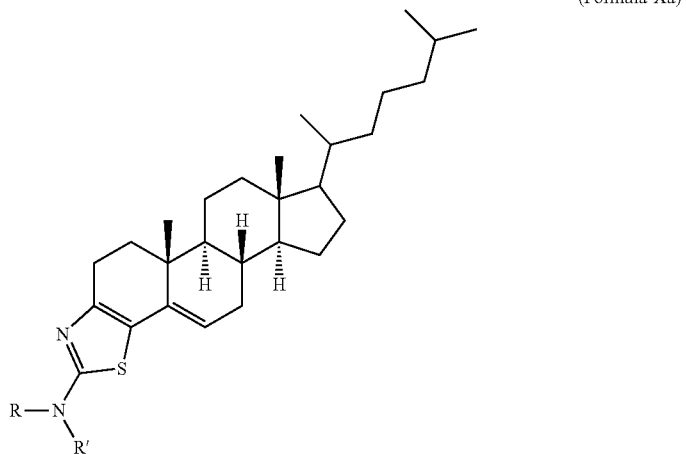

(Formula Xa)

| Compound ID | R = | R' = |
|---|---|---|
| X.16 | H | 2,4-dimethoxy-phenyl |
| X.17 | H | 2-methoxy, 5-chloro-phenyl |
| X.18 | H | pyrind-2-yl |
| X.19 | H | pyrimidin-2-yl |

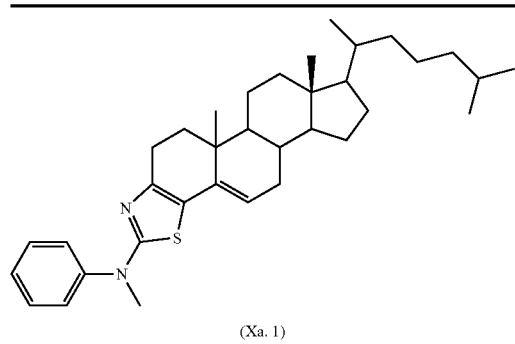

(Xa.1)

C-17 Alkenyl Derivatives

Thiazolo-andostenone derivatives may be prepared according to Scheme 17 via expoxidation of the A-ring from compounds having a C-17 OH- and alkynyl-group

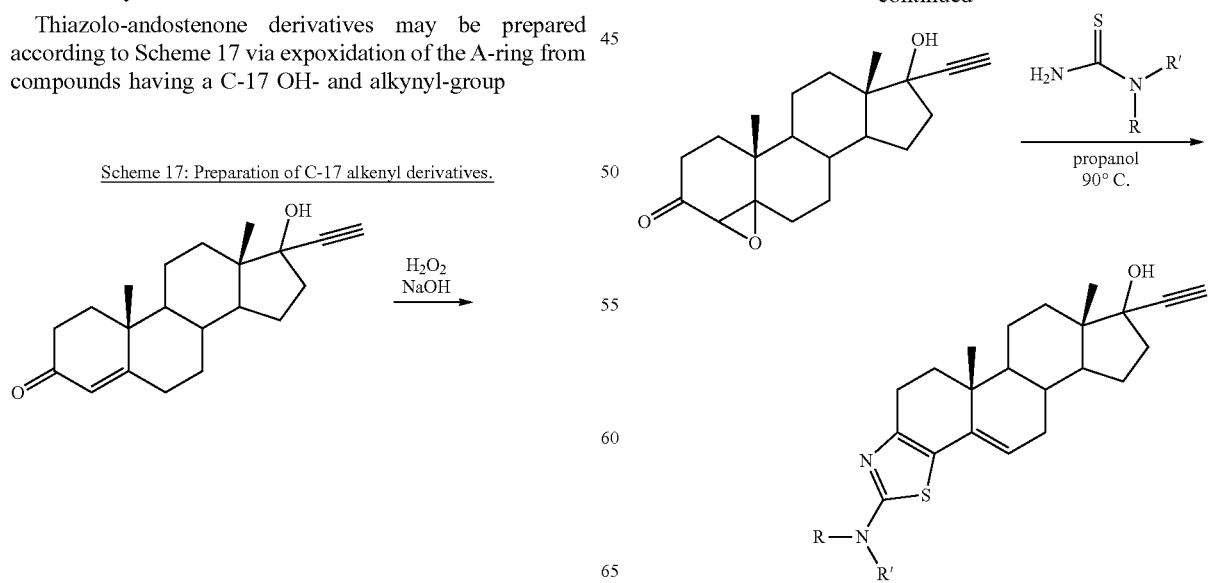

Scheme 17: Preparation of C-17 alkenyl derivatives.

Suitably, the $R^1$ and $R^2$ group may be any substituent described herein. Exemplary compounds include, without limitation, those shown in Table 10.

TABLE 10

Exemplary compounds of Formula XI.

(Formula XIa)

| Compound ID | R = | R' = |
|---|---|---|
| XI.1 | H | H |
| XI.2 | H | 2,4-difluoro-phenyl |
| XI.3 | H | 2-nitro-phenyl |
| XI.4 | H | 2,4-dimethoxy-phenyl |
| XI.5 | H | pyrind-2-yl |
| XI.6 | H | pyrimidin-2-yl |

D-Ring Lactam Derivatives

D-ring lactams may also be prepared according to Scheme 18.

Scheme 18: Preparation of carboxylate derivatives.

Suitably, D-ring lactams may be prepared by reacting a C-17 oxime, such as any of the C-17 oximes described herein, with thionyl chloride. Suitably, the R group may be any thiazolo substituent described herein.

B-Ring Derivatives

Saturated B-ring derivatives may be prepared by hydrogenating an unsaturated B-ring in the presence of a catalyst such as Pd/C. Schemes 19 and 20 provide exemplary method for preparing saturated B-ring derivatives starting with a compound of Formula II or Formula III, respectively.

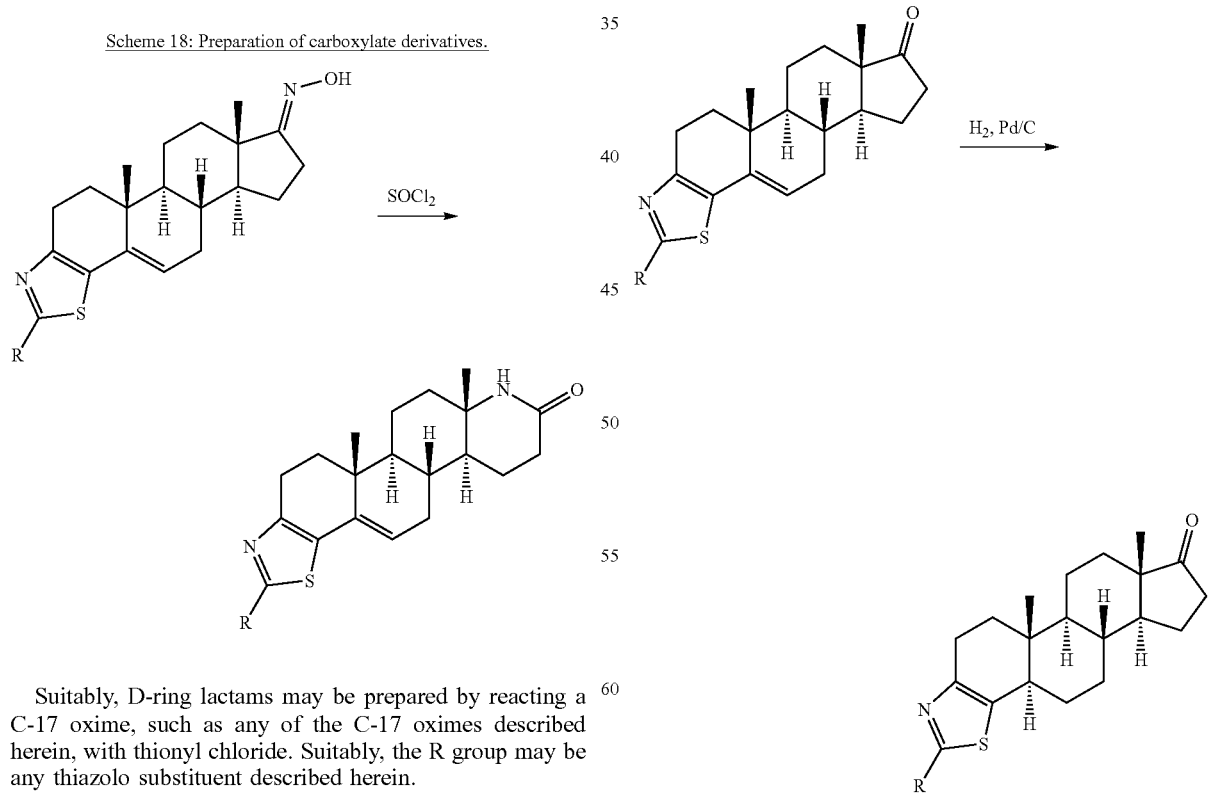

Scheme 19: Preparation of saturated B-ring derivatives.

(Formula IIc)

Scheme 20: Preparation of saturated B-ring derivatives.

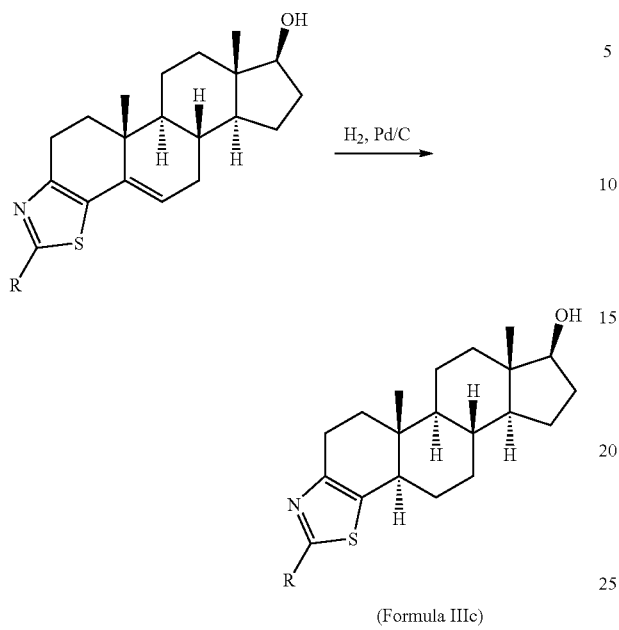

(Formula IIIc)

Suitably, the R group may be any thiazolo substituent described herein. Exemplary compounds include, without limitation, those shown in Table 11.

TABLE 11

Exemplary compounds of Formula IIc.

(Formula IIc)

| Compound ID | R = |
|---|---|
| II.1 | methyl |
| II.2 | benzyl |
| II.3 | pyrind-2-yl |
| II.4 | 4-hydroxy-phenyl |
| II.5 | 2-chloro-phenyl |
| II.7 | 3-methyl-phenyl |
| II.8 | 4-methyl-phenyl |
| II.9 | 3-methoxy-phenyl |
| II.10 | 4-methoxy-phenyl |
| II.11 | 2-hydroxy-phenyl |
| II.12 | 3-fluoro-phenyl |
| II.13 | 4-fluoro-phenyl |
| II.14 | 3-chloro-phenyl |
| II.15 | 4-chloro-phenyl |
| II.16 | 4-bromo-phenyl |
| II.17 | 3-hydroxy-phenyl |
| II.18 | 2-methyl-benzyl |

Saturated B-ring derivatives may be prepared according to Scheme 20 from compounds having a C-17 hydroxyl-group. Exemplary compounds include, without limitation, those shown in Table 12.

TABLE 12

Exemplary compounds of Formula IIIc.

(Formula IIIc)

| Compound ID | R = |
|---|---|
| III.1 | methyl |
| III.3 | benzyl |
| III.4 | pyrind-2-yl |
| III.5 | 4-hydroxy-phenyl |
| III.6 | 2-hydroxy-phenyl |
| III.8 | 2-chloro-phenyl |
| III.10 | 3-methyl-phenyl |
| III.11 | 4-methyl-phenyl |
| III.12 | 3-methoxy-phenyl |
| III.13 | 4-methoxy-phenyl |
| III.15 | 3-fluoro-phenyl |
| III.16 | 4-fluoro-phenyl |
| III.17 | 3-chloro-phenyl |
| III.18 | 4-chloro-phenyl |
| III.19 | 4-bromo-phenyl |
| III.21 | 3-hydroxy-phenyl |
| III.22 | 2-methyl-benzyl |

Saturated B-ring derivatives comprising a hydroxyl group may be prepared according to Scheme 21.

Scheme 21: Preparation of saturated B-ring derivatives.

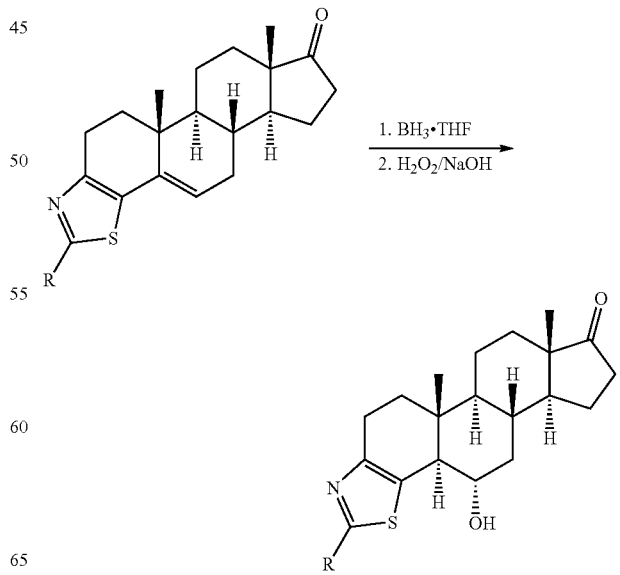

Suitably, the R group may be any thiazolo substituent described herein. Exemplary compounds include, without limitation, those shown in Table 13.

TABLE 13

Exemplary compounds of Formula VIII.

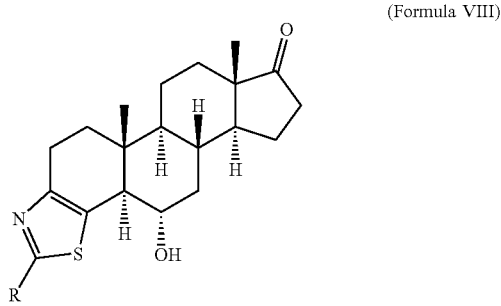

(Formula VIII)

| Compound ID | R = |
|---|---|
| VIII.1 | methyl |
| VIII.2 | benzyl |
| VIII.3 | pyrind-2-yl |
| VIII.4 | 4-hydroxy-phenyl |
| VIII.5 | 2-chloro-phenyl |
| VIII.6 | 3-methyl-phenyl |
| VIII.7 | 4-methyl-phenyl |
| VIII.8 | 3-methoxy-phenyl |
| VIII.9 | 4-methoxy-phenyl |
| VIII.10 | 2-hydroxy-phenyl |
| VIII.11 | 3-fluoro-phenyl |
| VIII.12 | 4-fluoro-phenyl |
| VIII.13 | 3-chloro-phenyl |
| VIII.14 | 4-chloro-phenyl |
| VIII.15 | 4-bromo-phenyl |
| VIII.16 | 3-hydroxy-phenyl |
| VIII.17 | 2-rnethyl-benzyl |

Saturated B-ring derivatives comprising two hydroxyl groups may be prepared according to Scheme 22.

Scheme 22: Preparation of saturated B-ring derivatives.

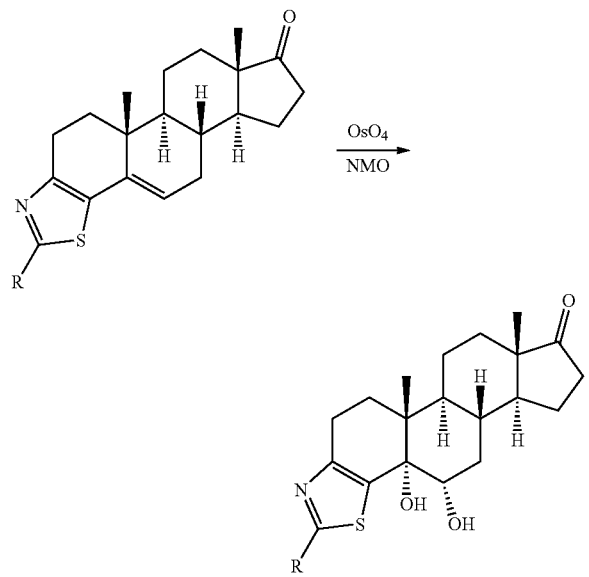

Suitably, the R group may be any thiazolo substituent described herein. Exemplary compounds include, without limitation, those shown in Table 14.

TABLE 14

Exemplary compounds of formula IX.

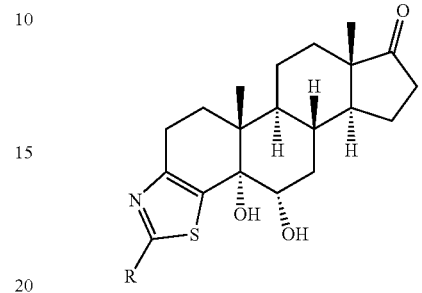

(Formula IX)

| Compound ID | R = |
|---|---|
| IX.1 | methyl |
| IX.2 | benzyl |
| IX.3 | pyrind-2-yl |
| IX.4 | 4-hydroxy-phenyl |
| IX.5 | 2-chloro-phenyl |
| IX.6 | 3-methyl-phenyl |
| IX.7 | 4-methyl-phenyl |
| IX.8 | 3-methoxy-phenyl |
| IX.9 | 4-methoxy-phenyl |
| IX.10 | 2-hydroxy-phenyl |
| IX.11 | 3-fluoro-phenyl |
| IX.12 | 4-fluoro-phenyl |
| IX.13 | 3-chloro-phenyl |
| IX.14 | 4-chloro-phenyl |
| IX.15 | 4-bromo-phenyl |
| IX.16 | 3-hydroxy-phenyl |
| IX.17 | 2-methyl-benzyl |

Pharmaceutical Compositions

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the compound at the site of action is about 2 to 10 μM.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (Pro-Solv SMCC™) Suitable lubricants, including agents that act on the flowability of the powder to be compressed, may include colloidal silicon dioxide, such as Aerosil® 200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurized aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form, which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures. The compounds for use according to the methods of disclosed herein may be administered as a single compound or a combination of compounds. For example, a compound that treats cancer activity may be administered as a single compound or in combination with another compound that treats cancer or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

Cytotoxic Agents and Methods for Inhibiting the Proliferation of or Killing Cancer Cells The compounds and pharmaceutical compositions disclosed herein may be used to inhibit the proliferation or a cell. As demonstrated in the Examples that follows, the compounds disclosed herein may be used to inhibit the proliferation of or kill cells (e.g., central nervous system, melanoma, ovarian cancer, renal cancer, prostate cancer, breast cancer including metastatic breast cancer, and cervical cancer cells). The method comprises contacting an effective amount of any of the compounds disclosed herein sufficient to result in at least 50% reduction in cell proliferation relative to control. Suitably, the method comprises contacting an effective amount of any of the compounds disclosed herein sufficient to result in at least 60%, at least 70%, at least 80%, at least 90%, at least 95%, at least 96%, at least 97%, at least 98%, or at least 99% reduction in cell proliferation relative to control.

Many of these compounds have shown promising activity against several cancer cell lines at 10 µM concentration. Compound (1S,2R,13R,14S,18S)-7-(3-fluorophenyl)-2,18-dimethyl-8-thia-6-azapentacyclo[11.7.0.02,10.05,9.014,18]icosa-5(9),7,10-trien-17-one (II.12) has shown −36.55 and −38.17 mean percent cell growth inhibition of NCI-H522 (NSCLC) and HCT-15 (Colon Cancer) cell lines respectively. Two cell lines, SF-295 and SF-539, of the Central Nervous System (CNS) cancer cell line panel were inhibited by −18.91 and −33.43 in mean growth percent scale. Similarly this compound has shown potent growth inhibition against several other cancer cell lines.

In vitro testing results of compounds (1S,2R,13R,14S,18S)-7-(3-fluoroanilino)-2,18-dimethyl-6-thia-8-azapentacyclo[11.7.0.02,10.05,9.014,18]icosa-5(9),7,10-trien-17-one (IIa.8) and (1S,2R,13R,14S,18S)-7-(2,4-dimethylanilino)-2,18-dimethyl-6-thia-8-azapentacyclo[11.7.0.02,10.05,9.014,18]icosa-5(9),7,10-trien-17-one (IIa.14) also show potent activity against several cancer cell lines, including the growth inhibition of leukemia cell lines: RPMI-8226 and SR with 50% growth inhibition ($GI_{50}$) values at submicromolar concentration. Two of the non-small cell lung cancer (NSCLC) cell lines were inhibited at low µM concentration. Compound IIa.8 inhibited the four of six central nervous system (CNS) cell lines with $GI_{50}$ values <2 µM concentration. Four cell lines of the colon cancer panel were also inhibited significantly by these compounds. Compound IIa.8 inhibited the growth of glioblastoma (SF-295) and gliosarcoma (SF-539) cell lines with $GI_{50}$ values 1.19 and 1.34 µM respectively. Demonstrating the significant anticancer properties of these compounds, five cell lines of melanoma panel and six cell lines of renal cancer panel were inhibited at low micromolar concentration. Ovarian cancer, prostate cancer, breast cancer cell lines were also inhibited with $GI_{50}$ values <2 µM (Table 18).

Anticancer Agents and Methods for Treating a Subject Having a Cancer.

The compounds and pharmaceutical composition disclosed herein may be used as anticancer agents to treat a subject having a cell proliferative disorder. As used herein, a "subject" may be interchangeable with "patient" or "individual" and means an animal, which may be a human or non-human animal, in need of treatment. A "subject in need of treatment" may include a subject having a disease, disorder, or condition that is responsive to therapy with the polycyclic compounds disclosed herein. For example, a "subject in need of treatment" may include a subject having a cell proliferative disease, disorder, or condition such as cancer (e.g., cancers such as multiple myeloma, leukemia, non-small cell lung cancer, colon cancer, cancer of the central nervous system, melanoma, ovarian cancer, renal cancer, prostate cancer, breast cancer including metastatic breast cancer, and cervical cancer).

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a cell proliferative disease or disorder.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Definitions

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as $C_1$-$C_{12}$ alkyl, $C_1$-$C_{10}$-alkyl, and $C_1$-$C_6$-alkyl, respectively.

The term "alkylene" refers to a diradical of an alkyl group. An exemplary alkylene group is —$CH_2CH_2$—.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like The term "heteroalkyl" as used herein refers to an "alkyl" group in which at least one carbon atom has been replaced with a heteroatom (e.g., an O, N, or S atom). One type of heteroalkyl group is an "alkoxyl" group The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$-alkenyl, $C_2$-$C_{10}$-alkenyl, and $C_2$-$C_6$-alkenyl, respectively The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a diradical of an cycloalkyl group.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a $C_5$-$C_{14}$, $C_5$-$C_{12}$, $C_5$-$C_8$, or $C_5$-$C_6$ membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using Cx-Cx nomenclature where x is an integer specifying the number of ring atoms. For example, a $C_3$-$C_7$ heterocyclyl group refers to a saturated or partially unsaturated 3- to 7-membered ring structure containing one to four heteroatoms, such as nitrogen, oxygen, and sulfur. The designation "$C_3$-$C_7$" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines, wherein substituents may include, for example, alkyl, cycloalkyl, heterocyclyl, alkenyl, and aryl.

The terms "alkoxyl" or "alkoxy" are art-recognized and refer to an alkyl group, as defined above, having an oxygen radical attached thereto. Representative alkoxyl groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

An "epoxide" is a cyclic ether with a three-atom ring typically include two carbon atoms and whose shape approximates an isosceles triangle. Epoxides can be formed by oxidation of a double bound where the carbon atoms of the double bond form an epoxide with an oxygen atom.

The term "carbonyl" as used herein refers to the radical —C(O)—.

The term "carboxamido" as used herein refers to the radical —C(O)NRR', where R and R' may be the same or different. R and R' may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" as used herein refers to a radical of the form —$R^1$C(O)N($R^2$)—, —$R^1$C(O)N($R^2$) $R^3$—, —C(O)$NR^2R^3$, or —C(O)$NH_2$, wherein $R^1$, $R^2$ and $R^3$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereo isomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Compositions comprising substantially purified stereoisomers, epimers, or enantiomers, or analogs or derivatives thereof are contemplated herein (e.g., a composition comprising at least about 90%, 95%, or 99% pure stereoisomer, epimer, or enantiomer.)

Miscellaneous

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Synthetic Methods

Thioamide Derivatives

β-bromoandrostenedione, thioamide, and sodium acetate was mixed in hexafluoroisopropanol (HFIP) for 12 hours to complete the reaction. Progress of the reaction was monitored by thin layer chromatography (TLC). After the completion of the reaction, HFIP was distilled out and the reaction mixture was suspended in methanol. Filtration followed by washing with water afforded the pure product in yield.

Solvent Selection

After the identification of the product II.19 in HFIP, we carried out the reaction in different solvents including different alcohols, and polar aprotic solvents: THF, DMSO, and DMF (Table 15). Refluxing the reaction mixture in DMF gave the decomposed products. Based on these observations, we can conclude that polar protic solvents are required for the product formation of this domino methodology and HFIP has the best properties of the solvent tested for the success of this reaction.

TABLE 15

Effect of solvent on percent yield

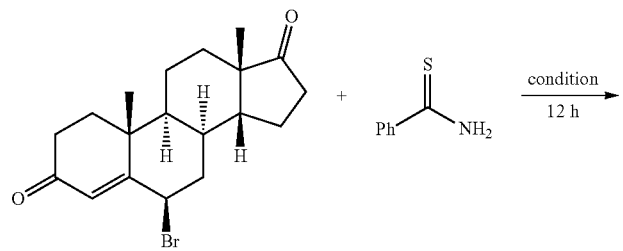

TABLE 15-continued

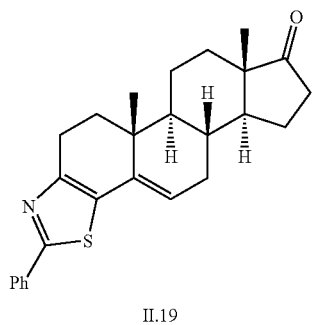

II.19

| Entry | Solvent | Temperature | Yield % |
|---|---|---|---|
| 1. | HFIP | reflux | 61 |
| 2. | TFE | reflux | 50 |
| 3. | $CH_3CO_2H$ | reflux | 20 |
| 4. | $CH_3OH$ | reflux | NR |
| 5. | EtOH | reflux | NR |
| 6. | EtOH | reflux | NR |
| 7. | iPrOH | reflux | NR |
| 8. | nPrOH | reflux | NR |
| 9. | tBuOH | reflux | NR |
| 10. | THF | reflux | NR |
| 11. | DMF | 100° C. | NR |
| 12. | DMF | reflux | NR |
| 13. | DMSO | 100° C. | NR |

Thiourea Deratives

β-bromoandrostenedione, thiourea, and sodium acetate was mixed in hexafluoroisopropanol (HFIP) for eight hours to complete the reaction. Progress of the reaction was monitored by thin layer chromatography (TLC). After the completion of the reaction, HFIP was distilled out and the reaction mixture was suspended in methanol. Filtration followed by washing with water afforded the pure product in yield.

NMR Data, and Mass Spectrometry Data (1S,2R,13R,14S,18S)-2,18-dimethyl-7-phenyl-8-thia-6-azapentacyclo[11.7.0.02,10.05,9.014,18]icosa-5(9),7,10-trien-17-one (II.19)

$^1$H NMR (300 MHz, $CDCl_3$) δ ppm: 7.92-7.90 (m, 2H), 7.46-7.40 (m, 3H), 5.86-5.84 (m, 1H), 3.05-2.86 (m, 2H), 2.56-2.34 (m, 2H), 2.20-1.80 (m, 6H), 1.68-1.16 (m, 7H), 1.09 (s, 3H), 0.95 (s, 3H); $^{13}$C NMR (75 MHz, $CDCl_3$) δ ppm: 220.8, 164.2, 150.4, 136.6, 133.8, 131.6, 129.7, 128.8, 126.3, 121.4, 51.7, 48.1, 47.6, 36.7, 35.8, 34.3, 31.3, 31.1, 30.8, 24.1, 21.8, 20.7, 18.7, 13.6. HRMS (ESI-FTMS, m/z): calcd for $C_{26}H_{30}NOS$ [M+H]$^+$ 404.2042, found 404.2046. Yield (245 mg, 61%).

(1S,2R,13R,14S,18S)-2,7,18-trimethyl-8-thia-6-azapentacyclo[11.7.0.02,10.05,9.014,18]icosa-5(9),7,10-trien-17-one (II.1)

$^1$H NMR (300 MHz, $CDCl_3$) δ ppm: 5.70-5.69 (m, 1H), 2.91-2.71 (m, 2H), 2.62 (s, 3H), 2.54-2.21 (m, 2H), 2.18-1.66 (m, 7H), 1.63-1.14 (m, 6H), 1.03 (s, 3H), 0.94 (s, 3H); $^{13}$C NMR (75 MHz, $CDCl_3$) δ ppm: 220.8, 162.7, 148.7, 136.5, 130.9, 120.5, 51.7, 48.1, 47.6, 36.7, 35.8, 34.3, 31.3, 31.1, 30.6, 23.9, 21.8, 20.7, 19.4, 18.6, 13.6. HRMS (ESI-FTMS, m/z): calcd for $C_{21}H_{28}NOS$ [M+H]$^+$ 342.1886, found 342.1890. Yield (177 mg, 52%).

(1S,2R,13R,14S,18S)-2,18-dimethyl-7-phenyl-8-thia-6-azapentacyclo[11.7.0.02,10.05,9.014,18]icosa-5(9),7,10-trien-17-one (II.2)

$^1$H NMR (300 MHz, $CDCl_3$) δ ppm: 7.40-7.21 (m, 5H), 5.67-5.65 (m, 1H), 4.25 (s, 2H), 2.95-2.74 (m, 2H), 2.50 (dd, J=8.7, 19.1 Hz, 1H), 2.34-2.25 (m, 1H), 2.18-1.29 (m, 13H), 1.22-1.10 (m, 1H), 1.03 (s, 3H), 0.93 (s, 3H); $^{13}$C NMR (75 MHz, $CDCl_3$) δ ppm: 220.8, 166.9, 148.9, 137.9, 136.5, 131.6, 129.0, 128.7, 127.0, 120.7, 51.7, 48.1, 47.6, 40.7, 36.7, 35.8, 34.3, 31.3, 31.1, 30.6, 24.0, 21.8, 20.7, 18.6, 13.6. Yield (233 mg, 56%).

(1S,2R,13R,14S,18S)-2,18-dimethyl-7-(o-tolylmethyl)-8-thia-6-azapentacyclo[11.7.0.02,10.05,9.014,18]icosa-5(9),6,10-trien-17-one (II.18)

$^1$H NMR (300 MHz, $CDCl_3$) δ ppm: 7.27-7.22 (m, 4H), 5.63-5.62 (m, 1H), 4.25 (s, 2H), 2.95-2.74 (m, 2H), 2.49 (dd, J=8.7, 19.2 Hz, 1H), 2.34 (s, 3H), 2.34-2.28 (m, 1H), 2.17-1.78 (m, 7H), 1.58-1.14 (m, 6H), 1.03 (s, 3H), 0.93 (s, 3H); $^{13}$C NMR (75 MHz, $CDCl_3$) δ ppm: 220.8, 167.3, 148.8, 136.7, 136.5, 136.3, 131.3, 130.5, 130.0, 127.5, 126.3, 120.6, 51.7, 48.1, 47.6, 37.8, 36.6, 35.8, 34.3, 31.3, 31.1, 30.6, 24.0, 21.8, 20.7, 19.6, 18.6, 13.6. Yield (237 mg, 55%).

(1S,2R,13R,14S,18S)-2,18-dimethyl-7-(m-tolyl)-8-thia-6-azapentacyclo[11.7.0.02,10.05,9.014,18]icosa-5(9),7,10-trien-17-one (II.7)

$^1$H NMR (300 MHz, $CDCl_3$) δ ppm: 7.76 (s, 1H), 7.69 (d, J=7.6 Hz, 1H), 7.33-7.28 (m, 1H), 7.21 (d, J=7.4 Hz, 1H), 5.85-5.84 (m, 1H), 3.05-2.82 (m, 2H), 2.55-2.34 (m, 5H), 2.19-1.80 (m, 7H), 1.68-1.25 (m, 5H), 1.22-1.16 (m, 1H), 1.09 (s, 3H), 0.95 (s, 3H); $^{13}$C NMR (75 MHz, $CDCl_3$) δ ppm: 220.7, 164.4, 150.4, 138.6, 136.6, 133.7, 131.4, 130.5, 128.7, 126.8, 123.6, 121.3, 51.7, 48.2, 47.6, 36.7, 35.8, 34.3, 31.4, 31.1, 30.8, 24.1, 21.8, 21.3, 20.7, 18.7, 13.6. HRMS (ESI-FTMS, m/z): calcd for $C_{27}H_{32}NOS$ [M+H]$^+$ 418.2199, found 418.2204. Yield (246 mg, 59%)

(1S,2R,13R,14S,18S)-2,18-dimethyl-7-(p-tolyl)-8-thia-6-azapentacyclo[11.7.0.02,10.05,9.014,18]icosa-5(9),7,10-trien-17-one (II.8)

$^1$H NMR (300 MHz, CDCl$_3$) δ ppm: 7.80 (d, J=8.0 Hz, 2H), 7.23 (d, J=8.2 Hz, 2H), 5.83-5.52 (m, 1H), 3.03-2.87 (m, 2H), 2.55-2.33 (m, 2H), 2.39 (s, 3H), 2.19-1.80 (m, 7H), 1.68-1.15 (m, 6H), 1.08 (s, 3H), 0.94 (s, 3H); $^{13}$C NMR (75 MHz, CDCl$_3$) δ ppm: 220.8, 164.5, 150.2, 140.0, 136.6, 131.1, 129.5, 126.3, 121.2, 51.7, 48.1, 47.6, 36.7, 35.8, 34.3, 31.3, 31.1, 30.8, 24.1, 21.8, 21.4, 20.7, 18.7, 13.6. HRMS (ESI-FTMS, m/z): calcd for $C_{27}H_{32}NOS$ [M+H]$^+$ 418.2199, found 418.2204. Yield (254 mg, 61%).

(1S,2R,13R,14S,18S)-7-(3-methoxyphenyl)-2,18-dimethyl-8-thia-6-azapentacyclo[11.7.0.02,10.05,9.014,18]icosa-5(9),7,10-trien-17-one (II.9)

$^1$H NMR (300 MHz, CDCl$_3$) δ ppm: 7.47 (m, 2H), 7.32 (d, J=8.2 Hz, 1H), 6.95-6.92 (m, 1H), 5.83 (s, 1H), 3.87 (s, 3H), 3.02-2.80 (m, 2H), 2.53-2.33 (m, 2H), 2.17-1.78 (m, 7H), 1.65-1.13 (m, 7H), 1.06 (s, 3H), 0.92 (m, 3H); $^{13}$C NMR (75 MHz, CDCl$_3$) δ ppm: 220.7, 164.0, 159.9, 150.3, 136.5, 135.1, 131.7, 129.8, 121.5, 119.0, 116.0, 110.9, 55.4, 51.6, 48.1, 47.5, 36.7, 35.8, 34.3, 31.3, 31.1, 30.7, 24.1, 21.8, 20.7, 18.7, 13.6. HRMS (ESI-FTMS, m/z): calcd for $C_{27}H_{32}NO_2S$ [M+H]$^+$ 434.2148, found 434.2154. Yield (286 mg, 66%).

(1S,2R,13R,14S,18S)-7-(4-methoxyphenyl)-2,18-dimethyl-8-thia-6-azapentacyclo[11.7.0.02,10.05,9.014,18]icosa-5(9),7,10-trien-17-one (II.10)

$^1$H NMR (300 MHz, CDCl$_3$) δ ppm: 7.86 (d, J=8.6 Hz, 2H), 6.94 (d, J=8.7 Hz, 2H), 5.82-5.81 (m, 1H), 3.86 (s, 3H), 3.02-2.86 (m, 2H), 2.55-2.33 (m, 2H), 2.19-1.81 (m, 6H), 1.68-1.16 (m, 7H), 1.09 (s, 3H), 0.95 (s, 3H); $^{13}$C NMR (75 MHz, CDCl$_3$) δ ppm: 220.7, 164.2, 160.9, 150.2, 136.7, 130.6, 127.8, 126.8, 120.9, 114.2, 55.3, 51.7, 48.2, 47.6, 36.7, 35.8, 34.3, 31.4, 31.1, 30.8, 24.1, 21.8, 20.7, 18.7, 13.6. HRMS (ESI-FTMS, m/z): calcd for $C_{27}H_{32}NO_2S$ [M+H]$^+$ 434.2148, found 434.2153. Yield (259 mg, 66%).

(1S,2R,13R,14S,18S)-7-(3-hydroxy)-2,18-dimethyl-8-thia-6-azapentacyclo[11.7.0.02,10.05,9.014,18]icosa-5(9),7,10-trien-17-one (II. 17)

$^1$H NMR (300 MHz, CDCl$_3$+DMSO-d$_6$) δ ppm: 12.13 (br s, 1H), 7.49 (d, J=7.7 Hz, 1H), 7.19 (t, J=8.2 Hz, 1H), 6.88 (d, J=8.2 Hz, 1H), 6.81 (t, J=7.4 Hz, 1H), 5.78 (br s, 1H), 2.87-2.74 (m, 2H), 2.51-2.31 (m, 2H), 2.07-1.71 (m, 6H), 1.60-1.12 (m, 7H), 0.98 (s, 3H), 0.84 (s, 3H); $^{13}$C NMR (75 MHz, CDCl$_3$+DMSO-d$_6$) δ ppm: 220.3, 164.9, 156.6, 147.6, 135.6, 130.9, 129.2, 126.7, 121.7, 118.8, 117.2, 116.7, 51.2, 47.6, 47.1, 36.3, 35.3, 33.6, 30.9, 30.7, 30.3, 23.2, 21.4, 20.3, 18.3, 13.2. HRMS (ESI-FTMS, m/z): calcd for $C_{26}H_{29}NOS$ [M+H]$^+$ 420.1992, found 420.1997. Yield (230 mg, 55%).

(1S,2R,13R,14S,18S)-7-(3-hydroxy)-2,18-dimethyl-8-thia-6-azapentacyclo[11.7.0.02,10.05,9.014,18]icosa-5(9),7,10-trien-17-one (II.17)

$^1$H NMR (300 MHz, CDCl$_3$+DMSO-d$_6$) δ ppm: 9.41 (d, J=5.2 Hz, 1H), 7.27-7.13 (m, 3H), 6.77 (d, J=7.9 Hz, 1H), 5.77 (s, 1H), 2.89-2.70 (m, 2H), 2.43-2.30 (m, 2H), 2.04-1.72 (m, 8H), 1.60-1.11 (m, 7H), 0.99 (s, 3H), 0.84 (s, 3H); $^{13}$C NMR (75 MHz, CDCl$_3$+DMSO-d$_6$) δ ppm: 219.7, 163.4, 158.0, 150.3, 136.3, 134.8, 131.4, 130.1, 121.9, 117.3, 117.1, 112.9, 51.4, 48.0, 47.3, 36.6, 35.7, 34.1, 31.4, 31.0, 30.7, 24.1, 21.8, 20.7, 18.8, 13.7. Yield (273 mg, 65%)

(1S,2R,13R,14S,18S)-7-(4-hydroxy)-2,18-dimethyl-8-thia-6-azapentacyclo[11.7.0.02,10.05,9.014,18]icosa-5(9),7,10-trien-17-one (II.4)

$^1$H NMR (300 MHz, CDCl$_3$+DMSO-d$_6$) δ ppm: 9.90 (s, 1H), 7.67 (d, J=8.3 Hz, 2H), 6.81 (d, J=8.3 Hz, 2H), 5.74 (s, 1H), 2.85-2.69 (m, 2H), 2.50-2.27 (m, 2H), 2.06-1.71 (m, 6H), 1.62-1.15 (m, 7H), 1.00 (s, 3H), 0.84 (s, 3H); $^1$H NMR (300 MHz, CDCl$_3$+DMSO-d$_6$) δ ppm: 219.7, 163.8, 159.7, 150.1, 136.5, 130.0, 127.9, 125.0, 121.5, 116.1, 51.3, 48.0, 47.3, 36.6, 35.7, 34.2, 31.5, 31.0, 30.6, 24.2, 21.8, 20.7, 18.9, 13.7. HRMS (ESI-FTMS, m/z): calcd for $C_{26}H_{29}NO_2S$ [M+H]$^+$ 420.1992, found 420.1997. Yield (281 mg, 67%).

(1S,2R,13R,14S,18S)-7-(3,4-dihydroxyphenyl)-2,18-dimethyl-8-thia-6-azapentacyclo[11.7.0.02,10.05,9.014,18]icosa-5(9),6,10-trien-17-one (II.20)

$^1$H NMR (300 MHz, CDCl$_3$+DMSO-d$_6$) δ ppm: Yield (252 mg, 58%). 8.95 (s, 1H), 8.78 (s, 1H), 7.30 (d, J=2.0 Hz, 1H), 7.13 (dd, J=2.0, 8.1 Hz, 1H), 6.74 (d, J=8.2 Hz, 1H), 5.68 (br s), 2.83-2.71 (m, 2H), 2.50-2.29 (m, 3H), 2.07-1.73 (m, 7H), 1.56-1.12 (m, 6H), 0.98 (s, 3H), 0.84 (s, 3H); $^1$H NMR (75 MHz, CDCl$_3$+DMSO-d$_6$) δ ppm: 220.1, 164.2, 149.8, 147.6, 145.5, 136.4, 130.0, 125.7, 120.9, 118.2, 115.9, 113.6, 51.4, 48.0, 47.4, 36.6, 35.7, 34.2, 31.4, 31.0, 30.6, 24.1, 21.7, 20.6, 18.7, 13.6.

(1S,2R,13R,14S,18S)-7-(3-fluorophenyl)-2,18-dimethyl-8-thia-6-azapentacyclo[11.7.0.02,10.05,9.014,18]icosa-5(9),7,10-trien-17-one (II.12)

$^1$H NMR (300 MHz, CDCl$_3$) δ ppm: 7.69 (m, 2H), 7.42-7.35 (m, 1H), 7.12-7.06 (m, 1H), 5.88-5.85 (m, 1H), 3.04-2.88 (m, 2H), 2.53-2.11 (m, 2H), 2.08-1.81 (m, 7H), 1.69-1.20 (m, 6H), 1.09 (s, 3H), 0.95 (s, 3H); $^1$H NMR (75 MHz, CDCl3) δ ppm: 220.6, 163.0 ($^1J_{CF}$=244.9 Hz), 162.5, 150.7, 136.5, 135.9 ($^3J_{CF}$=8.0 Hz), 132.3, 130.4 ($^3J_{CF}$=8.3 Hz), 122.0, 121.9, 116.5 ($^2J_{CF}$=21.3 Hz), 113.0 ($^2J_{CF}$=23.3 Hz), 51.7, 48.1, 47.6, 36.7, 35.8, 34.2, 31.4, 31.1, 30.8, 24.1, 21.8, 20.7, 18.7, 13.6. HRMS (ESI-FTMS, m/z): calcd for $C_{26}H_{29}FNOS$ [M+H]$^+$ 422.1948, found 422.1951. Yield (252 mg, 60%).

(1S,2R,13R,14S,18S)-7-(4-fluorophenyl)-2,18-dimethyl-8-thia-6-azapentacyclo[11.7.0.02,10.05,9.014,18]icosa-5(9),7,10-trien-17-one (II.13)

$^1$H NMR (300 MHz, CDCl$_3$) δ ppm: 7.91-7.87 (m, 2H), 7.11 (t, J=8.5 Hz, 2H), 5.84-5.83 (m, 1H), 3.03-2.86 (m, 2H), 2.56-2.34 (m, 2H), 2.20-1.80 (m, 7H), 1.68-1.18 (m, 6H), 1.08 (s, 3H), 0.95 (s, 3H); $^{13}$C NMR (75 MHz, CDCl$_3$) δ ppm: 220.8, 163.6 ($^1J_{CF}$=248.6 Hz), 162.9, 150.4, 136.5, 131.7, 130.2, 128.2 ($^3J_{CF}$=8.3 Hz), 121.5, 116.0 (2JCF=21.8 Hz), 51.7, 48.1, 47.6, 36.7, 35.8, 34.3, 31.3, 31.1, 30.8, 24.1, 21.8, 20.7, 18.7, 13.6. HRMS (ESI-FTMS, m/z): calcd for $C_{26}H_{29}FNOS$ [M+H]$^+$ 422.1948, found 422.1953. Yield (256 mg, 61%).

(1S,2R,13R,14S,18S)-7-(3-chlorophenyl)-2,18-dimethyl-8-thia-6-azapentacyclo[11.7.0.02,10.05,9.014,18]icosa-5(9),7,10-trien-17-one (II.14)

$^1$H NMR (300 MHz, CDCl$_3$) δ ppm: 7.93 (s, 1H), 7.79-7.75 (m, 1H), 2.36-7.32 (m, 2H), 5.88-5.87 (m, 1H), 3.04-2.81 (m, 2H), 2.56-2.34 (m, 2H), 2.20-1.81 (m, 6H), 1.66-1.32 (m, 6H), 1.26-1.19 (m, 1H), 1.08 (s, 3H), 0.95 (s, 3H); $^{13}$C NMR (75 MHz, CDCl$_3$) δ ppm: 220.8, 162.3, 150.7, 136.4, 135.4, 134.9, 132.4, 130.1, 129.6, 126.2, 124.4, 122.0, 51.7, 48.1, 47.6, 36.7, 35.8, 34.2, 31.3, 31.1, 30.8, 24.1, 21.8, 20.7, 18.7, 13.6. HRMS (ESI-FTMS, m/z): calcd for C$_{26}$H$_{29}$ClNOS [M+H]$^+$ 438.1653, found 438.1654. Yield (214 mg, 49%).

(1S,2R,13R,14S,18S)-7-(4-chlorophenyl)-2,18-dimethyl-8-thia-6-azapentacyclo[11.7.0.02,10.05,9.014,18]icosa-5(9),6,10-trien-17-one (II.15)

Recrystallized from acetonitrile
$^1$H NMR (300 MHz, CDCl$_3$) δ ppm: 7.85 (d, J=8.4 Hz, 2H), 7.40 (J=8.5 Hz, 2H), 5.86-5.85 (m, 1H), 3.03-2.87 (m, 2H), 2.56-2.37 (m, 2H), 2.20-1.80 (m, 6H), 1.65-1.34 (m, 6H), 1.26-1.21 (m, 1H), 1.08 (s, 3H), 0.95 (s, 3H); $^{13}$C NMR (75 MHz, CDCl$_3$) δ ppm: 220.7, 162.7, 150.6, 136.5, 135.5, 132.3, 132.0, 129.0, 127.5, 121.8, 51.7, 48.1, 47.6, 36.7, 35.8, 34.2, 31.3, 31.1, 30.8, 24.1, 21.8, 20.7, 18.7, 13.6. HRMS (ESI-FTMS, m/z): calcd for C$_{26}$H$_{29}$ClNOS [M+H]$^+$ 438.1653, found 438.1656. Yield (222 mg, 51%).

(1S,2R,13R,14S,18S)-7-(4-bromophenyl)-2,18-dimethyl-8-thia-6-azapentacyclo[11.7.0.02,10.05,9.014,18]icosa-5(9),7,10-trien-17-one (II.16)

$^1$H NMR (300 MHz, CDCl$_3$) δ ppm: 7.78 (d, J=8.3 Hz, 2H), 7.55 (d, J=8.3 Hz, 2H), 5.86-5.85 (m, 1H), 3.03-2.87 (m, 2H), 2.56-2.33 (m 2H), 2.20-1.81 (m, 7H), 1.68-1.31 (m, 5H), 1.26-1.17 (m, 1H), 1.08 (s, 3H), 0.95 (s, 3H); $^{13}$C NMR (75 MHz, CDCl$_3$) δ ppm: 222.2, 164.2, 152.1, 138.0, 134.2, 133.6, 133.5, 129.2, 125.3, 123.3, 53.1, 49.6, 49.0, 38.2, 37.3, 35.7, 32.8, 32.6, 32.3, 25.6, 23.3, 22.2, 20.1, 15.1. HRMS (ESI-FTMS, m/z): calcd for C$_{26}$H$_{29}$BrNOS [M+H]$^+$ and [M+2+H]$^+$482.1148, 484.1128, found 482.1149, 484.1129 respectively. Yield (216 mg, 45%).

(1S,2R,13R,14S,18S)-2,18-dimethyl-7-[4-(trifluoromethyl)phenyl]-8-thia-6-azapentacyclo[11.7.0.02,10.05,9.014,18]icosa-5(9),7,10-trien-17-one (II.21)

$^1$H NMR (300 MHz, CDCl$_3$) δ ppm: 8.02 (d, J=8.1 Hz, 2H), 7.68 (d, J=8.2 Hz, 2H), 5.91-5.89 (m, 1H), 3.07-2.84 (m, 2H), 2.57-2.39 (m, 2H), 2.21-1.82 (m, 7H), 1.69-1.19 (m, 6H), 1.09 (s, 3H), 0.96 (s, 3H); $^{13}$C NMR (75 MHz, CDCl$_3$) δ ppm: 220.8, 162.0, 151.0, 136.9, 136.4, 132.9, 131.3, 130.9, 126.4, 125.9-125.7 (m),122.3, 122.1, 51.7, 48.1, 47.6, 36.7, 35.8, 34.2, 31.3, 31.1, 30.8, 24.1, 21.8, 20.7, 18.7, 13.6. Yield (268 mg, 57%).

(1S,2R,13R,14S,18S)-2,18-dimethyl-7-(3-nitrophenyl)-8-thia-6-azapentacyclo[11.7.0.02,10.05,9.014,18]icosa-5(9),6,10-trien-17-one (II.22)

$^1$H NMR (300 MHz, CDCl$_3$) δ ppm: 8.74 (s, 1H), 8.24 (d, J=7.7 Hz, 2H), 7.61 (t, J=7.9 Hz, 1H), 5.93-5.91 (m, 1H), 305-2.84 (m, 2H), 2.57-2.37 (m, 2H), 2.21-1.82 (m, 7H), 1.70-1.25 (m, 6H), 1.10 (s, 3H), 0.96 (s, 3H); $^{13}$C NMR (75 MHz, CDCl$_3$) δ ppm: 220.2, 150.6, 160.4, 148.1, 135.9, 135.0, 132.8, 131.2, 129.4, 123.4, 122.2, 120.6, 51.2, 47.6, 47.1, 36.3, 35.3, 33.7, 30.9, 30.6, 30.4, 23.6, 21.3, 20.3, 18.2, 13.2.

(1S,2R,13R,14S,18S)-2,18-dimethyl-7-(2-pyridyl)-8-thia-6-azapentacyclo[11.7.0.02,10.05,9.014,18]icosa-5(9),7,10-trien-17-one (II.3)

$^1$H NMR (300 MHz, CDCl$_3$) δ ppm: 8.59 (s, 1H), 8.13 (d, J=7.6 Hz, 1H), 7.76 (t, J=7.5 Hz, 1H), 7.27 (s, 1H), 5.94 (s, 1H), 3.02-2.84 (m, 2H), 2.54-2.38 (m, 2H), 2.18-1.79 (m, 7H), 1.67-1.20 (m, 6H), 1.07 (s, 3H), 0.93 (s, 3H); $^{13}$C NMR (75 MHz, CDCl$_3$) δ ppm: 220.7, 164.8, 151.5, 150.8, 149.4, 136.8, 136.6, 133.9, 124.0, 122.2, 119.3, 51.7, 48.1, 47.5, 36.6, 35.8, 34.3, 31.3, 31.1, 30.8, 24.1, 21.8, 20.7, 18.7, 13.6. HRMS (ESI-FTMS, m/z): calcd for C$_{25}$H$_{29}$N$_2$OS [M+H]$^+$ 405.1995, found 405.2000. Yield (153 mg, 38%).

(1S,2R,13R,14S,17S,18S)-7-(4-fluorophenyl)-2,18-dimethyl-8-thia-6-azapentacyclo[11.7.0.02,10.05, 9.014,18]icosa-5(9),6,10-trien-17-ol (III.15)

A solution of compound II.19 (210.5 mg, 0.5 mmol) in methanol was cooled in ice and NaBH$_4$ (189 mg, 5 mmol) was added portionwise and the reaction mixture was stirred overnight. After completion of the reaction, aqueous 10% HCl was added and the reaction was stirred for two hour to precipitate the product. Filtration and washing with water gave the pure product (203 mg, 96%).

$^1$H NMR (300 MHz, CDCl$_3$) δ ppm: 7.69-7.63 (m, 1H), 7.42-7.34 (m, 1H), 7.12-7.05 (m, 1H), 5.85-5.83 (m, 1H), 3.69 (t, J=8.3 Hz, 1H), 3.04-2.81 (m, 2H), 2.31-2.22 (m, 1H), 2.18-2.05 (m, 2H), 1.93-1.28 (m, 10H), 1.22-1.11 (m, 3H), 1.07 (s, 3H), 0.82 (s, 3H); $^{13}$C NMR (75 MHz, CDCl$_3$) δ ppm: 163.5 ($^1$J=244.9 Hz), 162.4 ($^4$J=3.1 Hz), 150.5, 136.3, 135.9 ($^3$J=8.0 Hz), 132.5, 130.4 ($^3$J=8.2 Hz), 122.6, 122.1 ($^4$J=2.8 Hz), 116.5 ($^2$J=21.1 Hz), 113.1 ($^2$J=23.3 Hz), 81.7, 51.3, 48.1, 42.8, 36.7, 36.5, 34.3, 31.5, 31.5, 30.5, 24.1, 23.4, 21.0, 18.7, 11.0. HRMS (ESI-FTMS, m/z): calcd for C$_{26}$H$_{30}$NOS [M+H]$^+$ 428.2105, found 424.2107. Yield (407 mg, 96%)

[(1S,2R,13R,14S,17S,18S)-7-(3-fluorophenyl)-2,18-dimethyl-8-thia-6-azapentacyclo[11.7.0.02,10.05, 9.014,18]icosa-5(9),6,10-trien-17-yl] acetate A solution of compound III.15 (150 mg, 0.35 mmol) in dichloromethane (CH$_2$Cl$_2$, 4 mL)) was cooled in ice and acetic anhydride (1 mL) and pyridine (0.2 mL) were added and reaction mixture was stirred for 24 hours at room temperature. After the completion of the reaction, CH$_2$Cl$_2$ was removed by evaporation and 5 mL methanol was added to the reaction mixture followed by adding 10 mL water. The precipitate was filtered and washed with water to get the pure product (158 mg, 0.34 mmol, 96%).

$^1$H NMR (300 MHz, CDCl$_3$) δ ppm: 7.68-7.62 (m, 2H), 7.42-7.34 (m, 1H), 7.00 (dd, J=2.4, 9.0 Hz, 1H), 5.85-5.83 (m, 1H), 4.64 (t, J=8.0 Hz, 1H), 3.03-2.81 (m, 2H), 2.32-2.11 (m, 3H), 2.07 (s, 3H), 1.87-1.68 (m, 6H), 1.61-1.09 (m, 6H), 1.06 (s, 3H), 0.86 (s, 3H); $^{13}$C NMR (75 MHz, CDCl$_3$) δ ppm: 171.2, 163.0 ($^1$J=244.8 Hz), 162.4 ($^4$J=3.0 Hz), 150.6, 136.4, 136.0 ($^3$J=8.0 Hz), 132.5, 130.4 ($^3$J=8.2 Hz), 122.4, 122.0 ($^4$J=2.9 Hz), 116.4 ($^2$J=21.3 Hz), 113.1 ($^2$J=23.2 Hz), 82.6, 51.0, 47.9, 42.4, 36.6, 34.3, 31.4, 31.3, 27.5, 24.1, 23.5, 21.0, 20.9, 18.7, 12.0. HRMS (ESI-FTMS, m/z): calcd for C$_{28}$H$_{33}$FNO$_2$S [M+H]$^+$ 466.2211, found 466.2214.

(1S,2R,13R,14S,18S)-7-amino-2,18-dimethyl-6-thia-8-azapentacyclo[11.7.0.02,10.05,9.014,18]icosa-5(9),7,10-trien-17-one (IIa.1)

¹H NMR (300 MHz, DMSO-d₆+TFA-d) δ ppm: 5.54 (s, 1H), 2.60-2.26 (m, 4H), 2.06-1.66 (m, 7H), 1.52-1.02 (m, 6H), 0.96 (s, 3H), 0.81 (s, 3H); ¹H NMR (75 MHz, DMSO-d₆+TFA-d) 6 ppm: 219.7, 168.0, 134.3, 133.1, 121.1, 116.5, 51.1, 47.6, 47.2, 36.6, 35.5, 32.8, 31.4, 30.9, 30.2, 21.6, 21.5, 20.5, 18.5, 13.5. HRMS (ESI-FTMS, m/z): calcd for $C_{20}H_{27}N_2OS$ [M+H]⁺ 343.1839, found 343.1843. Yield (1.258 g, 3.67 mmol, 91%).

(1S,2R,13R,14S,18S)-7-(ethylamino)-2,18-dimethyl-6-thia-8-azapentacyclo[11.7.0.02,10.05,9.014,18]icosa-5(9),7,10-trien-17-one (IIa.30)

¹H NMR (300 MHz, CDCl₃) δ ppm: 5.40-5.38 (m, 1H), 3.29 (q, J=7.2 Hz, 2H), 2.66-2.63 (m, 2H), 2.49 (dd, J=8.3, 18.8 Hz, 1H), 2.39-2.27 (m, 1H), 2.17-1.75 (m, 7H), 1.65-1.14 (m, 7H), 1.28 (t, J=7.2 Hz, 3H), 1.05 (s, 3H), 0.92 (s, 3H); ¹³C NMR (75 MHz, CDCl₃) δ ppm: 221.0, 167.1, 145.6, 136.9, 119.0, 116.2, 51.8, 48.1, 47.6, 40.6, 36.9, 35.8, 34.3, 31.4, 31.2, 30.5, 24.0, 21.8, 20.6, 18.7, 14.7, 13.6. (Yield (263 mg, 0.71 mmol, 71%)

(1S,2R,13R,14S,18S)-7-(butylamino)-2,18-dimethyl-6-thia-8-azapentacyclo[11.7.0.02,10.05,9.014,18]icosa-7,10-dien-17-one (IIa.31)

¹H NMR (300 MHz, CDCl₃) δ ppm: 5.40-5.38 (m, 1H), 3.25 (t, J=7.0 Hz, 2H), 2.66-2.63 (m, 2H), 2.49 (dd, J=8.4, 18.8 Hz, 1H), 2.27-2.39 (m, 1H), 2.08-1.75 (m, 7H), 1.67-1.20 (m, 11H), 1.06 (s, 3H), 0.95 (t, J=7.2 Hz, 3H), 0.92 (s, 3H); ¹³C NMR (75 MHz, CDCl₃) δ ppm: 221.0, 167.2, 145.8, 137.0, 119.1, 116.1, 51.8, 48.1, 47.6, 45.6, 36.6, 35.8, 34.3, 31.4, 31.4, 31.2, 30.5, 24.1, 21.8, 20.6, 20.0, 18.7, 13.7, 13.6. Yield (310 mg, 0.78 mmol, 78%)

(1S,2R,13R,14S,18S)-7-(allylamino)-2,18-dimethyl-6-thia-8-azapentacyclo[11.7.0.02,10.05,9.014,18]icosa-5(9),7,10-trien-17-one (IIa.3)

¹H NMR (300 MHz, CDCl₃) δ ppm: 5.99-5.86 (m, 1H), 2.60 (bs s, 1H), 5.40-5.19 (m, 3H), 3.92-3.90 (m, 2H), 2.66-2.63 (m, 2H), 2.57-2.44 (dd, J=8.5, 18.9 Hz, 1H), 2.39-2.27 (m, 1H), 2.18-1.66 (m, 8H), 1.63-1.14 (m, 7H), 1.06 (s, 3H), 0.93 (s, 3H); ¹³C NMR (75 MHz, CDCl₃) δ ppm: 221.0, 166.8, 145.9, 136.9, 133.6, 119.6, 117.1, 116.4, 51.8, 48.16, 48.12, 47.6, 36.6, 35.8, 34.3, 31.4, 31.2, 30.5, 24.1, 21.8, 20.6, 18.7, 13.6. Yield (278 mg, 0.73 mmol, 73%)

(1S,2R,13R,14S,18S)-2,18-dimethyl-7-(2-phenylethylamino)-6-thia-8-azapentacyclo [11.7.0.02,10.05, 9.014,18]icosa-5(9),7,10-trien-17-one (IIa.2)

¹H NMR (300 MHz, CDCl₃) δ ppm: 7.35-7.22 (m, 5H), 5.41-5.40 (m, 1H), 3.53 (t, J=6.9 Hz, 2H), 2.95 (t, J=6.9 Hz, 2H), 2.66-2.63 (m, 2H), 2.49 (dd, J=8.8, 19.0 Hz, 1H), 2.40-2.28 (m, 1H), 2.18-1.76 (m, 7H), 1.66-1.16 (m, 6H), 1.06 (s, 3H), 0.93 (m, 3H). ¹H NMR (75 MHz, CDCl₃) δ ppm: 220.8, 167.1, 143.6, 138.0, 136.4, 128.8, 128.7, 126.7, 118.9, 117.2, 51.7, 48.1, 47.5, 47.4, 36.7, 35.8, 35.3, 34.0, 31.3, 31.2, 30.5, 23.4, 21.8, 20.6, 18.7, 13.6. HRMS (ESI-FTMS, m/z): calcd for $C_{28}H_{34}N_2OS$ [M+H]⁺ 447.2465, found 447.2470. Yield (334 mg, 0.75 mmol, 75%).

(1S,2R,13R,14S,18S)-7-(benzylamino)-2,18-dimethyl-6-thia-8-azapentacyclo[11.7.0.02,10.05,9.014, 18]icosa-5(9),7,10-trien-17-one (IIa.5)

¹H NMR (300 MHz, CDCl₃) δ ppm: 7.36-7.27 (m, 5H), 5.95 (br s, 1H), 5.39-5.38 (m, 1H), 4.48 (m, 2H), 2.63-2.60 (m, 2H), 2.53-2.44 (m, 1H), 2.38-2.26 (m, 1H), 2.17-1.76 (m, 7H), 1.65-1.27 (m, 5H), 1.22-1.14 (m, 1H), 1.05 (s, 3H), 0.94 (s, 3H); ¹H NMR (75 MHz, CDCl₃) δ ppm: ¹H NMR (75 MHz, CDCl₃) δ ppm: 220.9, 166.8, 146.0, 137.6, 136.9, 128.7, 127.7, 127.5, 119.6, 116.4, 51.8, 49.7, 48.1, 47.6, 36.6, 35.8, 34.3, 31.4, 31.2, 30.5, 24.1, 21.8, 20.6, 18.7, 13.6. HRMS (ESI-FTMS, m/z): calcd for $C_{27}H_{32}N_2OS$ [M+H]⁺ 433.2308, found 433.2312. Yield (341 mg, 0.79 mmol, 79%)

(1S,2R,13R,14S,18S)-2,18-dimethyl-7-(3-morpholinopropylamino)-6-thia-8-azapentacyclo [11.7.0.02,10.05,9.014,18]icosa-5(9),7,10-trien-17-one (IIa.4)

¹H NMR (300 MHz, CDCl₃) δ ppm: 5.38-5.37 (m, 1H), 3.75 (t, J=4.5 Hz, 4H), 3.39 (t, J=6.2 Hz, 2H), 2.67-2.63 (m, 2H), 2.52-2.44 (m, 7H), 2.36-2.30 (m, 1H), 2.18-1.76 (m, 9H), 1.66-1.15 (m, 7H), 1.06 (s, 3H), 0.92 (s, 3H); ¹H NMR (75 MHz, CDCl₃) δ ppm: 221.1, 166.9, 146.1, 137.1, 119.0, 116.1, 67.0, 57.5, 53.7, 51.8, 48.1, 47.6, 45.3, 36.6, 35.8, 34.3, 31.4, 31.2, 30.5, 24.8, 24.1, 21.8, 20.6, 18.7, 13.6. Yield (351 mg, 0.75 mmol, 75%)

(1S,2R,13R,14S,18S)-7-anilino-2,18-dimethyl-6-thia-8-azapentacyclo[11.7.0.02,10.05,9.014,18]icosa-5(9),7,10-trien-17-one (IIa.6)

¹H NMR (300 MHz, CDCl₃) δ ppm: 7.39-7.32 (m, 4H), 7.11-7.06 (m, 1H), 5.48-5.47 (m, 1H), 2.72-2.67 (m, 2H), 2.54-2.45 (m, 1H), 2.40-2.28 (m, 1H), 2.18-1.77 (m, 7H), 1.63-1.15 (m, 6H), 1.07 (s, 3H), 0.93 (s, 3H); ¹H NMR (75 MHz, CDCl3) δ ppm: 221.0, 162.2, 145.4, 140.2, 136.6, 129.4, 123.2, 120.3, 118.6, 117.5, 51.7, 48.1, 47.6, 36.7, 35.8, 34.2, 31.4, 31.2, 30.6, 24.0, 21.8, 20.6, 18.7, 13.6. Yield (359 mg, 0.86 mg, 86%)

(1S,2R,13R,14S,18S)-2,18-dimethyl-7-(4-methylanilino)-6-thia-8-azapentacyclo[11.7.0.02,10.05, 9.014,18]icosa-5(9),7,10-trien-17-one (IIa.32)

¹H NMR (300 MHz, CDCl₃) δ ppm: 7.27-7.14 (m, 4H), 5.45-5.44 (m, 1H), 2.69-2.67 (m, 2H), 2.54-2.45 (m, 1H), 2.38-2.34 (m, 4H), 2.18-1.77 (m, 6H), 1.66-1.16 (m, 7H), 1.07 (s, 3H), 0.93 (s, 3H); ¹³C NMR (75 MHz, CDCl₃) δ ppm: 220.9, 163.3, 145.3, 137.7, 136.7, 133.2, 129.9, 119.9, 119.4, 117.2, 51.8, 48.1, 47.6, 36.7, 35.8, 34.2, 31.4, 31.2, 30.5, 23.9, 21.8, 20.8, 20.6, 18.7, 13.6. HRMS (ESI-FTMS, m/z): calcd for $C_{28}H_{34}N_2OS$ [M+H]⁺ 447.2465, found 447.2470. Yield (397 mg, 0.92 mmol, 92%)

(1S,2R,13R,14S,18S)-7-(2-methoxyanilino)-2,18-dimethyl-6-thia-8-azapentacyclo[11.7.0.02,10.05, 9.014,18]icosa-5(9),7,10-trien-17-one (IIa.15)

¹H NMR (300 MHz, CDCl₃) δ ppm: 7.91-7.88 (m, 1H), 7.01-6.96 (m, 2H), 6.91-6.88 (m, 1H), 5.51-5.50 (m, 1H), 3.90 (s, 3H), 2.76-2.71 (m, 2H), 2.54-2.45 (m, 1H), 2.38-2.32 (m, 1H), 2.18-1.79 (m, 7H), 1.67-1.21 (m, 6H), 1.08 (s, 3H), 0.94 (m, 3H); 13C NMR (75 MHz, CDCl₃) δ ppm: 221.0, 160.8, 147.5, 145.7, 136.7, 129.7, 122.0, 121.0, 120.6, 117.5, 116.1, 110.1, 55.7, 51.8, 48.1, 47.6, 36.7, 35.8, 34.3, 31.4, 31.2, 30.6, 24.0, 21.8, 20.6, 18.7, 13.6. HRMS (ESI-FTMS, m/z): calcd for $C_{27}H_{33}N_2O_2S$ [M+H]$^+$ 449.2257, found 449.2264. Yield (367 mg, 0.82 mmol, 82%)

(1S,2R,13R,14S,18S)-2,18-dimethyl-7-[4-(trifluoromethoxy)anilino]-6-thia-8-azapentacyclo[11.7.0.0²,¹⁰.0⁵,⁹.0¹⁴,¹⁸]icosa-5(9),7,10-trien-17-one (IIa.19)

$^1$H NMR (300 MHz, CDCl$_3$) δ ppm: 7.46 (d, J=8.8 Hz, 2H), 7.30 (d, J=9.2 Hz, 2H), 5.57-5.56 (m, 1H), 2.90-2.66 (m, 2H), 2.53-2.44 (m, 1H), 2.38-2.32 (m, 1H), 2.17-1.74 (m, 7H), 1.65-1.59 (m, 6H), 1.03 (s, 3H), 0.91 (s, 3H); $^1$H NMR (300 MHz, CDCl$_3$) δ ppm: 220.3, 165.6, 147.5, 135.5, 133.8, 133.2, 123.1, 122.6, 122.0, 117.1, 51.5, 47.6, 47.4, 36.8, 35.7, 32.8, 31.1, 31.0, 30.4, 21.7, 20.8, 20.5, 18.5, 13.6. HRMS (ESI-FTMS, m/z): calcd for $C_{27}H_{30}F_3N_2O_2S$ [M+H]$^+$ 503.1975, found 503.1977. Yield (376 mg, 0.75 mmol, 75%)

(1S,2R,13R,14S,18S)-7-(3-hydroxyanilino)-2,18-dimethyl-6-thia-8-azapentacyclo[11.7.0.0²,¹⁰.0⁵,⁹.0¹⁴,¹⁸]icosa-5(9),7,10-trien-17-one (IIa.17)

$^1$H NMR (300 MHz, DMSO-d$_6$) δ ppm: 9.80 (br s, 1H), 9.11 (br s, 1H), 7.09 (s, 1H), 6.99-6.88 (m, 2H), 6.31 (d, J=7.7 Hz, 1H), 5.35 (s, 1H), 2.62-2.57 (m, 2H), 2.42-2.24 (m, 2H), 2.06-1.70 (m, 7H), 1.59-1.08 (m, 6H), 0.98 (s, 3H), 0.83 (s, 3H); $^1$H NMR (300 MHz, DMSO-d$_6$) δ ppm: 219.8, 160.7, 158.1, 145.7, 142.3, 136.7, 129.6, 119.7, 117.4, 108.9, 108.5, 104.7, 51.5, 48.0, 47.3, 36.5, 35.7, 34.2, 31.5, 31.1, 30.5, 24.3, 21.8, 20.6, 18.8, 13.7. HRMS (ESI-FTMS, m/z): calcd for $C_{28}H_{31}N_2O_2S$ [M+H]$^+$ 435.2101, found 435.2106. Yield (312 mg, 0.72 mmol, 72%)

(1S,2R,13R,14S,18S)-7-(2-fluoroanilino)-2,18-dimethyl-6-thia-8-azapentacyclo[11.7.0.0²,¹⁰.0⁵,⁹.0¹⁴,¹⁸]icosa-5(9),7,10-trien-17-one (IIa.33)

$^1$H NMR (300 MHz, CDCl$_3$) δ ppm: 8.05-8.00 (m, 1H), 7.18-7.08 (m, 2H), 7.01-6.94 (m, 1H), 5.53-5.51 (m, 1H), 2.80-2.65 (m, 2H), 2.50 (dd, J=8.9, 19.1 Hz, 1H), 2.41-2.29 (m, 1H), 2.19-1.78 (m, 7H), 1.67-1.15 (m, 6H), 1.08 (s, 3H), 0.94 (s, 3H); $^{13}$C NMR (75 MHz, CDCl$_3$) δ ppm: 220.9, 160.2, 151.98 (d, $^1J_{CF}$=241.5 Hz), 145.8, 136.6, 128.69 d, $^3J_{CF}$=10.3 Hz), 124.69 (d, $^4J_{C-F}$=3.7 Hz), 122.5 (d, $^4J_{C-F}$=7.2 Hz), 121.5, 118.5, 118.1, 115.1 (d, $^2J_{C-F}$=18.8 Hz), 51.7, 48.1, 47.6, 36.7, 35.8, 34.2, 31.4, 31.2, 30.6, 24.1, 21.8, 20.6, 18.7, 13.6. Yield (348 mg, 0.80 mmol, 80%).

(1S,2R,13R,14S,18S)-7-(3-fluoroanilino)-2,18-dimethyl-6-thia-8-azapentacyclo[11.7.0.0²,¹⁰.0⁵,⁹.0¹⁴,¹⁸]icosa-5(9),7,10-trien-17-one (IIa.8)

$^1$H NMR (300 MHz, CDCl$_3$) δ ppm: 7.37-7.23 (m, 2H), 7.05-7.02 (m, 1H), 6.78-6.71 (m, 1H), 5.53-5.52 (m, 1H), 2.79-2.70 (m, 2H), 2.55-2.46 (m, 1H), 2.39-2.33 (m, 1H), 2.19-1.79 (m, 7H), 1.67-1.18 (m, 6H), 1.08 (s, 3H), 0.94 (s, 3H); $^{13}$H NMR (75 MHz, CDCl$_3$) δ ppm: 220.8, 163.4 (d, $^1J_{C-F}$=243.4 Hz), 160.6, 145.6, 141.8 (d, $^3J_{C-F}$=10.6 Hz), 136.5, 130.5 (d, $^3J_{C-F}$=9.6 Hz), 121.3, 118.1, 113.4 ($^4J_{C-F}$=2.7 Hz), 109.3 (d, $^2J_{C-F}$=21.2 Hz), 105.1 (d, $^2J_{C-F}$=25.9 Hz), 51.8, 48.1, 47.6, 36.7, 35.8, 34.2, 31.4, 31.1, 30.6, 24.0, 21.8, 20.6, 18.7, 13.6. HRMS (ESI-FTMS, m/z): calcd for $C_{26}H_{30}FN_2OS$ [M+H]$^+$ 437.2057, found 437.2063. Yield (361 mg, 0.83 mmol, 83%)

(1S,2R,13R,14S,18S)-7-(4-fluoroanilino)-2,18-dimethyl-8-thia-6-azapentacyclo[11.7.0.0²,¹⁰.0⁵,⁹.0¹⁴,¹⁸]icosa-5(9),6,10-trien-17-one (IIa.9)

$^1$H NMR (300 MHz, CDCl$_3$) δ ppm: 7.6-7.32 (m, 2H), 7.09-7.03 (m, 2H), 5.45 (s, 1H), 2.69-2.67 (m, 2H), 2.50 (dd, J=8.7, 19.2 Hz, 1H), 2.36-2.31 (m, 1H), 2.18-1.76 (m, 6H), 1.66-1.16 (m, 6H), 1.06 (s, 3H), 0.98 (s, 3H); $^{13}$C NMR (75 MHz, CDCl$_3$) δ ppm: 163.6, 159.1 (d, $^1J$=241.7 Hz), 144.9, 136.5, 136.4 (d, $^4J$=2.5 Hz), 121.6 (d, $^3J$=7.9 Hz), 119.8, 117.7, 116.2 (d, $^2J$=22.5 Hz), 77.2, 51.7, 48.0, 47.6, 36.6, 35.8, 34.2, 31.3, 31.1, 30.5, 23.9, 21.8, 20.6, 18.7, 13.6. HRMS (ESI-FTMS, m/z): calcd for $C_{26}H_{30}FN_2OS$ [M+H]$^+$ 437.2057, found 437.2052.

(1S,2R,13R,14S,18S)-7-(2-chloroanilino)-2,18-dimethyl-6-thia-8-azapentacyclo[11.7.0.0²,¹⁰.0⁵,⁹.0¹⁴,¹⁸]icosa-5(9),7,10-trien-17-one (IIa.11)

$^1$H NMR (300 MHz, CDCl$_3$) δ ppm: 8.08 (d, J=8.1 Hz, 1H), 7.39 (d, J=7.9 Hz, 1H), 7.32-7.27 (m, 1H), 6.96 (t, J=7.5 Hz, 1H), 5.53 (s, 1H), 2.81-2.68 (m, 2H), 2.54-2.45 (m, 1H), 2.38-2.32 (m, 1H), 2.18-1.78 (m, 7H), 1.67-1.18 (m, 6H), 1.08 (s, 3H), 0.94 (s, 3H); $^1$H NMR (75 MHz, CDCl$_3$) δ ppm: 220.9, 159.9, 145.8, 136.7, 136.5, 129.4, 127.8, 122.7, 121.8, 121.7, 118.3, 117.8, 51.7, 48.1, 47.6, 36.7, 35.8, 34.2, 31.3, 31.2, 30.6, 24.1, 21.8, 20.6, 18.7, 13.6. HRMS (ESI-FTMS, m/z): calcd for $C_{26}H_{30}ClN_2OS$ [M+H]$^+$ 453.1762, found 453.1767. Yield (334 mg, 0.74 mmol, 74%)

3-[[(1S,2R,13R,14S,18S)-2,18-dimethyl-17-oxo-6-thia-8-azapentacyclo[11.7.0.0²,¹⁰.0⁵,⁹.0¹⁴,¹⁸]icosa-5(9),7,10-trien-7-yl]amino]benzoic acid (IIa.34)

$^1$H NMR (300 MHz, CDCl$_3$+DMSO-d$_6$) δ ppm: 8.07 (s, 1H), 7.89-7.86 (m, 1H), 7.48-7.45 (m, 1H), 7.29-7.24 (m, 1H), 5.37-5.36 (m, 1H), 2.68-2.59 (m, 2H), 2.42-2.24 (m, 2H), 2.06-1.69 (m, 7H), 1.58-1.04 (m, 7H), 0.98 (s, 3H), 0.83 (s, 3H); $^{13}$C NMR (75 MHz, CDCl$_3$+DMSO-d$_6$) δ ppm: 220.1, 168.0, 160.4, 145.9, 141.4, 136.6, 131.6, 128.9, 122.2, 121.3, 120.3, 118.2, 117.6, 51.6, 48.0, 47.4, 36.5, 35.7, 34.2, 31.4, 31.1, 30.5, 24.3, 21.8, 20.6, 18.8, 13.7. Yield (332 mg, 0.72 mmol, 72%).

4-[[(1S,2R,13R,14S,18S)-2,18-dimethyl-17-oxo-6-thia-8-azapentacyclo[11.7.0.0²,¹⁰.0⁵,⁹.0¹⁴,¹⁸]icosa-5(9),7,10-trien-7-yl]amino]benzoic acid (IIa.23)

$^1$H NMR (300 MHz, CDCl$_3$) δ ppm: 10.56 (br s, 1H), 7.87 (d, J=8.5 Hz, 2H), 7.70 (d, J=8.7 Hz, 2H), 2.71-2.66 (m, 2H), 2.45-2.36 (m, 1H), 2.31-2.27 (m, 1H), 2.07-1.67 (m, 7H), 1.59-1.02 (m, 7H), 0.99 (s, 3H), 0.82 (s, 3H); $^{13}$C NMR (75 MHz, CDCl$_3$) δ ppm: 220.0, 167.4, 159.5, 146.1, 145.2, 136.5, 131.1, 123.1, 121.1, 118.8, 116.4, 51.3, 48.0, 47.3, 36.5, 35.7, 34.2, 31.5, 31.0, 30.4, 24.3, 21.8, 20.6, 18.9, 13.7. Yield (346 mg, 0.75 mmol, 75%).

(1S,2R,13R,14S,18S)-2,18-dimethyl-7-(2-nitroanilino)-6-thia-8-azapentacyclo[11.7.0.0²,¹⁰.0⁵,⁹.0¹⁴,¹⁸]icosa-5(9),7,10-trien-17-one (IIa.13)

$^1$H NMR (300 MHz, CDCl$_3$) δ ppm: 10.62 (br s, 1H), 8.72 (d, J=8.6 Hz, 1H), 8.26 (d, J=8.4 Hz, 1H), 7.66-7.61 (m, 1H), 7.05-7.00 (m, 1H), 5.61-5.60 (m, 1H), 2.87-2.70 (m, 2H), 2.55-2.35 (m, 2H), 2.19-1.79 (m, 7H), 1.68-1.19 (m, 7H), 1.09 (s, 3H), 0.94 (s, 3H); $^{13}$C NMR (75 MHz, CDCl$_3$) δ ppm: 220.7, 157.8, 146.4, 137.8, 136.3, 136.3, 133.9, 126.2, 124.3, 120.5, 119.7, 119.2, 51.7, 48.1, 47.6, 36.7, 35.8, 34.2, 31.4, 31.1, 30.6, 24.2, 21.8, 20.6, 18.7, 13.6. HRMS (ESI-FTMS, m/z): calcd for C$_{26}$H$_{30}$N$_3$O$_3$S [M+H]$^+$ 464.2002, found 464.2008. Yield (375 mg, 0.81 mmol, 81%)

(1S,2R,13R,14S,18S)-7-(2,4-difluoroanilino)-2,18-dimethyl-6-thia-8-azapentacyclo[11.7.0.02,10.05, 9.014,18]icosa-5(9),7,10-trien-17-one (IIa.10)

$^1$H NMR (300 MHz, CDCl$_3$) δ ppm: 8.08-8.00 (m, 1H), 6.93-6.88 (m, 2H), 5.50-5.49 (m, 1H), 2.75-2.70 (m, 2H), 2.55-2.45 (m, 1H), 2.38-2.32 (m, 1H), 2.19-1.78 (m, 7H), 1.67-1.18 (m, 6H), 1.08 (s, 3H), 0.94 (s, 3H); $^1$H NMR (75 MHz, CDCl$_3$) δ ppm: 220.8, 160.8, 157.5 (dd, $^{1,3}J_{C-F}$=243.3, 11.2 Hz), 151.6 (dd, $^{1,3}J_{C-F}$=244.9, 11.9 Hz), 145.9, 136.5, 125.2 (dd, $^{3,4}J_{C-F}$=10.9, 3.6 Hz), 121.5, 120.3 (d, $^3J_{CF}$=8.9 Hz), 118.1, 111.2 (dd, $^{2,3}J_{C-F}$=21.7, 3.7 Hz), 104.1 (d, $^2J_{CF}$=22.9 Hz), 103.8 (d, $^2J_{C-F}$=22.9 Hz), 51.8, 48.1, 47.6, 36.7, 35.8, 34.2, 31.4, 31.2, 30.6, 24.1, 21.8, 20.6, 18.7, 13.6. HRMS (ESI-FTMS, m/z): calcd for C$_{26}$H$_{29}$F$_2$N$_2$OS [M+H]$^+$ 455.1963, found 455.1968. Yield (349 mg, 0.77 mmol, 77%).

(1S,2R,13R,14S,18S)-7-(2,4-dimethylanilino)-2,18-dimethyl-6-thia-8-azapentacyclo[11.7.0.02,10.05, 9.014,18]icosa-5(9),7,10-trien-17-one (IIa.14)

$^1$H NMR (300 MHz, CDCl$_3$) δ ppm: 7.40 (d, J=7.8 Hz, 1H), 7.13-6.98 (m, 2H), 5.40-5.39 (m, 1H), 2.68-2.65 (m, 2H), 2.49 (dd, J=8.8, 18.9 Hz, 1H), 2.33 (s, 3H), 2.28 (s, 3H), 2.21-1.76 (m, 7H), 1.65-1.42 (m, 7H), 1.06 (s, 3H), 0.93 (s, 3H); $^{13}$C NMR (75 MHz, CDCl$_3$) δ ppm: 221.0, 165.2, 145.1, 136.7, 135.9, 135.1, 131.8, 130.9, 127.6, 122.3, 119.8, 117.0, 51.7, 48.1, 47.6, 36.6, 35.8, 34.2, 31.4, 31.1, 30.5, 23.8, 21.8, 20.9, 20.6, 18.7, 17.7, 13.6. Yield (338 mg, 0.76 mmol, 76%).

(1S,2R,13R,14S,18S)-7-(5-chloro-2-methoxy-anilino)-2,18-dimethyl-6-thia-8-azapentacyclo[11.7.0.02,10.05,9.014,18]icosa-5(9),7,10-trien-17-one (IIa.20)

$^1$H NMR (300 MHz, CDCl$_3$) δ ppm: 8.10 (d, J=2.3 Hz, 1H), 7.64 (br s, 1H), 6.91 (dd, J=2.3, 8.5 Hz, 1H), 6.78 (d, J=8.6 Hz, 1H), 5.53-5.52 (m, 1H), 3.89 (s, 3H), 2.82-2.67 (m, 2H), 2.52-2.51 (m, 1H), 2.38-2.33 (m, 1H), 2.18-1.78 (m, 7H), 1.67-1.20 (m, 7H), 1.08 (s, 3H), 0.94 (s, 3H); $^{13}$C NMR (75 MHz, CDCl$_3$) δ ppm: 220.8, 159.5, 146.0, 145.6, 136.6, 130.7, 126.2, 121.5, 120.8, 118.1, 115.9, 110.6, 56.0, 51.7, 48.1, 47.6, 36.7, 35.8, 34.2, 31.4, 31.2, 30.6, 24.2, 21.8, 20.7, 18.7, 13.6. HRMS (ESI-FTMS, m/z): calcd for C$_{27}$H$_{32}$ClN$_2$O$_2$S [M+H]$^+$ 483.1868, found 483.1871. Yield (366 mg, 0.76 mmol, 76%).

(1S,2R,13R,14S,18S)-7-(2,5-dimethoxyanilino)-2,18-dimethyl-6-thia-8-azapentacyclo[11.7.0.02,10.05, 9.014,18]icosa-5(9),7,10-trien-17-one (IIa.16)

$^1$H NMR (300 MHz, CDCl$_3$) δ ppm: 7.63 (d, J=2.7 Hz, 1H), 6.80 (d, J=8.8 Hz, 1H), 6.48 (dd, J=2.8, 8.7 Hz, 1H), 5.51-5.50 (m, 1H), 3.85 (s, 3H), 3.81 (s, 3H), 2.76-2.71 (m, 2H), 2.54-2.45 (m, 1H), 2.38-2.32 (m, 1H), 2.18-1.78 (m, 6H), 1.66-1.17 (m, 7H), 1.08 (s, 3H), 0.93 (s, 3H); $^{13}$C NMR (75 MHz, CDCl$_3$) δ ppm: 221.0, 160.3, 154.0, 145.6, 141.8, 136.6, 130.4, 120.9, 117.7, 110.7, 105.1, 103.6, 56.3, 55.7, 51.7, 48.1, 47.6, 36.7, 35.8, 34.2, 31.4, 31.2, 30.6, 24.1, 21.8, 20.6, 18.7, 13.6. HRMS (ESI-FTMS, m/z): calcd for C$_{28}$H$_{35}$N$_2$O$_3$S [M+H]$^+$ 479.2363, found 479.2367. Yield (334, 0.70 mmol, 70%)

(1S,2R,13R,14S,18S)-2,18-dimethyl-7-(N-methyl-anilino)-6-thia-8-azapentacyclo[11.7.0.02,10.05, 9.014,18]icosa-5(9),7,10-trien-17-one (IIa.6)

$^1$H NMR (300 MHz, CDCl$_3$) δ ppm: 7.45-7.38 (m, 4H), 7.30-7.27 (m, 1H), 5.33-5.31 (m, 1H), 3.53 (s, 3H), 2.78-2.70 (m, 2H), 2.52-2.43 (m, 1H), 2.34-2.23 (m, 1H), 2.13-1.77 (m, 7H), 1.61-1.28 (m, 5H), 1.22-1.13 (m, 1H), 1.06 (s, 3H), 0.98 (s, 3H); $^{13}$C NMR (75 MHz, CDCl$_3$) δ ppm: 220.9, 167.1, 146.3, 146.2, 136.9, 129.7, 126.5, 125.3, 120.2, 116.7, 51.8, 48.1, 47.6, 40.1, 36.5, 35.8, 34.4, 31.4, 31.2, 30.5, 24.2, 21.8, 20.6, 18.7, 13.6. HRMS (ESI-FTMS, m/z): calcd for C$_{27}$H$_{33}$N$_2$OS [M+H]$^+$ 433.2308, found 433.2312. Yield (315 mg, 0.73 mmol, 73%).

(1S,2R,13R,14S,18S)-2,18-dimethyl-7-(2-pyridylamino)-6-thia-8-azapentacyclo[11.7.0.02,10.05, 9.014,18]icosa-5(9),7,10-trien-17-one (IIa.21)

$^1$H NMR (300 MHz, CDCl$_3$) δ ppm: 8.35 (d, J=4.7 Hz, 1H), 7.57 (t, J=7.6 Hz, 1H), 6.89-6.85 (m, 2H), 5.71 (d, J=2.4 Hz, 1H), 2.76-2.73 (m, 2H), 2.54-2.34 (m, 2H), 2.18-1.78 (m, 7H), 1.67-1.22 (m, 7H), 1.07 (s, 3H), 0.94 (s, 3H); $^{13}$C NMR (75 MHz, CDCl$_3$) δ ppm: 221.0, 158.3, 151.4, 146.9, 143.0, 137.7, 136.8, 122.8, 117.5, 116.3, 110.7, 51.8, 48.1, 47.6, 36.5, 35.8, 34.3, 31.4, 31.2, 30.6, 23.7, 21.8, 20.7, 18.7, 13.6. HRMS (ESI-FTMS, m/z): calcd for C$_{25}$H$_{30}$N$_3$OS [M+H]$^+$ 420.2104, found 420.2109. Yield (314 mg, 0.75 mmol, 75%).

(1S,2R,13R,14S,18S)-2,18-dimethyl-7-(pyrimidin-2-ylamino)-6-thia-8-azapentacyclo[11.7.0.02,10.05, 9.014,18]icosa-5(9),7,10-trien-17-one (IIa.22)

$^1$H NMR (300 MHz, CDCl$_3$+DMSO-d$_6$+TFA-d) δ ppm: 8.64 (d, J=4.9 Hz, 2H), 7.07 (t, J=4.9 Hz, 1H), 5.74-5.73 (m, 1H), 2.74-2.58 (m, 2H), 2.37-2.26 (m, 2H), 2.00-1.64 (m, 7H), 1.53-1.07 (m, 6H), 0.94 (s, 3H), 0.78 (s, 3H); $^{13}$C NMR (75 MHz, CDCl$_3$+DMSO-d$_6$+TFA-d) δ ppm: 219.8, 159.4, 155.2, 134.3, 132.4, 122.4, 121.5, 115.6, 114.7, 51.2, 47.6, 47.2, 36.3, 35.4, 32.8, 31.2, 30.8, 30.2, 21.4, 20.3, 20.2, 18.1, 13.2. Yield (273 mg, 0.65 mmol, 65%).

N-[(1S,2R,13R,14S,18S)-2,18-dimethyl-17-oxo-8-thia-6-azapentacyclo[11.7.0.02,10.05,9.014,18] icosa-5(9),6,10-trien-7-yl]acetamide (IIb.1)

$^1$H NMR (300 MHz, CDCl3) δ 5.48 (s, 1H), 2.55-2.38 (m, 2H), 2.15-2.00 (m, 5H), 1.76-1.50 (m, 7H), 1.40-1.36 (m, 1H), 1.25-0.90 (m, 6H), 0.83-0.81 (m, 1H), 0.62 (s, 3H), 0.53 (s, 3H); $^{13}$C NMR (75 MHz, CDCl3) δ=219.8, 168.2, 158.7, 133.3, 132.0, 123.7, 123.0, 51.0, 47.2, 47.0, 36.2, 35.2, 32.5, 32.5, 30.7, 30.5, 30.1, 23.0, 21.3, 20.2, 18.0, 13.1. HRMS (ESI-FTMS, m/z): calcd for C$_{22}$H$_{29}$N$_2$O$_2$S+[M+H]$^+$ 385.1944, found 385.1948. Yield (364 mg, 0.95 mmol, 95%).

(1S,2R,13R,14S,17S,18S)-2,7,18-trimethyl-8-thia-6-azapentacyclo[11.7.0.02,10.05,9.014,18]icosa-5(9), 6,10-trien-17-ol (III.1)

$^1$H NMR (300 MHz, CDCl$_3$) δ ppm: 5.83-5.81 (m, 1H), 3.70 (t, J=8.3 Hz, 1H), 2.81-2.61 (m, 2H), 2.39 (s, 3H), 2.33-2.25 (m, 1H), 2.17-2.08 (m, 2H), 1.93-1.89 (m, 1H), 1.84-1.26 (m, 9H), 1.21-1.01 (m, 3H), 1.01 (s, 3H), 0.82 (s, 3H); $^{13}$C NMR (75 MHz, CDCl$_3$) δ ppm: 168.3, 134.6, 134.2, 124.9, 123.2, 81.6, 51.2, 47.8, 42.8, 36.6, 36.3, 33.3, 31.4, 31.3, 30.3, 23.5, 23.3, 21.4, 20.9, 18.5, 11.1.

(1S,2R,13R,14S,17S,18S)-2,18-dimethyl-7-phenyl-8-thia-6-azapentacyclo[11.7.0.02,10.05,9.014,18]icosa-5(9),6,10-trien-17-ol (III.2)

$^1$H NMR (300 MHz, CDCl$_3$) δ ppm: 7.41-7.35 (m, 5H), 5.81-5.79 (m, 1H), 3.68 (t, J=8.3 Hz, 1H), 3.21 (dd, J=4.8, 17.2 Hz, 1H), 2.96-2.87 (m, 1H), 2.26-2.03 (m, 3H), 1.91-1.87 (m, 1H), 1.81-1.03 (m, 12H), 0.99 (s, 3H), 0.79 (s, 3H); $^{13}$C NMR (75 MHz, CDCl$_3$) δ ppm: 171.9, 141.1, 134.3, 133.8, 133.3, 129.4, 129.3, 128.5, 125.9, 81.5, 51.1, 47.7, 42.7, 36.8, 36.2, 32.9, 31.4, 31.3, 30.3, 23.3, 21.1, 20.9, 18.5, 11.0.

(1S,2R,13R,14S,17S,18S)-2,18-dimethyl-7-(o-tolyl)-8-thia-6-azapentacyclo[11.7.0.02,10.05,9.014,18]icosa-5(9),6,10-trien-17-ol (III.14)

$^1$H NMR (300 MHz, DMSO-d6) δ ppm: 7.75 (s, 1H), 7.30-7.25 (m, 3H), 5.85 (s, 1H), 3.71 (t, J=8.8 Hz, 1H), 3.05-2.82 (m, 2H), 2.61 (s, 3H), 2.30-2.26 (m, 1H), 2.14-2.09 (m, 2H), 1.93-1.13 (m, 13H), 1.09 (s, 3H), 0.83 (s, 3H); $^{13}$C NMR (75 MHz, CDCl$_3$) δ ppm: 163.7, 136.42, 136.20, 132.4, 131.4, 129.9, 129.5, 126.1, 122.5, 81.7, 51.3, 48.1, 42.8, 36.7, 36.5, 34.3, 31.59, 31.53, 30.48, 23.9, 23.4, 21.5, 21.0, 18.7, 11.1. HRMS (ESI-FTMS, m/z): calcd for C$_{27}$H$_{34}$NOS [M+H]$^+$ 420.2356, found 420.2362.

(1S,2R,13R,14S,17S,18S)-2,18-dimethyl-7-(m-tolyl)-8-thia-6-azapentacyclo[11.7.0.02,10.05,9.014,18]icosa-5(9),6,10-trien-17-ol (III.10)

$^1$H NMR (300 MHz, CDCl$_3$) δ ppm: 7.76 (s, 1H), 7.69 (d, J=7.6 Hz, 1H), 7.33-7.27 (m, 1H), 7.21 (d, J=7.4 Hz, 1H), 5.82 (s, 1H), 3.68 (t, J=8.4 Hz, 1H), 3.03-2.81 (m, 2H), 2.41 (s, 3H), 2.30-2.24 (m, 1H), 2.17-2.04 (m, 2H), 1.91-1.27 (m, 11H), 1.19-1.10 (m, 2H), 1.07 (s, 3H), 0.82 (s, 3H); $^{13}$C NMR (75 MHz, CDCl$_3$) δ ppm: 164.3, 150.2, 138.6, 136.5, 133.8, 131.7, 130.5, 128.7, 126.8, 123.6, 122.0, 81.7, 51.3, 48.1, 42.8, 36.6, 36.5, 34.4, 31.58, 31.52, 30.4, 24.2, 23.4, 21.3, 21.0, 18.7, 11.0. HRMS (ESI-FTMS, m/z): calcd for C$_{27}$H$_{33}$NOS [M+H]$^+$ 420.2356, found 420.2361.

(1S,2R,13R,14S,17S,18S)-7-(3-methoxyphenyl)-2,18-dimethyl-8-thia-6-azapentacyclo[11.7.0.02,10.05,9.014,18]icosa-5(9),6,10-trien-17-ol (III.12)

$^1$H NMR (300 MHz, CDCl$_3$+DMSO-d6) δ ppm: 7.59 (s, 1H), 7.43 (d, J=7.4 Hz, 1H), 7.30 (t, J=7.8 Hz, 1H), 6.95 (d, J=8.3 Hz, 1H), 5.84 (s, 1H), 3.82 (s, 3H), 3.50 (t, J=8.5 Hz, 1H), 3.00 (dd, J=5.2, 17.7 Hz, 1H), 2.84-2.76 (m, 1H), 2.23-2.17 (m, 1H), 2.06-2.01 (m, 1H), 1.91-1.16 (m, 11H), 1.06-0.98 (m, 3H), 0.96 (s, 3H), 0.68 (s, 3H); $^{13}$C NMR (75 MHz, CDCl$_3$) δ ppm: 166.2, 160.5, 143.7, 134.3, 132.4, 130.7, 128.4, 126.2, 120.9, 120.4, 111.9, 81.5, 56.7, 51.1, 47.8, 42.8, 36.9, 36.3, 33.2, 31.5, 31.1, 30.3, 23.3, 22.1, 21.0, 18.9, 11.1. HRMS (ESI-FTMS, m/z): calcd for C$_{27}$H$_{34}$NO$_2$S [M+H]$^+$ 436.2305, found 436.2302.

(1S,2R,13R,14S,17S,18S)-7-(3-ethoxyphenyl)-2,18-dimethyl-8-thia-6-azapentacyclo[11.7.0.02,10.05,9.014,18]icosa-5(9),6,10-trien-17-ol (III.20)

$^1$H NMR (300 MHz, DMSO-d6) δ ppm: 7.41-7.32 (m, 3H), 6.99 (d, J=7.2 Hz, 1H), 5.76 (s, 1H), 4.06 (t, J=6.4 Hz, 2H), 3.42 (t, J=7.9 Hz, 1H), 3.14-2.73 (m, 2H), 2.16 (d, J=17.8 Hz, 1H), 2.01 (d, J=9.1 Hz, 1H), 1.78-1.39 (m, 5H), 1.33 (t, J=6.7 Hz, 3H), 1.35-1.30 (m, 6H), 1.20-0.99 (m, 3H), 0.94 (s, 3H), 0.65 (s, 3H); $^{13}$C NMR (75 MHz, DMSO-d6) δ ppm: 163.0, 159.3, 150.4, 136.2, 134.7, 131.8, 130.8, 123.1, 118.8, 116.9, 111.3, 80.3, 63.7, 51.2, 48.0, 43.5, 42.7, 36.7, 36.5, 34.1, 31.5, 30.2, 24.1, 23.4, 21.0, 18.9, 15.0, 11.6. HRMS (ESI-FTMS, m/z): calcd for C$_{28}$H$_{36}$NO$_2$S [M+H]$^+$ 450.2461, found 450.2456.

(1S,2R,13R,14S,17S,18S)-7-(2-hydroxyphenyl)-2,18-dimethyl-8-thia-6-azapentacyclo[11.7.0.02,10.05,9.014,18]icosa-5(9),6,10-trien-17-ol (III.6)

$^1$H NMR (300 MHz, CDCl$_3$) δ ppm: 7.98 (d, J=7.9 Hz, 1H), 7.38 (t, J=7.9 Hz, 1H), 7.09 (J=9.0 Hz, 1H), 6.96 (t, J=7.8 Hz, 1H), 5.98 (s, 1H), 3.43 (t, J=8.0 Hz, 1H), 2.94-2.72 (m, 2H), 2.21-2.15 (m, 1H), 2.06-2.03 (m, 1H), 1.84-1.30 (m, 9H), 1.21-1.17 (m, 1H), 1.03-0.95 (m, 2H), 0.94 (s, 3H), 0.59 (s, 3H); $^{13}$C NMR (75 MHz, CDCl$_3$) δ ppm: 161.9, 156.6, 141.9, 134.3, 134.0, 131.8, 127.2, 124.8, 120.0, 117.1, 114.6, 80.2, 51.0, 47.8, 42.5, 36.5, 36.4, 33.0, 31.3, 31.1, 29.8, 23.0, 21.3, 20.7, 18.1, 11.0. HRMS (ESI-FTMS, m/z): calcd for C$_{26}$H$_{31}$NO$_2$S [M+H]$^+$ 422.2148, found 422.2151.

(1S,2R,13R,14S,17S,18S)-7-(4-hydroxyphenyl)-2,18-dimethyl-8-thia-6-azapentacyclo[11.7.0.02,10.05,9.014,18]icosa-5(9),6,10-trien-17-ol (III.5)

$^1$H NMR (300 MHz, CDCl$_3$+DMSO-d6) δ ppm: 7.71 (d, J=8.6 Hz, 2H), 6.84 (d, J=8.3 Hz, 2H), 5.73 (s, 1H), 3.46 (t, J=8.3 Hz, 1H), 2.87-2.72 (m, 1H), 2.22-2.16 (m, 1H), 2.04-2.01 (m, 1H), 1.81-1.18 (m, 12H), 1.06-0.97 (m, 3H), 0.97 (s, 3H), 0.63 (s, 3H); $^{13}$C APT NMR (75 MHz, CDCl$_3$+DMSO-d6) δ ppm: 164.1, 160.2, 148.9, 136.1, 130.2, 128.2, 124.0, 122.4, 116.3, 80.4, 51.3, 48.1, 42.8, 36.7, 36.6, 34.1, 31.58, 31.51, 30.2, 23.8, 23.4, 21.1, 18.9, 11.6. HRMS (ESI-FTMS, m/z): calcd for C$_{26}$H$_{31}$NO$_2$S [M+H]$^+$ 422.2148, found 422.2151.

4-[(1S,2R,13R,14S,17S,18S)-17-hydroxy-2,18-dimethyl-8-thia-6-azapentacyclo[11.7.0.02,10.05,9.014,18]icosa-5(9),6,10-trien-7-yl]benzene-1,2-diol (III.7)

$^1$H NMR (300 MHz, DMSO-d6) δ ppm: 7.32 (s, 1H), 7.19 (d, J=8.2 Hz, 1H), 6.82 (d, J=8.2 Hz, 1H), 5.70 (s, 1H), 3.43 (t, J=8.0 Hz, 1H), 2.83-2.66 (m, 2H), 2.17-2.11 (m, 1H), 2.01-1.97 (m, 1H), 1.78-1.10 (m, 11H), 1.03-0.88 (m, 3H), 0.94 (s, 3H), 0.65 (s, 3H); $^{13}$C NMR (75 MHz, DMSO-d6) δ ppm: 164.3, 148.9, 148.7, 146.1, 136.0, 130.0, 124.3, 122.5, 118.7, 116.5, 113.6, 80.3, 51.1, 48.0, 42.7, 36.7, 36.5, 34.0, 31.5, 31.4, 30.2, 23.8, 23.4, 21.0, 18.9, 11.6. HRMS (ESI-FTMS, m/z): calcd for C$_{26}$H$_{32}$NO$_3$S [M+H]$^+$ 438.2097, found 438.2099.

(1S,2R,13R,14S,17S,18S)-7-(3-fluorophenyl)-2,18-dimethyl-8-thia-6-azapentacyclo[11.7.0.02,10.05,9.014,18]icosa-5(9),6,10-trien-17-ol (III.15)

$^1$H NMR (300 MHz, CDCl$_3$) δ ppm: 7.69-7.63 (m, 2H), 7.40-7.34 (m, 1H), 7.09 (dt, J=2.5, 8.4 Hz, 1H), 5.85-5.83 (m, 1H), 3.69 (t, J=8.3 Hz, 1H), 3.04-2.81 (m, 2H), 2.31-2.22 (m, 1H), 2.18-2.05 (m, 2H), 1.93-1.28 (m, 10H), 1.22-1.02 (m, 3H), 1.07 (s, 3H), 0.82 (s, 3H); $^{13}$C NMR (75 MHz, CDCl$_3$) δ ppm: 163.0 (d, $^1$J=244.9 Hz), 162.4 (d, $^4$J=3.1 Hz), 150.5, 136.3, 135.9 (d, $^3$J=8.0 Hz), 132.5, 130.4

(d, ³J=8.2 Hz), 122.6, 122.1 (d, ⁴J=2.8 Hz), 116.5 (d, ²J=21.1 Hz), 113.1 (d, ²J=23.3 Hz), 81.7, 51.3, 48.1, 42.8, 36.7, 36.5, 34.3, 31.57, 31.54, 30.5, 24.1, 23.4, 21.0, 18.7, 11.0. HRMS (ESI-FTMS, m/z): calcd for $C_{26}H_{30}NOSF$ [M+H]⁺ 424.2105, found 424.2107.

(1S,2R,13R,14S,17S,18S)-7-(4-fluorophenyl)-2,18-dimethyl-8-thia-6-azapentacyclo[11.7.0.02,10.05, 9.014,18]icosa-5(9),6,10-trien-17-ol (III.16)

¹H NMR (300 MHz, CDCl₃) δ ppm: 7.90 (dd, J=5.3, 8.7 Hz, 2H), 7.11 (t, J=8.6 Hz, 2H), 5.82 (m, 1H), 3.70 (t, J=8.4 Hz, 1H), 3.03-2.91 (m, 2H), 2.31-2.25 (m, 1H), 2.18-2.08 (m, 2H), 1.92-1.28 (m, 10H), 1.22-1.02 (m, 3H), 1.07 (s, 3H), 0.82 (s, 3H); ¹³C NMR (75 MHz, CDCl₃) δ ppm: 163.6 (d, J¹=248.3 Hz), 162.8, 150.4, 136.4, 131.9, 130.3 (d, J⁴=3.2 Hz), 128.2 (d, J³=8.3 Hz), 122.1, 115.9 (d, J²=21.8 Hz), 81.7, 51.3, 48.1, 42.8, 36.7, 36.5, 34.3, 31.58, 31.52, 30.5, 24.2, 23.4, 21.0, 18.7, 11.0. HRMS (ESI-FTMS, m/z): calcd for $C_{26}H_{30}NOSF$ [M+H]⁺ 424.2105, found 424.2106.

(1S,2R,13R,14S,17S,18S)-7-(4-chlorophenyl)-2,18-dimethyl-8-thia-6-azapentacyclo[11.7.0.02,10.05, 9.014,18]icosa-5(9),6,10-trien-17-ol (III.18)

¹H NMR (300 MHz, CDCl₃) δ ppm: 7.85 (d, J=7.9 Hz, 2H), 7.39 (d, J=7.9 Hz, 2H), 5.84-5.83 (m, 1H), 3.70 (t, J=8.1 Hz, 1H), 3.02-2.81 (m, 2H), 2.31-2.25 (m, 1H), 2.18-2.08 (m, 2H), 1.92-1.28 (m, 11H), 1.22-1.02 (m, 2H), 1.07 (s, 3H), 0.82 (s, 3H); ¹³C NMR (75 MHz, CDCl₃) δ ppm: 162.5, 150.5, 136.4, 135.5, 132.4, 132.3, 129.0, 127.5, 122.4, 81.7, 51.3, 48.1, 42.8, 36.7, 36.5, 34.3, 31.58, 31.54, 30.5, 24.2, 23.4, 21.0, 18.7, 11.0. HRMS (ESI-FTMS, m/z): calcd for $C_{26}H_{30}ClNOS$ [M+H]⁺ 440.1809, 442.1782, found 440.1815, 442.1785.

(1S,2R,13R,14S,17S,18S)-7-(4-bromophenyl)-2,18-dimethyl-8-thia-6-azapentacyclo[11.7.0.02,10.05, 9.014,18]icosa-5(9),6,10-trien-17-ol (III.19)

¹H NMR (300 MHz, CDCl₃) δ ppm: 7.83 (d, J=8.5 Hz, 2H), 7.56 (d, J=8.6 Hz, 2H), 5.85-5.53 (m, 1H), 3.69 (t, J=8.3 Hz, 1H), 3.07-2.82 (m, 2H), 2.31-2.21 (m, 1H), 2.17-2.05 (m, 2H), 1.92-1.27 (m, 10H), 1.21-1.01 (m, 2H), 1.06 (s, 3H), 0.82 (s, 3H); ¹³C NMR (75 MHz, CDCl₃) δ ppm: 162.7, 150.2, 136.3, 132.5, 132.3, 132.0, 127.7, 124.0, 122.7, 81.7, 51.3, 48.1, 42.8, 36.7, 36.4, 34.2, 31.56, 31.53, 30.4, 24.0, 23.3, 21.0, 18.7, 11.0. HRMS (ESI-FTMS, m/z): calcd for $C_{26}H_{31}NOSBr$ [M+H]⁺ 484.1304 and 486.1285, found 484.1306 and 486.1285.

(1S,2R,13R,14S,17S,18S)-2,18-dimethyl-7-(2-pyridyl)-8-thia-6-azapentacyclo[11.7.0.02,10.05, 9.014,18]icosa-5(9),6,10-trien-17-ol (III.4)

¹H NMR (300 MHz, CDCl₃+DMSO-d6) δ ppm: 8.51 (s, 1H), 8.02 (d, J=7.6 Hz, 1H), 7.82 (t, J=7.6 Hz, 1H), 7.35-7.34 (m, 1H), 5.80 (s, 1H), 3.42 (t, J=8.1 Hz, 1H), 2.86-2.69 (m, 2H), 2.18-2.12 (m, 1H), 2.02-1.98 (m, 1H), 1.79-1.14 (m, 11H), 1.05-0.85 (m, 3H), 0.92 (s, 3H), 0.63 (s, 3H); ¹³C NMR (300 MHz, CDCl₃+DMSO-d6) δ ppm: 163.7, 150.75, 150.71, 149.3, 137.8, 136.2, 134.1, 124.8, 123.4, 119.5, 80.4, 51.2, 48.0, 42.7, 36.6, 36.5, 34.1, 31.5, 31.4, 30.1, 24.1, 23.3, 21.0, 18.8, 11.4. HRMS (ESI-FTMS, m/z): calcd for $C_{25}H_{31}N_2OS$ [M+H]⁺ 407.2152, found 407.2153.

(1S,2R,13R,14S,17S,18S)-2,18-dimethyl-7-(methylamino)-8-thia-6-azapentacyclo[11.7.0.02,10.05, 9.014,18]icosa-5(9),6,10-trien-17-ol (IIIa.2)

¹H NMR (300 MHz, DMSO-d6) δ ppm: 10.14 (br s, 1H), 5.48 (s, 1H), 3.45 (br s, 1H), 3.00 (s, 3H), 2.68-2.49 (m, 2H), 2.19-2.14 (m, 1H), 2.00-1.97 (m, 1H), 1.84-1.13 (m, 11H), 1.05-0.95 (m, 3H), 0.95 (s, 3H), 0.66 (s, 3H); ¹³C NMR (75 MHz, DMSO-d6) δ ppm: 166.9, 134.6, 121.0, 116.4, 80.3, 51.2, 47.8, 42.7, 36.7, 36.6, 33.1, 32.3, 31.6, 31.1, 30.2, 23.4, 21.2, 20.9, 18.8, 11.6. HRMS (ESI-FTMS, m/z): calcd for $C_{21}H_{31}N_2OS$ [M+H]⁺ 359.2152, found 359.2149.

(1S,2R,13R,14S,17S,18S)-7-(ethylamino)-2,18-dimethyl-8-thia-6-azapentacyclo[11.7.0.02,10.05,9.014, 18]icosa-5(9),6,10-trien-17-ol (IIIa.3)

¹H NMR (300 MHz, DMSO-d6) δ ppm: 5.48 (s, 1H), 3.48-3.42 (m, 3H), 2.19-2.13 (m, 3H), 2.01-1.97 (m, 1H), 1.86-1.45 (m, 6H), 1.38-1.25 (m, 4H), 1.20 (t, J=7.2 Hz, 3H), 1.05-1.01 (m, 3H), 0.95 (s, 3H), 0.66 (s, 3H); ¹³C NMR (75 MHz, DMSO-d6) δ ppm: 165.6, 134.6, 121.0, 116.2, 80.3, 51.2, 47.8, 42.7, 41.0, 36.7, 36.6, 33.1, 31.6, 31.1, 30.2, 23.4, 21.2, 20.9, 18.8, 14.0, 11.7. HRMS (ESI-FTMS, m/z): calcd for $C_{22}H_{33}N_2OS$ [M+H]⁺ 373.2308, found 373.2300.

(1S,2R,13R,14S,17S,18S)-7-(butylamino)-2,18-dimethyl-8-thia-6-azapentacyclo[11.7.0.02,10.05,9.014, 18]icosa-5(9),6,10-trien-17-ol (IIIa.4)

¹H NMR (300 MHz, DMSO-d6) δ ppm: 9.84 (br s, 1H), 5.51-5.49 (m, 1H), 3.69 (t, J=8.3 Hz, 1H), 3.29 (q, J=6.8 Hz, 2H), 2.76-2.59 (m, 2H), 2.28-2.22 (m, 1H), 1.19-2.01 (m, 2H), 1.92-1.88 (m, 1H), 1.76-1.24 (m, 15H), 1.18-1.00 (m, 3H), 0.98 (s, 3H), 0.93 (t, J=7.2 Hz, 3H), 0.79 (s, 3H); ¹³C NMR (75 MHz, DMSO-d6) δ ppm: 168.3, 134.0, 132.9, 121.4, 116.3, 81.5, 51.2, 47.7, 42.7, 40.3, 40.0, 36.8, 36.3, 33.0, 31.5, 31.1, 30.3, 30.2, 23.3, 20.9, 19.9, 18.6, 13.5, 11.0. HRMS (ESI-FTMS, m/z): calcd for $C_{24}H_{37}N_2OS$ [M+H]⁺ 401.2621, found 401.2608.

(1S,2R,13R,14S,17S,18S)-7-(allylamino)-2,18-dimethyl-8-thia-6-azapentacyclo[11.7.0.02,10.05,9.014, 18]icosa-5(9),6,10-trien-17-ol (IIIa.6)

¹H NMR (300 MHz, CDCl3+MeOD-d4) δ ppm: 5.92-5.79 (m, 1H), 5.54-5.53 (m, 1H), 5.40-5.31 (m, 2H), 3.99 (d, J=5.4 Hz, 2H), 3.60 (t, J=8.4 Hz, 1H), 3.33-3.31 (m, 1H), 2.74-2.57 (m, 2H), 2.27-2.18 (m, 1H), 2.07-1.23 (m, 15H), 1.15-0.97 (m, 4H), 1.01 (s, 3H), 0.76 (s, 3H); ¹³C NMR (75 MHz, CDCl3+MeOD-d4) δ ppm: 167.1, 133.7, 132.7, 129.9, 122.1, 119.1, 117.7, 80.9, 76.9, 51.1, 49.1, 42.6, 36.6, 36.2, 32.9, 31.5, 31.0, 29.4, 23.1, 20.8, 20.5, 18.3, 10.8. HRMS (ESI-FTMS, m/z): calcd for $C_{23}H_{33}N_2OS$ [M+H]⁺ 385.2308, found 385.2302.

(1S,2R,13R,14S,17S,18S)-2,18-dimethyl-7-(2-phenylethylamino)-8-thia-6-azapentacyclo[11.7.0.02, 10.05,9.014,18]icosa-5(9),6,10-trien-17-ol (IIIa.5)

¹H NMR (300 MHz, CDCl₃+DMSO-d6) δ ppm: 10.31 (br s, 1H), 7.28-7.23 (m, 4H), 7.22-7.17 (m, 1H), 5.44 (s, 1H), 3.67-3.66 (m, 1H), 3.48-3.43 (m, 2H), 2.93 (t, J=7.3 Hz, 2H), 2.70-2.55 (m, 2H), 2.00-1.13 (m, 12H), 1.05-0.95 (m, 3H), 0.95 (s, 3H), 0.67 (s, 3H); ¹³C APT NMR (75 MHz, CDCl₃+DMSO-d6) δ ppm: 166.1, 137.9, 134.2, 132.9, 129.1, 128.7, 126.8, 121.4, 116.8, 80.4, 51.2, 47.7, 42.7, 36.6, 34.3, 33.0, 31.5, 31.1, 30.1, 23.4, 20.9, 18.7, 11.5.

(1S,2R,13R,14S,17S,18S)-7-anilino-2,18-dimethyl-8-thia-6-azapentacyclo[11.7.0.0²,¹⁰.0⁵,⁹.0¹⁴,¹⁸] icosa-5(9),6,10-trien-17-ol (IIIa.10)

$^1$H NMR (300 MHz, DMSO-d6) δ ppm: 7.58 (d, J=8.1 Hz, 2H), 7.31 (t, J=7.7 Hz, 2H), 6.99 (t, J=7.1 Hz, 1H), 5.39 (s, 1H), 3.45 (t, J=7.7 Hz, 1H), 2.63-2.58 (m, 2H), 2.18-2.12 (m, 1H), 1.98-1.94 (m, 1H), 1.80-1.17 (m, 12H), 1.05-1.01 (m, 3H), 0.97 (s, 3H), 0.67 (s, 3H); $^{13}$C NMR (75 MHz, DMSO-d6) δ ppm: 161.6, 143.3, 140.6, 136.1, 129.6, 122.9, 119.3, 119.2, 118.7, 80.3, 51.3, 48.1, 42.8, 36.8, 36.5, 34.0, 31.6, 31.2, 30.2, 23.6, 23.4, 21.0, 19.0, 11.7. HRMS (ESI-FTMS, m/z): calcd for $C_{26}H_{32}N_2OS$ [M+H]$^+$ 421.2308, found 421.2313.

(1S,2R,13R,14S,17S,18S)-2,18-dimethyl-7-(4-methylanilino)-8-thia-6-azapentacyclo[11.7.0.0²,¹⁰.0⁵,⁹.0¹⁴,¹⁸]icosa-5(9),6,10-trien-17-ol (IIIa.33)

$^1$H NMR (300 MHz, CDCl$_3$) δ ppm: 7.24 (s, 4H), 5.49 (s, 1H), 3.68 (t, J=8.4 Hz, 1H), 2.85-2.58 (m, 2H), 2.37 (s, 3H), 2.25-2.04 (m, 5H), 1.92-1.88 (m, 1H), 1.78-1.24 (m, 7H), 1.17-1.01 (m, 3H), 1.01 (s, 3H), 0.79 (s, 3H); $^{13}$C APT NMR (75 MHz, CDCl$_3$) δ ppm: 166.2, 137.6, 134.5, 133.9, 132.7, 130.6, 122.0, 121.8, 116.7, 81.5, 51.1, 47.7, 42.7, 36.8, 36.3, 33.0, 31.5, 31.1, 30.2, 23.3, 21.0, 20.9, 20.8, 18.6, 11.1. HRMS (ESI-FTMS, m/z): calcd for $C_{27}H_{35}N_2OS$ [M+H]$^+$ 435.2465, found 435.2449.

(1S,2R,13R,14S,17S,18S)-2,18-dimethyl-7-(N-methylanilino)-8-thia-6-azapentacyclo[11.7.0.0²,¹⁰.0⁵,⁹.0¹⁴,¹⁸]icosa-5(9),6,10-trien-17-ol (IIIa.9)

$^1$H NMR (300 MHz, CDCl$_3$) δ ppm: 7.55-7.48 (m, 3H), 7.35 (d, J=7.3 Hz, 2H), 5.39 (s, 1H), 3.66 (t, J=8.3 Hz, 1H), 3.22 (dd, J=4.1, 17.8 Hz, 1H), 2.86-2.78 (m, 1H), 2.17-2.01 (m, 3H), 1.88 (d, J=12.4 Hz, 1H), 1.74-1.21 (m, 12H), 1.16-0.95 (m, 3H), 1.00 (s, 3H), 0.77 (s, 3H); $^{13}$C APT NMR (75 MHz, CDCl$_3$) δ ppm: 167.9, 143.8, 135.9, 134.2, 131.0, 130.1, 125.5, 121.6, 118.3, 81.6, 51.2, 47.7, 44.0, 42.7, 36.7, 36.3, 33.5, 31.0, 30.3, 23.3, 21.3, 21.3, 20.8, 18.6, 11.0. HRMS (ESI-FTMS, m/z): calcd for $C_{27}H_{35}N_2OS$ [M+H]$^+$ 435.2465, found 435.2449.

(1S,2R,13R,14S,17S,18S)-7-(2,5-dimethoxyanilino)-2,18-dimethyl-8-thia-6 azapentacyclo[11.7.0.0²,10.05,9.014,18]icosa-5(9),6,10-trien-17-ol (IIIa.19)

$^1$H NMR (300 MHz, CDCl$_3$) δ ppm: 7.51 (d, J=2.8 Hz, 1H), 6.82 (d, J=8.8 Hz, 1H), 6.53 (dd, J=2.8, 8.8 Hz, 1H), 5.50-5.49 (m, 1H), 3.86 (s, 3H), 3.81 (s, 3H), 3.69 (t, J=8.5 Hz, 1H), 2.76-2.71 (m, 2H), 2.26-2.01 (m, 3H), 1.91-1.87 (m, 1H), 1.80-1.26 (m, 10H), 1.21-1.10 (m, 3H), 1.06 (s, 3H), 0.81 (s, 3H); $^{13}$C APT NMR (75 MHz, CDCl$_3$) δ ppm: 160.0, 153.2, 143.4, 141.4, 135.5, 129.3, 119.9, 118.0, 110.2, 105.0, 103.2, 81.0, 55.5, 55.0, 50.6, 47.3, 42.0, 35.9, 35.7, 33.5, 30.8, 30.5, 29.7, 23.0, 22.6, 20.2, 18.0, 10.3.

(1S,2R,13R,14S,17S,18S)-7-(3-hydroxyanilino)-2,18-dimethyl-8-thia-6-azapentacyclo[11.7.0.0²,¹⁰.0⁵,⁹.0¹⁴,¹⁸]icosa-5(9),6,10-trien-17-ol (IIIa.20)

$^1$H NMR (300 MHz, CDCl$_3$+MeOD-d3) δ ppm: 9.62 (d, J=8.1 Hz, 1H), 7.28-7.16 (m, 1H), 6.80 (d, J=7.5 Hz, 1H), 6.46 (s, 2H), 5.74 (s, 1H), 4.41 (s, 1H), 3.46-3.42 (m, 1H), 2.88-2.68 (m, 2H), 2.26-2.15 (m, 1H), 2.05-2.00 (m, 1H), 1.91-1.13 (m, 10H), 1.05-0.83 (m, 3H), 0.97 (s, 3H), 0.67 (s, 3H); $^{13}$C NMR (75 MHz, CDCl$_3$+MeOD-d3) δ ppm: 163.2, 158.2, 150.3, 136.3, 134.8, 131.5, 130.3, 122.6, 117.4, 117.1, 112.8, 80.4, 51.2, 48.1, 42.7, 36.7, 36.6, 34.2, 31.5, 30.2, 24.2, 23.4, 21.0, 18.9, 11.5.

(1S,2R,13R,14S,17S,18S)-2,18-dimethyl-7-[4-(trifluoromethoxy)7niline]-8-thia-6-azapentacyclo [11.7.0.0²,¹⁰.0⁵,⁹.0¹⁴,¹⁸]icosa-5(9),6,10-trien-17-ol (IIIa.22)

$^1$H NMR (300 MHz, CDCl$_3$) δ ppm: 7.44 (d, J=8.9 Hz, 2H), 7.31 (d, J=8.6 Hz, 2H), 5.56 (s, 1H), 3.69 (t, J=8.2 Hz, 1H), 2.88-2.67 (m, 2H), 2.28-2.07 (m, 3H), 1.93-1.88 (m, 1H), 1.77-1.27 (m, 8H), 1.20-1.03 (m, 3H), 1.03 (s, 3H), 0.80 (s, 3H); $^{13}$C APT (75 MHz, CDCl$_3$) δ ppm: 165.5, 147.4, 135.5, 133.7, 132.9, 122.9, 122.6, 118.6, 117.3, 81.6, 51.1, 47.7, 42.7, 36.8, 36.3, 32.9, 31.5, 31.1, 30.3, 23.3, 20.9, 20.8, 18.6, 11.0.

(1S,2R,13R,14S,17S,18S)-7-(3-fluoroanilino)-2,18-dimethyl-8-thia-6-azapentacyclo[11.7.0.0²,¹⁰.0⁵,⁹.0¹⁴,¹⁸]icosa-5(9),6,10-trien-17-ol (IIIa.11)

$^1$H NMR (300 MHz, CDCl$_3$) δ ppm: 7.45-7.39 (m, 1H), 7.19 (d, J=8.1 Hz, 1H), 7.14 (d, J=9.3 Hz, 1H), 7.01 (t, J=8.0 Hz, 1H), 5.58 (s, 1H), 3.69 (t, J=8.3 Hz, 1H), 2.87-2.75 (m, 2H), 2.28-2.06 (m, 5H), 1.92 (d, J=12.0 Hz, 1H), 1.81-1.25 (m, 8H), 1.18-1.09 (m, 3H), 1.02 (s, 3H), 0.80 (s, 3H); $^{13}$C (75 MHz, CDCl$_3$) δ ppm: 165.0, 163.0 (d, $^1$J=247.5 Hz), 138.3 (d, $^3$J=10.0 Hz), 133.7, 132.8, 131.5 (d, $^3$J=9.2 Hz), 122.7, 117.5, 116.8 (d, $^4$J=3.0 Hz), 114.0 (d, $^2$J=20.9 Hz), 108.4 (d, $^2$J=25.0 Hz), 81.6, 77.2, 51.1, 47.7, 42.8, 36.8, 36.3, 32.9, 31.5, 31.1, 30.2, 23.3, 20.9, 18.6, 11.1. HRMS (ESI-FTMS, m/z): calcd for $C_{26}H_{32}FN_2OS$ [M+H]$^+$ 439.2214, found 439.2210.

(1S,2R,13R,14S,17S,18S)-7-(4-fluoroanilino)-2,18-dimethyl-8-thia-6-azapentacyclo[11.7.0.0²,¹⁰.0⁵,⁹.0¹⁴,¹⁸]icosa-5(9),6,10-trien-17-ol (IIIa.12)

$^1$H NMR (300 MHz, CDCl$_3$) δ ppm: 7.38 (dd, J=4.6, 8.9 Hz, 2H), 7.11 (t, J=8.6 Hz, 2H), 5.44 (s, 1H), 3.47 (t, J=8.3 Hz, 1H), 2.70 (dd, J=4.8, 17.8 Hz, 1H), 2.57-2.50 (m, 2H), 2.17-2.11 (m, 1H), 1.98-1.15 (m, 10H), 1.10-0.93 (m, 3H), 0.93 (s, 3H), 0.66 (s, 3H); $^{13}$C NMR (75 MHz, CDCl$_3$) δ ppm: 166.7, 161.3 (d, $^1$J=247.0 Hz), 133.8, 133.1, 132.8, 124.4 (d, $^3$J=8.3 Hz), 122.3, 117.2 (d, $^2$J=23.0 Hz), 117.0, 81.5, 51.1, 47.7, 42.7, 36.8, 36.3, 33.0, 31.5, 31.1, 30.3, 23.3, 21.0, 20.9, 18.6, 11.1. HRMS (ESI-FTMS, m/z): calcd for $C_{26}H_{32}FN_2OS$ [M+H]$^+$ 439.2214, found 439.2215.

(1S,2R,13R,14S,17S,18S)-7-(2,4-difluoroanilino)-2,18-dimethyl-8-thia-6-azapentacyclo[11.7.0.0²,¹⁰.0⁵,⁹.0¹⁴,¹⁸]icosa-5(9),6,10-trien-17-ol (IIIa.13)

$^1$H NMR (300 MHz, DMSO-d6+CDCl$_3$) δ ppm: 7.67 (s, 1H), 7.19 (s, 1H), 7.04 (t, J=8.4 Hz, 1H), 5.47 (s, 1H), 3.45 (t, J=8.1 Hz, 1H), 2.68-2.57 (m, 2H), 2.18-2.12 (m, 1H), 1.98-1.95 (m, 1H), 1.81-1.16 (m, 11H), 1.04-1.00 (m, 3H), 0.95 (s, 3H), 0.66 (s, 3H); $^1$H NMR (300 MHz, DMSO-d6+CDCl$_3$) δ ppm: 165.7, 162.8-159.6 (m), 157.7-154.5 (m), 135.7, 134.3, 127.7, 122.1, 121.6, 119.1, 112.6 (d, $^2$J=22.3 Hz), 105.5 (t, $^2$J=25.6 Hz), 80.4, 51.2, 47.8, 42.7, 37.5, 36.6, 33.2, 31.5, 31.2, 30.1, 23.3, 21.5, 20.9, 18.7, 11.4. HRMS (ESI-FTMS, m/z): calcd for $C_{26}H_{31}F_2N_2OS$ [M+H]$^+$ 457.2120, found 457.2115.

(1S,2R,13R,14S,17S,18S)-2,18-dimethyl-7-[3-(trifluoromethoxy)anilino]-8-thia-6-azapentacyclo[11.7.0.0²,¹⁰.0⁵,⁹.0¹⁴,¹⁸]icosa-5(9),6,10-trien-17-ol (IIIa.34)

$^1$H NMR (300 MHz, DMSO-d6) δ ppm: 10.60 (br s, 1H), 8.09 (s, 1H), 7.85 (d, J=8.1 Hz, 1H), 7.50 (t, J=7.9 Hz, 1H), 7.24 (d, J=7.6 Hz, 1H), 5.39 (s, 1H), 3.43 (t, J=8.3 Hz, 1H), 2.64-2.15 (m, 2H), 2.16-2.10 (m, 1H), 1.96-1.92 (m, 1H), 1.78-1.15 (m, 12H), 1.03-0.81 (m, 3H), 0.95 (s, 3H), 0.65 (s, 3H); $^1$H NMR (300 MHz, DMSO-d6) δ ppm: 159.9, 145.7, 142.0, 136.4, 130.4, 130.0 (d, $^2$J=31.0 Hz), 124.6 (d, $^1$J=270.6 Hz), 120.8, 120.8, 119.0, 117.6, 113.3 (d, $^3$J=3.9 Hz), 80.3, 51.3, 48.1, 42.7, 36.8, 36.5, 34.2, 31.6, 31.2, 30.2, 24.3, 23.4, 21.0, 18.9, 11.0. HRMS (ESI-FTMS, m/z): calcd for $C_{26}H_{32}F_3N_2OS$ [M+H]$^+$ 457.2120, found 505.2130.

(1S,2R,13R,14S,17S,18S)-2,18-dimethyl-7-[3-(trifluoromethyl)anilino]-8-thia-6-azapentacyclo[11.7.0.0²,¹⁰.0⁵,⁹.0¹⁴,¹⁸]icosa-5(9),6,10-trien-17-ol (IIIa.36)

$^1$H NMR (300 MHz, DMSO-d6) δ ppm: 7.64-7.58 (m, 4H), 5.60-5.58 (m, 1H), 4.49 (br s, 1H), 3.69 (t, J=8.5 Hz, 1H), 2.98-2.67 (m, 2H), 2.29-2.16 (m, 1H), 2.12-2.06 (m, 2H), 1.98-1.88 (m, 1H), 1.81-1.06 (m, 12H), 1.03 (s, 3H), 0.81 (s, 3H); $^{13}$C APT NMR (75 MHz, DMSO-d6) δ ppm: 165.1, 137.6, 133.6, 133.0, 132.7, 132.3, 130.8, 124.4, 123.68-123.63 (m), 122.9, 117.9, 117.6-117.5 (m), 81.6, 51.1, 47.7, 42.7, 36.8, 36.3, 32.9, 31.5, 31.1, 30.3, 23.3, 20.9, 20.8, 18.6. 11.0. HRMS (ESI-FTMS, m/z): calcd for $C_{27}H_{32}F_3N_2OS$ [M+H]$^+$ 489.2181, found 489.2185.

3-[[(1S,2R,13R,14S,17S,18S)-17-hydroxy-2,18-dimethyl-8-thia-6-azapentacyclo[11.7.0.0²,¹⁰.0⁵,⁹.0¹⁴,¹⁸]icosa-5(9),6,10-trien-7-yl]amino]benzoic acid (IIIa.35)

$^1$H NMR (300 MHz, DMSO-d6) δ ppm: 8.18 (s, 1H), 7.95 (d, J=8.3 Hz, 1H), 7.49 (d, J=7.6 Hz, 1H), 7.40 (t, J=7.8 Hz, 1H), 5.37 (s, 1H), 3.44 (t, J=8.3 Hz, 1H), 2.62 (br s, 2H), 2.17-2.11 (m, 1H), 1.97-1.93 (m, 1H), 1.79-1.16 (m, 12H), 1.04-1.00 (m, 3H), 0.96 (s, 3H), 0.66 (s, 3H); $^{13}$C NMR (75 MHz, DMSO-d6) δ ppm: 167.7, 160.3, 145.5, 141.6, 136.5, 131.8, 129.5, 122.4, 121.5, 120.3, 118.7, 118.2, 80.3, 51.3, 48.1, 42.8, 36.8, 36.5, 34.2, 31.6, 31.3, 30.2, 24.3, 23.4, 21.0, 19.0, 11.7. HRMS (ESI-FTMS, m/z): calcd for $C_{27}H_{33}N_2O_3S$ [M+H]$^+$ 465.2206, found 465.2212.

4-[[(1S,2R,13R,14S,17S,18S)-17-hydroxy-2,18-dimethyl-8-thia-6-azapentacyclo[11.7.0.0²,¹⁰.0⁵,⁹.0¹⁴,¹⁸]icosa-5(9),6,10-trien-7-yl]amino]benzoic acid (IIIa.26)

$^1$H NMR (300 MHz, DMSO-d6) δ ppm: 7.86 (d, J=8.8 Hz, 2H), 7.69 (d, J=8.8 Hz, 2H), 5.41 (s, 1H), 3.43 (s, 1H), 2.47-2.53 (m, 2H), 2.27-2.12 (m, 1H), 1.98-1.94 (m, 1H), 1.79-1.18 (m, 12H), 1.04-1.01 (m, 3H), 0.96 (s, 3H), 0.66 (s, 3H); $^{13}$C NMR (75 MHz, DMSO-d6) δ ppm: 167.5, 159.5, 146.0, 145.2, 136.5, 131.1, 123.1, 121.2, 119.1, 116.4, 80.4, 51.3, 48.1, 42.8, 36.8, 36.5, 34.2, 31.6, 31.3, 30.2, 24.4, 23.4, 21.0, 19.0, 11.7. HRMS (ESI-FTMS, m/z): calcd for $C_{27}H_{33}N_2O_3S$ [M+H]$^+$ 465.2206, found 465.2215.

(1S,2R,13R,14S,17S,18S)-2,18-dimethyl-7-(2-nitroanilino)-8-thia-6-azapentacyclo[11.7.0.0²,¹⁰.0⁵,⁹.0¹⁴,¹⁸]icosa-5(9),6,10-trien-17-ol (IIIa.16)

$^1$H NMR (300 MHz, CDCl$_3$) δ ppm: 8.64 (d, J=7.3 Hz, 1H), 8.25 (d, J=7.1 Hz, 1H), 7.63 (t, J=7.4 Hz, 1H), 7.04 (t, J=7.3 Hz, 1H), 5.57 (s, 1H), 3.68 (t, J=8.8 Hz, 1H), 2.80-2.77 (m, 2H), 2.28-2.23 (m, 1H), 2.09-1.96 (m, 2H), 1.91-1.87 (m, 1H), 1.78-1.30 (m, 10H), 1.20-1.07 (3H), 0.99 (s, 3H), 0.77 (s, 3H); $^{13}$C APT NMR (75 MHz, CDCl$_3$) δ ppm: 157.2, 144.6, 136.6, 135.4, 135.1, 133.5, 125.3, 123.3, 119.9, 119.6, 118.5, 80.8, 50.4, 47.2, 41.9, 35.7, 35.5, 33.3, 30.7, 30.4, 29.5, 23.1, 22.4, 20.0, 17.8, 10.1. HRMS (ESI-FTMS, m/z): calcd for $C_{26}H_{32}N_3O_3S$ [M+H]$^+$ 466.2159, found 466.2157.

(1S,2R,13R,14S,17S,18S)-2,18-dimethyl-7-(2-pyridylamino)-8-thia-6-azapentacyclo[11.7.0.0²,¹⁰.0⁵,⁹.0¹⁴,¹⁸]icosa-5(9),6,10-trien-17-ol (IIIa.24)

$^1$H NMR (300 MHz, CDCl$_3$+DMSO-d6) δ ppm: 8.35 (d, J=4.4 Hz, 1H), 7.79 (t, J=7.5 Hz, 1H), 7.47 (d, J=8.3 Hz, 1H), 7.10 (t, J=5.6 Hz, 1H), 5.65 (s, 1H), 3.45 (t, J=8.3 Hz, 1H), 2.84-2.77 (m, 1H), 2.64-2.50 (m, 1H), 2.18-2.12 (m, 1H), 2.00-1.96 (m, 1H), 1.86-1.13 (m, 10H), 1.03-0.92 (m, 3H), 0.92 (s, 3H), 0.65 (s, 3H); $^{13}$C NMR (75 MHz, CDCl$_3$+DMSO-d6) δ ppm: 158.7, 149.0, 144.7, 139.9, 134.5, 134.1, 121.9, 119.1, 113.6, 81.0, 51.2, 47.8, 42.7, 36.6, 36.4, 33.2, 31.4, 31.2, 30.1, 23.3, 21.1, 20.9, 18.6, 11.4. HRMS (ESI-FTMS, m/z): calcd for $C_{25}H_{32}N_3OS$ [M+H]$^+$ 422.2261, found 422.2254.

N-[(1S,2R,13R,14S,17S,18S)-17-hydroxy-2,18-dimethyl-8-thia-6-azapentacyclo[11.7.0.0²,¹⁰.0⁵,⁹.0¹⁴,¹⁸]icosa-5(9),6,10-trien-7-yl]acetamide (IIIa.37)

$^1$H NMR (300 MHz, CDCl$_3$) δ 5.74-5.73 (m, 1H), 3.69 (t, J=8.2 Hz, 1H), 2.74-2.73 (m, 2H), 2.26-2.23 (m, 4H), 2.17-2.02 (m, 2H), 1.91-1.87 (m, 1H), 1.77-1.64 (m, 4H), 1.55-1.26 (m, 4H), 1.16-1.06 (m, 3H), 1.03 (s, 3H), 0.81 (s, 3H); $^{13}$C NMR (75 MHz, CDCl$_3$) δ=167.6, 155.9, 141.7, 135.8, 125.5, 120.5, 120.4, 81.7, 51.3, 48.0, 42.8, 36.5, 34.2, 31.5, 31.3, 30.4, 23.4, 23.38, 23.34, 21.0, 18.6, 11.0.

(1S,2R,13R,14S,17S,18S)-7-(4-hydroxyphenyl)-2,18-dimethyl-8-thia-6-azapentacyclo[11.7.0.0²,¹⁰.0⁵,⁹.0¹⁴,¹⁸]icosa-5(9),6,10-trien-17-ol (IIIa.38)

$^1$H NMR (300 MHz, CDCl$_3$+DMSO-d6) δ ppm: 7.71 (d, J=8.6 Hz, 2H), 6.84 (d, J=8.3 Hz, 2H), 5.73 (s, 1H), 3.46 (t, J=8.3 Hz, 1H), 2.87-2.72 (m, 1H), 2.22-2.16 (m, 1H), 2.04-2.01 (m, 1H), 1.81-1.18 (m, 12H), 1.06-0.97 (m, 3H), 0.97 (s, 3H), 0.63 (s, 3H); $^{13}$C APT NMR (75 MHz, CDCl$_3$+DMSO-d6) δ ppm: 164.1, 160.2, 148.9, 136.1, 130.2, 128.2, 124.0, 122.4, 116.3, 80.4, 51.3, 48.1, 42.8, 36.7, 36.6, 34.1, 31.58, 31.51, 30.2, 23.8, 23.4, 21.1, 18.9, 11.6. HRMS (ESI-FTMS, m/z): calcd for $C_{26}H_{31}NO_2S$ [M+H]$^+$ 422.2148, found 422.2151.

[(E)-[(1S,2R,13R,14S,17S,18S)-7-amino-2,18-dimethyl-8-thia-6-azapentacyclo[11.7.0.0²,¹⁰.0⁵,⁹.0¹⁴,¹⁸]icosa-5(9),6,10-trien-17-ylidene]amino]urea (IVa.1)

$^1$H NMR (300 MHz, CDCl$_3$) δ 6.12 (br s, 2H), 5.46 (s, 1H), 2.72-2.14 (m, 5H), 1.98-1.65 (m, 6H), 1.45-1.13 (m, 6H), 0.97 (s, 3H), 0.83 (s, 3H).

17-(1,5-dimethylhexyl)-2,18-dimethyl-8-thia-6-azapentacyclo[11.7.0.02,10.05,9.014,18]icosa-5(9),6,10-trien-7-amine (X.1)

$^1$H NMR (300 MHz, DMSO-d$_6$): δ 5.40-5.38 (m, 1H), 4.92 (s, 1H), 2.65-2.62 (m, 2H), 2.20-2.16 (m, 1H), 2.07-1.94 (m, 2H), 1.87-1.03 (m, 26H), 0.93 (d, J=6.4 Hz, 3H), 0.89-0.86 (m, 6H), 0.71 (s, 2H); $^{13}$C NMR (75 MHz, DMSO-d$_6$) δ 167.6, 155.7, 142.7, 136.0, 125.8, 56.7, 56.1, 47.9, 42.3, 39.7, 39.5, 36.4, 36.1, 35.8, 34.3, 31.7, 31.4, 28.2, 28.0, 24.2, 23.8, 23.3, 22.8, 22.5, 21.4, 18.7, 18.5. HRMS (ESI-FTMS Mass (m/z): calcd for C$_{28}$H$_{44}$N$_2$S [M+H]$^+$=441.3298, found 441.3294.

17-(1,5-dimethylhexyl)-N-(2,4-dimethylphenyl)-2,18-dimethyl-8-thia-6-azapentacyclo[11.7.0.02,10.05,9.014,18]icosa-5(9),6,10-trien-7-amine (X.12)

$^1$H NMR (300 MHz, DMSO-d$_6$): δ 7.41 (d, J=7.8 Hz, 1H), 6.83-6.81 (m, 2H), 5.39-5.38 (m, 1H), 2.68-2.66 (m, 2H), 2.32 (s, 3H), 2.27 (s, 3H), 2.20 (br s, 1H), 2.15-2.12 (m, 1H), 2.07 (br s, 1H), 2.03 (br s, 1H), 1.97 (br s, 1H), 1.84-1.73 (m, 4H), 1.68-1.60 (m, 6H), 1.55-1.49 (m, 2H), 1.46-1.44 (m, 1H), 1.40-1.31 (m, 5H), 1.26 (br s, 1H), 1.21 (d, J=4.6 Hz, 1H), 1.18-1.10 (m, 8H), 1.04 (s, 3H), 0.94 (d, J=6.4 Hz, 3H), 0.89-0.86 (m, 8H), 0.72 (s, 3H); $^{13}$C NMR (75 MHz, DMSO-d$_6$) δ 164.4, 145.4, 136.5, 136.0, 134.7, 131.7, 130.3, 127.6, 121.8, 120.5, 118.0, 56.8, 56.1, 48.0, 42.3, 39.7, 39.5, 36.5, 36.1, 35.8, 34.3, 31.6, 31.5, 28.3, 28.0, 24.2, 24.0, 23.8, 22.8, 22.5, 21.3, 20.8, 18.7, 17.7, 11.9. HRMS (ESI-FTMS Mass (m/z): calcd for C$_{36}$H$_{52}$N$_2$S [M+H]$^+$=545.3924, found 545.3927.

N-(2,5-dimethoxyphenyl)-17-(1,5-dimethylhexyl)-2,18-dimethyl-8-thia-6-azapentacyclo[11.7.0.02,10.05,9.014,18]icosa-5(9),6,10-trien-7-amine (X.16)

$^1$H NMR (300 MHz, DMSO-d$_6$): δ 7.64-7.63 (m, 1H), 6.79 (d, J=8.7 Hz, 1H), 6.48-6.44 (m, 1H), 5.49 (s, 1H), 3.85-3.81 (m, 6H), 2.75-2.73 (m, 2H), 2.24-2.18 (m, 1H), 2.03 (t, J=12.8 Hz, 2H), 1.84-1.72 (m, 7H), 1.65-1.47 (m, 4H), 1.41-1.34 (m, 3H), 1.27 (br s, 1H), 1.22 (d, J=4.5 Hz, 1H), 1.13-1.11 (m, 7H), 1.05 (s, 4H), 0.94 (d, J=6.3 Hz, 3H), 0.88 (d, J=6.3 Hz, 6H), 0.72 (s, 3H); $^{13}$C NMR (75 MHz, DMSO-d$_6$) δ 159.6, 153.6, 145.1, 141.3, 136.0, 130.1, 120.8, 118.3, 110.3, 104.6, 103.1, 56.3, 55.8, 55.7, 55.3, 47.6, 41.9, 39.3, 39.1, 36.2, 35.7, 35.4, 33.9, 31.3, 31.1, 27.8, 27.6, 23.8, 23.4, 22.4, 22.1, 20.9, 18.3, 11.5. HRMS (ESI-FTMS Mass (m/z): calcd for C$_{36}$H$_{52}$N$_2$O$_2$S [M+H]$^+$=577.3822, found 577.3824.

N-(2-chlorophenyl)-17-(1,5-dimethylhexyl)-2,18-dimethyl-8-thia-6-azapentacyclo[11.7.0.02,10.05,9.014,18]icosa-5(9),6,10-trien-7-amine (X.9)

$^1$H NMR (300 MHz, DMSO-d$_6$): δ 8.07 (d, J=8.1 Hz, 1H), 7.38 (d, J=7.9 Hz, 1H), 7.31-7.27 (m, 1H), 6.95 (t, J=7.4 Hz, 1H), 5.52 (s, 1H), 2.76-2.71 (m, 2H), 2.25-2.19 (m, 1H), 2.04 (t, J=12.3 Hz, 2H), 1.88-1.78 (m, 2H), 1.72-1.61 (m, 4H), 1.56-1.42 (m, 4H), 1.39-1.32 (m, 3H), 1.28 (br s, 1H), 1.23 (d, J=4.7 Hz, 1H), 1.17-1.12 (m, 7H), 1.06 (s, 4H), 0.94 (d, J=6.4 Hz, 3H), 0.88 (d, J=6.5 Hz, 6H), 0.73 (s, 3H); $^{13}$C NMR (75 MHz, DMSO-d$_6$) δ 159.6, 145.6, 136.8, 136.3, 129.4, 127.8, 122.5, 122.2, 121.5, 119.4, 117.7, 56.7, 56.1, 48.0, 42.3, 39.7, 39.5, 36.6, 36.1, 35.8, 34.3, 31.5, 28.2, 28.0, 24.2, 23.8, 22.8, 22.5, 21.3, 18.7, 11.9. HRMS (ESI-FTMS Mass (m/z): calcd for C$_{34}$H$_{47}$ClN$_2$S [M+H]$^+$=551.3221, 553.3195, found 551.3229, 553.3208.

N-allyl-17-(1,5-dimethylhexyl)-2,18-dimethyl-8-thia-6-azapentacyclo[11.7.0.02,10.05,9.014,18]icosa-5(9),6,10-trien-7-amine (X.2)

$^1$H NMR (300 MHz, DMSO-d$_6$): δ 5.95-5.86 (m, 1H), 5.67 (br s, 1H), 5.37-5.16 (m, 3H), 3.89 (s, 2H), 2.63-2.60 (m, 2H), 2.20-2.14 (m, 1H), 2.04-1.92 (m, 3H), 1.85-1.01 (m, 32H), 0.91 (d, J=6.3 Hz, 5H), 0.86 (d, J=6.3 Hz, 5H), 0.69 (s, 3H); $^{13}$C NMR (75 MHz, DMSO-d$_6$) δ 166.4, 145.2, 136.3, 133.3, 119.4, 117.0, 116.6, 56.4, 55.7, 47.7, 47.6, 41.9, 39.3, 39.1, 36.1, 35.7, 35.4, 33.9, 31.2, 31.1, 27.8, 27.6, 23.8, 23.4, 22.4, 22.1, 20.9, 18.3, 11.5. HRMS (ESI-FTMS Mass (m/z): calcd for C$_{31}$H$_{48}$N$_2$S [M+H]$^+$=481.3611, found 481.3599.

17-(1,5-dimethylhexyl)-2,18-dimethyl-N-(2-nitrophenyl)-8-thia-6-azapentacyclo[11.7.0.02,10.05,9.014,18]icosa-5(9),6,10-trien-7-amine (X.11)

$^1$H NMR (300 MHz, DMSO-d$_6$): δ 8.72-8.69 (m, 1H), 8.27-8.24 (m, 1H), 7.66-7.60 (m, 1H), 7.04-6.98 (m, 1H), 5.59 (s, 1H), 2.87-2.80 (m, 2H), 2.28-2.19 (m, 1H), 2.09-2.02 (m, 2H), 1.88-1.79 (m, 2H), 1.73-1.62 (m, 4H), 1.58-1.47 (m, 3H), 1.44-1.35 (m, 4H), 1.28-1.27 (m, 1H), 1.23 (d, J=4.2 Hz, 1H), 1.18-1.08 (m, 7H), 1.06 (s, 3H), 0.94 (d, J=6.4 Hz, 3H), 0.90-0.87 (m, 6H), 0.73 (s, 3H); $^{13}$C NMR (75 MHz, DMSO-d$_6$) δ 157.6, 146.3, 138.0, 136.3, 136.0, 133.8, 126.2, 124.8, 120.8, 120.3, 119.1, 56.7, 56.1, 48.0, 42.3, 39.7, 39.5, 36.6, 36.1, 35.8, 34.2, 31.8, 31.5, 28.2, 28.0, 24.3, 24.2, 23.8, 22.8, 22.5, 21.3, 18.6, 11.9. HRMS (ESI-FTMS Mass (m/z): calcd for C$_{34}$H$_{47}$N$_3$O$_2$S [M+H]$^+$=562.3462, found 562.3453.

17-(1,5-dimethylhexyl)-2,18-dimethyl-N-[2-(trifluoromethyl)phenyl]-8-thia-6-azapentacyclo[11.7.0.02,10.05,9.014,18]icosa-5(9),6,10-trien-7-amine (X.6)

$^1$H NMR (300 MHz, DMSO-d$_6$): δ 8.04 (d, J=8.2 Hz, 1H), 7.63-7.52 (m, 2H), 7.14 (t, J=7.5 Hz, 1H), 5.49 (s, 1H), 2.74 (s, 2H), 2.24-2.18 (m, 1H), 2.04 (t, J=12.3 Hz, 2H), 1.85-1.77 (m, 2H), 1.72-1.61 (m, 4H), 1.56-1.47 (m, 3H), 1.42-1.35 (m, 5H), 1.23 (s, 1H), 1.23 (d, J=3.7 Hz, 1H), 1.18-1.08 (m, 9H), 1.06 (s, 4H), 0.94 (d, J=6.3 Hz, 4H), 0.88 (d, J=6.5 Hz, 7H), 0.73 (s, 3H); $^{13}$C NMR (75 MHz, DMSO-d$_6$) 160.64, 145.4, 138.5, 136.2, 133.1, 126.7-126.6 (m), 125.9, 122.7, 122.3, 120.6, 119.5, 118.6 (d, J=29.5 Hz), 56.7, 56.1, 48.0, 42.3, 39.7, 39.5, 36.6, 36.1, 35.8, 34.2, 31.7, 31.5, 28.2, 28.0, 24.2, 24.0, 23.8, 22.8, 22.5, 21.3, 18.7, 11.9. HRMS (ESI-FTMS Mass (m/z): calcd for C$_{35}$H$_{47}$F$_3$N$_2$S [M+H]$^+$=585.3485, found 585.3482.

17-(1,5-dimethylhexyl)-2,18-dimethyl-N-(2-pyridyl)-8-thia-6-azapentacyclo[11.7.0.02,10.05,9.014,18]icosa-5(9),6,10-trien-7-amine (X.18)

$^1$H NMR (300 MHz, DMSO-d$_6$): δ 8.36-8.35 (m, 1H), 7.72-7.42 (m, 1H), 6.88-6.83 (m, 2H), 5.70-5.68 (m, 1H), 2.75-2.74 (m, 2H), 2.26-2.21 (m, 1H), 2.04 (t, J=12.0 Hz, 2H), 1.87-1.05 (m, 29H), 0.94 (d, J=6.4 Hz, 3H), 0.90-0.80 (m, 7H), 0.703 (s, 3H); $^{13}$C NMR (75 MHz, DMSO-d$_6$) δ 158.2, 151.6, 147.0, 143.1, 137.5, 136.6, 123.2, 118.5, 116.1, 110.6, 56.8, 56.1, 48.0, 42.3, 39.7, 39.5, 36.4, 36.1, 35.8, 34.4, 31.7, 31.5, 28.2, 28.0, 24.2, 24.0, 23.8, 22.8, 22.5, 21.4, 18.7, 11.9. HRMS (ESI-FTMS Mass (m/z): calcd for $C_{33}H_{47}N_3S$ [M+H]$^+$=518.3563, found 518.3550.

17-(1,5-dimethylhexyl)-2,18-dimethyl-N-pyrimidin-2-yl-8-thia-6-azapentacyclo[11.7.0.02,10.05,9.014,18]icosa-5(9),6,10-trien-7-amine (X.19)

$^1$H NMR (300 MHz, DMSO-d$_6$): δ 8.67-8.65 (m, 2H), 6.90-6.86 (m, 1H), 5.69 (s, 1H), 2.90-2.75 (m, 2H), 2.25-2.19 (m, 1H), 2.08-2.01 (m, 2H), 1.94-1.81 (m, 2H), 1.79-1.61 (m, 3H), 1.56-1.46 (m, 3H), 1.43-1.32 (m, 4H), 1.27 (br s, 1H), 1.22 (d, J=3.7 Hz, 1H), 1.14-1.11 (m, 8H), 1.04 (s, 4H), 0.94 (d, J=6.2 Hz, 3H), 0.88 (d, J=6.5 Hz, 7H), 0.73 (s, 3H); $^{13}$C NMR (75 MHz, DMSO-d$_6$) δ 157.9, 157.0, 156.7, 144.2, 136.7, 124.4, 118.6, 113.5, 56.8, 56.1, 48.0, 42.3, 39.7, 39.5, 36.4, 36.2, 35.8, 34.4, 31.7, 31.5, 28.2, 28.0, 24.2, 23.9, 22.8, 22.5, 21.4, 18.7, 18.6, 11.9. HRMS (ESI-FTMS Mass (m/z): calcd for $C_{32}H_{46}N_4S$ [M+H]$^+$=519.3516, found 519.3518.

17-(1,5-dimethylhexyl)-N,2,18-trimethyl-N-phenyl-8-thia-6-azapentacyclo[11.7.0.02,10.05,9.014,18]icosa-5(9),6,10-trien-7-amine (Xa.1)

$^1$H NMR (300 MHz, DMSO-d$_6$): δ 7.44-7.33 (m, 4H), 7.30-7.24 (m, 1H), 5.31-5.29 (m, 1H), 3.53 (s, 3H), 2.74-2.69 (m, 2H), 2.16-2.11 (m, 1H), 2.07-1.97 (m, 2H), 1.86-1.74 (m, 2H), 1.66-1.58 (m, 3H), 1.55-1.43 (m, 3H), 1.40-1.29 (m, 4H), 1.25-1.24 (m, 1H), 1.20 (d, J=4.5 Hz, 1H), 1.14-1.07 (m, 7H), 1.03 (s, 4H), 0.93 (d, J=6.4 Hz, 3H), 0.89-0.86 (m, 6H), 0.71 (s, 3H); $^{13}$C NMR (75 MHz, DMSO-d$_6$) δ 166.9, 146.4, 146.0, 136.7, 129.6, 126.4, 125.2, 120.5, 117.8, 56.8, 56.1, 48.0, 42.3, 40.0, 39.7, 39.5, 36.4, 36.1, 35.8, 34.4, 31.6, 31.5, 28.2, 28.0, 24.3, 24.2, 23.8, 22.8, 22.5, 21.3, 18.7, 11.9. HRMS (ESI-FTMS Mass (m/z): calcd for $C_{35}H_{50}N_2S$ [M+H]$^+$=531.3767, found 531.3753.

N-(2,4-dimethoxyphenyl)-17-(1,5-dimethylhexyl)-2,18-dimethyl-8-thia-6-azapentacyclo[11.7.0.02,10.05,9.014,18]icosa-5(9),6,10-trien-7-amine (X.16)

$^1$H NMR (300 MHz, DMSO-d$_6$): δ 7.76-7.73 (m, 1H), 6.51 (s, 1H), 5.44 (s, 1H), 3.83 (d, J=12.3 Hz, 6H), 2.72-2.70 (m, 2H), 2.22-2.16 (m, 1H), 2.03 (t, J=12.6 Hz, 2H), 1.84-1.80 (m, 2H), 1.76-1.60 (m, 4H), 1.55-1.45 (m, 3H), 1.41-1.34 (m, 5H), 1.26 (br s, 1H), 1.22 (d, J=3.6 Hz, 1H), 1.13-1.11 (m, 9H), 1.04 (s, 5H), 0.94 (d, J=6.1 Hz, 4H), 0.88 (d, J=6.5 Hz, 7H), 0.72 (s, 3H); $^{13}$C NMR (75 MHz, DMSO-d$_6$) δ 162.2, 155.7, 149.6, 145.6, 136.6, 123.6, 120.3, 118.5, 118.2, 103.6, 99.0, 56.8, 56.1, 55.7, 55.6, 48.0, 42.3, 39.7, 39.5, 36.5, 36.1, 35.8, 34.4, 31.7, 31.5, 28.2, 28.0, 24.2, 24.2, 22.8, 22.5, 21.3, 18.7, 11.9. HRMS (ESI-FTMS Mass (m/z): calcd for $C_{36}H_{52}N_2O_2S$ [M+H]$^+$=577.3822, found 577.3812.

N-(5-chloro-2-methoxy-phenyl)-17-(1,5-dimethylhexyl)-2,18-dimethyl-8-thia-6-azapentacyclo[11.7.0.02,10.05,9.014,18]icosa-5(9),6,10-trien-7-amine (X.17)

$^1$H NMR (300 MHz, DMSO-d$_6$): δ 8.11-8.10 (m, 1H), 6.92-6.88 (m, 1H), 6.78-6.75 (m, 1H), 5.52 (s, 1H), 3.88 (s, 3H), 2.77-2.71 (m, 2H), 2.24-2.18 (m, 1H), 2.08-2.04 (m, 3H), 1.84-1.72 (m, 3H), 1.65-1.53 (m, 5H), 1.51-1.47 (m, 5H), 1.41-1.34 (m, 7H), 1.27 (br s, 1H), 1.22 (d, J=3.6 Hz, 1H), 1.15-1.13 (m, 10H), 1.05 (s, 4H), 0.94 (d, J=6.3 Hz, 4H), 0.88 (d, J=6.5 Hz, 7H), 0.72 (s, 3H); $^{13}$C NMR (75 MHz, DMSO-d$_6$) δ 159.3, 145.8, 145.6, 136.4, 130.8, 126.1, 121.8, 120.7, 119.2, 115.9, 110.6, 56.7, 56.1, 55.9, 48.0, 42.3, 39.7, 39.5, 36.6, 36.1, 35.8, 34.3, 31.7, 31.5, 28.26, 28.04, 24.2, 23.8, 22.8, 22.5, 21.3, 18.7, 11.9. HRMS (ESI-FTMS Mass (m/z): calcd for $C_{35}H_{49}ClN_2OS$ [M+H]$^+$=581.3327, 583.3301, found 581.3321, 583.3307.

17-(1,5-dimethylhexyl)-N-(2-methoxyphenyl)-2,18-dimethyl-8-thia-6-azapentacyclo[11.7.0.02,10.05,9.014,18]icosa-5(9),6,10-trien-7-amine (X.14)

$^1$H NMR (300 MHz, DMSO-d$_6$): δ 7.94-7.90 (m, 1H), 7.02-6.96 (m, 2H), 6.90-6.87 (m, 1H), 5.49 (s, 1H), 3.87 (s, 3H), 2.75 (s, 2H), 2.24-2.18 (m, 1H), 2.04 (t, J=12.2 Hz, 2H), 1.88-1.77 (m, 2H), 1.72-1.61 (m, 4H), 1.56-1.46 (m, 5H), 1.41-1.131 (m, 4H), 1.27 (s, 1H), 1.22 (d, J=4.2 Hz, 1H), 1.18-1.08 (m, 9H), 1.05 (s, 4H), 0.94 (d, J=6.3 Hz, 4H), 0.88 (d, J=6.5 Hz, 8H), 0.73 (s, 3H); $^{13}$C NMR (75 MHz, DMSO-d$_6$) δ 160.5, 147.3, 145.5, 136.5, 129.8, 121.7, 121.0, 118.6, 116.0, 110.0, 56.8, 56.1, 55.7, 48.0, 42.3, 39.7, 39.5, 36.6, 36.1, 35.8, 34.2, 31.7, 31.5, 28.2, 28.0, 24.2, 23.8, 22.8, 22.5, 21.3, 18.7, 11.9. HRMS (ESI-FTMS Mass (m/z): calcd for $C_{35}H_{50}N_2OS$ [M+H]$^+$=547.3717, found 547.3711.

N-[3,5-bis(trifluoromethyl)phenyl]-17-(1,5-dimethylhexyl)-2,18-dimethyl-8-thia-6-azapentacyclo[11.7.0.02,10.05,9.014,18]icosa-5(9),6,10-trien-7-amine (X.10)

$^1$H NMR (300 MHz, DMSO-d$_6$): δ 7.88 (s, 2H), 7.48 (s, 1H), 5.55 (s, 1H), 2.76 (s, 2H), 2.26-2.16 (m, 1H), 2.05 (t, J=12.3 Hz, 2H), 1.86-1.78 (m, 3H), 1.73-1.62 (m, 5H), 1.55-1.47 (m, 4H), 1.41-1.35 (m, 5H), 1.27 (s, 1H), 1.22 (d, J=3.8 Hz, 1H), 1.14-1.11 (m, 8H), 1.05 (s, 3H), 0.94 (d, J=6.4 Hz, 4H), 0.88 (d, J=6.1 Hz, 7H), 0.73 (s, 3H); $^{13}$C NMR (75 MHz, DMSO-d$_6$) δ 159.5, 145.2, 141.8, 136.0, 133.2-131.9 (m), 123.1 (d, J=270 Hz), 122.6, 120.2, 117.0, 115.2, 56.7, 57.1, 47.9, 42.3, 39.6, 39.5, 36.6, 36.1, 35.8, 34.2, 31.7, 31.5, 28.2, 28.0, 24.2, 24.1, 23.8, 22.8, 22.5, 21.3, 18.7, 18.6, 11.9. HRMS (ESI-FTMS Mass (m/z): calcd for $C_{36}H_{46}F_6N_2S$ [M+H]$^+$=653.3359, found 653.3350.

N-(2,4-difluorophenyl)-17-(1,5-dimethylhexyl)-2,18-dimethyl-8-thia-6-azapentacyclo[11.7.0.02,10.05,9.014,18]icosa-5(9),6,10-trien-7-amine (X.8)

$^1$H NMR (300 MHz, DMSO-d$_6$): δ 8.06-7.98 (m, 1H), 6.92-6.87 (m, 2H), 5.48 (s, 1H), 2.72 (s, 2H), 2.23-2.17 (m, 1H), 2.04 (t, J=12.2 Hz, 2H), 1.85-1.77 (m, 2H), 1.71-1.60 (m, 4H), 1.55-1.45 (m, 3H), 1.41-1.34 (m, 5H), 1.26 (s, 1H), 1.21 (d, J=4.6 Hz, 1H), 1.13-1.11 (m, 8H), 1.04 (s, 4H), 0.93 (d, J=6.4 Hz, 5H), 0.88 (d, J=6.4 Hz, 6H), 0.72 (s, 3H); $^{13}$C NMR (75 MHz, DMSO-d$_6$) δ 160.9, 157.6 (dd, J=10.9, 10.9 Hz), 152.3 (dd, J=11.7, 13.4 Hz), 145.5, 136.3, 125.3-125.1 (m), 121.6, 120.5 (d, J=9.1 Hz), 119.2, 111.4-111.0 (m), 104.2, 103.6 (m), 56.7, 56.1, 48.0, 42.3, 39.4, 39.5, 36.5, 36.1, 35.8, 34.2, 31.7, 31.5, 28.2, 28.0, 24.2, 24.1, 23.8, 22.8, 22.5, 21.3, 18.7, 11.9. HRMS (ESI-FTMS Mass (m/z): calcd for $C_{34}H_{46}F_2N_2S$ [M+H]$^+$=553.3423, found 553.3416.

17-(1,5-dimethylhexyl)-2,18-dimethyl-N-(2,4,6-trimethylphenyl)-8-thia-6-azapentacyclo[11.7.0.02,10.05,9.014,18]icosa-5(9),6,10-trien-7-amine (X.13)

$^1$H NMR (300 MHz, DMSO-d$_6$): δ 6.96 (s, 2H), 5.27 (s, 1H), 2.57-2.50 (m, 2H), 2.32-2.28 (m, 9H), 2.22-1.02 (m, 35H), 0.93-0.86 (m, 10H), 0.70 (s, 3H); $^{13}$C NMR (75 MHz,

DMSO-d$_6$) δ 167.8, 145.8, 137.6, 136.7, 134.7, 129.4, 128.8, 119.9, 117.3, 56.8, 56.0, 48.0, 42.3, 39.6, 39.5, 36.5, 36.1, 35.7, 34.3, 31.6, 31.5, 28.2, 28.0, 24.2, 24.0, 23.8, 22.8, 22.5, 21.3, 21.0, 18.7, 18.7, 18.1, 11.9. HRMS (ESI-FTMS Mass (m/z): calcd for C$_{37}$H$_{54}$N$_2$S [M+H]$^+$=559.4080, found 559.4080.

17-(1,5-dimethylhexyl)-2,18-dimethyl-N-phenyl-8-thia-6-azapentacyclo[11.7.0.0$^{2,10}$.0$^{5,9}$.0$^{14,18}$]icosa-5(9),6,10-trien-7-amine (X.5)

$^1$H NMR (300 MHz, DMSO-d$_6$): δ 7.35-7.27 (m, 4H), 7.16-7.04 (m, 1H), 5.47 (br s, 1H), 2.70-2.68 (m, 2H), 2.23-2.17 (m, 1H), 2.08-1.97 (m, 3H), 1.85-1.04 (m, 37H), 0.94 (d, J=6.4 Hz, 4H), 0.89-0.87 (m, 7H), 0.72 (s, 3H); $^{13}$C NMR (75 MHz, DMSO-d$_6$) 140.1, 136.4, 129.2, 122.9, 120.7, 120.5, 118.7, 118.3, 56.8, 56.1, 48.0, 42.3, 39.7, 39.5, 36.6, 35.8, 34.3, 31.7, 31.5, 30.9, 28.2, 28.0, 24.2, 24.0, 23.8, 22.8, 22.5, 21.3, 18.7, 11.9. HRMS (ESI-FTMS Mass (m/z): calcd for C$_{34}$H$_{48}$N$_2$S [M+H]$^+$=517.3611, found 517.3614.

17-(1,5-dimethylhexyl)-2,18-dimethyl-N-(p-tolyl)-8-thia-6-azapentacyclo[11.7.0.0$^{2,10}$.0$^{5,9}$.0$^{14,18}$]icosa-5(9),6,10-trien-7-amine (X.7)

$^1$H NMR (300 MHz, DMSO-d$_6$): δ 7.24-7.14 (m, 4H), 5.44-5.42 (m, 1H), 2.68-2.66 (m, 2H), 2.34 (s, 3H), 2.22-2.16 (m, 1H), 2.07-1.96 (m, 2H), 1.85-1.04 (m, 29H), 0.94 (d, J=6.4 Hz, 3H), 0.89-0.87 (m, 7H), 0.72 (s, 3H); $^{13}$C NMR (75 MHz, DMSO-d$_6$) 162.8, 145.1, 137.8, 136.5, 133.0, 129.9, 120.9, 119.3, 118.3, 56.8, 56.1, 48.0, 42.3, 39.7, 39.5, 36.5, 36.1, 35.8, 34.3, 31.7, 31.5, 28.2, 28.0, 24.2, 24.0, 23.8, 22.8, 22.5, 21.3, 20.8, 18.7, 11.9. HRMS (ESI-FTMS Mass (m/z): calcd for C$_{35}$H$_{50}$N$_2$S [M+H]$^+$=531.3767, found 531.3767.

N-benzyl-17-(1,5-dimethylhexyl)-2,18-dimethyl-8-thia-6-azapentacyclo[11.7.0.0$^{2,10}$.0$^{5,9}$.0$^{14,18}$]icosa-5(9),6,10-trien-7-amine (X.3)

$^1$H NMR (300 MHz, DMSO-d$_6$): δ 7.37-7.28 (m, 5H), 5.38-5.36 (m, 1H), 4.48 (s, 2H), 2.64-2.61 (m, 1H), 2.26-2.15 (m, 1H), 2.07-1.94 (m, 4H), 1.87-1.02 (m, 28H), 0.93 (d, J=6.4 Hz, 3H), 0.89-0.86 (m, 8H), 0.71 (s, 4H); $^{13}$C NMR (75 MHz, DMSO-d$_6$) 166.9, 144.1, 137.1, 136.3, 128.7, 127.8, 127.6, 119.6, 118.1, 56.7, 56.1, 49.8, 47.9, 42.3, 39.7, 39.5, 36.5, 36.1, 35.8, 34.2, 31.6, 31.5 28.2, 28.0, 24.2, 23.8, 23.7, 22.8, 22.5, 21.3, 18.7, 11.9. HRMS (ESI-FTMS Mass (m/z): calcd for C$_{35}$H$_{50}$N$_2$S [M+H]$^+$=531.3767, found 531.3765.

7-amino-17-ethynyl-2,18-dimethyl-8-thia-6-azapentacyclo[11.7.0.0$^{2,10}$.0$^{5,9}$.0$^{14,18}$]icosa-5(9),6,10-trien-17-ol (XI.1)

$^1$H NMR (300 MHz, DMSO-d$_6$): δ 5.41-5.40 (m, 1H), 2.67-2.58 (m, 3H), 2.36-2.24 (m, 2H), 2.21-2.17 (m, 1H), 2.08-1.98 (m, 3H), 1.83-1.66 (m, 7H), 2.67-1.34 (m, 5H), 1.21-1.15 (m, 1H), 1.04-1.03 (m, 3H), 0.91-0.89 (m, 4H); $^{13}$C NMR (75 MHz, DMSO-d$_6$): δ 165.3, 135.9, 120.9, 118.8, 87.3, 79.8, 74.1, 59.0, 50.7, 47.5, 46.6, 38.9, 36.6, 34.0, 32.4, 32.1, 31.1, 23.2, 23.1, 21.0, 18.6, 12.7. HRMS (ESI-FTMS Mass (m/z): calcd for C$_{22}$H$_{28}$N$_2$OS [M+H]$^+$ 369.1995 found 369.1981.

17-ethynyl-2,18-dimethyl-7-(pyrimidin-2-ylamino)-8-thia-6-azapentacyclo[11.7.0.0$^{2,10}$.0$^{5,9}$.0$^{14,18}$]icosa-5(9),6,10-trien-17-ol (XI.6)

$^1$H NMR (300 MHz, DMSO-d$_6$): δ 8.64 (s, 2H), 7.05-6.90 (m, 1H), 5.70 (s, 1H), 3.09-2.79 (m, 2H), 2.59 (s, 1H), 2.29-2.03 (m, 9H), 1.78-1.47 (m, 10H), 1.19-1.04 (m, 4H), 0.90 (s, 3H); $^{13}$C NMR (75 MHz, DMSO-d$_6$): δ 181.3, 158.0, 157.3, 143.1, 136.6, 123.4, 118.2, 115.6, 113.6, 88.9, 50.6, 47.7, 46.6, 40.9, 36.3, 34.2, 32.6, 32.1, 31.3, 30.9, 23.6, 23.2, 21.0, 18.7, 12.9. HRMS (ESI-FTMS Mass (m/z): calcd for C$_{26}$H$_{30}$N$_4$OS [M+H]$^+$ 447.2213 found 447.2207.

17-ethynyl-2,18-dimethyl-7-(2-nitroanilino)-8-thia-6-azapentacyclo[11.7.0.0$^{2,10}$.0$^{5,9}$.0$^{14,18}$]icosa-5(9),6,10-trien-17-ol (XI.3)

$^1$H NMR (300 MHz, DMSO-d$_6$): δ 8.66 (d, J=8.5 Hz, 1H), 8.27-8.24 (m, 1H), 7.66-7.61 (m, 1H), 7.03 (t, J=8.0 Hz, 1H), 5.58-5.57 (m, 1H), 2.89-2.76 (m, 2H), 2.60 (s, 1H), 2.38-2.22 (m, 2H), 2.10-1.99 (m, 3H), 1.86-1.28 (m, 11H), 1.24-1.15 (m, 1H), 1.07 (s, 3H), 0.92 (s, 3H); $^{13}$C NMR (75 MHz, DMSO-d$_6$): δ 158.0, 145.9, 137.7, 136.3, 136.0, 134.1, 126.2, 124.4, 120.7, 120.4, 119.3, 87.4, 79.8, 74.1, 50.7, 47.6, 46.6, 38.9, 36.6, 34.2, 32.5, 32.1, 31.3, 24.1, 23.1, 21.0, 18.7, 12.7. HRMS (ESI-FTMS Mass (m/z): calcd for C$_{28}$H$_{31}$N$_3$O$_3$S [M+H]$^+$ 490.2159 found 490.2154.

17-ethynyl-2,18-dimethyl-7-(2-pyridylamino)-8-thia-6-azapentacyclo[11.7.0.0$^{2,10}$.0$^{5,9}$.0$^{14,18}$]icosa-5(9),6,10-trien-17-ol (XI.5)

$^1$H NMR (300 MHz, DMSO-d$_6$): δ 7.58 (s, 1H), 6.88-6.82 (m, 1H), 6.23-5.99 (m, 2H), 4.94 (s, 1H), 1.95-1.82 (m, 3H), 1.56-1.27 (m, 7H), 1.02-0.63 (m, 11H), 0.43-0.11 (m, 7H); $^{13}$C NMR (75 MHz, DMSO-d$_6$): δ 177.0, 158.6, 150.0, 145.8, 138.9, 137.0, 135.2, 117.9, 116.0, 110.6, 86.6, 79.0, 73.2, 49.9, 46.8, 45.8, 38.1, 35.6, 33.2, 31.7, 31.3, 30.4, 22.3, 21.5, 21.1, 20.2, 17.8, 11.9. HRMS (ESI-FTMS Mass (m/z): calcd for C$_{27}$H$_{31}$N$_3$OS [M+H]$^+$ 446.2261 found 446.2264.

(1S,2R,13R,14S,17R,18S)-7-(2,4-dimethoxyanilino)-17-ethynyl-2,18-dimethyl-6-thia-8-azapentacyclo[11.7.0.0$^{2,10}$.0$^{5,9}$.0$^{14,18}$]icosa-5(9),7,10-trien-17-ol (XI.4)

$^1$H NMR (300 MHz, DMSO-d$_6$): δ 7.61-7.59 (m, 1H), 6.51-6.48 (m, 2H), 5.42-5.40 (m, 1H), 3.85-3.81 (m, 6H), 2.73-2.62 (m, 1H), 2.58 (s, 1H), 2.36-2.18 (m, 2H), 2.08-1.97 (m, 4H), 1.82-1.65 (m, 7H), 1.60-1.29 (m, 6H), 1.21-1.14 (m, 1H), 1.05 (s, 3H), 0.90 (s, 4H); $^{13}$C NMR (75 MHz, DMSO-d$_6$): δ 163.9, 156.9, 150.8, 143.2, 136.1, 122.6, 120.2, 119.4, 118.3, 103.8, 99.2, 87.4, 97.7, 74.0, 55.7, 55.6, 50.7, 47.6, 46.6, 38.9, 36.6, 34.1, 32.5, 32.1, 31.1, 23.4, 23.1, 21.0, 18.7, 12.7. HRMS (ESI-FTMS Mass (m/z): calcd for C$_{30}$H$_{36}$N$_2$O$_3$S [M+H]$^+$ 505.2519 found 505.2518.

(1S,2R,13R,14S,17R,18S)-7-(2,4-difluoroanilino)-17-ethynyl-2,18-dimethyl-6-thia-8-azapentacyclo[11.7.0.0$^{2,10}$.0$^{5,9}$.0$^{14,18}$]icosa-5(9),7,10-trien-17-ol (XI.2)

$^1$H NMR (300 MHz, DMSO-d$_6$): δ 7.99-7.91 (m, 1H), 7.02-6.86 (m, 2H), 5.47-5.45 (m, 1H), 2.74-2.72 (m, 2H), 2.61-2.58 (m, 1H), 2.35-2.20 (m, 2H), 2.07-2.02 (m, 2H), 1.78-1.68 (m, 7H), 1.61-1.34 (m, 5H), 1.26-1.19 (m, 1H), 1.06-1.00 (m, 3H), 0.91-0.89 (m, 4H); $^{13}$C NMR (75 MHz,

DMSO-$d_6$): δ 163.9, 152.7 (dd, J=245.7 Hz), 144.7, 136.1, 124.9 (d, J=10.8 Hz), 124.8, 121.1 (d, J=22.8 Hz), 118.9, 111.4 (d, J=3.86 Hz), 104.4-103.8 (m), 87.4, 79.8, 74.0, 50.7, 47.6, 46.6, 38.9, 36.6, 34.2, 32.5, 32.1, 31.1, 23.9, 23.1, 21.0, 18.7, 12.7. HRMS (ESI-FTMS Mass (m/z): calcd for $C_{28}H_{30}F_2N_2OS$ [M+H]$^+$ 481.2120 found 481.2113.

Crystal Structures opment: assessment of bioactivity profiles within the National Cancer Institute anticancer screening data. Molec Cancer Therap 2007; 6: 2261-70; Shoemaker RH. The NCI60 human tumor cell line anticancer drug screen. Nature Rev Cancer 2006; 6: 813-23; Phillips L R et al. Liquid chromatographic determination of NSC 737664 (ABT-888: an inhibitor of poly(ADP-ribose) polymerase (PARP)) in

TABLE 16

Crystal structure data for compound II.12, II.13, and acetylated II.12.

| | II.12 | II.13 | Acetylated II.12 |
|---|---|---|---|
| Identification code | k93k | k91k | k92k |
| Empirical formula | C26 H28 F N O S | C26 H28 F N O S | C28 H32 F N O2 S |
| Formula weight | 421.55 | 421.55 | 465.6 |
| Temperature | 200(2) K | 200(2) K | 200(2) K |
| Wavelength | 0.71073 Å | 0.71073 Å | 0.71073 Å |
| Crystal system | Orthorhombic | Monoclinic | Monoclinic |
| Space group | P2$_1$2$_1$2$_1$ | P2$_1$ | P2$_1$ |
| Unit cell dimensions | a = 7.212(4) Å, α = 90° | a = 9.603(2) Å, α = 90° | a = 10.190(8) Å, α = 90° |
| | b = 8.116(4) Å, β = 90° | b = 7.0203(16) Å, β = 93.616(3)° | b = 6.636(5) Å, β = 104.79(2)° |
| | c = 36.696(17) Å, γ = 90° | c = 15.771(4) Å, γ = 90° | c = 18.242(14) Å, γ = 90° |
| Volume | 2147.8(18) Å3 | 1061.1(4) Å3 | 1192.6(16) Å3 |
| Z | 4 | 2 | 2 |
| Density (calculated) | 1.304 Mg/m3 | 1.319 Mg/m3 | 1.297 Mg/m3 |
| Absorption coefficient | 0.177 mm-1 | 0.179 mm-1 | 0.169 mm-1 |
| F(000) | 896 | 448 | 496 |
| Crystal size | 0.640 × 0.600 × 0.300 mm3 | 0.410 × 0.340 × 0.140 mm3 | 0.600 × 0.460 × 0.320 mm3 |
| Theta range for data collection | 2.220 to 29.128°. | 2.125 to 30.980°. | 2.067 to 31.571°. |
| Index ranges | −9 <= h <= 9, −10 <= k <= 11, −50 <= l <= 50 | −13 <= h <= 13, −10 <= k <= 10, −22 <= l <= 22 | −14 <= h <= 14, −9 <= k <= 9, −26 <= l <= 26 |
| Reflections collected | 20296 | 13514 | 15271 |
| Independent reflections | 5683 [R(int) = 0.0571] | 6650 [R(int) = 0.0372] | 7639 [R(int) = 0.0370] |
| Completeness to theta = 25.242° | 99.90% | 100.00% | 99.70% |
| Absorption correction | Multi-scan | Multi-scan | Multi-scan |
| Max. and min. transmission | 0.7465 and 0.6156 | 0.7465 and 0.6544 | 0.7462 and 0.6313 |
| Refinement method | Full-matrix least-squares on F2 | Full-matrix least-squares on F2 | Full-matrix least-squares on F2 |
| Data/restraints/parameters | 5683/0/273 | 6650/1/273 | 7639/1/301 |
| Goodness-of-fit on F2 | 1.051 | 1.027 | 1.039 |
| Final R indices [I > 2sigma(I)] | R1 = 0.0590, wR2 = 0.1269 | R1 = 0.0466, wR2 = 0.0920 | R1 = 0.0461, wR2 = 0.1074 |
| R indices (all data) | R1 = 0.0826, wR2 = 0.1372 | R1 = 0.0686, wR2 = 0.1040 | R1 = 0.0640, = 0.1212 |
| Absolute structure parameter | 0.11(5) | 0.05(4) | 0.02(4) |
| Extinction coefficient | n/a | n/a | n/a |
| Largest diff. peak and hole | 0.290 and −0.348 e.Å$^{-3}$ | 0.321 and −0.247 e.Å$^{-3}$ | 0.332 and −0.241 e.Å$^{-3}$ |

In Vitro Testing

Synthesized compounds were submitted to the NCI Development Therapeutics Program (DTP) and screened against 60 different human tumor cell lines, representing leukemia, melanoma and cancers of the lung, colon, brain, ovary, breast, prostate, and kidney cancers. See Su G, et al. Integrated metabolome and transriptome analysis of the NCI60 dataset. BMC Bioinformatics 2011; 12 (suppl 1): S36; Sokilde R, et al. Global microRNA analysis of the NCI-60 cancer cell panel. Molec Cancer Therap 2011; 10: 375-84; Park E S et al. Integrative analysis of proteomic signatures, mutations, and drug responsiveness in the NCI 60 cancer cell lines set. Molec Cancer Therap 2010; 9: 257-67; Covell D G et al. Anticancer medicines in development: plasma and urine in a phase 0 clinical trial. J Liq Chromatogr Relat Technol 2009; 32: 261-72; Boyd, M. R. et al. Some Practical Considerations and Applications of the National Cancer Institute In Vitro Anticancer Drug Discovery Screen. Drug Development Research 34: 91-109, 1995; Grever, M. R. et al., The National Cancer Institute: Cancer Drug Discovery and Development Program. Seminars in Oncology, Vol. 19, No. 6, pp 622-638, 1992; Alley, M. C. et al. Feasibility of Drug Screening with Panels of Human Tumor Cell Lines Using a Microculture Tetrazolium Assay. Cancer Research 48: 589-601, 1988. One dose and five dose data are presented in Tables 17 and 18, respectively.

IC50 is the concentration of a drug that inhibits a biological activity by 50%. e.g. the drug could be reducing the activity of an enzyme by 50%. GI50 would be the concentration of the anti-cancer drug that inhibits the growth of cancer cells by 50% (in other words, after giving the drug, there is a 50% reduction in cancer cell proliferation). LC50 stands for "Lethal Concentration". TGI=Tumor growth inhibition.

TABLE 17

One dose NCI analysis.

| Panel/Cell Line | II.12 Growth Percent | III.5 Growth Percent | IIa.8 Growth Percent | IIa.14 Growth Percent | IIa.6 Growth Percent | IIa.17 Growth Percent |
|---|---|---|---|---|---|---|
| Leukemia | | | | | | |
| CCRF-CEM | 15.82 | 13.10 | 4.95 | 7.99 | 44.17 | 12.99 |
| HL-60(TB) | 34.18 | 22.65 | 8.58 | 9.29 | 44.55 | 45.99 |
| K-562 | 7.01 | 13.87 | −0.51 | 5.33 | | 4.81 |
| MOLT-4 | 5.82 | −23.23 | −3.78 | −0.31 | 45.63 | 5.52 |
| RPMI-8226 | −2.88 | −36.92 | −22.26 | −3.52 | 48.36 | −13.60 |
| SR | 5.11 | 5.95 | −11.87 | −0.63 | 31.74 | 3.61 |
| Non-small Cell Lung Cancer | | | | | | |
| A549/ATCC | 55.01 | 52.15 | 35.39 | 61.13 | 47.72 | 55.43 |
| EKVX | 68.33 | 63.56 | 46.43 | 51.95 | 78.34 | 71.36 |
| HOP-62 | 50.54 | 46.75 | 20.40 | 45.74 | 70.07 | 27.50 |
| HOP-92 | 74.28 | | 68.93 | 65.93 | 78.79 | 64.31 |
| NCI-H226 | 65.84 | 109.87 | 71.91 | 72.85 | 83.39 | 94.46 |
| NCI-H23 | 62.70 | 74.72 | 55.09 | 54.16 | 79.64 | 63.65 |
| NCI-H322M | 69.34 | 92.82 | 55.83 | 79.50 | 89.66 | 72.84 |
| NCI-H460 | 53.88 | 41.91 | 51.98 | 45.78 | 38.69 | 43.90 |
| NCI-H522 | −36.55 | 41.21 | −43.73 | 24.64 | 8.26 | −56.41 |
| Colon Cancer | | | | | | |
| COLO 205 | 44.55 | 77.66 | 47.59 | 62.35 | 48.79 | 34.38 |
| HCC-2998 | 79.47 | 95.33 | 75.50 | 84.48 | 82.14 | 81.46 |
| HCT-116 | 0.51 | 43.80 | −68.78 | −27.32 | 32.71 | −23.66 |
| HCT-15 | −38.17 | 29.48 | 6.88 | 0.81 | 35.23 | −47.90 |
| HT29 | 5.21 | 19.90 | −3.32 | 3.81 | 10.25 | −29.01 |
| KM12 | 46.48 | 60.79 | 38.74 | 44.55 | 33.11 | 34.70 |
| SW-620 | 3.81 | 71.71 | 4.62 | 4.35 | 44.14 | −4.13 |
| CNS Cancer | | | | | | |
| SF-268 | 52.39 | 48.55 | 55.66 | 46.93 | 73.87 | 43.09 |
| SF-295 | −18.91 | −36.24 | −18.79 | 63.77 | 42.68 | −47.70 |
| SF-539 | −33.43 | 8.02 | −5.93 | 8.46 | 51.35 | −41.82 |
| SNB-19 | 60.01 | 71.05 | 62.83 | 44.03 | 54.72 | 57.90 |
| SNB-75 | 44.61 | 26.42 | 18.66 | 35.14 | 73.17 | 37.28 |
| U251 | 18.77 | 20.08 | 15.66 | 18.36 | 36.99 | 18.85 |
| Melanoma | | | | | | |
| LOX IMVI | 1.34 | 25.37 | 6.22 | −16.56 | 66.30 | −52.69 |
| MALME-3M | 37.62 | 72.42 | 22.82 | 27.34 | 55.43 | 35.26 |
| M14 | 57.14 | 60.54 | 44.82 | 37.85 | 41.12 | 54.77 |
| MDA-MB-435 | 49.24 | 91.96 | 35.93 | 16.89 | 2.34 | 42.59 |
| SK-MEL-2 | 32.06 | 44.94 | 21.81 | 72.63 | 49.76 | 29.07 |
| SK-MEL-28 | 48.00 | 53.31 | 39.44 | 50.77 | 72.19 | 41.25 |
| SK-MEL-5 | 61.51 | 71.98 | 32.06 | 51.38 | 32.53 | 64.76 |
| UACC-257 | 77.45 | 66.19 | 73.04 | 65.55 | 67.13 | 79.56 |
| UACC-62 | 34.85 | 28.69 | 37.50 | 39.03 | 38.23 | 28.83 |
| Ovarian Cancer | | | | | | |
| IGROV1 | 0.60 | 80.66 | 60.02 | 17.68 | 67.27 | −12.12 |
| OVCAR-3 | 7.89 | 38.63 | −5.24 | −6.33 | 36.20 | −3.79 |
| OVCAR-4 | 65.10 | 81.75 | 59.21 | 59.62 | 83.97 | 52.06 |
| OVCAR-5 | 87.24 | 106.38 | 65.53 | 59.08 | 98.72 | 109.51 |
| OVCAR-8 | 28.53 | 74.18 | 39.56 | 31.69 | 76.81 | 17.89 |
| NCI/ADR-RES | 68.33 | 76.79 | 55.43 | 53.35 | 43.96 | 78.93 |
| SK-OV-3 | 17.92 | 38.63 | −18.44 | 78.49 | 79.14 | 37.28 |
| Renal Cancer | | | | | | |
| 786-0 | −10.07 | 8.35 | −13.93 | 5.54 | 58.79 | −0.52 |
| A498 | | 49.45 | 22.95 | 66.68 | 50.67 | |
| ACHN | 11.90 | 46.04 | 1.56 | 32.28 | 93.66 | 5.12 |
| CAKI-1 | 36.88 | 61.32 | 50.45 | 49.83 | 61.11 | 37.11 |
| RXF 393 | −22.47 | −46.32 | −28.44 | 28.78 | 79.66 | −6.67 |
| SN12C | 42.89 | 96.68 | 28.50 | 26.21 | 77.26 | 46.55 |
| TK-10 | 24.03 | 89.27 | 20.27 | 63.32 | 91.08 | 10.18 |
| UO-31 | 1.08 | 9.33 | −26.89 | 34.25 | 79.34 | 22.19 |

TABLE 17-continued

One dose NCI analysis.

Prostate Cancer

| | | | | | | |
|---|---|---|---|---|---|---|
| PC-3 | 35.02 | 49.49 | 19.1.2 | 15.83 | 71.01 | 28.08 |
| DU-145 | 22.88 | 63.77 | 17.23 | 25.93 | 79.22 | 12.72 |

Breast Cancer

| | | | | | | |
|---|---|---|---|---|---|---|
| MCF7 | 10.76 | 42.59 | 4.46 | 18.18 | 32.55 | −25.89 |
| MDA-MB-231/ATCC | 62.02 | 56.24 | 38.20 | 26.55 | 68.22 | 39.51 |
| HS 578T | 27.43 | 4.16 | 35.44 | 45.27 | 54.53 | 7.41 |
| BI-549 | 23.16 | 59.26 | −8.61 | 2.85 | 45.19 | 17.42 |
| T-47D | 3.07 | 67.74 | −0.76 | 41.81 | 65.84 | −8.55 |
| MDA-MB-468 | 29.20 | 81.03 | −2.99 | 16.97 | 29.56 | 32.20 |

| Panel/Cell Line | IIIa.10 Growth Percent | IVb.1 Growth Percent | IIa.2 Growth Percent | IIa.35 Growth Percent | IIa.10 Growth Percent | IIa.19 Growth Percent |
|---|---|---|---|---|---|---|

Leukemia

| | | | | | | |
|---|---|---|---|---|---|---|
| CCRF-CEM | 0.74 | −5.86 | 8.44 | 8.33 | 10.07 | 5.05 |
| HL-60(TB) | 15.69 | 42.82 | 1.45 | 8.98 | 21.35 | 43.98 |
| K-562 | 4.96 | −38.55 | 5.14 | 10.77 | 2.15 | 8.20 |
| MOLT-4 | 6.79 | 13.35 | 4.71 | 10.99 | 3.63 | 4.15 |
| RPMI-8226 | −32.33 | −6.28 | −5.28 | −24.54 | −20.85 | 2.88 |
| SR | 8.06 | −21.79 | 0.92 | 9.60 | .71 | 16.86 |

Non-small Cell Lung Cancer

| | | | | | | |
|---|---|---|---|---|---|---|
| A549/ATCC | 57.08 | 0.92 | 87.76 | 79.28 | 61.70 | 67.03 |
| EKVX | 73.21 | −4.54 | 92.45 | 98.04 | 78.36 | 78.41 |
| HOP-62 | 34.18 | 75.49 | 101.67 | 92.69 | 87.08 | 80.02 |
| HOP-92 | 103.92 | 46.57 | 66.42 | 125.71 | 77.08 | 74.98 |
| NCI-H226 | 63.92 | 107.87 | 84.07 | 102.70 | 84.23 | 74.91 |
| NCI-H23 | 67.34 | −44.30 | 66.61 | 70.16 | 66.21 | 75.47 |
| NCI-H322M | 78.38 | 52.42 | 91.89 | 93.36 | 84.48 | 77.29 |
| NCI-H460 | 6.06 | −38.65 | 72.80 | 65.57 | 60.86 | 53.27 |
| NCI-H522 | 25.77 | −18.57 | 44.08 | −55.25 | 42.56 | 89.13 |

Colon Cancer

| | | | | | | |
|---|---|---|---|---|---|---|
| COLO 205 | 57.13 | 34.98 | 90.61 | 38.45 | 54.33 | 67.03 |
| HCC-2998 | 98.16 | 63.85 | 105.58 | 97.70 | 71.64 | 96.47 |
| HCT-116 | −81.48 | 6.35 | 21.16 | −72.37 | −23.35 | 7.77 |
| HCT-15 | −30.18 | −47.82 | 22.48 | −67.96 | 7.76 | 38.33 |
| HT29 | −38.50 | 13.20 | 34.29 | 10.26 | 30.06 | 12.95 |
| KM12 | 15.64 | 20.47 | 74.67 | 46.68 | 57.14 | 53.51 |
| SW-620 | −19.44 | −59.20 | 35.34 | −32.15 | 7.16 | 43.34 |

CNS Cancer

| | | | | | | |
|---|---|---|---|---|---|---|
| SF-268 | 9.68 | −6.41 | 83.93 | 58.35 | 70.67 | 68.55 |
| SF-295 | 7.36 | 45.72 | 68.44 | 52.47 | 50.99 | −2.71 |
| SF-539 | −34.31 | 87.19 | 64.79 | −3.84 | 49.60 | −5.40 |
| SNB-19 | 26.54 | −9.98 | 80.20 | 64.60 | 74.13 | 56.49 |
| SNB-75 | −5.43 | 99.02 | 85.55 | 41.74 | 69.43 | 68.60 |
| U251 | −30.05 | −69.94 | 60.12 | 19.48 | 40.73 | 34.08 |

Melanoma

| | | | | | | |
|---|---|---|---|---|---|---|
| LOX IMVI | −81.48 | −67.61 | 70.22 | −8.01 | −49.65 | 34.82 |
| MALME-3M | 71.16 | 3.07 | 73.32 | 29.71 | 69.51 | 76.83 |
| M14 | 53.44 | −51.14 | 85.36 | 58.13 | 57.76 | 83.90 |
| MDA-MB-435 | 3.47 | −58.82 | 58.12 | 35.34 | 51.52 | 77.59 |
| SK-MEL-2 | 51.68 | | 92.09 | 72.46 | 76.42 | 61.81 |
| SK-MEL-28 | 27.28 | 13.00 | 83.31 | 77.86 | 84.36 | 65.29 |
| SK-MEL-5 | 34.54 | 20.55 | 65.96 | 62.03 | 76.86 | 95.89 |
| UACC-257 | 69.33 | 105.26 | 87.36 | 73.38 | 71.94 | 84.04 |
| UACC-62 | 39.84 | 38.92 | 75.59 | 55.82 | 67.65 | 63.42 |

Ovarian Cancer

| | | | | | | |
|---|---|---|---|---|---|---|
| IGROV1 | 11.15 | 2.90 | 87.98 | 13.07 | 62.11 | 93.62 |
| OVCAR-3 | −31.62 | −32.35 | 6.41 | −31.67 | −4.15 | 37.42 |
| OVCAR-4 | 64.10 | −19.07 | 74.22 | 57.12 | 66.68 | 63.99 |
| OVCAR-5 | 92.21 | 72.93 | 100.34 | 116.69 | 91.77 | 91.93 |
| OVCAR-8 | −8.95 | −2.26 | 72.09 | 35.92 | 45.20 | 66.51 |
| NCI/ADR-RES | 36.29 | −5.32 | 70.16 | 68.59 | 67.57 | 81.59 |
| SK-OV-3 | 89.65 | 100.67 | 111.53 | 107.77 | 84.10 | 69.90 |

Renal Cancer

| | | | | | | |
|---|---|---|---|---|---|---|
| 786-0 | −49.68 | −9.65 | 4.36 | −3.03 | −27.72 | 30.50 |
| A498 | | 91.62 | 86.92 | 100.87 | 77.80 | 75.00 |
| ACHN | 36.78 | 32.38 | 73.78 | −17.29 | 37.67 | 71.59 |

TABLE 17-continued

| One dose NCI analysis. | | | | | | |
|---|---|---|---|---|---|---|
| CAKI-1 | 49.02 | 62.97 | 73.48 | 47.13 | 38.44 | 60.44 |
| RXF 393 | −32.33 | 7.08 | 20.01 | −16.18 | 5.60 | −32.25 |
| SN12C | 10.11 | 18.09 | 68.49 | 30.38 | 64.13 | 71.17 |
| TK-10 | 65.01 | 49.21 | 91.34 | 22.82 | 50.24 | 98.20 |
| UO-31 | 26.06 | 85.84 | 50.44 | −48.83 | 42.87 | 54.33 |
| Prostate Cancer | | | | | | |
| PC-3 | 39.21 | 57.29 | 38.82 | 39.10 | 52.88 | 38.59 |
| DU-145 | 14.25 | 31.1.1 | 33.94 | 10.45 | 24.05 | 66.11 |
| Breast Cancer | | | | | | |
| MCF7 | 29.18 | −55.62 | 20.41 | 3.11 | 14.62 | 17.08 |
| MDA-MB-231/ATCC | 35.75 | 35.18 | 83.12 | 35.27 | 76.10 | 73.45 |
| HS 578T | 3.65 | 36.38 | 75.51 | 53.60 | 55.28 | 38.46 |
| BT-549 | 19.16 | 107.48 | 60.37 | 45.59 | 59.58 | 53.50 |
| T-47D | 16.35 | −21.02 | 75.21 | 10.57 | 48.94 | 41.82 |
| MDA-MB-468 | −1.00 | −46.23 | 32.92 | −36.91 | 23.25 | 69.12 |

TABLE 18

Five dose NCI analysis.

| | III.5 | | | IIa.8 | | | IIa.14 | | |
|---|---|---|---|---|---|---|---|---|---|
| Panel/Cell Line | GI50 | TGI | LC50 | GI50 | TGI | LC50 | GI50 | TGI | LC50 |
| Leukemia | | | | | | | | | |
| CCRF-CEM | 2.05E-6 | 4.72E-5 | >1.00E-4 | 1.90E-6 | >1.00E-4 | >1.00E-4 | 2.45E-6 | >1.00E-4 | >1.00E-4 |
| HL-60(TB) | 4.08E-6 | >1.00E-4 | >1.00E-4 | 2.73E-6 | 8.00E-6 | >1.00E-4 | 2.47E-6 | 6.03E-6 | >1.00E-4 |
| K-562 | 3.48E-6 | >1.00E-4 | >1.00E-4 | 1.86E-6 | | >1.00E-4 | 2.86E-6 | >1.00E-4 | >1.00E-4 |
| MOLT-4 | 1.93E-6 | >1.00E-4 | >1.00E-4 | 1.68E-6 | 2.83E-5 | >1.00E-4 | 2.49E-6 | >1.00E-4 | >1.00E-4 |
| RPM1-8226 | 3.78E-6 | 2.50E-6 | >1.00E-4 | 8.59E-7 | 3.90E-6 | >1.00E-4 | 2.43E-6 | 6.25E-6 | >1.00E-4 |
| SR | 1.37E-6 | 3.38E-5 | >1.00E-4 | 8.59E-7 | | >1.00E-4 | 2.32E-6 | >1.00E-4 | >1.00E-4 |
| Non-small Cell Lung Cancer | | | | | | | | | |
| A549/ATCC | 5.95E-6 | >1.00E-4 | >1.00E-4 | 2.58E-6 | 7.50E-6 | >1.00E-4 | 3.50E-6 | >1.00E-4 | >1.00E-4 |
| EKVX | 7.29E-6 | >1.00E-4 | >1.00E-4 | 2.50E-6 | 1.85E-5 | >1.00E-4 | 2.13E-6 | | >1.00E-4 |
| HOP-62 | 5.25E-6 | 5.05E-5 | >1.00E-4 | 2.07E-6 | 5.34E-6 | 2.45E-6 | 2.43E-6 | >1.00E-4 | >1.00E-4 |
| HOP-92 | | | | 2.25E-6 | 4.17E-6 | 7.73E-6 | 1.72E-6 | 3.86E-6 | 8.68E-6 |
| NCI-H226 | 2.74E-5 | >1.00E-4 | >1.00E-4 | 2.35E-6 | 5.70E-6 | 8.15E-5 | 2.35E-6 | | >1.00E-4 |
| NCI-H23 | 1.40E-5 | >1.00E-4 | >1.00E-4 | 2.27E-6 | 9.08E-6 | 7.77E-5 | 2.01E-6 | 4.85E-6 | >1.00E-4 |
| NCI-H322M | 3.11E-5 | >1.00E-4 | >1.00E-4 | 3.60E-6 | 2.89E-6 | >1.00E-4 | 4.28E-6 | >1.00E-4 | >1.00E-4 |
| NCI-H460 | 4.94E-6 | >1.00E-4 | >1.00E-4 | 2.52E-6 | 5.58E-6 | >1.00E-4 | 2.70E-6 | 8.39E-6 | >1.00E-4 |
| NCI-H522 | 2.26E-5 | >1.00E-4 | >1.00E-4 | 1.63E-6 | 3.06E-6 | 5.75E-6 | 1.68E-6 | 3.28E-6 | 6.43E-6 |
| Colon Cancer | | | | | | | | | |
| COLO 205 | 9.14E-6 | >1.00E-4 | >1.00E-4 | 2.16E-6 | 4.81E-6 | 2.44E-5 | 2.50E-6 | 6.54E-6 | >1.00E-4 |
| HCC-2998 | 3.19E-5 | >1.00E-4 | >1.00E-4 | 3.55E-6 | 1.46E-5 | 8.80E-5 | 1.90E-6 | 3.74E-6 | |
| HCT-116 | 2.37E-6 | 2.74E-5 | >1.00E-4 | 1.59E-6 | 3.24E-6 | 6.58E-6 | 1.49E-6 | 2.85E-6 | 5.46E-6 |
| HCT-15 | 2.43E-6 | 2.07E-5 | >1.00E-4 | 1.58E-6 | 4.08E-6 | 1.47E-5 | 2.68E-6 | | >1.00E-4 |
| HT29 | 3.13E-6 | 2.04E-5 | >1.00E-4 | 1.49E-6 | 3.51E-6 | 8.28E-6 | 2.55E-6 | 7.04E-6 | >1.00E-4 |
| KM12 | 7.24E-6 | >1.00E-4 | >1.00E-4 | 3.00E-6 | 1.24E-5 | 7.92E-5 | 2.78E-6 | | 1.00E-4 |
| SW-620 | 8.40E-6 | >1.00E-4 | >1.00E-4 | 2.33E-6 | 4.99E-6 | >1.00E-4 | 2.70E-6 | | >1.00E-4 |
| CNS Cancer | | | | | | | | | |
| SF-268 | 5.32E-6 | >1.00E-4 | >1.00E-4 | 3.09E-6 | 1.11E-5 | >1.00E-4 | 2.77E-6 | | >1.00E-4 |
| SF-295 | 4.13E-7 | 2.03E-6 | 8.20E-6 | 1.19E-6 | 2.97E-6 | 7.37E-6 | 1.81E-6 | 4.10E-6 | |
| SF-539 | 4.54E-7 | 3.23E-6 | 9.17E-5 | 1.34E-6 | 2.94E-6 | 6.45E-6 | 1 62E-6 | 3.08E-6 | 5.86E-6 |
| SNB-19 | 7.95E-6 | >1.00E-4 | >1.00E-4 | 2.33E-6 | 5.69E-6 | 2.27E-6 | 2.12E-6 | 5.09E-6 | >1.00E-4 |
| SNB-75 | 1.84E-6 | 2.57E-5 | >1.00E-4 | 1.52E-6 | 4.94E-6 | >1.00E-4 | 2.19E-6 | 9.75E-5 | >1.00E-4 |
| U251 | 2.23E-6 | 6.73E-5 | >1.00E-4 | 1.59E-6 | 3.68E-6 | 8.51E-6 | I.69E-6 | 3.21E-6 | 6.10E-6 |
| Melanoma | | | | | | | | | |
| LOX IMVI | 2.67E-6 | 1.46E-5 | >1.00E-4 | 1.67E-6 | 3.21E-6 | 6.16E-6 | 1.64E-6 | 3.13E-6 | 5.96E-6 |
| MALME-3M | 3.76E-6 | >1.00E-4 | >1.00E-4 | 1.94E-6 | 5.04E-6 | 2.67E-5 | 1.99E-6 | 5.55E-6 | >1.00E-4 |
| M14 | 2.86E-6 | 2.93E-5 | >1.00E-4 | 2.36E-6 | 7.23E-6 | 8.14E-5 | 1.85E-6 | 3.79E-6 | |
| MDA-MB-435 | 1.64E-5 | >1.00E-4 | >1.00E-4 | 2.74E-6 | 1.31E-5 | >1.00E-4 | 3.02E-6 | >1.00E-4 | >1.00E-4 |
| SK-MEL-2 | 4.42E-6 | 6.94E-5 | >1.00E-4 | 1.86E-6 | 5.19E-6 | 2.67E-5 | 2.19E-6 | 4.74E-6 | 2.27E-5 |
| SK-MEL-28 | 3.05E-6 | 6.60E-5 | >1.00E-4 | 1.52E-6 | 4.27E-6 | 1.99E-6 | 2.31E-6 | 6.08E-6 | >1.00E-4 |
| SK-MEL-5 | 3.15E-6 | 1.31E-5 | 4.85E-5 | 2.02E-6 | 4.32E-6 | 9 24E-6 | 1.86E-6 | 3.73E-6 | 7.47E-6 |
| UACC-257 | 1.19E-5 | >1.00E-4 | >1.00E-4 | 5.47E-6 | 6.45E-5 | >1.00E-4 | 3.70E-6 | >1.00E-4 | >1.00E-4 |
| UACC-62 | 2.43E-6 | 7.64E-6 | >1.00E-4 | 1.54E-6 | 3.12E-6 | 6.31E-6 | 1.72E-6 | 3.94E-6 | 9.02E-6 |

TABLE 18-continued

Five dose NCI analysis.

Ovarian Cancer

| | | | | | | | | | |
|---|---|---|---|---|---|---|---|---|---|
| IGROV1 | 1.11E−5 | >1.00E−4 | >1.00E−4 | 1.89E−6 | 3.83E−6 | 7.76E−6 | 2.11E−6 | 5.14E−6 | >1.00E−4 |
| OVCAR-3 | 8.67E−6 | 8.37E−5 | >1.00E−4 | 1.72E−6 | 3.30E−6 | 6.34E−6 | 2.18E−6 | 5.03E−6 | 3.825E−5 |
| OVCAR-4 | 7.24E−6 | >1.00E−4 | >1.00E−4 | 2.71E−6 | >1.00E−4 | >1.00E−4 | 2.83E−6 | >1.00E−4 | >1.00E−4 |
| OVCAR-5 | 1.33E−5 | >1.00E−4 | >1.00E−4 | 2.73E−6 | 1.80E−5 | >1.00E−4 | 2.90E−6 | >1.00E−4 | >1.00E−4 |
| OVCAR-8 | 4.09E−6 | >1.00E−4 | >1.00E−4 | 2.79E−6 | 7.98E−6 | 6.87E−5 | 2.63E−6 | 7.26E−6 | >1.00E−4 |
| NCI/ADR-RES | 6.77E−6 | >1.00E−4 | >1.00E−4 | 2.81E−6 | 1.72E−5 | >1.00E−4 | 2.90E−6 | >1.00E−4 | >1.00E−4 |
| SK-OV-3 | 1.90E−5 | >1.00E−4 | >1.00E−4 | 2.33E−6 | 6.10E−6 | >1.00E−4 | 9.85E−6 | >1.00E−4 | >1.00E−4 |

Renal Cancer

| | | | | | | | | | |
|---|---|---|---|---|---|---|---|---|---|
| 786-0 | 4.23E−7 | 2.39E−6 | 2.12E−5 | 1.43E−6 | 2.83E−6 | 5.61E−6 | 1.62E−6 | 3.07E−6 | 5.84E−6 |
| A498 | 3.51E−6 | 2.13E−5 | >1.00E−4 | 2.16E−6 | 6.77E−6 | >1.00E−4 | 2.54E−6 | | >1.00E−4 |
| ACHN | 7.55E−6 | >1.00E−4 | >1.00E−4 | 1.78E−6 | 3.24E−6 | 5.92E−6 | 2.08E−6 | 4.53E−6 | |
| CAKI-1 | 4.12E−6 | >1.00E−4 | >1.00E−4 | 1.99E−6 | 5.73E−6 | 3.81E−5 | 2.83E−6 | >1.00E−4 | >1.00E−4 |
| RXF 393 | 3.77E−7 | 1.31E−6 | 8.58E−6 | 1.45E−6 | 3.25E−6 | 7.31E−6 | 1.74E−6 | 3.23 E−6 | 6.01E−6 |
| SN12C | | >1.00E−4 | >1.00E−4 | 2.36E−6 | 6.02E−6 | 3.60E−5 | 2.17E−6 | 5.06E−6 | >1.00E−4 |
| TK-10 | >1.00E−4 | >1.00E−4 | >1.00E−4 | 1.97E−6 | 4.15E−6 | 8.72E−6 | 2.46E−6 | 6.70E−6 | >1.00E−4 |
| UO-31 | 2.48E−6 | 2.04E−5 | >1.00E−4 | 1.67E−6 | 3.59E−6 | 7.69E−6 | 1.34E−6 | 2.86E−6 | 6.12E−6 |

Prostate Cancer

| | | | | | | | | | |
|---|---|---|---|---|---|---|---|---|---|
| PC-3 | | | | 1.88E−6 | 3.87E−6 | 7.94E−6 | 1.86E−6 | 4.53E−6 | 4.00E−4 |
| DU-145 | 9.54E−6 | >1.00E−4 | >1.00E−4 | 1.93E−6 | 4.87E−6 | 2.74E−5 | 2.04E−6 | 5.18E−6 | >1.00E−4 |

Breast Cancer

| | | | | | | | | | |
|---|---|---|---|---|---|---|---|---|---|
| MCF7 | 3.34E−6 | 2.15E−5 | >1.00E−4 | 1.37E−6 | 3.28E−6 | 7.87E−6 | 2.31E−6 | >1.00E−4 | >1.00E−4 |
| MDA-MB-231/ATCC | 6.98E−6 | 3.29E−5 | >1.00E−4 | 2.11E−6 | 4.59E−6 | 9.99E−6 | 2.33E−6 | 7.92E−6 | >1.00E−4 |
| HS 578T | 1.59E−6 | 6.01E−5 | >1.00E−4 | 3.14E−6 | >1.00E−4 | >1.00E−4 | 3.75E−6 | >1.00E−4 | >1.00E−4 |
| BT-549 | 1.14E−6 | 1.94E−5 | >1.00E−4 | 1.54E−6 | 3.62E−6 | 8.49E−6 | 1.49E−6 | 2.94E−6 | 5.80E−6 |
| T-47D | 1.03E−5 | >1.00E−4 | >1.00E−4 | 2.22E−6 | 6.95E−6 | >1.00E−4 | 2.89E−6 | >1.00E−4 | >1.00E−4 |
| MDA-MB-468 | 5.13E−6 | 4.16E−5 | >1.00E−4 | 2.01E−6 | 4.18E−6 | | 1.93E−6 | 3.93E−6 | 8.01E−6 |

| | IIa.17 | | | IIIa.10 | | | IVb.1 | | |
|---|---|---|---|---|---|---|---|---|---|
| Panel/Cell Line | GI50 | TGI | LC50 | GI50 | TGI | LC50 | GI50 | TGI | LC50 |

Leukemia

| | | | | | | | | | |
|---|---|---|---|---|---|---|---|---|---|
| CCRF-CEM | 2.84E−6 | >1.00E−4 | >1.00E−4 | 1.60E−6 | 2.71E−5 | >1.00E−4 | 2.80E−7 | 1.62E−6 | >1.00E−4 |
| HL-60(TB) | | | | 2.02E−6 | 6.87E−6 | >1.00E−4 | 2.73E−6 | 7.95E−6 | >1.00E−4 |
| K-562 | 2.79E−6 | >1.00E−4 | >1.00E−4 | 2.45E−6 | 1.26E−5 | >1.00E−4 | 1.81E−6 | 5.08E−6 | 4.04E−5 |
| MOLT-4 | 2.84E−6 | >1.00E−4 | 1.00E−4 | 1.87E−6 | 8.07E−6 | >1.00E−4 | 2.64E−6 | 7.02E−6 | 9.33E−5 |
| RPMI-8226 | 2.73E−6 | 7.44E−6 | >1.00E−4 | 4.65E−7 | 2.47E−6 | >1.00E−4 | 3.00E−7 | 1.37E−6 | >1.00E−4 |
| SR | 2.58E−6 | >1.00E−4 | >1.00E−4 | 2.41E−7 | 6.10E−6 | >1.00E−4 | 1.29E−6 | 4.33E−6 | >1.00E−4 |

Non-small Cell Lung Cancer

| | | | | | | | | | |
|---|---|---|---|---|---|---|---|---|---|
| A549/ATCC | 2.64E−5 | >1.00E−4 | >1.00E−4 | 2.41E−6 | 6.02E−6 | 4.62E−5 | 2.02E−6 | 3.89E−6 | 7.51E−6 |
| EKVX | 2.88E−5 | >1.00E−4 | >1.00E−4 | 2.75E−6 | 9.26E−6 | 6.38E−5 | 1.80E−6 | 3.63E−6 | 7.32E−6 |
| HOP-62 | 2.24E−5 | >1.00E−4 | >1.00E−4 | 2.47E−6 | 6.54E−6 | >1.00E−4 | 1.84E−6 | 3.47E−6 | 6.54E−6 |
| HOP-92 | 1.87E−5 | 6.79E−5 | >1.00E−4 | 2.84E−6 | 6.77E−6 | 2.74E−5 | 1.51E−6 | 3.16E−6 | 6.60E−6 |
| NCI-H226 | 7.36 | 4.50E−5 | >1.00E−4 | 2.40E−6 | 5.57E−6 | >1.00E−4 | 2.09E−6 | 4.91E6 | 1.74E−5 |
| NCI-H23 | 1.81E−5 | >1.00E−4 | >1.00E−4 | 2.03E−6 | 5.04E−6 | 2.37E−5 | 1.78E−6 | 3.32E−6 | 6.21E−6 |
| NCI-H322M | 5.05E−5 | >1.00E−4 | >1.00E−4 | 2.88E−6 | 1.11E−5 | 3.52E−5 | 1.77E−6 | 3.55E−6 | 7.14E−6 |
| NCI-H460 | 4.65E−6 | 2.79E−5 | >1.00E−4 | 1.95E−6 | 4.04E−6 | 8.37E−6 | 1.92E−6 | 3.61E−6 | 6.79E−6 |
| NCI-H522 | 6.60E−6 | 2.36E−5 | 6.93E−5 | 1.90E−6 | 4.50E−6 | 1.43E−5 | 1.93E−6 | 4.06E−6 | 8.55E−6 |

Colon Cancer

| | | | | | | | | | |
|---|---|---|---|---|---|---|---|---|---|
| COLO 205 | 1.23E−5 | 3.74E−5 | >1.00E−4 | 2.45E−6 | 5.61E−6 | 5.08E−5 | 2.06E−6 | 4.37E−6 | 9.25E−6 |
| HCC-2998 | 1.82E−5 | 4.48E−5 | >1.00E−4 | 1.97E−6 | 3.56E−6 | 6.42E−6 | 1.74E−6 | 3.28E−6 | 6.15E−6 |
| HCT-116 | 1.91E−6 | 4.17E−6 | 9.09E−6 | 1.51E−6 | 3.01E−6 | 6.01E−6 | 2.09E−6 | 4.35E−6 | 9.07E−6 |
| HCT-15 | 2.53E−6 | 9.71E−6 | >1.00E−4 | 1.60E−6 | 5.15E−6 | 3.06E−5 | 1.46E−6 | 2.86E−6 | 5.60E−6 |
| HT29 | 3.90E−6 | 1.76E−5 | 7.52E−5 | 2.13E−6 | 4.45E−6 | | 1.88E−6 | 3.73E−6 | 7.41E−6 |
| KM12 | 8.27E−6 | 2.94E−5 | 9.47E−5 | 1.68E−6 | 3.12E−6 | 5.77E−6 | 2.01E−6 | 4.01E−6 | 6.79E−6 |
| SW-620 | 3.38E−6 | 1.56E−5 | >1.00E−4 | 2.27E−6 | 5.36E−6 | 2.32E−5 | 1.69E−6 | 3.39E−6 | 8.55E−6 |

CNS Cancer

| | | | | | | | | | |
|---|---|---|---|---|---|---|---|---|---|
| SF-268 | 5.95E−6 | 7.00E−5 | >1.00E−4 | 1.66E−6 | 3.32E−6 | 6.62E−6 | 1.78E−6 | 4.11E−6 | 9.48E−6 |
| SF-295 | 8.98E−6 | >1.00E−4 | >1.00E−4 | 1.06E−6 | 2.98E−6 | 8.38E−6 | 1.61E−6 | 3.03E−6 | 5.71E−6 |
| SF-539 | 3.04E−6 | 1.33E−5 | 7.99E−5 | 1.19E−6 | 2.62E−6 | 5.74E−6 | 2.05E−6 | 5.23E−6 | 1.98E−5 |
| SNB-19 | 1.29E−5 | >1.00E−4 | >1.00E−4 | 1.86E−6 | 3.77E−6 | 7.65E−6 | 1.87E−6 | 3.62E−6 | 7.01E−6 |
| SNB-75 | 5.40E−6 | 7.25E−5 | >1.00E−4 | 1.49E−6 | 3.05E−6 | 6.24E−6 | 1.58E−6 | 3.50E−6 | 7.76E−6 |
| U251 | 4.41E−6 | 1.93E−5 | 5.86E−5 | 1.36E−6 | 2.79E−6 | 5.70E−6 | 1.77E−6 | 3.22E−6 | 5.86E−6 |

Melanoma

| | | | | | | | | | |
|---|---|---|---|---|---|---|---|---|---|
| LOX IMVI | 3.22E−6 | 1.08E−5 | 4.81E−5 | 1.33E−6 | 2.77E−6 | 5.78E−6 | 1.71E−6 | 3.12E−6 | 5.72E−6 |
| MALME-3M | 2.12E−5 | >1.00E−4 | >1.00E−4 | 2.19E−6 | 5.89E−6 | 2.19E−5 | 1.76E−6 | 3.49E−6 | 6.90E−6 |
| M14 | 7.88E−6 | 5.09E−5 | >1.00E−4 | 1.84E−6 | 4.27E−6 | 9.90E−6 | 1.94E−6 | 3.77E−6 | 7.31E−6 |
| MDA-MB-435 | 3.49E−6 | >1.00E−4 | >1.00E−4 | 2.25E−6 | 7.03E−6 | 2.97E−5 | 1.33E−6 | 2.70E−6 | 5.49E−6 |

TABLE 18-continued

Five dose NCI analysis.

| | | | | | | | | | |
|---|---|---|---|---|---|---|---|---|---|
| SK-MEL-2 | 1.71E−5 | 6.08E−5 | >1.00E−4 | 2.51E−6 | 5.64E−6 | 2.22E−5 | 1.98E−6 | 4.58E−6 | 1.24E−5 |
| SK-MEL-28 | 2.05E−5 | >1.00E−4 | >1.00E−4 | 1.68E−6 | 3.99E−6 | 9.49E−6 | 1.63E−6 | 3.10E−6 | 5.88E−6 |
| SK-MEL-5 | 1.02E−5 | 2.60E−5 | 6.25E−5 | 1.82E−6 | 3.41E−6 | 6.40E−6 | 1.57E−6 | 2.97E−6 | 5.61E−6 |
| UACC-257 | 2.38E−5 | 9.45E−5 | >1.00E−4 | 2.54E−6 | 6.68E−6 | 3.05E−5 | 2.40E−6 | 5.83E−6 | 2.57E−5 |
| UACC-62 | 9.54E−6 | 2.96E−4 | 8.97E−5 | 1.83E−6 | 3.96E−6 | 8.55E−6 | 1.63E−6 | 3.13E−6 | 5.98E−6 |
| Ovarian Cancer | | | | | | | | | |
| IGROV1 | 8.21E−6 | >1.00E−4 | >1.00E−4 | 2.78E−6 | 7.85E−6 | >1.00E−4 | 1.78E−6 | 3.43E−6 | 6.63E−6 |
| OVCAR-3 | 4.41E−6 | 5.08E−5 | >1.00E−4 | 1.28E−6 | 2.62E−6 | 5.37E−6 | 1.87E−6 | 3.44E−6 | 6.34E−6 |
| OVCAR-4 | 1.89E−5 | >1.00E−4 | >1.00E−4 | 3.13E−6 | 1.54E−5 | 5.68E−5 | 1.74E−6 | 3.17E−6 | 5.78E−6 |
| OVCAR-5 | 2.45E−5 | >1.00E−4 | >1.00E−4 | 2.68E−6 | 7.86E−6 | 3.40E−5 | 1.71E−6 | 3.19−E6 | 5.96E−6 |
| OVCAR-8 | 7.61E−6 | >1.00E−4 | >1.00E−4 | 3.43E−6 | 1.49E−5 | 9.37E−5 | 1.85E−6 | 3.63E−6 | 7.11E−6 |
| NCI/ADR-RES | 6.34E−6 | >1.00E−4 | >1.00E−4 | 3.39E−6 | 9.17E−5 | >1.00E−4 | 1.94E−6 | 3.87E−6 | 7.71E−6 |
| SK-OV-3 | 3.40E−5 | >1.00E−4 | >1.00E−4 | 5.16E−6 | 1.79E−5 | 5.12E−5 | 6.21E−6 | 2.23E−6 | 6.67E−5 |
| Renal Cancer | | | | | | | | | |
| 786-0 | 3.02E−6 | 1.31E−5 | >1.00E−4 | 1.22E−6 | 3.30E−6 | 8 87E−6 | 1.39E−6 | 2.82E−6 | 5.96E−6 |
| A498 | 2.88E−5 | >1.00E−4 | >1.00E−4 | 2.16E−6 | 5.66E−6 | 2.07E−5 | 2.10E−6 | 6 83E−6 | 2.78E−5 |
| ACHN | 7.81E−6 | 2.95E−5 | >1.00E−4 | 1.71E−6 | 3.25E−6 | 6.19E−6 | 1.80E−6 | 3.19E−6 | 5.68E−6 |
| CAKI-1 | 1.30E−5 | 3.02E−5 | 7.00E−5 | 2.32E−6 | 5.68E−6 | 1.92E−5 | 1.77E−6 | 3.64E−6 | 7.49E−6 |
| RXF 393 | 3.18E−6 | 1.42E−5 | 4.89E−5 | 7.98E−7 | 2.28E−6 | 5.81E−6 | 1.61E−6 | 3.23E−6 | 6.48E−6 |
| SN12C | 3.81E−6 | 2.53E−5 | >1.00E−4 | 1.65E−6 | 3.28E−6 | 6.53E−6 | 1.89E−6 | 3.45E−6 | 6.33E−6 |
| TK-10 | 7.47E−6 | 5.48E−5 | >1.00E−4 | 2.91E−6 | 6.63E−6 | 2.30E−5 | 2.29E−6 | 5.45E−6 | 1.93E−5 |
| UO-31 | 5.26E−6 | 1.94E−5 | 4.99E−5 | 1.67E−6 | 3.05E−6 | 5.56E−6 | 1.52E−6 | 2.88E−6 | 5.44E−6 |
| Prostate Cancer | | | | | | | | | |
| PC-3 | 5.52E−6 | 6.37E−5 | >1.00E−4 | 2.37E−6 | 5.84E−6 | 3.84E−5 | 1.25E−6 | 2.75E−6 | 6.01E−6 |
| DU-145 | 4.34E−6 | 4.09E−5 | >1.00E−4 | 1.70E−6 | 3.62E−6 | 7.68E−6 | 1.75E−6 | 3.41E−6 | 6.66E−6 |
| Breast Cancer | | | | | | | | | |
| MCF7 | 3.85E−6 | 3.28E−5 | >1.00E−4 | 1.80E−6 | 4.73E−6 | >1.00E−4 | 1.52E−6 | 3.14E−6 | 6.50E−6 |
| MDA-MB-231/ATCC | 1.34E−5 | >1.00E−4 | >1.00E−4 | 1.99E−6 | 4.63E−6 | 1.28E−5 | 1.70E−6 | 3.43E−6 | 6.90E−6 |
| HS 578T | 1.20E−5 | >1.00E−4 | >1.00E−4 | 2.16E−6 | 1.72E−5 | >1.00E−4 | 2.08E−6 | 5.15E−6 | >1.00E−4 |
| BT-549 | 4.58E−6 | 3.89R−5 | >1.00E−4 | 1.38E−6 | 4.31E−6 | 3.26E−5 | 2.84E−6 | 8.91E−6 | 8.85E−5 |
| T-47D | 3.50E−6 | >1.00E−4 | >1.00E−4 | 2.41E−6 | 7.59E6− | >1.00E−4 | 1.86E−6 | 3.80E−6 | 7.77E−6 |
| MDA-MB-468 | 3.59E−6 | 1.46E−5 | 5.47E−5 | 1.72E−6 | 3.38E−6 | 6.66E−6 | 1.60E−6 | 3.17E−6 | 6.30E−6 |

| | IIa.2 | | | IIa.35 | | | IIa.10 | | |
|---|---|---|---|---|---|---|---|---|---|
| Panel/Cell Line | GI50 | TGI | LC50 | GI50 | TGI | LC50 | GI50 | TGI | LC50 |
| Leukemia | | | | | | | | | |
| CCRF-CEM | 2.63E−6 | 4.04E−5 | >1.00E−4 | 2.47E−6 | >1.00E−4 | >1.00E−4 | 2.64E−6 | | >1.00E−4 |
| HL-60( TB) | 2.93E−6 | 9.10E−6 | >1.00E−4 | 2.57E−6 | 7.27E−6 | >1.00E−4 | | | >1.00E−4 |
| K-562 | 2.89E−6 | >1.00E−4 | >1.00E−4 | 2.96E−6 | >1.00E−4 | >1.00E−4 | 2.43E−6 | >1.00E−4 | >1.00E−4 |
| MOLT-4 | 2.58E−6 | >1.00E−4 | >1.00E−4 | 2.38E−6 | >1.00E−4 | >1.00E−4 | 2.44E−6 | >1.00E−4 | >1.00E−4 |
| RPMI-8226 | 1.79E−6 | 5.69E−6 | >1.00E−4 | 2.35E−6 | 7.07E−6 | >1.00E−4 | 1.88E−6 | | >1.00E−4 |
| SR | 3.07E−6 | >1.00E−4 | >1.00E−4 | 2.72E−6 | >1.00E−4 | >1.00E−4 | 2.90E−6 | | >1.00E−4 |
| Non-small Cell Lung Cancer | | | | | | | | | |
| A549/ATCC | 7.00E−6 | >1.00E−4 | >1.00E−4 | 4.42E−6 | >1.00E−4 | >1.00E−4 | | >1.00E−4 | >1.00E−4 |
| EKVX | 9.01E−5 | >1.00E−4 | >1.00E−4 | 1.04E−5 | 4.00E−4 | >1.00E−4 | | >1.00E−4 | >1.00E−4 |
| HOP-62 | 8.52E−6 | >1.00E−4 | >1.00E−4 | 3.28E−6 | 1.26E−5 | >1.00E−4 | | | >1.00E−4 |
| HOP-92 | 2.75E−6 | 9.10E−6 | >1.00E−4 | 2.39E6 | 5.65E−6 | >1.00E−4 | | | >1.00E−4 |
| NCI-H226 | 2.42E−6 | 6.57E−6 | >1.00E−4 | 2.86E−6 | 8.52E−6 | >1.00E−4 | 1.83E−6 | | |
| NCI-H23 | 5.03E−6 | >1.00E−4 | >l.00E−4 | 3.96E−6 | >1.00E−4 | >1.00E−4 | | | >1.00E−4 |
| NCI-H322M | 9.69E−5 | >1.00E−4 | >1.00E−4 | 6.40E−6 | >1.00E−4 | >1.00E−4 | | >1.00E−4 | >1.00E−4 |
| NCI-H460 | 4.47E−6 | >1.00E−4 | >1.00E−4 | 3.01E−6 | 1.05E−5 | >1.00E−4 | | | >1.00E−4 |
| NCI-H522 | 1.78E−6 | 3.64E−6 | 7.45E−6 | 1.42E−6 | 2.96E−6 | 6.18E−6 | 1.84E−6 | | |
| Colon Cancer | | | | | | | | | |
| COLO 205 | 3.03E−6 | 8.77E−6 | >1.00E−4 | 2.00E−6 | 3.90E−6 | 7.61E−6 | | | |
| HCC-2998 | 8.19E−6 | >1.00E−4 | >1.00E−4 | 4.11E−6 | >1.00E−4 | >1.00E−4 | | | |
| HCT-116 | 2.87E−6 | 1.23E−5 | >1.00E−4 | 1.90E−6 | | | 1.67E−6 | | |
| HCT-15 | 1.57E−6 | 4.49E−6 | 8.87E−5 | 1.66E−6 | 4.40E−6 | >1.00E−4 | 1.70E−6 | | >1.00E−4 |
| HT29 | 2.21E−6 | 8.11E−6 | >1.00E−4 | 2.13E−6 | 5.59E−6 | >1.00E−4 | 2.24E−6 | | >1.00E−4 |
| KM12 | 3.60E−6 | >1.00E−4 | >1.00E−4 | 1.93E−6 | 4.06E−6 | | | | |
| SW-620 | 2.30E−6 | 5.28E−6 | >1.00E−4 | 2.08E−6 | 4.73E−6 | >1.00E−4 | 2.40E−6 | | >1.00E−4 |
| CNS Cancer | | | | | | | | | |
| SF-268 | 4.62E−6 | >1.00E−4 | >1.00E−4 | 3.37E−6 | 4.00E−4 | >1.00E−4 | | | >1.00E−4 |
| SF-295 | 1.89E−5 | >1.00E−4 | >1.00E−4 | 5.26E−6 | 3.59E−5 | >1.00E−4 | | >1.00E−4 | >1.00E−4 |
| SF-539 | 1.69E−6 | 3.62E−6 | 7.75E−6 | 1.76E−6 | 3.59E−6 | 7.34E−6 | 1.63E−6 | | |
| SNB-19 | 9.75E−5 | >1.00E−4 | >1.00E−4 | 1.09E−5 | >1.00E−4 | >1.00E−4 | | >1.00E−4 | >1.00E−4 |
| SNB-75 | 2.67E−6 | | >1.00E−4 | 2.76E−6 | >1.00E−4 | >1.00E−4 | | | >1.00E−4 |
| U251 | 4.97E−6 | >1.00E−4 | >1.00E−4 | 3.06E−6 | 2.19E−5 | >1.00E−4 | | >1.00E−4 | >1.00E−4 |

TABLE 18-continued

Five dose NCI analysis.

Melanoma

| | | | | | | | | | |
|---|---|---|---|---|---|---|---|---|---|
| LOX IMVI | 1.70E−6 | 3.17E−6 | 5.91E−6 | 1.58E−6 | 3.04E−6 | | 1.71E−6 | | |
| MALME-3M | 2.18E−6 | 6.82E−6 | >1.00E−4 | 1.81E−6 | 4.03E−6 | 8.96E−6 | | | >1.00E−4 |
| M14 | 3.63E−6 | >1.00E−4 | >1.00E−4 | 2.68E−6 | | >1.00E−4 | | | >1.00E−4 |
| MDA-MB-435 | 3.01E−6 | >1.00E−4 | >1.00E−4 | 2.08E−6 | 5.32E−6 | >1.00E−4 | | | >1.00E−4 |
| SK-MEL-2 | 1.70E−5 | >1.00E−4 | >1.00E−4 | 6.98E−6 | >1.00E−4 | >1.00E−4 | | | >1.00E−4 |
| SK-MEL-28 | 3.37E−6 | 1.89E−5 | >1.00E−4 | 2.08E6 | 4.75E−6 | >1.00E−4 | | | |
| SK-MEL-5 | 4.57E−6 | 5.27E−5 | >1.00E−4 | 4.33E−6 | 3.19E−5 | >1.00E−4 | 1.88E−6 | | |
| UACC-257 | 4.92E−6 | 7.98E−5 | >1.00E−4 | 1.86E6 | 4.62E−6 | >1.00E−4 | | | >1.00E−4 |
| UACC-62 | 2.67E−6 | 1.06E−5 | >1.00E−4 | 1.76E−6 | 4.02E−6 | 9.19E−6 | | | >1.00E−4 |

Ovarian Cancer

| | | | | | | | | | |
|---|---|---|---|---|---|---|---|---|---|
| IGROV1 | 2.60E−6 | 6.18E−6 | 6.56E−5 | 1.99E−6 | 5.02E−6 | >1.00E−4 | | | >1.00E−4 |
| OVCAR-3 | 2.08E−6 | 4.83E−6 | >1.00E−4 | 1.71E−6 | 3.38E−6 | 6.70E−6 | 1.90E−6 | | |
| OVCAR-4 | 3 93E−6 | >1.00E−4 | >1.00E−4 | 2.03E−6 | | >1.00E−4 | | >1.00E−4 | >1.00E−4 |
| OVCAR-5 | 4.44E−6 | 6.59E−5 | >1.00E−4 | 3.91E−6 | >1.00E−4 | >1.00E−4 | | >1.00E−4 | >1.00E−4 |
| OVCAR-8 | 2.77E−6 | >1.00E−4 | >1.00E−4 | 3.22E−6 | >1.00E−4 | > 1.00E−4 | 2.96E−6 | >1.00E−4 | >1.00E−4 |
| NCI/ADR-RES | 2.31E−6 | 7.52E−6 | >1.00E−4 | 3.27E−6 | >1.00E−4 | >1.00E−4 | | | >1.00E−4 |
| SK-OV-3 | >1.00E−4 | >1.00E−4 | >1.00E−4 | 1.23E−5 | >1.00E−4 | >1.00E−4 | | >1.00E−4 | >1.00E−4 |

Renal Cancer

| | | | | | | | | | |
|---|---|---|---|---|---|---|---|---|---|
| 786-0 | 2.82E−6 | 9.61E−6 | >1.00E−4 | 1.80E6 | 3.82 | | | | |
| A498 | 4.43E−6 | >1.00E−4 | >1.00E−4 | 1.42E−5 | 8.06E−5 | >1.00E−4 | | >1.00E−4 | |
| ACHN | 1.96E−6 | 3.75E−6 | 7.19E−6 | 2.92E−6 | 9.29E−6 | 3.66E−5 | 1.81E−6 | | |
| CAKI-1 | 3.13E−6 | 1.11E−5 | >1.00E−4 | 1.93E−6 | 3.97E−6 | | | | >1.00E−4 |
| RXF 393 | 1.73E−6 | 4.49E−6 | 3.09E−5 | 1.78E−6 | 4.14E−6 | | 1.57E−6 | | |
| SN12C | 2.89E−6 | >1.00E−4 | >1.00E−4 | 2.91E−6 | >1.00E−4 | >1.00E−4 | | | >1.00E−4 |
| TK-10 | 4.15E−6 | >1.00E−4 | >1.00E−4 | 2.01E−6 | 4.40E−6 | 9.60E−6 | 2.80E−6 | | |
| UO-31 | 4.03E−6 | 2.51E−5 | >1 00E−4 | 1.54E−6 | 2.90E−6 | 9.49E−6 | | | |

Prostate Cancer

| | | | | | | | | | |
|---|---|---|---|---|---|---|---|---|---|
| PC-3 | 3.35E−6 | >1.00E−4 | >1.00E−4 | 2.49E−6 | 8.15E−6 | >1.00E−4 | | | >1.00E−4 |
| DU-145 | 3.64E−6 | >1.00E−4 | >1.00E−4 | 1.66E−6 | 3.14E−6 | | 1.98E−6 | | |

Breast Cancer

| | | | | | | | | | |
|---|---|---|---|---|---|---|---|---|---|
| MCF7 | 2.68E−6 | >1.00E−4 | >1.00E−4 | 1.66E−6 | 4.26E−6 | >1.00E−4 | | | >1.00E−4 |
| MDA-MB-231/ATCC | 3.40E−6 | 2.14E−5 | >1.00E−4 | 3.22E−6 | | >1.00E−4 | | | |
| HS 578T | 2.85E−6 | >1.00E−4 | >1.00E−4 | 3.38E−6 | >1.00E−4 | >1.00E−4 | | >1.00E−4 | >1.00E−4 |
| BT-549 | 2.42E−6 | >1.00E−4 | >1.00E−4 | 3.13E−6 | >1.00E−4 | >1.00E−4 | | >1.00E−4 | >1.00E−4 |
| T-47D | 3.05E−6 | 2.52E−5 | >1.00E−4 | 1.95E−6 | 5.03E−6 | >1.00E−4 | 2.25E−6 | | >1.00E−4 |
| MDA-MB-468 | 2 99E−6 | 1.03E−5 | >1.00E−4 | 2.17E−6 | 5.80E−6 | >1.00E−4 | 1.75E−6 | | |

| | IIa.19 | | |
|---|---|---|---|
| Panel/Cell Line | GI50 | TGI | LC50 |

Leukemia

| | | | |
|---|---|---|---|
| CCRF-CEM | 1.42E−6 | >1.00E−4 | >1.00E−4 |
| HL-60(TB) | 1.93E−6 | 4.44E−6 | >1.00E−4 |
| K-562 | 1.87E−6 | 6.64E−6 | >1.00E−4 |
| MOLT-4 | 1.53E−6 | 1.19E−5 | >1.00E−4 |
| RPMI-8226 | 1.02E−6 | 3.77E−6 | >1.00E−4 |
| SR | 2.74E−6 | >1.00E−4 | >1.00E−4 |

Non-small Cell Lung Cancer

| | | | |
|---|---|---|---|
| A549/ATCC | 3.35E−6 | 1.61E−5 | 7.35E−5 |
| EKVX | 2.63E−6 | 1.74E−5 | 9.57E−5 |
| HOP-62 | 1.92E−6 | 4.19E−6 | 9.14E−6 |
| HOP-92 | 1.43E−6 | 3.44E−6 | 8.26E−6 |
| NCI-H226 | 6.37E−6 | 4.41E−5 | >1.00E−4 |
| NCI-H23 | 3.73E−6 | 2.17E−5 | 9.46E−5 |
| NCI-H322M | 6.05E−6 | 4.89E−5 | >1.00E−4 |
| NCI-H460 | 3.25E−6 | 1.18E−5 | 4.19E−5 |
| NCI-H522 | 2.14E−6 | 4.56E−6 | 9.70E−6 |

Colon Cancer

| | | | |
|---|---|---|---|
| COLO 205 | 2.61E−6 | 6.76E−6 | 5.87E5 |
| HCC-2998 | 5.32E−6 | 1.86E−5 | 5.12E5 |
| HCT-116 | 1.28E−6 | 2.78E6 | |
| HCT-15 | 1.69E−6 | 4.10E−6 | 9.97E−6 |
| HT29 | 2.39E−6 | 1.09E−5 | >1.00E−4 |
| KM12 | 3.56E−6 | 1.50E−5 | >1.00E−4 |
| SW-620 | 2.21E−6 | 5.00E−6 | 1.85E−5 |

TABLE 18-continued

Five dose NCI analysis.

| CNS Cancer | | | |
|---|---|---|---|
| SF-268 | 3.01E−6 | 1.23E−5 | 5.73E−5 |
| SF-295 | 7.00E−7 | 2.44E−6 | 7.16E−6 |
| SF-539 | 1.05E−6 | 2.72E−6 | 7.07E−6 |
| SNB-19 | 2.12E−6 | 9.93E−6 | 4.60E−5 |
| SNB-75 | 1.88E−6 | 6.23E−6 | 2.96E−5 |
| U251 | 1.09E−6 | 3.26E−6 | 9.78E−6 |
| Melanoma | | | |
| LOX IMVI | 1.74E−6 | 3.18E−6 | 5.82E−6 |
| MALME-3M | 3.45E−6 | 1.68E−5 | 8.45E−5 |
| M14 | 3.29E−6 | 8.72E−6 | 4.66E−5 |
| MDA-MB-435 | 2.72E−6 | 1.01E−5 | 4.42E−5 |
| SK-MEL-2 | 3.00E−6 | 1.16E−5 | 5.56E−5 |
| SK-MEL-28 | 1.88E−6 | 7.98E−6 | 4.92E−5 |
| SK-MEL-5 | 2.62E−6 | 7.41E−6 | 4.14E−5 |
| UACC-257 | 4.89E−6 | 2.88E−5 | >1.00E−4 |
| UACC-62 | 3.03E6 | 1.03E−5 | >1.00E−4 |
| Ovarian Cancer | | | |
| IGROV1 | 3.32E−6 | 1.08E−5 | >1.00E−4 |
| OVCAR-3 | 1.94E−6 | 4.14E−6 | 8.82E−6 |
| OVCAR-4 | 3.31E−6 | 2.58E−5 | >1.00E−4 |
| OVCAR-5 | 9.06E−6 | 4.03E−5 | >1.00E−4 |
| OVCAR-8 | 3.49E−6 | 2.50E−5 | >1.00E−4 |
| NCI/ADR-RES | 3.93E−6 | 2.02E−5 | >1.00E−4 |
| SK-OV-3 | 3.03E−6 | 1.00E−5 | 8.39E−5 |
| Renal Cancer | | | |
| 786-0 | 1.45E−6 | 3.28E−6 | 7.45E−6 |
| A498 | 2.09E−6 | 5.77E−6 | 2.14E−5 |
| ACHN | 3.27E−6 | 1.08E−5 | 6.03E−5 |
| CAKI-1 | 3.21E6 | 1.32E−5 | 3.99E−5 |
| RXF 393 | 5.00E−7 | 2.21E−6 | 8.59E−6 |
| SN12C | 3.44E−6 | 1.61E−5 | 8.91E−5 |
| TK-10 | 4.82E−6 | 3.20E−5 | >1.00E−4 |
| UO-31 | 2.06E−6 | 4.73E−6 | 1.26E−5 |
| Prostate Cancer | | | |
| PC-3 | | | |
| DU-145 | 4.31E−6 | 2.51E−5 | >1.00E−4 |
| Breast Cancer | | | |
| MCF7 | 1.82E−6 | 4.14E−6 | 9.42E−6 |
| MDA-MB-231/ATCC | 2.42E−6 | 7.84E−6 | 6.51E−5 |
| HS 578T | 1.48E−6 | 5.22E−6 | >1.00E−4 |
| BT-549 | 1.78E−6 | 7.42E−6 | 6.90E−5 |
| T-47D | 2.15E−6 | 6.43E−6 | 6.75E−5 |
| MDA-MB-468 | 2.09E−6 | 4.44E−6 | |

Anti-Melanoma Studies of Thiazole-Androstane Derivatives

Materials and Methods

Cytotoxicity Assay: Melanoma cells (~4000 cells in each well) were incubated in a 96 well plates at 37° C. in 5% $CO_2$ for 24 hours. Compounds were added in triplicates and the plate was further incubated for 24 hours. DMSO and dacarbazine were added as technical and positive controls respectively. Next day resazurin was added and the plate was further incubated for 6 hours followed by reading the plate at 544 nm (excitation) and 590 nm (emission) using BMG Labtech Fluostar Optima plate reader. $IC_{50}$ values were determined by using Graphpad Prism.

On day 1, the cell line trypsinized and centrifuged to form cell pellet. The pellet was diluted in media, then counted using Countess automated cell counter. Approximately 4000 cells (198 uL) per well plated in 63 of 64 inner wells. A control well of 200 uL growth media was also prepared. Wells closest to plate perimeter were filled with 200 uL PBS to prevent inner well evaporation. The 96 well plates are incubated in 37° C. incubator at 5% $CO_2$ for 24 hours.

On day 2, compounds were added (in triplicate) along with DMSO/Dacarbazine controls (2 uL) added to bring wells to volume of 200 μL. The 96 well plates are incubated in 37° C. incubator at 5% $CO_2$ for 24 hours.

On day 3, 40 μL of 0.15 mg/ml reszurin solution added to wells. Samples were placed in a 37° C. incubator at 5% $CO_2$ for 6 hours. Excitation and emission for fluorescence measured at 544 nm and 590 nm using BMG Labtech Fluostar Optima plate reader Percent viability determined by taking average of each triplicate well fluorescence and subtracting GM well reading to remove the background signal. This difference is then divided by the average of the negative control (DMSO) wells to determine percent viability.

$IC_{50}$s were determined by using cereal dilution of compound to determine viability. Viabilities and concentration of cells are analyzed in Graphpad Prism by creating sigmoidal curve graph, which will determine the $IC_{50}$ concentration.

We analyzed the ability of the thiazole-androstane derivatives to inhibit growth in various melanoma cell lines. The growth inhibition against melanoma cell lines of various compound is shown below in Tables 19 and 20. Inhibition results are reported as the $IC_{50}$ concentration in μM of the indicated compound or as the percent viability (% inhibition) of the indicated compound. NA=not available.

Without being limited by theory, the compounds that showed the most promising results were compounds IIa.32, IIa.11, IIIa.12, IIIa.13, and IIIa.33 as these compounds had some of the lowest $IC_{50}$s in various melanoma cell lines. Compounds IIIa.33 is of particular interest as this compound exhibited $IC_{50}$s<10 μM for cell lines LOX IMVI, SK-MEL-28, and SK-MEL-25; an $IC_{50}$ of 13 μM was observed in cell line HFF-1.

TABLE 19

Growth Inhibition against Melanoma Cell Lines of various Compounds of Formula II and Formula IIa.

| Compound | LOX-IMVI (% inhibition) | LOX IMVI ($IC_{50}$) | SK-MEL-25 (% inhibition) | SK-MEL-25 ($IC_{50}$) | SK-MEL-28 (% inhibition) | SK-MEL-28 ($IC_{50}$) | SK-MEL-5 (% inhibition) |
|---|---|---|---|---|---|---|---|
| IIa.1 | NA | | NA | | 1 | | 29 |
| IIa.30 | NA | | 4 | | 67 | | 26 |
| IIa.31 | 43 | | 74 | | 93 | | 69 |
| IIa.3 | 16 | | 68 | | 65 | | 57 |
| IIa.5 | NA | | 6 | | 97 | | 46 |
| IIa.2 | 45 | | 59 | | 79 | | 73 |
| IIa.4 | 42 | | 66 | | NA | | 74 |
| IIa.7 | 19 | | | | 43 | | |
| IIa.32 | 61 | 9 | 87 | 5 | 63 | >20 | |
| IIa.15 | 19 | | 67 | | 13 | | 76 |
| IIa.19 | NA | | 24 | | 97 | | 43 |
| IIa.17 | 37 | | 79 | | 87 | | |
| IIa.33 | 48 | | 77 | | 66 | | 87 |
| IIa.8 | 79 | >20 | 88 | 10 | 90 | >20 | 84 |
| IIa.9 | 40 | | 61 | | 90 | | 58 |
| IIa.11 | 61 | 12 | 96 | 9 | 88 | >20 | 84 |
| IIa.34 | 45 | | 59 | | 73 | | 80 |
| IIa.23 | 38 | | 71 | | 78 | | 43 |
| IIa.13 | 33 | | 58 | | 6 | | 36 |
| IIa.10 | 10 | | 34 | | 14 | | 48 |
| IIa.14 | NA | | 15 | | NA | | NA |
| IIa.20 | 33 | | 83 | | 95 | | 70 |
| IIa.16 | NA | | 70 | | 86 | | 81 |
| IIa.6 | 7 | | 60 | | 60 | | 63 |
| IIa.21 | 29 | | 58 | | 93 | | 88 |
| IIa.22 | NA | | 3 | | 4 | | 15 |
| IIb.1 | NA | | 31 | | 16 | | 5 |
| II.1 | NA | | 16 | | 5 | | 25 |
| II.2 | 17 | | 69 | | 98 | | 77 |
| II.7 | 11 | | 85 | | 89 | | 29 |
| II.8 | 11 | | 20 | | 44 | | 26 |
| II.9 | 13 | | | | | | |
| II.23 | 52 | | | | | | |
| II.24 | 10 | | | | | | |
| II.10 | 2 | | | | | | |
| II.11 | 35 | | | | | | |
| II.17 | 17 | | | | | | |
| II.4 | 16 | | | | | | |
| II.13 | 11 | | | | | | |
| II.14 | 13 | | | | | | |
| II.15 | 3 | | | | | | |
| II.25 | 89 | | | | | | |
| II.16 | 88 | | | | | | |
| II.21 | 91 | | | | | | |
| II.22 | 95 | | | | | | |
| II.3 | 47 | | | | | | |

TABLE 20

Growth Inhibition against Melanoma Cell Lines of various Compounds of Formula III and Formula IIIa.

| Compound | LOX-IMVI (% viability) | LOX IMVI (IC$_{50}$) | SK-MEL-28 (% viability) | SK-MEL-28 IC$_{50}$ | SK-MEL-5 (% viability) | SK-MEL-25 (% viability) | SK-MEL-25 IC$_{50}$ | MALME-3M (% viability) | HFF-1 (IC$_{50}$) |
|---|---|---|---|---|---|---|---|---|---|
| IIIa.2 | 14 | | 1.9 | | 2.02 | 6.21 | | 59.51 | |
| IIIa.3 | 6 | >20 | 2.00 | | 2.46 | 5.06 | | 51.83 | |
| IIIa.4 | 2 | 7.672 | 1.69 | | 2.1 | 2.63 | 16 | 4.96 | |
| IIIa.6 | 11 | >20 | 2.04 | | 3.52 | 3.79 | | 29.73 | |
| IIIa.5 | 10 | 11 | 4.28 | | 3.49 | 9.39 | | 55.63 | |
| IIIa.10 | 27 | | 13.79 | | 14.72 | 13.15 | >20 | 68.28 | |
| IIIa.33 | 6 | 4.636 | 0.90 | 6 | 1.21 | 7.53 | 6 | 23.03 | 13 |
| IIIa.39 | 51 | | 3.71 | | 6.75 | 6.33 | | 45.95 | |
| IIIa.12 | 12 | 5.203 | 2.35 | 10 | 3.66 | 7.33 | 7 | 35.97 | 24 |
| IIIa.13 | | 6.425 | 3.92 | 11 | 4.9 | 8.72 | 8 | 20.83 | 25 |
| IIIa.35 | 89 | | 66.69 | | 106.21 | 54.19 | | 122.92 | |
| IIIa.26 | 79 | | 69.56 | | 93.06 | 37.03 | | 113.38 | |
| IIIa.16 | 67 | | 8.47 | | 10.22 | 26.7 | | 102.39 | |
| IIIa.24 | | >20 | 1.50 | | 2.25 | 1.76 | | 10.69 | >20 |
| IIIa.37 | | | 62.56 | | 48.52 | 39.57 | >20 | 104.91 | |
| III.1 | | | 58 | | | | | | |
| III.6 | | | 32 | | | | | | |
| III.7 | | | 11 | | | | | | |
| III.19 | | | 58 | | | | | | |
| III.4 | | | 86 | | | | | | |

I claim:

1. A compound of formula

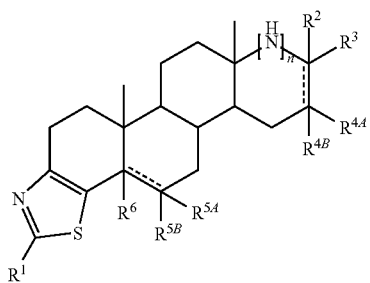

or a salt thereof
wherein R$^1$ is selected from
(1) —NR$^{7A}$R$^{7B}$ and R$^{7A}$ and R$^{7B}$ are independently selected from hydrogen; acetyl; a branched or unbranched, substituted or unsubstituted C$_1$-C$_{12}$ alkyl; a branched or unbranched, substituted or unsubstituted C$_2$-C$_{12}$ alkenyl; a branched or unbranched, substituted or unsubstituted C$_2$-C$_{12}$ alkynyl; a branched or unbranched, substituted or unsubstituted C$_3$-C$_{12}$ cycloalkyl; a branched or unbranched, substituted or unsubstituted C$_6$-C$_{12}$ aryl; a branched or unbranched, substituted or unsubstituted C$_6$-C$_{12}$ arylalkyl; a branched or unbranched, substituted or unsubstituted C$_3$-C$_{12}$ heterocyclyl; or a branched or unbranched, substituted or unsubstituted C$_3$-C$_{12}$ heterocyclylalkyl; or (2) hydrogen, a branched or unbranched, substituted or unsubstituted C$_1$-C$_{12}$ alkyl, a branched or unbranched, substituted or unsubstituted C$_2$-C$_{12}$ alkenyl, a branched or unbranched, substituted or unsubstituted C$_2$-C$_{12}$ alkynyl, a branched or unbranched, substituted or unsubstituted C$_3$-C$_{12}$ cycloalkyl, a branched or unbranched, substituted or unsubstituted C$_6$-C$_{12}$ aryl, a branched or unbranched, substituted or unsubstituted C$_6$-C$_{12}$ arylalkyl, or a branched or unbranched, substituted or unsubstituted C$_3$-C$_{12}$ heterocyclyl; or (3) —NR$^{7A}$R$^{7B}$ and R$^{7A}$ and R$^{7B}$ together are selected from a branched or unbranched, substituted or unsubstituted C$_2$-C$_{12}$ alkylene; a branched or unbranched, substituted or unsubstituted C$_2$-C$_{12}$ ether; or a branched or unbranched, substituted or unsubstituted, secondary, tertiary, or quaternary amine; and wherein
(1) R$^{4A}$ and R$^{4B}$ are each hydrogen and
(A) one of R$^2$ or R$^3$ is selected from hydrogen and the other from a hydroxyl group; or
(B) R$^2$ and R$^3$ together are selected from an oxo group; or
(C) R$^2$ and R$^3$ together are selected from a =N—NR$^{10A}$R$^{10B}$ and
(i) R$^{10A}$ and R$^{10B}$ are independently selected from hydrogen; a branched or unbranched, substituted or unsubstituted C$_1$-C$_{12}$ alkyl; a branched or unbranched, substituted or unsubstituted C$_2$-C$_{12}$ alkenyl; a branched or unbranched, substituted or unsubstituted C$_2$-C$_{12}$ alkynyl; a branched or unbranched, substituted or unsubstituted C$_3$-C$_{12}$ cycloalkyl; a branched or unbranched, substituted or unsubstituted C$_6$-C$_{12}$ aryl; a branched or unbranched, substituted or unsubstituted C$_6$-C$_{12}$ arylalkyl; or a branched or unbranched, substituted or unsubstituted C$_3$-C$_{12}$ heterocyclyl; or
(ii) R$^{10A}$ and R$^{10B}$ together is selected a branched or unbranched, substituted or unsubstituted C$_2$-C$_{12}$ alkylene; a branched or unbranched, substituted or unsubstituted C$_2$-C$_{12}$ ether; a branched or unbranched, substituted or unsubstituted, secondary, tertiary, or quaternary amine; or
(D) R$^2$ and R$^3$ together are selected from =NOH; or
(E) R$^2$ and R$^3$ together are selected from =NN(H)C(=Z)R$^8$ wherein Z is selected from oxygen and sulfur and R$^8$ is selected from hydrogen; a branched or unbranched, substituted or unsubstituted C$_1$-C$_{12}$ alkyl; a branched or unbranched, substituted or unsubstituted C$_2$-C$_{12}$ alkenyl; a branched or unbranched, substituted or unsubstituted $C_2$-$C_{12}$ alkynyl; a branched or unbranched, substituted or unsubstituted $C_3$-$C_{12}$ cycloalkyl; a branched or unbranched, substituted or unsubstituted $C_6$-$C_{12}$ aryl; a branched or unbranched, substituted or unsubstituted $C_6$-$C_{12}$ arylalkyl; a branched or unbranched, substituted or unsubstituted $C_3$-$C_{12}$ heterocyclyl; or a branched or unbranched, substituted or unsubstituted, secondary, tertiary, or quaternary amine; or (F) one of $R^2$ or $R^3$ is selected from hydrogen and the other from —OC(=Z)$R^9$ wherein Z is selected from oxygen and sulfur and $R^9$ is selected from hydrogen; a branched or unbranched, substituted or unsubstituted $C_1$-$C_{12}$ alkyl; a branched or unbranched, substituted or unsubstituted $C_2$-$C_{12}$ alkenyl; a branched or unbranched, substituted or unsubstituted $C_2$-$C_{12}$ alkynyl; a branched or unbranched, substituted or unsubstituted $C_3$-$C_{12}$ cycloalkyl; a branched or unbranched, substituted or unsubstituted $C_6$-$C_{12}$ aryl; a branched or unbranched, substituted or unsubstituted $C_6$-$C_{12}$ arylalkyl; a branched or unbranched, substituted or unsubstituted $C_3$-$C_{12}$ heterocyclyl; or a branched or unbranched, substituted or unsubstituted, secondary, tertiary, or quaternary amine; or (G) $R^1$ is the —$NR^{7A}R^{7B}$ and one of $R^2$ or $R^3$ is selected from hydrogen and the other from a branched or unbranched, substituted or unsubstituted $C_1$-$C_{12}$ alkyl; or (H) one of $R^2$ or $R^3$ is selected from a hydroxyl group and the other from $C_2$-$C_{12}$ alkynyl; and (2) $R^{4A}$ and $R^{4B}$ are together hydrogen and (A) $R^2$ and $R^3$ together are selected from a cyano group; or (B) $R^2$ and $R^3$ together are selected from a branched or unbranched,
substituted or unsubstituted $C_6$-$C_{12}$ aryl; and
wherein (1) $R^{5A}$ and $R^{5B}$ are together hydrogen and $R^6$ is not present; or (2) each of $R^{5A}$ and $R^{5B}$ is hydrogen and $R^6$ is hydrogen; or (3) one of $R^{5A}$ and $R^5$ is hydrogen and the other is a hydroxyl group and $R^6$ is selected from hydrogen or a hydroxyl group; and wherein n is equal to 0 or 1.

2. The compound of claim 1, wherein the compound is a compound of Formula II

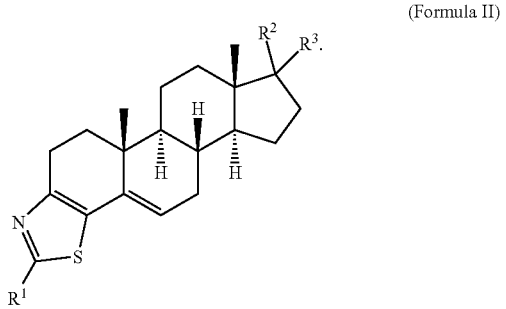

(Formula II)

3. The compound of claim 2, wherein $R^{7A}$ and $R^{7B}$ are independently selected from hydrogen; the branched or unbranched, substituted or unsubstituted $C_1$-$C_{12}$ alkyl; the branched or unbranched, substituted or unsubstituted $C_2$-$C_{12}$ alkenyl; the branched or unbranched, substituted or unsubstituted $C_2$-$C_{12}$ alkynyl; the branched or unbranched, substituted or unsubstituted $C_3$-$C_{12}$ cycloalkyl; the branched or unbranched, substituted or unsubstituted $C_6$-$C_{12}$ aryl; the branched or unbranched, substituted or unsubstituted $C_6$-$C_{12}$ arylalkyl; the branched or unbranched, substituted or unsubstituted $C_3$-$C_{12}$ heterocyclyl; the branched or unbranched, substituted or unsubstituted $C_3$-$C_{12}$ heterocyclylalkyl.

4. The compound of claim 1, wherein the compound is the compound of Formula IIIa

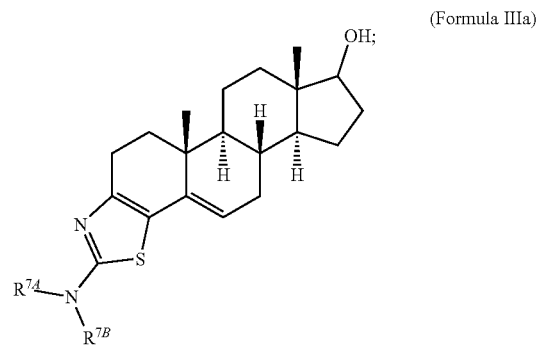

(Formula IIIa)

the compound of Formula IIa

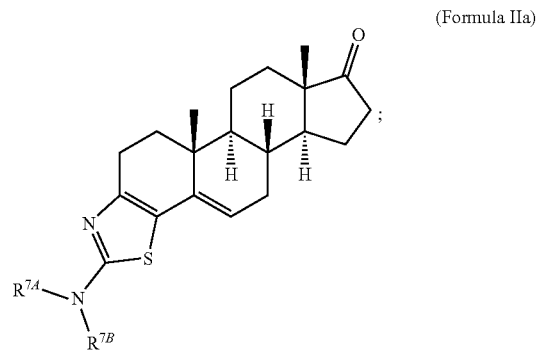

(Formula IIa)

the compound of Formula IVa

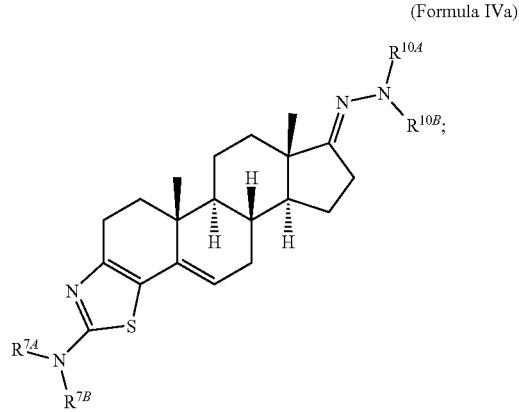

(Formula IVa)

the compound of Formula Va
the compound of Formula Xa
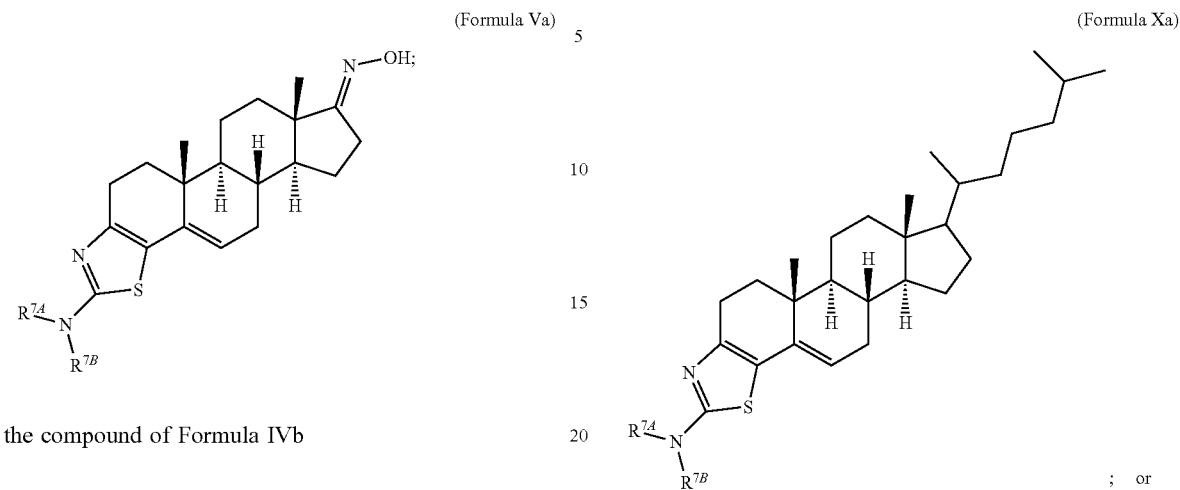
(Formula Va)
(Formula Xa)
the compound of Formula IVb
the compound of Formula XI
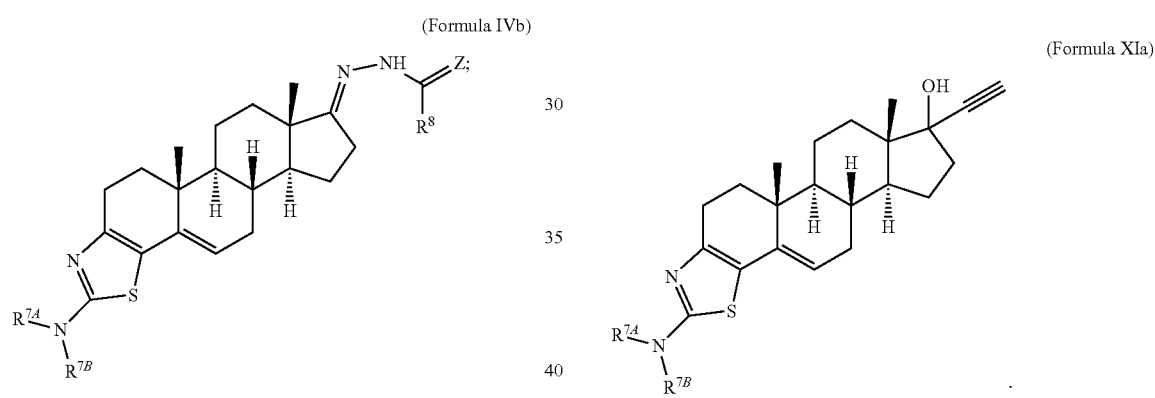
(Formula IVb)
(Formula XIa)
the compound of Formula VIIa
5. The compound of claim 1, wherein the compound is a compound of Formula I
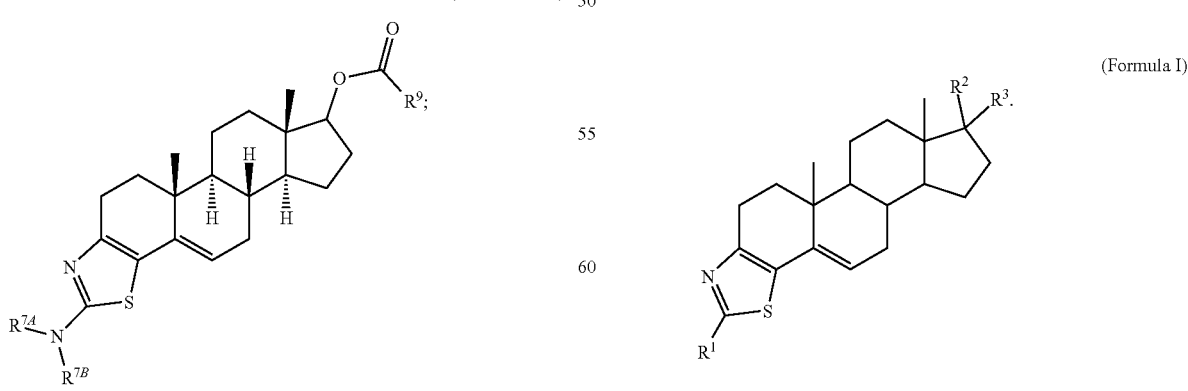
(Formula VIIa)
(Formula I)
6. The compound of claim 5, wherein the compound is a compound of Formula III

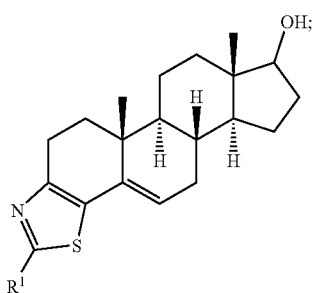
the compound of Formula II
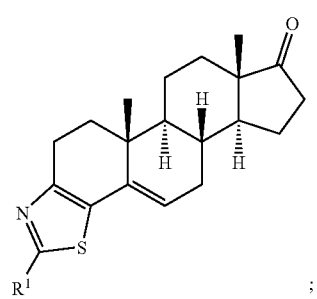
a compound of Formula IV
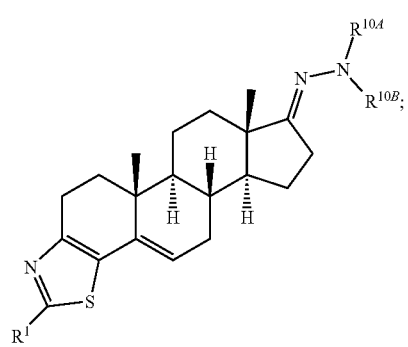
a compound of Formula V
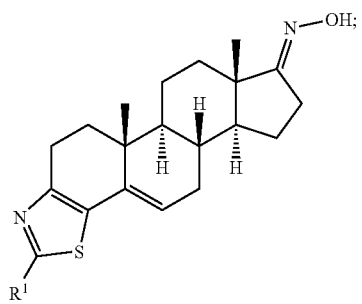
a compound of Formula VI
(Formula III)
(Formula II)
(Formula IV)
(Formula V)
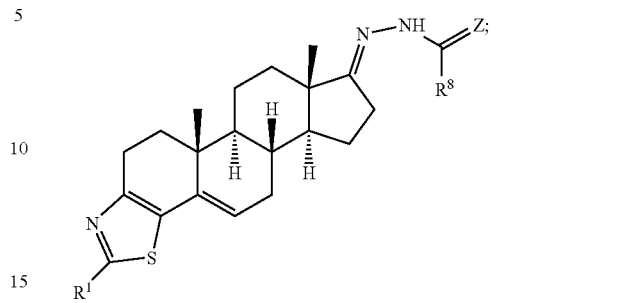
a compound of Formula VII
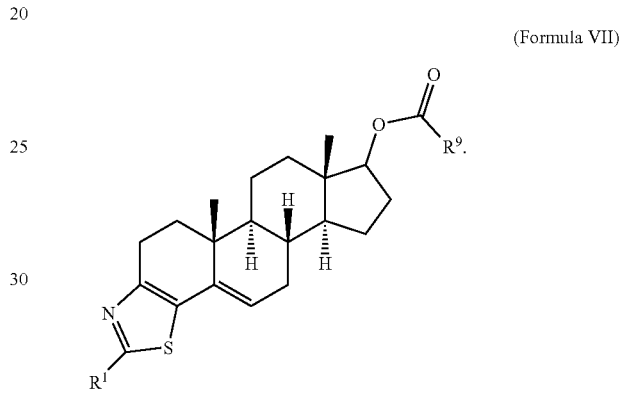
7. The compound of claim 1, wherein the compound is a compound of Formula VIII
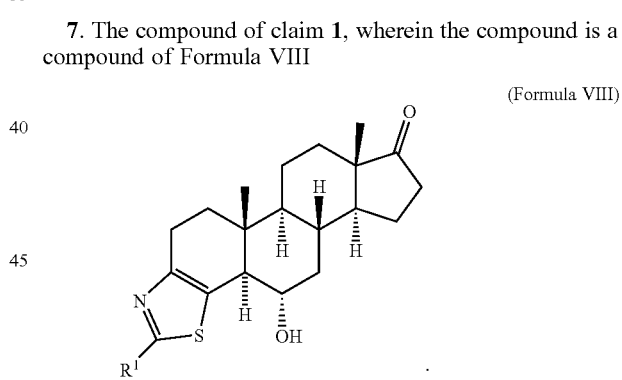
8. The compound of claim 1, wherein the compound is a compound of Formula IX
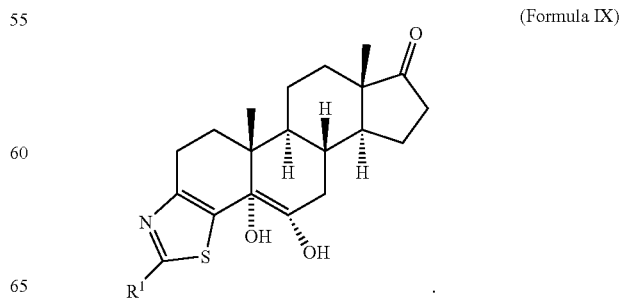
(Formula VI)
(Formula VII)
(Formula VIII)
(Formula IX)

9. The compound of claim 1, wherein the compound is any one of the compounds:

(5aR,5bS,7aS,10aS,10bR)-2,5a,7a-trimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-benzyl-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-(pyridin-2-yl)-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(4-hydroxyphenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(2-chlorophenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(4-carboxyphenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(3-methylphenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(4-methylphenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(3-methoxyphenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(4-methoxyphenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(2-hydroxyphenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(3-fluorophenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(4-fluorophenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(3-chlorophenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(4-chlorophenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(4-bromophenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(3-hydroxyphenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(2-methylbenzyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-phenyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(3,4-dihydroxyphenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(4-trifluoromethylphenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(3-nitrophenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(3-ethoxyphenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-(3-((5-(trifluoromethyl)pyridin-2-yl)oxy)phenyl)-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(3,5-dichloro-phenyl)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-amino-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-(phenethylamino)-4,5,5a,5b,6,7,7a,9,10,10a,10b,11,12,12a-tetradecahydro-8H-cyclopenta[7,8]phenanthro[2,1-d]thiazol-8-one;

(5ar,5bs,7as,10as,10br)-5a,7a-dimethyl-2-(prop-2-en-1-ylamino)-4,5,5a,5b,6,7,7a,9,10,10a,10b,11,12,12a-tetradecahydro-8h-cyclopenta[7,8]phenanthro[2,1-d]thiazol-8-one;

(5aR,5bS,7aS,10aS,10bR)-5a,7a-dimethyl-2-((3-morpholinopropyl)amino)-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(benzylamino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-(phenylamino)-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-(methyl(phenyl)amino)-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-((3-fluorophenyl)amino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-((4-fluorophenyl)amino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-((2,4-difluorophenyl)amino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-((2-chlorophenyl)amino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-((4-chlorophenyl)amino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-((2-nitrophenyl)amino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-((2,4-dimethylphenyl)amino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-((2-methoxyphenyl)amino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-((2,6-dimethyoxyphenyl)amino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-((3-hydroxyphenyl)amino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-((4-hydroxyphenyl)amino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-((4-trifluoromethoxyphenyl)amino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-((2-methoxy,5-chlorophenyl)amino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-((pyrind-2-yl)amino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-((pyrimidin-2-yl)amino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-((4-carboxyphenyl)amino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-((piperidin-1-yl)amino)-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-((morpholino)amino)-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-((4-methylpiperazin-1-yl)amino)-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-((4-ethylpiperazin-1-yl)amino)-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-((4-ethan-2-ol-piperazin-1-yl)amino)-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-((piperazin-1-yl)amino)-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-(ethylamino)-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-2-(butylamino)-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-((4-methylphenyl)amino)-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-((2-fluorophenyl)amino)-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-((3-carboxyphenyl)amino)-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR)-5a,7a-dimethyl-2-((4-hydroxyphenyl)amino)-4,5,5a,5b,6,7,7a,9,10,10a,10b,11,12,12a-tetradecahydro-8H-cyclopenta[7,8]phenanthro[2,1-d]thiazol-8-one;

N-((5aR,5bS,7aS,10aS,10bR)-5a,7a-dimethyl-8-oxo-5,5a,5b,6,7,7a,8,9,10,10a,10b,11,12,12a-tetradecahydro-4H-cyclopenta[7,8]phenanthro[2,1-d]thiazol-2-yl)acetamide;

N-((5aR,5bS,7aS,10aS,10bR)-5a,7a-dimethyl-8-oxo-5,5a,5b,6,7,7a,8,9,10,10a,10b,11,12,12a-tetradecahydro-4H-cyclopenta[7,8]phenanthro[2,1-d]thiazol-2-yl)-N-phenethylacetamide;

N-allyl-N-((5aR,5bS,7aS,10aS,10bR)-5a,7a-dimethyl-8-oxo-5,5a,5b,6,7,7a,8,9,10,10a,10b,11,12,12a-tetradecahydro-4H-cyclopenta[7,8]phenanthro[2,1-d]thiazol-2-yl)acetamide;

N-((5aR,5bS,7aS,10aS,10bR)-5a,7a-dimethyl-8-oxo-5,5a,5b,6,7,7a,8,9,10,10a,10b,11,12,12a-tetradecahydro-4H-cyclopenta[7,8]phenanthro[2,1-d]thiazol-2-yl)-N-(3-morpholinopropyl)acetamide;

N-benzyl-N-((5aR,5bS,7aS,10aS,10bR)-5a,7a-dimethyl-8-oxo-5,5a,5b,6,7,7a,8,9,10,10a,10b,11,12,12a-tetradecahydro-4H-cyclopenta[7,8]phenanthro[2,1-d]thiazol-2-yl)acetamide;

N-((5aR,5bS,7aS,10aS,10bR)-5a,7a-dimethyl-8-oxo-5,
5a,5b,6,7,7a,8,9,10,10a,10b,11,12,12a-tetradecahydro-
4H-cyclopenta[7,8]phenanthro[2,1-d]thiazol-2-yl)-N-
phenylacetamide;

N-((5aR,5bS,7aS,10aS,10bR)-5a,7a-dimethyl-8-oxo-5,
5a,5b,6,7,7a,8,9,10,10a,10b,11,12,12a-tetradecahydro-
4H-cyclopenta[7,8]phenanthro[2,1-d]thiazol-2-yl)-N-
(3-fluorophenyl)acetamide;

N-((5aR,5bS,7aS,10aS,10bR)-5a,7a-dimethyl-8-oxo-5,
5a,5b,6,7,7a,8,9,10,10a,10b,11,12,12a-tetradecahydro-
4H-cyclopenta[7,8]phenanthro[2,1-d]thiazol-2-yl)-N-
(4-fluorophenyl)acetamide;

N-(2,4-difluorophenyl)-N-((5aR,5bS,7aS,10aS,10bR)-5a,
7a-dimethyl-8-oxo-5,5a,5b,6,7,7a,8,9,10,10a,10b,11,
12,12a-tetradecahydro-4H-cyclopenta[7,8]phenanthro
[2,1-d]thiazol-2-yl)acetamide;

N-(2-chlorophenyl)-N-((5aR,5bS,7aS,10aS,10bR)-5a,7a-
dimethyl-8-oxo-5,5a,5b,6,7,7a,8,9,10,10a,10b,11,12,
12a-tetradecahydro-4H-cyclopenta[7,8]phenanthro[2,
1-d]thiazol-2-yl)acetamide;

N-(4-chlorophenyl)-N-((5aR,5bS,7aS,10aS,10bR)-5a,7a-
dimethyl-8-oxo-5,5a,5b,6,7,7a,8,9,10,10a,10b,11,12,
12a-tetradecahydro-4H-cyclopenta[7,8]phenanthro[2,
1-d]thiazol-2-yl)acetamide;

2-(N-((5aR,5bS,7aS,10aS,10bR)-5a,7a-dimethyl-8-oxo-
5,5a,5b,6,7,7a,8,9,10,10a,10b,11,12,12a-tetradeca-
hydro-4H-cyclopenta[7,8]phenanthro[2,1-d]thiazol-2-
yl)acetamido)phenyl nitrate;

N-((5aR,5bS,7aS,10aS,10bR)-5a,7a-dimethyl-8-oxo-5,
5a,5b,6,7,7a,8,9,10,10a,10b,11,12,12a-tetradecahydro-
4H-cyclopenta[7,8]phenanthro[2,1-d]thiazol-2-yl)-N-
(2,4-dimethylphenyl)acetamide;

N-((5aR,5bS,7aS,10aS,10bR)-5a,7a-dimethyl-8-oxo-5,
5a,5b,6,7,7a,8,9,10,10a,10b,11,12,12a-tetradecahydro-
4H-cyclopenta[7,8]phenanthro[2,1-d]thiazol-2-yl)-N-
(2-methoxyphenyl)acetamide;

N-(2,5-dimethoxyphenyl)-N-((5aR,5bS,7aS,10aS,10bR)-
5a,7a-dimethyl-8-oxo-5,5a,5b,6,7,7a,8,9,10,10a,10b,
11,12,12a-tetradecahydro-4H-cyclopenta[7,8]
phenanthro[2,1-d]thiazol-2-yl)acetamide;

N-((5aR,5bS,7aS,10aS,10bR)-5a,7a-dimethyl-8-oxo-5,
5a,5b,6,7,7a,8,9,10,10a,10b,11,12,12a-tetradecahydro-
4H-cyclopenta[7,8]phenanthro[2,1-d]thiazol-2-yl)-N-
(3-methoxyphenyl)acetamide;

N-((5aR,5bS,7aS,10aS,10bR)-5a,7a-dimethyl-8-oxo-5,
5a,5b,6,7,7a,8,9,10,10a,10b,11,12,12a-tetradecahydro-
4H-cyclopenta[7,8]phenanthro[2,1-d]thiazol-2-yl)-N-
(3-methoxyphenyl)acetamide;

N-((5aR,5bS,7aS,10aS,10bR)-5a,7a-dimethyl-8-oxo-5,
5a,5b,6,7,7a,8,9,10,10a,10b,11,12,12a-tetradecahydro-
4H-cyclopenta[7,8]phenanthro[2,1-d]thiazol-2-yl)-N-
(4-methoxyphenyl)acetamide;

N-((5aR,5bS,7aS,10aS,10bR)-5a,7a-dimethyl-8-oxo-5,
5a,5b,6,7,7a,8,9,10,10a,10b,11,12,12a-tetradecahydro-
4H-cyclopenta[7,8]phenanthro[2,1-d]thiazol-2-yl)-N-
(4-(trifluoromethyl)phenoxy)acetamide;

N-(5-chloro-2-methoxyphenyl)-N-((5aR,5bS,7aS,10aS,
10bR)-5a,7a-dimethyl-8-oxo-5,5a,5b,6,7,7a,8,9,10,
10a,10b,11,12,12a-tetradecahydro-4H-cyclopenta[7,8]
phenanthro[2,1-d]thiazol-2-yl)acetamide;

N-((5aR,5bS,7aS,10aS,10bR)-5a,7a-dimethyl-8-oxo-5,
5a,5b,6,7,7a,8,9,10,10a,10b,11,12,12a-tetradecahydro-
4H-cyclopenta[7,8]phenanthro[2,1-d]thiazol-2-yl)-N-
(pyrimidin-2-yl)acetamide;

4-(N-((5aR,5bS,7aS,10aS,10bR)-5a,7a-dimethyl-8-oxo-
5,5a,5b,6,7,7a,8,9,10,10a,10b,11,12,12a-tetradeca-
hydro-4H-cyclopenta[7,8]phenanthro[2,1-d]thiazol-2-
yl)acetamido)benzoic acid;

(5aR,5bS,7aS,10aS,10bR)-2,5a,7a-trimethyl-5,5a,5b,6,7,
7a,8,9,10,10a,10b,11-dodecahydro-4H-cyclopenta[7,8]
phenanthro[2,1-d]thiazol-8-ol;

(5aR,5bS,7aS,10aS,10bR)-5a,7a-dimethyl-2-phenyl-5,
5a,5b,6,7,7a,8,9,10,10a,10b,11-dodecahydro-4H-cy-
clopenta[7,8]phenanthro[2,1-d]thiazol-8-ol;

(5aR,5bS,7aS,10aS,10bR)-2-benzyl-5a,7a-dimethyl-5,5a,
5b,6,7,7a,8,9,10,10a,10b,11-dodecahydro-4H-cyclo-
penta[7,8]phenanthro[2,1-d]thiazol-8-ol;

(5aR,5bS,7aS,10aS,10bR)-5a,7a-dimethyl-2-(pyridin-2-
yl)-5,5a,5b,6,7,7a,8,9,10,10a,10b,11-dodecahydro-4H-
cyclopenta[7,8]phenanthro[2,1-d]thiazol-8-ol;

(5aR,5bS,7aS,10aS,10bR)-2-(4-hydroxyphenyl)-5a,7a-
dimethyl-5,5a,5b,6,7,7a,8,9,10,10a,10b,11-dodeca-
hydro-4H-cyclopenta[7,8]phenanthro[2,1-d]thiazol-8-
ol;

(5aR,5bS,7aS,10aS,10bR)-2-(2-hydroxyphenyl)-5a,7a-
dimethyl-5,5a,5b,6,7,7a,8,9,10,10a,10b,11-dodeca-
hydro-4H-cyclopenta[7,8]phenanthro[2,1-d]thiazol-8-
ol;

4-((5aR,5bS,7aS,10aS,10bR)-8-hydroxy-5a,7a-dimethyl-
5,5a,5b,6,7,7a,8,9,10,10a,10b,11-dodecahydro-4H-cy-
clopenta[7,8]phenanthro[2,1-d]thiazol-2-yl)benzene-1,
2-diol;

(5aR,5bS,7aS,10aS,10bR)-2-(2-chlorophenyl)-5a,7a-di-
methyl-5,5a,5b,6,7,7a,8,9,10,10a,10b,11-dodecahydro-
4H-cyclopenta[7,8]phenanthro[2,1-d]thiazol-8-ol;

4-((5aR,5bS,7aS,10aS,10bR)-8-hydroxy-5a,7a-dimethyl-
5,5a,5b,6,7,7a,8,9,10,10a,10b,11-dodecahydro-4H-cy-
clopenta[7,8]phenanthro[2,1-d]thiazol-2-yl)benzoic
acid;

(5aR,5bS,7aS,10aS,10bR)-5a,7a-dimethyl-2-(4-meth-
ylphenyl)-5,5a,5b,6,7,7a,8,9,10,10a,10b,11-dodeca-
hydro-4H-cyclopenta[7,8]phenanthro[2,1-d]thiazol-8-
ol;

(5aR,5bS,7aS,10aS,10bR)-5a,7a-dimethyl-2-(3-meth-
ylphenyl)-5,5a,5b,6,7,7a,8,9,10,10a,10b,11-dodeca-
hydro-4H-cyclopenta[7,8]phenanthro[2,1-d]thiazol-8-
ol;

(5aR,5bS,7aS,10aS,10bR)-2-(3-methoxyphenyl)-5a,7a-
dimethyl-5,5a,5b,6,7,7a,8,9,10,10a,10b,11-dodeca-
hydro-4H-cyclopenta[7,8]phenanthro[2,1-d]thiazol-8-
ol;

(5aR,5bS,7aS,10aS,10bR)-2-(4-methoxyphenyl)-5a,7a-
dimethyl-5,5a,5b,6,7,7a,8,9,10,10a,10b,11-dodeca-
hydro-4H-cyclopenta[7,8]phenanthro[2,1-d]thiazol-8-
ol;

(5aR,5bS,7aS,10aS,10bR)-5a,7a-dimethyl-2-(2-meth-
ylphenyl)-5,5a,5b,6,7,7a,8,9,10,10a,10b,11-dodeca-
hydro-4H-cyclopenta[7,8]phenanthro[2,1-d]thiazol-8-
ol;

(5aR,5bS,7aS,10aS,10bR)-2-(3-fluorophenyl)-5a,7a-di-
methyl-5,5a,5b,6,7,7a,8,9,10,10a,10b,11-dodecahydro-
4H-cyclopenta[7,8]phenanthro[2,1-d]thiazol-8-ol;

(5aR,5bS,7aS,10aS,10bR)-2-(4-fluorophenyl)-5a,7a-di-
methyl-5,5a,5b,6,7,7a,8,9,10,10a,10b,11-dodecahydro-
4H-cyclopenta[7,8]phenanthro[2,1-d]thiazol-8-ol;

(5aR,5bS,7aS,10aS,10bR)-2-(3-chlorophenyl)-5a,7a-di-
methyl-5,5a,5b,6,7,7a,8,9,10,10a,10b,11-dodecahydro-
4H-cyclopenta[7,8]phenanthro[2,1-d]thiazol-8-ol;

(5aR,5bS,7aS,10aS,10bR)-2-(4-chlorophenyl)-5a,7a-di-
methyl-5,5a,5b,6,7,7a,8,9,10,10a,10b,11-dodecahydro-
4H-cyclopenta[7,8]phenanthro[2,1-d]thiazol-8-ol;

(5aR,5bS,7aS,10aS,10bR)-2-(4-bromophenyl)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,10aS,10bR)-2-(3-ethoxyphenyl)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-amino-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-5a,7a-dimethyl-2-(methylamino)-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-(ethylamino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-(butylamino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-5a,7a-dimethyl-2-(phenethylamino)-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-(allylamino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-5a,7a-dimethyl-2-((3-morpholinopropyl)amino)-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-(benzylamino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-5a,7a-dimethyl-2-(methyl(phenyl)amino)-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-5a,7a-dimethyl-2-(phenylamino)-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-((4-fluorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-((3-fluorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-((4-chlorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-((2-chlorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-((2,4-difluorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-5a,7a-dimethyl-2-((2-nitrophenyl)amino)-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-((2,4-dimethylphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-((2-methoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-((2,5-dimethoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-((3-hydroxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-((4-methoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-5a,7a-dimethyl-2-((4-(trifluoromethoxy)phenyl)amino)-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-((5-chloro-2-methoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-5a,7a-dimethyl-2-(pyridin-2-ylamino)-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-5a,7a-dimethyl-2-(pyrimidin-2-ylamino)-5,5a,5b,6,7,7a,8,9,10,10a,10b,11-dodecahydro-4H-cyclopenta[7,8]phenanthro[2,1-d]thiazol-8-ol;

4-(((5aR,5bS,7aS,8S,10aS,10bR)-8-hydroxy-5a,7a-dimethyl-5,5a,5b,6,7,7a,8,9,10,10a,10b,11-dodecahydro-4H-cyclopenta[7,8]phenanthro[2,1-d]thiazol-2-yl)amino)benzoic acid;

(5aR,5bS,7aS,8S,10aS,10bR)-5a,7a-dimethyl-2-((piperidin-1-yl)amino)-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-5a,7a-dimethyl-2-(morpholinoamino)-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-5a,7a-dimethyl-2-((4-methylpiperazin-1-yl)amino)-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-((4-ethylpiperazin-1-yl)amino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-2-((4-ethyl-2-hydroxypiperazin-1-yl)amino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-5a,7a-dimethyl-2-(piperazin-1-ylamino)-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-5a,7a-dimethyl-2-(4-methylphenylamino)-5,5a,5b,6,7,7a,8,9,10,10a,10b,11-dodecahydro-4H-cyclopenta[7,8]phenanthro[2,1-d]thiazol-8-ol;

(5aR,5bS,7aS,8S,10aS,10bR)-5a,7a-dimethyl-2-((3-(trifluoromethoxy)phenyl)amino)-5,5a,5b,6,7,7a,8,9,10,10a,10b,11-dodecahydro-4H-cyclopenta[7,8]phenanthro[2,1-d]thiazol-8-ol;

3-(((5aR,5bS,7aS,8S,10aS,10bR)-8-hydroxy-5a,7a-dimethyl-5,5a,5b,6,7,7a,8,9,10,10a,10b,11-dodecahydro-4H-cyclopenta[7,8]phenanthro[2,1-d]thiazol-2-yl)amino)benzoic acid;

(5aR,5bS,7aS,8S,10aS,10bR)-5a,7a-dimethyl-2-((3-(trifluoromethyl)phenyl)amino)-5,5a,5b,6,7,7a,8,9,10,10a,10b,11-dodecahydro-4H-cyclopenta[7,8]phenanthro[2,1-d]thiazol-8-ol;

N-((5aR,5bS,7aS,8S,10aS,10bR)-8-hydroxy-5a,7a-dimethyl-5,5a,5b,6,7,7a,8,9,10,10a,10b,11-dodecahydro-4H-cyclopenta[7,8]phenanthro[2,1-d]thiazol-2-yl)acetamide;

(5aR,5bS,7aS,8S,10aS,10bR)-2-((4-hydroxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,10aS,10bR,E)-8-hydrazineylidene-5a,7a-dimethyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-8-hydrazineylidene-5a,7a-dimethyl-N-phenethyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-N-allyl-8-hydrazineylidene-5a,7a-dimethyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-8-hydrazineylidene-5a,7a-dimethyl-N-(3-morpholinopropyl)-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-N-benzyl-8-hydrazineylidene-5a,7a-dimethyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-8-hydrazineylidene-N,5a,7a-trimethyl-N-phenyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-8-hydrazineylidene-5a,7a-dimethyl-N-phenyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-N-(4-fluorophenyl)-8-hydrazineylidene-5a,7a-dimethyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-N-(3-fluorophenyl)-8-hydrazineylidene-5a,7a-dimethyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-N-(3-chlorophenyl)-8-hydrazineylidene-5a,7a-dimethyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-N-(4-chlorophenyl)-8-hydrazineylidene-5a,7a-dimethyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-N-(2,4-difluorophenyl)-8-hydrazineylidene-5a,7a-dimethyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-8-hydrazineylidene-5a,7a-dimethyl-N-(2-nitrophenyl)-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-N-(2,4-dimethylphenyl)-8-hydrazineylidene-5a,7a-dimethyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-8-hydrazineylidene-N-mesityl-5a,7a-dimethyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-8-hydrazineylidene-N-(2-methoxyphenyl)-5a,7a-dimethyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-N-(2,5-dimethoxyphenyl)-8-hydrazineylidene-5a,7a-dimethyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-N-(2,5-dimethoxyphenyl)-8-hydrazineylidene-5a,7a-dimethyl-5,5a,5b,6,7,7a,8,9,10,10a,10b,11-dodecahydro-4H-cyclopenta[7,8]phenanthro[2,1-d]thiazol-2-amine;

3-(((5aR,5bS,7aS,10aS,10bR,E)-8-hydrazineylidene-5a,7a-dimethyl-5,5a,5b,6,7,7a,8,9,10,10a,10b,11-dodecahydro-4H-cyclopenta[7,8]phenanthro[2,1-d]thiazol-2-yl)amino)phenol;

(5aR,5bS,7aS,10aS,10bR,E)-8-hydrazineylidene-N-(4-methoxyphenyl)-5a,7a-dimethyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-8-hydrazineylidene-5a,7a-dimethyl-N-(4-(trifluoromethoxy)phenyl)-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-N-(5-chloro-2-methoxyphenyl)-8-hydrazineylidene-5a,7a-dimethyl-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-8-hydrazineylidene-5a,7a-dimethyl-N-(pyrimidin-2-yl)-5,5a,5b,6,7,7a,8,9,10,10a,10b,11-dodecahydro-4H-cyclopenta[7,8]phenanthro[2,1-d]thiazol-2-amine;

4-(((5aR,5bS,7aS,10aS,10bR,E)-8-hydrazineylidene-5a,7a-dimethyl-5,5a,5b,6,7,7a,8,9,10,10a,10b,11-dodecahydro-4H-cyclopenta[7,8]phenanthro[2,1-d]thiazol-2-yl)amino)benzoic acid;

(5aR,5bS,7aS,10aS,10bR,E)-8-hydrazineylidene-5a,7a-dimethyl-N-(piperidin-1-yl)-5,5a,5b,6,7,7a,8,9,10,10a,10b,11-dodecahydro-4H-cyclopenta[7,8]phenanthro[2,1-d]thiazol-2-amine;

N-((5aR,5bS,7aS,10aS,10bR,E)-8-hydrazineylidene-5a,7a-dimethyl-5,5a,5b,6,7,7a,8,9,10,10a,10b,11-dodecahydro-4H-cyclopenta[7,8]phenanthro[2,1-d]thiazol-2-yl)morpholin-4-amine;

(5aR,5bS,7aS,10aS,10bR,E)-8-hydrazineylidene-5a,7a-dimethyl-N-(4-methylpiperazin-1-yl)-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-8-hydrazineylidene-5a,7a-dimethyl-N-(4-ethylpiperazin-1-yl)-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-8-hydrazineylidene-5a,7a-dimethyl-N-(4-ethan-2-ol-piperazin-1-yl)-5,5a,5b,6,7,7a,8,9,10,10a,10b,11-dodecahydro-4H-cyclopenta[7,8]phenanthro[2,1-d]thiazol-2-amine;

(5aR,5bS,7aS,10aS,10bR,E)-8-hydrazineylidene-5a,7a-dimethyl-N-(piperazin-1-yl)-5,5a,5b,6,7,7a,8,9,10,10a,10b,11-dodecahydro-4H-cyclopenta[7,8]phenanthro[2,1-d]thiazol-2-amine;

(E)-2-((5aR,5bS,7aS,10aS,10bR)-2-amino-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-5a,7a-dimethyl-2-(phenethylamino)-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-5a,7a-dimethyl-2-(prop-2-en-1-ylamino)-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-5a,7a-dimethyl-2-((3-morpholinopropyl)amino)-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-2-(benzylamino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-5a,7a-dimethyl-2-(phenylamino)-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-5a,7a-dimethyl-2-(methyl(phenyl)amino)-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-2-((4-fluorophenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-2-((3-fluorophenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-2-((2,4-difluorophenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-2-((4-chlorophenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-2-((2-chlorophenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-5a,7a-dimethyl-2-((2-nitrophenyl)amino)-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-2-((2,4-dimethylphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-2-((2,4,6-trimethylphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-2-((2-methoxyphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-2-((2,5-dimethoxyphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-2-((3-hydroxyphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-2-((4-methoxyphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-5a,7a-dimethyl-2-((4-(trifluoromethyl)phenoxy)amino)-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-2-((5-chloro-2-methoxyphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-5a,7a-dimethyl-2-(pyridin-2-ylamino)-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-5a,7a-dimethyl-2-(pyrimidin-2-ylamino)-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

4-(((5aR,5bS,7aS,10aS,10bR,E)-8-(2-carbamoylhydrazineylidene)-5a,7a-dimethyl-5,5a,5b,6,7,7a,8,9,10,10a,10b,11-dodecahydro-4H-cyclopenta[7,8]phenanthro[2,1-d]thiazol-2-yl)amino)benzoic acid;

(E)-2-((5aR,5bS,7aS,10aS,10bR)-5a,7a-dimethyl-2-(piperidin-1-ylamino)-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-5a,7a-dimethyl-2-(morpholinoamino)-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-5a,7a-dimethyl-2-((4-methylpiperazin-1-yl)amino)-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-5a,7a-dimethyl-2-((4-ethylpiperazin-1-yl)amino)-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-2-((4-(2-hydroxyethyl)piperazin-1-yl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-5a,7a-dimethyl-2-(piperazin-1-ylamino)-4,5,5a,5b,6,7,7a,9,10,10a,10b,11-dodecahydro-8H-cyclopenta[7,8]phenanthro[2,1-d]thiazol-8-ylidene)hydrazine-1-carboxamide;

(E)-2-((5aR,5bS,7aS,10aS,10bR)-2-amino-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-5a,7a-dimethyl-2-(phenethylamino)-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-5a,7a-dimethyl-2-(prop-2-en-1-ylamino)-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-5a,7a-dimethyl-2-((3-morpholinopropyl)amino)-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-2-(benzylamino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-5a,7a-dimethyl-2-(phenylamino)-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-5a,7a-dimethyl-2-(methyl(phenyl)amino)-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-2-((4-fluorophenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-2-((3-fluorophenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-2-((2,4-difluorophenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-2-((4-chlorophenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-2-((2-chlorophenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-5a,7a-dimethyl-2-((2-nitrophenyl)amino)-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-2-((2,4-dimethylphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-2-((2,4,6-trimethylphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-2-((2-methoxyphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-2-((2,5-dimethoxyphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-2-((3-hydroxyphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-2-((4-methoxyphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-5a,7a-dimethyl-2-((4-(trifluoromethyl)phenoxy)amino)-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-2-((5-chloro-2-methoxyphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-5a,7a-dimethyl-2-(pyridin-2-ylamino)-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-5a,7a-dimethyl-2-(pyrimidin-2-ylamino)-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

4-(((5aR,5bS,7aS,10aS,10bR,E)-8-(2-carbamothioylhydrazineylidene)-5a,7a-dimethyl-5,5a,5b,6,7,7a,8,9,10,10a,10b,11-dodecahydro-4H-cyclopenta[7,8]phenanthro[2,1-d]thiazol-2-yl)amino)benzoic acid;

(E)-2-((5aR,5bS,7aS,10aS,10bR)-5a,7a-dimethyl-2-(piperidin-1-ylamino)-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-5a,7a-dimethyl-2-(morpholinoamino)-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-5a,7a-dimethyl-2-((4-methylpiperazin-1-yl)amino)-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-2-((4-ethylpiperazin-1-yl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-2-((4-(2-hydroxyethyl)piperazin-1-yl)amino)-5a,7a-dimethyl-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(E)-2-((5aR,5bS,7aS,10aS,10bR)-5a,7a-dimethyl-2-(piperazin-1-ylamino)-4,5,5a,5b,6,7,7a,9,10,10a,10b,11-dodecahydro-8H-cyclopenta[7,8]phenanthro[2,1-d]thiazol-8-ylidene)hydrazine-1-carbothioamide;

(5aR,5bS,7aS,10aS,10bR,E)-2-amino-5a,7a-dimethyl-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-5a,7a-dimethyl-2-(phenethylamino)-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-5a,7a-dimethyl-2-(prop-2-en-1-ylamino)-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-5a,7a-dimethyl-2-((3-morpholinopropyl)amino)-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-2-(benzylamino)-5a,7a-dimethyl-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-5a,7a-dimethyl-2-(phenylamino)-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-5a,7a-dimethyl-2-(methyl(phenyl)amino)-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-2-((4-fluorophenyl)amino)-5a,7a-dimethyl-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-2-((3-fluorophenyl)amino)-5a,7a-dimethyl-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-2-((2,4-difluorophenyl)amino)-5a,7a-dimethyl-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-2-((4-chlorophenyl)amino)-5a,7a-dimethyl-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-2-((2-chlorophenyl)amino)-5a,7a-dimethyl-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-5a,7a-dimethyl-2-((2-nitrophenyl)amino)-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-2-((2,4-dimethylphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-2-((2,4,6-trimethylphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-2-((2-methoxyphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-2-((2,5-dimethoxyphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-2-((3-hydroxyphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-2-((4-methoxyphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-5a,7a-dimethyl-2-((4-(trifluoromethyl)phenoxy)amino)-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-2-((5-chloro-2-methoxyphenyl)amino)-5a,7a-dimethyl-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-5a,7a-dimethyl-2-(pyridin-2-ylamino)-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-5a,7a-dimethyl-2-(pyrimidin-2-ylamino)-4,5,5a,5b,6,7,7a,9,10,10a,10b,11-dodecahydro-8H-cyclopenta[7,8]phenanthro[2,1-d]thiazol-8-one oxime;

4-(((5aR,5bS,7aS,10aS,10bR,E)-8-(hydroxyimino)-5a,7a-dimethyl-5,5a,5b,6,7,7a,8,9,10,10a,10b,11-dodecahydro-4H-cyclopenta[7,8]phenanthro[2,1-d]thiazol-2-yl)amino)benzoic acid;

(5aR,5bS,7aS,10aS,10bR,E)-5a,7a-dimethyl-2-(piperidin-1-ylamino)-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-5a,7a-dimethyl-2-(morpholinoamino)-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-5a,7a-dimethyl-2-((4-methylpiperazin-1-yl)amino)-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-5a,7a-dimethyl-2-((4-ethylpiperazin-1-yl)amino)-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-2-((4-(2-hydroxyethyl)piperazin-1-yl)amino)-5a,7a-dimethyl-4,5,5a,5b,6,7,7a,9,10,10a,10b,11-dodecahydro-8H-cyclopenta[7,8]phenanthro[2,1-d]thiazol-8-one oxime;

(5aR,5bS,7aS,10aS,10bR,E)-5a,7a-dimethyl-2-(piperazin-1-ylamino)-4,5,5a,5b,6,7,7a,9,10,10a,10b,11-dodecahydro-8H-cyclopenta[7,8]phenanthro[2,1-d]thiazol-8-one oxime;

(5aR,5bS,7aS,8S,10aS,10bR)-2-acetamido-5a,7a-dimethyl-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-5a,7a-dimethyl-2-(phenethylamino)-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-2-(allylamino)-5a,7a-dimethyl-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-5a,7a-dimethyl-2-((3-morpholinopropyl)amino)-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-2-(benzylamino)-5a,7a-dimethyl-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-5a,7a-dimethyl-2-(phenylamino)-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-5a,7a-dimethyl-2-(methyl(phenyl)amino)-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-2-((4-fluorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-2-((3-fluorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-2-((2,4-difluorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-2-((2-chlorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-2-((4-chlorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-5a,7a-dimethyl-2-((2-nitrophenyl)amino)-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-2-((2,4-dimethylphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-2-((2-methoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-2-((2,5-dimethoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-2-((3-hydroxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-2-((4-methoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-5a,7a-dimethyl-2-((4-(trifluoromethoxy)phenyl)amino)-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-2-((5-chloro-2-methoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-5a,7a-dimethyl-2-(pyridin-2-ylamino)-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-5a,7a-dimethyl-2-(pyrimidin-2-ylamino)-5,5a,5b,6,7,7a,8,9,10,10a,10b,11-dodecahydro-4H-cyclopenta[7,8]phenanthro[2,1-d]thiazol-8-yl acetate;

4-(((5aR,5bS,7aS,8S,10aS,10bR)-8-acetoxy-5a,7a-dimethyl-5,5a,5b,6,7,7a,8,9,10,10a,10b,11-dodecahydro-4H-cyclopenta[7,8]phenanthro[2,1-d]thiazol-2-yl)amino)benzoic acid;

(5aR,5bS,7aS,8S,10aS,10bR)-5a,7a-dimethyl-2-(piperidin-1-ylamino)-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-5a,7a-dimethyl-2-(morpholinoamino)-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-5a,7a-dimethyl-2-((4-methylpiperazin-1-yl)amino)-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-2-((4-ethylpiperazin-1-yl)amino)-5a,7a-dimethyl-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-2-((4-ethyl-2-hydroxypiperazin-1-yl)amino)-5a,7a-dimethyl-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-5a,7a-dimethyl-2-(piperazin-1-ylamino)-5,5a,5b,6,7,7a,8,9,10,10a,10b,11-dodecahydro-4H-cyclopenta[7,8]phenanthro[2,1-d]thiazol-8-yl acetate;

(5aR,5bS,7aS,8S,10aS,10bR)-2-acetamido-5a,7a-dimethyl-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-5a,7a-dimethyl-2-(phenethylamino)-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-2-(allylamino)-5a,7a-dimethyl-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-5a,7a-dimethyl-2-((3-morpholinopropyl)amino)-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-2-(benzylamino)-5a,7a-dimethyl-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-5a,7a-dimethyl-2-(phenylamino)-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-5a,7a-dimethyl-2-(methyl(phenyl)amino)-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-2-((4-fluorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-2-((3-fluorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-2-((2,4-difluorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-2-((2-chlorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-2-((4-chlorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-5a,7a-dimethyl-2-((2-nitrophenyl)amino)-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-2-((2,4-dimethylphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-2-((2-methoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-2-((2,5-dimethoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-2-((3-hydroxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-2-((4-methoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-5a,7a-dimethyl-2-((4-(trifluoromethoxy)phenyl)amino)-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-2-((5-chloro-2-methoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-5a,7a-dimethyl-2-(pyridin-2-ylamino)-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-5a,7a-dimethyl-2-(pyrimidin-2-ylamino)-5,5a,5b,6,7,7a,8,9,10,10a,10b,11-dodecahydro-4H-cyclopenta[7,8]phenanthro[2,1-d]thiazol-8-yl propionate;

4-(((5aR,5bS,7aS,8S,10aS,10bR)-5a,7a-dimethyl-8-(propionyloxy)-5,5a,5b,6,7,7a,8,9,10,10a,10b,11-dodecahydro-4H-cyclopenta[7,8]phenanthro[2,1-d]thiazol-2-yl)amino)benzoic acid;

(5aR,5bS,7aS,8S,10aS,10bR)-5a,7a-dimethyl-2-(piperidin-1-ylamino)-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-5a,7a-dimethyl-2-(morpholinoamino)-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-5a,7a-dimethyl-2-((4-methylpiperazin-1-yl)amino)-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-2-((4-ethylpiperazin-1-yl)amino)-5a,7a-dimethyl-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-2-((4-ethyl-2-hydroxypiperazin-1-yl)amino)-5a,7a-dimethyl-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-5a,7a-dimethyl-2-(piperazin-1-ylamino)-5,5a,5b,6,7,7a,8,9,10,10a,10b,11-dodecahydro-4H-cyclopenta[7,8]phenanthro[2,1-d]thiazol-8-yl propionate;

(5aR,5bS,7aS,8S,10aS,10bR)-2-acetamido-5a,7a-dimethyl-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-5a,7a-dimethyl-2-(phenethylamino)-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-2-(allylamino)-5a,7a-dimethyl-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-5a,7a-dimethyl-2-((3-morpholinopropyl)amino)-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-2-(benzylamino)-5a,7a-dimethyl-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-5a,7a-dimethyl-2-(phenylamino)-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-5a,7a-dimethyl-2-(methyl(phenyl)amino)-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-2-((4-fluorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-2-((3-fluorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-2-((2,4-difluorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-2-((2-chlorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-2-((4-chlorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-5a,7a-dimethyl-2-((2-nitrophenyl)amino)-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-2-((2,4-dimethylphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-2-((2-methoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-2-((2,5-dimethoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-2-((3-hydroxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-2-((4-methoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-5a,7a-dimethyl-2-((4-(trifluoromethoxy)phenyl)amino)-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-2-((5-chloro-2-methoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-5a,7a-dimethyl-2-(pyridin-2-ylamino)-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-5a,7a-dimethyl-2-(pyrimidin-2-ylamino)-5,5a,5b,6,7,7a,8,9,10,10a,10b,11-dodecahydro-4H-cyclopenta[7,8]phenanthro[2,1-d]thiazol-8-yl butyrate;

4-(((5aR,5bS,7aS,8S,10aS,10bR)-8-(butyryloxy)-5a,7a-dimethyl-5,5a,5b,6,7,7a,8,9,10,10a,10b,11-dodecahydro-4H-cyclopenta[7,8]phenanthro[2,1-d]thiazol-2-yl)amino)benzoic acid;

(5aR,5bS,7aS,8S,10aS,10bR)-5a,7a-dimethyl-2-(piperidin-1-ylamino)-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-5a,7a-dimethyl-2-(morpholinoamino)-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-5a,7a-dimethyl-2-((4-methylpiperazin-1-yl)amino)-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-2-((4-ethylpiperazin-1-yl)amino)-5a,7a-dimethyl-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-2-((4-ethyl-2-hydroxypiperazin-1-yl)amino)-5a,7a-dimethyl-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-5a,7a-dimethyl-2-(piperazin-1-ylamino)-5,5a,5b,6,7,7a,8,9,10,10a,10b,11-dodecahydro-4H-cyclopenta[7,8]phenanthro[2,1-d]thiazol-8-yl butyrate;

(5aR,5bS,7aS,8S,10aS,10bR)-2-acetamido-5a,7a-dimethyl-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-5a,7a-dimethyl-2-(phenethylamino)-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-2-(allylamino)-5a,7a-dimethyl-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-5a,7a-dimethyl-2-((3-morpholinopropyl)amino)-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-2-(benzylamino)-5a,7a-dimethyl-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-5a,7a-dimethyl-2-(phenylamino)-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-5a,7a-dimethyl-2-(methyl(phenyl)amino)-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-2-((4-fluorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-2-((3-fluorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-2-((2,4-difluorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-2-((2-chlorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-2-((4-chlorophenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-5a,7a-dimethyl-2-((2-nitrophenyl)amino)-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-2-((2,4-dimethylphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-2-((2-methoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-2-((2,5-dimethoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-2-((3-hydroxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-2-((4-methoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-5a,7a-dimethyl-2-((4-(trifluoromethoxy)phenyl)amino)-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-2-((5-chloro-2-methoxyphenyl)amino)-5a,7a-dimethyl-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-5a,7a-dimethyl-2-(pyridin-2-ylamino)-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-5a,7a-dimethyl-2-(pyrimidin-2-ylamino)-5,5a,5b,6,7,7a,8,9,10,10a,10b,11-dodecahydro-4H-cyclopenta[7,8]phenanthro[2,1-d]thiazol-8-yl pentanoate;

4-(((5aR,5bS,7aS,8S,10aS,10bR)-5a,7a-dimethyl-8-(pentanoyloxy)-5,5a,5b,6,7,7a,8,9,10,10a,10b,11-dodecahydro-4H-cyclopenta[7,8]phenanthro[2,1-d]thiazol-2-yl)amino)benzoic acid;

(5aR,5bS,7aS,8S,10aS,10bR)-5a,7a-dimethyl-2-(piperidin-1-ylamino)-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-5a,7a-dimethyl-2-(morpholinoamino)-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-5a,7a-dimethyl-2-((4-methylpiperazin-1-yl)amino)-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-2-((4-ethylpiperazin-1-yl)amino)-5a,7a-dimethyl-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-2-((4-ethyl-2-hydroxypiperazin-1-yl)amino)-5a,7a-dimethyl-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aS,8S,10aS,10bR)-5a,7a-dimethyl-2-(piperazin-1-ylamino)-5,5a,5b,6,7,7a,8,9,10,10a,10b,11-dodecahydro-4H-cyclopenta[7,8]phenanthro[2,1-d]thiazol-8-yl pentanoate;

(5aR,5bS,7aR,10aS,10bS)-5a,7a-dimethyl-8-(6-methylheptan-2-yl)-5,5a,5b,6,7,7a,8,9,10,10a,10b,11-dodecahydro-4H-cyclopenta[7,8]phenanthro[2,1-d]thiazol-2-amine;

(5aR,5bS,7aR,10aS,10bS)-5a,7a-dimethyl-8-(6-methylheptan-2-yl)-N-allyl-5,5a,5b,6,7,7a,8,9,10,10a,10b,11-dodecahydro-4H-cyclopenta[7,8]phenanthro[2,1-d]thiazol-2-amine;

(5aR,5bS,7aR,10aS,10bS)-5a,7a-dimethyl-8-(6-methylheptan-2-yl)-N-benzyl-5,5a,5b,6,7,7a,8,9,10,10a,10b,11-dodecahydro-4H-cyclopenta[7,8]phenanthro[2,1-d]thiazol-2-amine;

(5aR,5bS,7aR,10aS,10bS)-5a,7a-dimethyl-8-(6-methylheptan-2-yl)-N-phenyl-5,5a,5b,6,7,7a,8,9,10,10a,10b,11-dodecahydro-4H-cyclopenta[7,8]phenanthro[2,1-d]thiazol-2-amine;

(5aR,5bS,7aR,10aS,10bS)—N,5a,7a-trimethyl-8-(6-methylheptan-2-yl)-N-phenyl-5,5a,5b,6,7,7a,8,9,10,10a,10b,11-dodecahydro-4H-cyclopenta[7,8]phenanthro[2,1-d]thiazol-2-amine;

(5aR,5bS,7aR,10aS,10bS)-5a,7a-dimethyl-8-(6-methylheptan-2-yl)-N-(2-(trifluoromethyl)phenyl)-5,5a,5b,6,7,7a,8,9,10,10a,10b,11-dodecahydro-4H-cyclopenta[7,8]phenanthro[2,1-d]thiazol-2-amine;

(5aR,5bS,7aR,10aS,10bS)-5a,7a-dimethyl-8-(6-methylheptan-2-yl)-N-(4-methylphenyl)-5,5a,5b,6,7,7a,8,9,10,10a,10b,11-dodecahydro-4H-cyclopenta[7,8]phenanthro[2,1-d]thiazol-2-amine;

(5aR,5bS,7aR,10aS,10bS)-5a,7a-dimethyl-8-(6-methylheptan-2-yl)-N-(2,4-difluorophenyl)-5,5a,5b,6,7,7a,8,9,10,10a,10b,11-dodecahydro-4H-cyclopenta[7,8]phenanthro[2,1-d]thiazol-2-amine;

(5aR,5bS,7aR,10aS,10bS)-5a,7a-dimethyl-8-(6-methylheptan-2-yl)-N-(2-chlorophenyl)-5,5a,5b,6,7,7a,8,9,10,10a,10b,11-dodecahydro-4H-cyclopenta[7,8]phenanthro[2,1-d]thiazol-2-amine;

(5aR,5bS,7aR,10aS,10bS)-5a,7a-dimethyl-8-(6-methylheptan-2-yl)-N-(3,5-ditrifluoromethylphenyl)-5,5a,5b,6,7,7a,8,9,10,10a,10b,11-dodecahydro-4H-cyclopenta[7,8]phenanthro[2,1-d]thiazol-2-amine;

(5aR,5bS,7aR,10aS,10bS)-5a,7a-dimethyl-8-(6-methylheptan-2-yl)-N-(2-nitrophenyl)-5,5a,5b,6,7,7a,8,9,10,10a,10b,11-dodecahydro-4H-cyclopenta[7,8]phenanthro[2,1-d]thiazol-2-amine;

(5aR,5bS,7aR,10aS,10bS)-5a,7a-dimethyl-8-(6-methylheptan-2-yl)-N-(2,4-dimethylphenyl)-5,5a,5b,6,7,7a,8,9,10,10a,10b,11-dodecahydro-4H-cyclopenta[7,8]phenanthro[2,1-d]thiazol-2-amine;

(5aR,5bS,7aR,10aS,10bS)-5a,7a-dimethyl-8-(6-methylheptan-2-yl)-N-(2,4,6-trimethylphenyl)-5,5a,5b,6,7,7a,8,9,10,10a,10b,11-dodecahydro-4H-cyclopenta[7,8]phenanthro[2,1-d]thiazol-2-amine;

(5aR,5bS,7aR,10aS,10bS)-5a,7a-dimethyl-8-(6-methylheptan-2-yl)-N-(2-methoxyphenyl)-5,5a,5b,6,7,7a,8,9,10,10a,10b,11-dodecahydro-4H-cyclopenta[7,8]phenanthro[2,1-d]thiazol-2-amine;

(5aR,5bS,7aR,10aS,10bS)-5a,7a-dimethyl-8-(6-methylheptan-2-yl)-N-(2,5-dimethoxyphenyl)-5,5a,5b,6,7,7a,8,9,10,10a,10b,11-dodecahydro-4H-cyclopenta[7,8]phenanthro[2,1-d]thiazol-2-amine;

(5aR,5bS,7aR,10aS,10bS)-5a,7a-dimethyl-8-(6-methylheptan-2-yl)-N-(2,4-dimethoxyphenyl)-5,5a,5b,6,7,7a,8,9,10,10a,10b,11-dodecahydro-4H-cyclopenta[7,8]phenanthro[2,1-d]thiazol-2-amine;

(5aR,5bS,7aR,10aS,10bS)-5a,7a-dimethyl-8-(6-methylheptan-2-yl)-N-(2-methoxy-5-chlorophenyl)-5,5a,5b, 6,7,7a,8,9,10,10a,10b,11-dodecahydro-4H-cyclopenta [7,8]phenanthro[2,1-d]thiazol-2-amine;

(5aR,5bS,7aR,10aS,10bS)-5a,7a-dimethyl-8-(6-methyl-heptan-2-yl)-N-(pyridin-2-yl)-5,5a,5b,6,7,7a,8,9,10, 10a,10b,11-dodecahydro-4H-cyclopenta[7,8] phenanthro[2,1-d]thiazol-2-amine;

(5aR,5bS,7aR,10aS,10bS)-5a,7a-dimethyl-8-(6-methyl-heptan-2-yl)-N-(pyrimidin-2-yl)-5,5a,5b,6,7,7a,8,9,10, 10a,10b,11-dodecahydro-4H-cyclopenta[7,8] phenanthro[2,1-d]thiazol-2-amine;

(5aR,5bS,7aS,10aS,10bR)-2-amino-8-ethynyl-5a,7a-dimethyl-5,5a,5b,6,7,7a,8,9,10,10a,10b,11-dodecahydro-4H-cyclopenta[7,8]phenanthro[2,1-d]thiazol-8-ol;

(5aR,5bS,7aS,10aS,10bR)-2-((2,4-difluorophenyl) amino)-8-ethynyl-5a,7a-dimethyl-5,5a,5b,6,7,7a,8,9, 10,10a,10b,11-dodecahydro-4H-cyclopenta[7,8] phenanthro[2,1-d]thiazol-8-ol;

(5aR,5bS,7aS,10aS,10bR)-8-ethynyl-5a,7a-dimethyl-2-((2-nitrophenyl)amino)-5,5a,5b,6,7,7a,8,9,10,10a,10b, 11-dodecahydro-4H-cyclopenta[7,8]phenanthro[2,1-d] thiazol-8-ol;

(5aR,5bS,7aS,10aS,10bR)-2-((2,4-dimethoxyphenyl) amino)-8-ethynyl-5a,7a-dimethyl-5,5a,5b,6,7,7a,8,9, 10,10a,10b,11-dodecahydro-4H-cyclopenta[7,8] phenanthro[2,1-d]thiazol-8-ol;

(5aR,5bS,7aS,10aS,10bR)-8-ethynyl-5a,7a-dimethyl-2-(pyridin-2-ylamino)-5,5a,5b,6,7,7a,8,9,10,10a,10b,11-dodecahydro-4H-cyclopenta[7,8]phenanthro[2,1-d]thiazol-8-ol;

(5aR,5bS,7aS,10aS,10bR)-8-ethynyl-5a,7a-dimethyl-2-(pyrimidin-2-ylamino)-5,5a,5b,6,7,7a,8,9,10,10a,10b, 11-dodecahydro-4H-cyclopenta[7,8]phenanthro[2,1-d] thiazol-8-ol;

(5aR,5bS,7aS,10aS,10bR,12aR)-2,5a,7a-trimethyl-4,5, 5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR,12aR)-2-benzyl-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR,12aR)-5a,7a-dimethyl-2-(pyridin-2-yl)-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR,12aR)-2-(4-hydroxyphenyl)-5a,7a-dimethyl-4,5,5a,5b,6,7,7a,9,10,10a,10b,11,12, 12a-tetradecahydro-8H-cyclopenta[7,8]phenanthro[2, 1-d]thiazol-8-one;

(5aR,5bS,7aS,10aS,10bR,12aR)-2-(2-chlorophenyl)-5a, 7a-dimethyl-4,5,5a,5b,6,7,7a,9,10,10a,10b,11,12,12a-tetradecahydro-8H-cyclopenta[7,8]phenanthro[2,1-d] thiazol-8-one;

(5aR,5bS,7aS,10aS,10bR,12aR)-5a,7a-dimethyl-2-(4-methylphenyl)-4,5,5a,5b,6,7,7a,9,10,10a,10b,11,12, 12a-tetradecahydro-8H-cyclopenta[7,8]phenanthro[2, 1-d]thiazol-8-one;

(5aR,5bS,7aS,10aS,10bR,12aR)-5a,7a-dimethyl-2-(3-methylphenyl)-4,5,5a,5b,6,7,7a,9,10,10a,10b,11,12, 12a-tetradecahydro-8H-cyclopenta[7,8]phenanthro[2, 1-d]thiazol-8-one;

(5aR,5bS,7aS,10aS,10bR,12aR)-2-(4-methoxyphenyl)-5a,7a-dimethyl-4,5,5a,5b,6,7,7a,9,10,10a,10b,11,12, 12a-tetradecahydro-8H-cyclopenta[7,8]phenanthro[2, 1-d]thiazol-8-one;

(5aR,5bS,7aS,10aS,10bR,12aR)-2-(3-methoxyphenyl)-5a,7a-dimethyl-4,5,5a,5b,6,7,7a,9,10,10a,10b,11,12, 12a-tetradecahydro-8H-cyclopenta[7,8]phenanthro[2, 1-d]thiazol-8-one;

(5aR,5bS,7aS,10aS,10bR,12aR)-2-(2-hydroxyphenyl)-5a,7a-dimethyl-4,5,5a,5b,6,7,7a,9,10,10a,10b,11,12, 12a-tetradecahydro-8H-cyclopenta[7,8]phenanthro[2, 1-d]thiazol-8-one;

(5aR,5bS,7aS,10aS,10bR,12aR)-2-(4-fluorophenyl)-5a, 7a-dimethyl-4,5,5a,5b,6,7,7a,9,10,10a,10b,11,12,12a-tetradecahydro-8H-cyclopenta[7,8]phenanthro[2,1-d] thiazol-8-one;

(5aR,5bS,7aS,10aS,10bR,12aR)-2-(3-fluorophenyl)-5a, 7a-dimethyl-4,5,5a,5b,6,7,7a,9,10,10a,10b,11,12,12a-tetradecahydro-8H-cyclopenta[7,8]phenanthro[2,1-d] thiazol-8-one;

(5aR,5bS,7aS,10aS,10bR,12aR)-2-(4-chlorophenyl)-5a, 7a-dimethyl-4,5,5a,5b,6,7,7a,9,10,10a,10b,11,12,12a-tetradecahydro-8H-cyclopenta[7,8]phenanthro[2,1-d] thiazol-8-one;

(5aR,5bS,7aS,10aS,10bR,12aR)-2-(3-chlorophenyl)-5a, 7a-dimethyl-4,5,5a,5b,6,7,7a,9,10,10a,10b,11,12,12a-tetradecahydro-8H-cyclopenta[7,8]phenanthro[2,1-d] thiazol-8-one;

(5aR,5bS,7aS,10aS,10bR,12aR)-2-(4-bromophenyl)-5a, 7a-dimethyl-4,5,5a,5b,6,7,7a,9,10,10a,10b,11,12,12a-tetradecahydro-8H-cyclopenta[7,8]phenanthro[2,1-d] thiazol-8-one;

(5aR,5bS,7aS,10aS,10bR,12aR)-2-(3-hydroxyphenyl)-5a,7a-dimethyl-4,5,5a,5b,6,7,7a,9,10,10a,10b,11,12, 12a-tetradecahydro-8H-cyclopenta[7,8]phenanthro[2, 1-d]thiazol-8-one;

(5aR,5bS,7aS,10aS,10bR,12aR)-5a,7a-dimethyl-2-(2-methylbenzyl)-4,5,5a,5b,6,7,7a,9,10,10a,10b,11,12, 12a-tetradecahydro-8H-cyclopenta[7,8]phenanthro[2, 1-d]thiazol-8-one;

(5aR,5bS,7aS,8S,10aS,10bR,12aR)-5a,7a-dimethyl-2-(2-methylbenzyl)-5,5a,5b,6,7,7a,8,9,10,10a,10b,11,12, 12a-tetradecahydro-4H-cyclopenta[7,8]phenanthro[2, 1-d]thiazol-8-ol (5aR,5bS,7aS,8S,10aS,10bR,12aR)-2-benzyl-5a,7a-dimethyl-5,5a,5b,6,7,7a,8,9,10,10a,10b, 11,12,12a-tetradecahydro-4H-cyclopenta[7,8] phenanthro[2,1-d]thiazol-8-ol;

(5aR,5bS,7aS,8S,10aS,10bR,12aR)-2,5a,7a-trimethyl-5, 5a,5b,6,7,7a,8,9,10,10a,10b,11,12,12a-tetradecahydro-4H-cyclopenta[7,8]phenanthro[2,1-d]thiazol-8-ol;

(5aR,5bS,7aS,8S,10aS,10bR,12aR)-5a,7a-dimethyl-2-(pyridin-2-yl)-5,5a,5b,6,7,7a,8,9,10,10a,10b,11,12, 12a-tetradecahydro-4H-cyclopenta[7,8]phenanthro[2, 1-d]thiazol-8-ol;

(5aR,5bS,7aS,8S,10aS,10bR,12aR)-2-(4-hydroxyphenyl)-5a,7a-dimethyl-5,5a,5b,6,7,7a,8,9,10,10a,10b,11, 12,12a-tetradecahydro-4H-cyclopenta[7,8]phenanthro [2,1-d]thiazol-8-ol;

(5aR,5bS,7aS,8S,10aS,10bR,12aR)-2-(3-hydroxyphenyl)-5a,7a-dimethyl-5,5a,5b,6,7,7a,8,9,10,10a,10b,11, 12,12a-tetradecahydro-4H-cyclopenta[7,8]phenanthro [2,1-d]thiazol-8-ol;

(5aR,5bS,7aS,8S,10aS,10bR,12aR)-2-(2-hydroxyphenyl)-5a,7a-dimethyl-5,5a,5b,6,7,7a,8,9,10,10a,10b,11, 12,12a-tetradecahydro-4H-cyclopenta[7,8]phenanthro [2,1-d]thiazol-8-ol;

(5aR,5bS,7aS,8S,10aS,10bR,12aR)-2-(2-chlorophenyl)-5a,7a-dimethyl-5,5a,5b,6,7,7a,8,9,10,10a,10b,11,12, 12a-tetradecahydro-4H-cyclopenta[7,8]phenanthro[2, 1-d]thiazol-8-ol;

(5aR,5bS,7aS,8S,10aS,10bR,12aR)-2-(3-chlorophenyl)-
5a,7a-dimethyl-5,5a,5b,6,7,7a,8,9,10,10a,10b,11,12,
12a-tetradecahydro-4H-cyclopenta[7,8]phenanthro[2,
1-d]thiazol-8-ol;

(5aR,5bS,7aS,8S,10aS,10bR,12aR)-2-(4-chlorophenyl)-
5a,7a-dimethyl-5,5a,5b,6,7,7a,8,9,10,10a,10b,11,12,
12a-tetradecahydro-4H-cyclopenta[7,8]phenanthro[2,
1-d]thiazol-8-ol;

(5aR,5bS,7aS,8S,10aS,10bR,12aR)-2-(3-methylphenyl)-
5a,7a-dimethyl-5,5a,5b,6,7,7a,8,9,10,10a,10b,11,12,
12a-tetradecahydro-4H-cyclopenta[7,8]phenanthro[2,
1-d]thiazol-8-ol;

(5aR,5bS,7aS,8S,10aS,10bR,12aR)-2-(4-methylphenyl)-
5a,7a-dimethyl-5,5a,5b,6,7,7a,8,9,10,10a,10b,11,12,
12a-tetradecahydro-4H-cyclopenta[7,8]phenanthro[2,
1-d]thiazol-8-ol;

(5aR,5bS,7aS,8S,10aS,10bR,12aR)-2-(4-fluorophenyl)-
5a,7a-dimethyl-5,5a,5b,6,7,7a,8,9,10,10a,10b,11,12,
12a-tetradecahydro-4H-cyclopenta[7,8]phenanthro[2,
1-d]thiazol-8-ol;

(5aR,5bS,7aS,8S,10aS,10bR,12aR)-2-(3-fluorophenyl)-
5a,7a-dimethyl-5,5a,5b,6,7,7a,8,9,10,10a,10b,11,12,
12a-tetradecahydro-4H-cyclopenta[7,8]phenanthro[2,
1-d]thiazol-8-ol;

(5aR,5bS,7aS,8S,10aS,10bR,12aR)-2-(4-bromophenyl)-
5a,7a-dimethyl-5,5a,5b,6,7,7a,8,9,10,10a,10b,11,12,
12a-tetradecahydro-4H-cyclopenta[7,8]phenanthro[2,
1-d]thiazol-8-ol;

(5aR,5bS,7aS,8S,10aS,10bR,12aR)-2-(4-methoxyphenyl)-5a,7a-dimethyl-5,5a,5b,6,7,7a,8,9,10,10a,10b,11,
12,12a-tetradecahydro-4H-cyclopenta[7,8]phenanthro
[2,1-d]thiazol-8-ol;

(5aR,5bS,7aS,8S,10aS,10bR,12aR)-2-(3-methoxyphenyl)-5a,7a-dimethyl-5,5a,5b,6,7,7a,8,9,10,10a,10b,11,
12,12a-tetradecahydro-4H-cyclopenta[7,8]phenanthro
[2,1-d]thiazol-8-ol;

(5aR,5bS,7aS,10aS,10bR,12S,12aS)-12-hydroxy-2,5a,
7a-trimethyl-4,5,5a,5b,6,7,7a,9,10,10a,10b,11,12,12a-
tetradecahydro-8H-cyclopenta[7,8]phenanthro[2,1-d]
thiazol-8-one;

(5aR,5bS,7aS,10aS,10bR,12S,12aS)-2-benzyl-12-hydroxy-5a,7a-dimethyl-4,5,5a,5b,6,7,7a,9,10,10a,10b,
11,12,12a-tetradecahydro-8H-cyclopenta[7,8]
phenanthro[2,1-d]thiazol-8-one;

(5aR,5bS,7aS,10aS,10bR,12S,12aS)-12-hydroxy-5a,7a-
dimethyl-2-(2-methylbenzyl)-4,5,5a,5b,6,7,7a,9,10,
10a,10b,11,12,12a-tetradecahydro-8H-cyclopenta[7,8]
phenanthro[2,1-d]thiazol-8-one;

(5aR,5bS,7aS,10aS,10bR,12S,12aS)-12-hydroxy-5a,7a-
dimethyl-2-(pyridin-2-yl)-4,5,5a,5b,6,7,7a,9,10,10a,
10b,11,12,12a-tetradecahydro-8H-cyclopenta[7,8]
phenanthro[2,1-d]thiazol-8-one;

(5aR,5bS,7aS,10aS,10bR,12S,12aS)-12-hydroxy-2-(4-
hydroxyphenyl)-5a,7a-dimethyl-4,5,5a,5b,6,7,7a,9,10,
10a,10b,11,12,12a-tetradecahydro-8H-cyclopenta[7,8]
phenanthro[2,1-d]thiazol-8-one;

(5aR,5bS,7aS,10aS,10bR,12S,12aS)-12-hydroxy-2-(3-
hydroxyphenyl)-5a,7a-dimethyl-4,5,5a,5b,6,7,7a,9,10,
10a,10b,11,12,12a-tetradecahydro-8H-cyclopenta[7,8]
phenanthro[2,1-d]thiazol-8-one;

(5aR,5bS,7aS,10aS,10bR,12S,12aS)-12-hydroxy-2-(2-
hydroxyphenyl)-5a,7a-dimethyl-4,5,5a,5b,6,7,7a,9,10,
10a,10b,11,12,12a-tetradecahydro-8H-cyclopenta[7,8]
phenanthro[2,1-d]thiazol-8-one;

(5aR,5bS,7aS,10aS,10bR,12S,12aS)-2-(4-chlorophenyl)-
12-hydroxy-5a,7a-dimethyl-4,5,5a,5b,6,7,7a,9,10,10a,
10b,11,12,12a-tetradecahydro-8H-cyclopenta[7,8]
phenanthro[2,1-d]thiazol-8-one;

(5aR,5bS,7aS,10aS,10bR,12S,12aS)-2-(3-chlorophenyl)-
12-hydroxy-5a,7a-dimethyl-4,5,5a,5b,6,7,7a,9,10,10a,
10b,11,12,12a-tetradecahydro-8H-cyclopenta[7,8]
phenanthro[2,1-d]thiazol-8-one;

(5aR,5bS,7aS,10aS,10bR,12S,12aS)-2-(2-chlorophenyl)-
12-hydroxy-5a,7a-dimethyl-4,5,5a,5b,6,7,7a,9,10,10a,
10b,11,12,12a-tetradecahydro-8H-cyclopenta[7,8]
phenanthro[2,1-d]thiazol-8-one;

(5aR,5bS,7aS,10aS,10bR,12S,12aS)-2-(4-bromophenyl)-
12-hydroxy-5a,7a-dimethyl-4,5,5a,5b,6,7,7a,9,10,10a,
10b,11,12,12a-tetradecahydro-8H-cyclopenta[7,8]
phenanthro[2,1-d]thiazol-8-one;

(5aR,5bS,7aS,10aS,10bR,12S,12aS)-2-(4-fluorophenyl)-
12-hydroxy-5a,7a-dimethyl-4,5,5a,5b,6,7,7a,9,10,10a,
10b,11,12,12a-tetradecahydro-8H-cyclopenta[7,8]
phenanthro[2,1-d]thiazol-8-one;

(5aR,5bS,7aS,10aS,10bR,12S,12aS)-2-(3-fluorophenyl)-
12-hydroxy-5a,7a-dimethyl-4,5,5a,5b,6,7,7a,9,10,10a,
10b,11,12,12a-tetradecahydro-8H-cyclopenta[7,8]
phenanthro[2,1-d]thiazol-8-one;

(5aR,5bS,7aS,10aS,10bR,12S,12aS)-2-(4-methylphenyl)-12-hydroxy-5a,7a-dimethyl-4,5,5a,5b,6,7,7a,9,10,
10a,10b,11,12,12a-tetradecahydro-8H-cyclopenta[7,8]
phenanthro[2,1-d]thiazol-8-one;

(5aR,5bS,7aS,10aS,10bR,12S,12aS)-2-(4-methylphenyl)-12-hydroxy-5a,7a-dimethyl-4,5,5a,5b,6,7,7a,9,10,
10a,10b,11,12,12a-tetradecahydro-8H-cyclopenta[7,8]
phenanthro[2,1-d]thiazol-8-one;

(5aR,5bS,7aS,10aS,10bR,12S,12aS)-12-hydroxy-2-(4-
methoxyphenyl)-5a,7a-dimethyl-4,5,5a,5b,6,7,7a,9,10,
10a,10b,11,12,12a-tetradecahydro-8H-cyclopenta[7,8]
phenanthro[2,1-d]thiazol-8-one;

(5aR,5bS,7aS,10aS,10bR,12S,12aS)-12-hydroxy-2-(3-
methoxyphenyl)-5a,7a-dimethyl-4,5,5a,5b,6,7,7a,9,10,
10a,10b,11,12,12a-tetradecahydro-8H-cyclopenta[7,8]
phenanthro[2,1-d]thiazol-8-one;

(5aR,5bS,7aS,10aS,10bR,12S,12aR)-12,12a-dihydroxy-
2,5a,7a-trimethyl-4,5,5a,5b,6,7,7a,9,10,10a,10b,11,12,
12a-tetradecahydro-8H-cyclopenta[7,8]phenanthro[2,
1-d]thiazol-8-one (5aR,5bS,7aS,10aS,10bR,12S,12aR)-2-benzyl-12,12a-dihydroxy-5a,7a-dimethyl-4,5,5a,5b,6,7,7a,9,10,10a,
10b,11,12,12a-tetradecahydro-8H-cyclopenta[7,8]
phenanthro[2,1-d]thiazol-8-one;

(5aR,5bS,7aS,10aS,10bR,12S,12aR)-12,12a-dihydroxy-
5a,7a-dimethyl-2-(2-methylbenzyl)-4,5,5a,5b,6,7,7a,9,
10,10a,10b,11,12,12a-tetradecahydro-8H-cyclopenta
[7,8]phenanthro[2,1-d]thiazol-8-one;

(5aR,5bS,7aS,10aS,10bR,12S,12aR)-12,12a-dihydroxy-
5a,7a-dimethyl-2-(pyridin-2-yl)-4,5,5a,5b,6,7,7a,9,10,
10a,10b,11,12,12a-tetradecahydro-8H-cyclopenta[7,8]
phenanthro[2,1-d]thiazol-8-one;

(5aR,5bS,7aS,10aS,10bR,12S,12aR)-12,12a-dihydroxy-
2-(4-hydroxyphenyl)-5a,7a-dimethyl-4,5,5a,5b,6,7,7a,
9,10,10a,10b,11,12,12a-tetradecahydro-8H-cyclopenta
[7,8]phenanthro[2,1-d]thiazol-8-one;

(5aR,5bS,7aS,10aS,10bR,12S,12aR)-12,12a-dihydroxy-
2-(3-hydroxyphenyl)-5a,7a-dimethyl-4,5,5a,5b,6,7,7a,
9,10,10a,10b,11,12,12a-tetradecahydro-8H-cyclopenta
[7,8]phenanthro[2,1-d]thiazol-8-one;

(5aR,5bS,7aS,10aS,10bR,12S,12aR)-12,12a-dihydroxy-
2-(2-hydroxyphenyl)-5a,7a-dimethyl-4,5,5a,5b,6,7,7a,
9,10,10a,10b,11,12,12a-tetradecahydro-8H-cyclopenta
[7,8]phenanthro[2,1-d]thiazol-8-one;

(5aR,5bS,7aS,10aS,10bR,12S,12aR)-2-(4-chlorophenyl)-12,12a-dihydroxy-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR,12S,12aR)-2-(3-chlorophenyl)-12,12a-dihydroxy-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR,12S,12aR)-2-(2-chlorophenyl)-12,12a-dihydroxy-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR,12S,12aR)-2-(4-bromophenyl)-12,12a-dihydroxy-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR,12S,12aR)-2-(4-fluorophenyl)-12,12a-dihydroxy-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5bS,7aS,10aS,10bR,12S,12aR)-2-(3-fluorophenyl)-12,12a-dihydroxy-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR,12S,12aR)-2-(4-methylphenyl)-12,12a-dihydroxy-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR,12S,12aR)-2-(3-methylphenyl)-12,12a-dihydroxy-5a,7a-dimethyl-4,5,5a,5b,6,7,7a,9,10,10a,10b,11,12,12a-tetradecahydro-8H-cyclopenta[7,8]phenanthro[2,1-d]thiazol-8-one;

(5aR,5bS,7aS,10aS,10bR,12S,12aR)-2-(4-methoxyphenyl)-12,12a-dihydroxy-5a,7a-dimethyl-4,5,5a,5b,6,7,7a,9,10,10a,10b,11,12,12a-tetradecahydro-8H-cyclopenta[7,8]phenanthro[2,1-d]thiazol-8-one; and (5aR,5bS,7aS,10aS,10bR,12S,12aR)-2-(3-methoxyphenyl)-12,12a-dihydroxy-5a,7a-dimethyl-4,5,5a,5b,6,7,7a,9,10,10a,10b,11,12,12a-tetradecahydro-8H-cyclopenta[7,8]phenanthro[2,1-d]thiazol-8-one.

10. A pharmaceutical composition comprising a therapeutically effective amount of the compound according to claim 1 and a pharmaceutically acceptable carrier, diluent, or excipient.

11. A method for inhibiting proliferation of or killing a cell comprising contacting the cell with the compound of claim 1, wherein the cell is melanoma.

12. A method for the treatment of a subject comprising administering to the subject a therapeutically effective amount of the compound of claim 1 or a pharmaceutical composition comprising a therapeutically effective amount of the compound of claim 1 and a pharmaceutically acceptable carrier, diluent, or excipient, wherein the subject has melanoma.

* * * * *